(12) United States Patent
Jaluria et al.

(10) Patent No.: US 11,352,612 B2
(45) Date of Patent: Jun. 7, 2022

(54) MANUFACTURING OF ALKALINE PHOSPHATASES

(71) Applicant: Alexion Pharmaceuticals, Inc., Boston, MA (US)

(72) Inventors: Pratik Jaluria, Madison, CT (US); Siguang Sui, Cheshire, CT (US)

(73) Assignee: Alexion Pharmaceuticals, Inc., Boston, MA (US)

(*) Notice: Subject to any disclaimer, the term of this patent is extended or adjusted under 35 U.S.C. 154(b) by 1002 days.

(21) Appl. No.: 15/751,498

(22) PCT Filed: Aug. 16, 2016

(86) PCT No.: PCT/US2016/047166
§ 371 (c)(1),
(2) Date: May 31, 2018

(87) PCT Pub. No.: WO2017/031114
PCT Pub. Date: Feb. 23, 2017

(65) Prior Publication Data
US 2018/0230445 A1  Aug. 16, 2018

Related U.S. Application Data

(60) Provisional application No. 62/206,001, filed on Aug. 17, 2015.

(51) Int. Cl.
*C12N 9/16* (2006.01)
*A61P 19/08* (2006.01)
*A61K 38/00* (2006.01)

(52) U.S. Cl.
CPC ............ *C12N 9/16* (2013.01); *A61P 19/08* (2018.01); *C12Y 301/03001* (2013.01); *A61K 38/00* (2013.01); *C12N 2500/22* (2013.01)

(58) Field of Classification Search
CPC ........ C12Y 301/03001; C12N 2500/60; C12N 9/16
See application file for complete search history.

(56) References Cited

U.S. PATENT DOCUMENTS

| | | | |
|---|---|---|---|
| 5,336,759 A | 8/1994 | Matsuo et al. |
| 5,338,830 A | 8/1994 | Matsuo et al. |
| 5,340,920 A | 8/1994 | Matsuo et al. |
| 5,352,770 A | 10/1994 | Matsuo |
| 5,428,130 A | 6/1995 | Capon et al. |
| 5,434,133 A | 7/1995 | Tanaka et al. |
| 5,583,108 A | 12/1996 | Wei et al. |
| 5,665,704 A | 9/1997 | Lowe et al. |
| 5,714,147 A | 2/1998 | Capon et al. |
| 5,767,239 A | 6/1998 | Immer et al. |
| 5,846,932 A | 12/1998 | Lowe et al. |
| 5,948,761 A | 9/1999 | Seilhamer et al. |
| 5,973,134 A | 10/1999 | Matsuo et al. |
| 6,020,168 A | 2/2000 | Matsuo et al. |
| 6,028,055 A | 2/2000 | Lowe et al. |
| 6,034,231 A | 3/2000 | Tanaka et al. |
| 6,290,952 B1 | 9/2001 | Poelstra et al. |
| 6,406,697 B1 | 6/2002 | Capon et al. |
| 6,407,211 B1 | 6/2002 | Burnett, Jr. et al. |
| 6,420,384 B2 | 7/2002 | Weigele et al. |
| 6,436,386 B1 | 8/2002 | Roberts et al. |
| 6,455,495 B1 | 9/2002 | Orgel et al. |
| 6,458,579 B2 | 10/2002 | Hopwood et al. |
| 6,525,022 B1 | 2/2003 | Lowe et al. |
| 6,541,610 B1 | 4/2003 | Smith |
| 6,743,425 B2 | 6/2004 | Nakao |
| 6,790,649 B1 | 9/2004 | Crine et al. |
| 6,818,619 B2 | 11/2004 | Burnett, Jr. et al. |
| 6,830,885 B1 | 12/2004 | Lanctot et al. |
| 6,849,714 B1 | 2/2005 | Bridon et al. |
| 6,887,470 B1 | 5/2005 | Bridon et al. |
| 6,905,689 B2 | 6/2005 | Schneidinger et al. |
| 6,946,484 B2 | 9/2005 | Adams et al. |
| 7,026,293 B2 | 4/2006 | Kitakaze |

(Continued)

FOREIGN PATENT DOCUMENTS

| | | |
|---|---|---|
| EP | 0478797 B1 | 4/1995 |
| EP | 0769554 A2 | 4/1997 |

(Continued)

OTHER PUBLICATIONS

Animal Cell Technology: Basic & Applied Aspects, vol. 13, Nov. 11-15, 2002. Ed. Yagasaki, Miura, Hatori & Nomura. Oguchi et al., "Control of Temperature and pH Enahnces Human Monoclonal Antibody Production in CHO Cell Culture", pp. 169-172.*
Kochanowski et al., "Medium and feed optimization for fed-batch production of a monoclonal antibody in CHO cells", BMC Proceedings 2011, 5(Suppl 8):p. 75.*
"Xcellerex™ XDR cell culture bioreactor systems", GE Healthcare Life Sciences, Feb. 2014, Retrieved from < https://www.cytivalifesciences.co.jp/catalog/pdf/29092925AA.pdf>.*
Fu-Hang et al., "Preliminary study on the effect of Zn2+ on the activities of peptidase and alkaline phosphatase," Marine Sciences. 27(3):64-65 (2003).

(Continued)

*Primary Examiner* — Suzanne M Noakes
(74) *Attorney, Agent, or Firm* — Clark & Elbing LLP

(57) ABSTRACT

A method for producing a recombinant polypeptide, comprising: (a) providing a 100 L to 25,000 L fed-batch bioreactor comprising (i) cells capable of expressing the recombinant polypeptide asfotase alfa (SEQ ID NO: 1), and (ii) a culture medium suitable for conducting such expression, the culture medium comprising about 25 µM to about 300 µM zinc; (b) culturing the cells under conditions suitable to express the recombinant asfotase alfa wherein the pH of the culture medium is about 6.7 to about 7.1, and wherein zinc is added into said culture medium such that the zinc concentration in the culture medium is maintained at a concentration of about 25 µM to about 300 µM of zinc.

18 Claims, 54 Drawing Sheets

Specification includes a Sequence Listing.

(56) References Cited

U.S. PATENT DOCUMENTS

| | | |
|---|---|---|
| 7,033,997 B2 | 4/2006 | Forssmann et al. |
| 7,070,974 B1 | 7/2006 | Desgroseillers et al. |
| 7,105,539 B2 | 9/2006 | Gravel et al. |
| 7,179,903 B2 | 2/2007 | McArthur et al. |
| 7,256,253 B2 | 8/2007 | Bridon et al. |
| 7,271,149 B2 | 9/2007 | Glaesner et al. |
| 7,276,481 B2 | 10/2007 | Golembo et al. |
| 7,341,838 B2 | 3/2008 | Buechler et al. |
| 7,365,091 B2 | 4/2008 | Gravel et al. |
| 7,384,917 B2 | 6/2008 | Burnett, Jr. et al. |
| 7,399,466 B2 | 7/2008 | Boileau |
| 7,414,107 B2 | 8/2008 | Larsen |
| 7,425,531 B2 | 9/2008 | Lanctot et al. |
| 7,427,498 B2 | 9/2008 | Crine et al. |
| 7,470,668 B2 | 12/2008 | Lanctot et al. |
| 7,488,713 B2 | 2/2009 | Vesely |
| 7,527,939 B2 | 5/2009 | Davey et al. |
| 7,563,769 B2 | 7/2009 | Bogin et al. |
| 7,625,564 B2 | 12/2009 | Wang et al. |
| 7,642,243 B2 | 1/2010 | Nakao et al. |
| 7,648,962 B2 | 1/2010 | James et al. |
| 7,662,773 B2 | 2/2010 | James et al. |
| 7,678,391 B2 | 3/2010 | Graham et al. |
| 7,732,406 B2 | 6/2010 | Mitrovic et al. |
| 7,736,653 B2 | 6/2010 | Kim et al. |
| 7,754,852 B2 | 7/2010 | Burnett, Jr. et al. |
| 7,763,712 B2 | 7/2010 | Crine et al. |
| 7,803,769 B2 | 9/2010 | Sullivan et al. |
| 7,803,901 B2 | 9/2010 | Burnett, Jr. et al. |
| 7,825,092 B2 | 11/2010 | Vesely |
| 7,846,900 B2 | 12/2010 | Vesely |
| 7,858,560 B2 | 12/2010 | Koster et al. |
| 7,919,591 B2 | 4/2011 | Sheffer et al. |
| 7,943,126 B2 | 5/2011 | Tomatsu et al. |
| 7,960,529 B2 | 6/2011 | Crine et al. |
| 8,058,242 B2 | 11/2011 | Alewood et al. |
| 8,691,208 B2 | 4/2014 | Tomatsu et al. |
| 9,266,939 B2 | 2/2016 | Crine et al. |
| 9,908,932 B2 | 3/2018 | Malanson et al. |
| 9,988,620 B2 | 6/2018 | Crine et al. |
| 10,000,532 B2 | 6/2018 | Crine et al. |
| 10,052,366 B2 | 8/2018 | Crine et al. |
| 10,449,236 B2 | 10/2019 | Marozsan et al. |
| 10,603,361 B2 | 3/2020 | Odrljin |
| 2002/0183276 A1 | 12/2002 | Millan et al. |
| 2003/0158132 A1 | 8/2003 | Kovesdi |
| 2004/0023916 A1 | 2/2004 | Millan et al. |
| 2004/0077537 A1 | 4/2004 | Schreiner |
| 2004/0234518 A1 | 11/2004 | Crine et al. |
| 2005/0113286 A1 | 5/2005 | Schreiner et al. |
| 2005/0142217 A1 | 6/2005 | Adams et al. |
| 2005/0202442 A1 | 9/2005 | Morris et al. |
| 2005/0244904 A1 | 11/2005 | Ng |
| 2005/0276796 A1 | 12/2005 | Tomatsu et al. |
| 2006/0014687 A1 | 1/2006 | Crine et al. |
| 2006/0019890 A1 | 1/2006 | Kapoun et al. |
| 2006/0074009 A1 | 4/2006 | James et al. |
| 2006/0110359 A1 | 5/2006 | Sanchez-Ramos et al. |
| 2006/0172929 A1 | 8/2006 | Rappold-Hoerbrand et al. |
| 2006/0228710 A1 | 10/2006 | Morris et al. |
| 2007/0041972 A1 | 2/2007 | Rother et al. |
| 2007/0042957 A1 | 2/2007 | Burnett et al. |
| 2007/0081984 A1 | 4/2007 | Tomatsu et al. |
| 2007/0081986 A1 | 4/2007 | Tomatsu et al. |
| 2007/0197434 A1 | 8/2007 | Nakao et al. |
| 2007/0281887 A1 | 12/2007 | Pan |
| 2007/0292966 A1 | 12/2007 | Prickett et al. |
| 2007/0293418 A1 | 12/2007 | Larsen |
| 2008/0032933 A1 | 2/2008 | Burnett et al. |
| 2008/0081768 A1 | 4/2008 | Watt et al. |
| 2008/0085862 A1 | 4/2008 | Kim et al. |
| 2008/0113411 A1 | 5/2008 | Sheffer et al. |
| 2008/0113412 A1 | 5/2008 | Sheffer et al. |
| 2008/0125574 A1 | 5/2008 | Sheffer et al. |
| 2008/0153747 A1 | 6/2008 | Alewood et al. |
| 2008/0161243 A1 | 7/2008 | Rosen et al. |
| 2008/0181903 A1 | 7/2008 | Bhaskar et al. |
| 2008/0182299 A1 | 7/2008 | Colocaru et al. |
| 2008/0194481 A1 | 8/2008 | Rosen et al. |
| 2008/0194682 A1 | 8/2008 | Golembo et al. |
| 2008/0227713 A1 | 9/2008 | Rotter |
| 2008/0293632 A1 | 11/2008 | Rappold-Hoerbrand et al. |
| 2008/0312142 A1 | 12/2008 | Nakao et al. |
| 2009/0011997 A1 | 1/2009 | Peri et al. |
| 2009/0023652 A1 | 1/2009 | Bell et al. |
| 2009/0053192 A1 | 2/2009 | Millan et al. |
| 2009/0069243 A1 | 3/2009 | Burnett, Jr. et al. |
| 2009/0092582 A1 | 4/2009 | Bogin et al. |
| 2009/0142347 A1 | 6/2009 | Millan |
| 2009/0170756 A1 | 7/2009 | Burnett, Jr. et al. |
| 2009/0221803 A1 | 9/2009 | Dall'Acqua et al. |
| 2009/0238814 A1 | 9/2009 | Tomatsu et al. |
| 2009/0240031 A1 | 9/2009 | Immer et al. |
| 2009/0247462 A1 | 10/2009 | Bogin et al. |
| 2009/0252729 A1 | 10/2009 | Farrington et al. |
| 2009/0258018 A1 | 10/2009 | Medich et al. |
| 2009/0275506 A1 | 11/2009 | Bakis et al. |
| 2009/0325195 A1 | 12/2009 | Davey et al. |
| 2010/0008979 A1 | 1/2010 | Tomatsu et al. |
| 2010/0055150 A1 | 3/2010 | Golembo et al. |
| 2010/0093678 A1 | 4/2010 | Della-Fera et al. |
| 2010/0160212 A1 | 6/2010 | Sheffer et al. |
| 2010/0168443 A1 | 7/2010 | Geysen |
| 2010/0184680 A1 | 7/2010 | Bevec |
| 2010/0197574 A1 | 8/2010 | Chen et al. |
| 2010/0204094 A1 | 8/2010 | Simari et al. |
| 2010/0204109 A1 | 8/2010 | Bevec |
| 2010/0204446 A1 | 8/2010 | Forssmann |
| 2010/0209958 A1 | 8/2010 | Nakao et al. |
| 2010/0216714 A1 | 8/2010 | James et al. |
| 2010/0221234 A1 | 9/2010 | Crine et al. |
| 2010/0240125 A1 | 9/2010 | Crine et al. |
| 2010/0249017 A1 | 9/2010 | Bevec et al. |
| 2010/0260706 A1 | 10/2010 | Bogin et al. |
| 2010/0261248 A1 | 10/2010 | Kim et al. |
| 2010/0297021 A1 | 11/2010 | Wendt et al. |
| 2010/0297119 A1* | 11/2010 | Crine .............. A61P 1/02 424/134.1 |
| 2010/0305031 A1 | 12/2010 | Wakabayashi et al. |
| 2010/0305051 A1 | 12/2010 | Burnett, Jr. et al. |
| 2010/0310561 A1 | 12/2010 | Canada et al. |
| 2010/0311660 A1 | 12/2010 | Simari et al. |
| 2010/0317600 A1 | 12/2010 | Immer et al. |
| 2010/0331256 A1 | 12/2010 | Wendt et al. |
| 2011/0152194 A1 | 6/2011 | Burnett, Jr. et al. |
| 2011/0250187 A1 | 10/2011 | Tomatsu et al. |
| 2011/0269684 A1 | 11/2011 | Burnett, Jr. et al. |
| 2011/0300143 A1 | 12/2011 | Sly et al. |
| 2012/0088771 A1 | 4/2012 | Millan |
| 2012/0164142 A1 | 6/2012 | Crine et al. |
| 2013/0108635 A1 | 5/2013 | Crine et al. |
| 2013/0323244 A1 | 12/2013 | Crine et al. |
| 2014/0193388 A1 | 7/2014 | Velders et al. |
| 2014/0194484 A1 | 7/2014 | Coats et al. |
| 2015/0353633 A1 | 12/2015 | Kakkis et al. |
| 2016/0052968 A1 | 2/2016 | Crine et al. |
| 2016/0097100 A1 | 4/2016 | Trent et al. |
| 2017/0175094 A1 | 6/2017 | Hatch |
| 2017/0360899 A1 | 12/2017 | Marozsan et al. |
| 2018/0230445 A1 | 8/2018 | Jaluria et al. |

FOREIGN PATENT DOCUMENTS

| | | |
|---|---|---|
| EP | 0771875 B1 | 5/1997 |
| EP | 0466174 B1 | 6/1997 |
| EP | 0475394 B1 | 6/1997 |
| EP | 0466175 B1 | 1/1998 |
| EP | 0477971 B1 | 1/1998 |
| EP | 0475290 B1 | 12/1998 |
| EP | 0475291 B1 | 12/1998 |
| EP | 0497368 B1 | 6/2002 |
| EP | 1492567 | 9/2003 |
| EP | 1502604 A1 | 2/2005 |
| EP | 1623994 A2 | 2/2006 |

(56) References Cited

FOREIGN PATENT DOCUMENTS

| | | |
|---|---|---|
| EP | 1759001 B1 | 3/2007 |
| EP | 1759710 A1 | 3/2007 |
| EP | 1985697 A1 | 10/2008 |
| EP | 2158319 | 3/2010 |
| EP | 2158319 B1 | 12/2011 |
| EP | 3250227 A2 | 12/2017 |
| JP | H0870875 A | 3/1996 |
| JP | 2000-327583 A | 11/2000 |
| JP | 2002-541776 A | 12/2002 |
| JP | 2007-511209 A | 5/2007 |
| JP | 2010-501026 A | 1/2010 |
| JP | 2010-526543 A | 8/2010 |
| JP | 2010-530222 A | 9/2010 |
| JP | 2011-504506 A | 2/2011 |
| WO | WO-92/20371 A1 | 11/1992 |
| WO | WO-94/20534 A1 | 9/1994 |
| WO | WO-95/05456 A1 | 2/1995 |
| WO | WO-95/13296 A1 | 5/1995 |
| WO | WO-95/33769 A1 | 12/1995 |
| WO | WO-98/17690 A1 | 4/1998 |
| WO | WO-98/35703 A2 | 8/1998 |
| WO | WO-99/46283 A1 | 9/1999 |
| WO | WO-00/18954 A2 | 4/2000 |
| WO | WO-00/50580 A2 | 8/2000 |
| WO | WO-00/53755 A2 | 9/2000 |
| WO | WO-00/64486 A2 | 11/2000 |
| WO | WO-00/69900 A2 | 11/2000 |
| WO | WO-01/36620 A2 | 5/2001 |
| WO | WO-01/44284 A2 | 6/2001 |
| WO | WO-01/80890 A2 | 11/2001 |
| WO | WO-02/15918 A2 | 2/2002 |
| WO | WO-02/47871 A1 | 6/2002 |
| WO | WO-02/067639 A1 | 8/2002 |
| WO | WO-02/068579 A2 | 9/2002 |
| WO | WO-02/074234 A2 | 9/2002 |
| WO | WO-03/074082 A1 | 9/2003 |
| WO | WO-03/079979 A2 | 10/2003 |
| WO | WO-03/092581 A2 | 11/2003 |
| WO | WO-03/094835 A2 | 11/2003 |
| WO | WO-2004/011498 A2 | 2/2004 |
| WO | WO-2004/022579 A2 | 3/2004 |
| WO | WO-2004/046194 A2 | 6/2004 |
| WO | WO-2004/047871 A2 | 6/2004 |
| WO | WO-2004/062555 A2 | 7/2004 |
| WO | WO-2004/074320 A2 | 9/2004 |
| WO | WO-2004/094460 A2 | 11/2004 |
| WO | WO-2005/000095 A2 | 1/2005 |
| WO | WO-2005/007809 A2 | 1/2005 |
| WO | WO-2005/042034 A1 | 5/2005 |
| WO | WO-2005/047337 A1 | 5/2005 |
| WO | WO-2005/070446 A1 | 8/2005 |
| WO | WO-2005/072055 A2 | 8/2005 |
| WO | WO-2005/087802 A2 | 9/2005 |
| WO | WO-2005/094890 A2 | 10/2005 |
| WO | WO-2005/098490 A1 | 10/2005 |
| WO | WO-2005/103263 A1 | 11/2005 |
| WO | WO-2005/110435 A1 | 11/2005 |
| WO | WO-2006/005140 A2 | 1/2006 |
| WO | WO-2006/026663 A1 | 3/2006 |
| WO | WO-2006/039480 A2 | 4/2006 |
| WO | WO-2006/060641 A2 | 6/2006 |
| WO | WO-2006/110743 A1 | 10/2006 |
| WO | WO-2006/116260 A2 | 11/2006 |
| WO | WO-2007/041645 A2 | 4/2007 |
| WO | WO-2007/071295 A1 | 6/2007 |
| WO | WO-2007/097923 A2 | 8/2007 |
| WO | WO-2007/130113 A2 | 11/2007 |
| WO | WO-2008/021872 A2 | 2/2008 |
| WO | WO-2008/030558 A2 | 3/2008 |
| WO | WO-2008/031045 A2 | 3/2008 |
| WO | WO-2008/053362 A2 | 5/2008 |
| WO | WO-2008/058016 A2 | 5/2008 |
| WO | WO-2008/079995 A2 | 7/2008 |
| WO | WO-2008/088422 A2 | 7/2008 |
| WO | WO-2008/109903 A1 | 9/2008 |
| WO | WO-2008/136611 A1 | 11/2008 |
| WO | WO-2008/138131 A1 | 11/2008 |
| WO | WO-2008/154226 A1 | 12/2008 |
| WO | WO-2009/006520 A1 | 1/2009 |
| WO | WO-2009/006732 A9 | 1/2009 |
| WO | WO-2009/015011 A1 | 1/2009 |
| WO | WO-2009/023270 A2 | 2/2009 |
| WO | WO-2009/033680 A2 | 3/2009 |
| WO | WO-2009/033724 A1 | 3/2009 |
| WO | WO-2009/033796 A1 | 3/2009 |
| WO | WO-2009/033807 A2 | 3/2009 |
| WO | WO-2009/034134 A2 | 3/2009 |
| WO | WO-2009/036448 A2 | 3/2009 |
| WO | WO-2009/040030 A1 | 4/2009 |
| WO | WO-2009/040031 A2 | 4/2009 |
| WO | WO-2009/040083 A2 | 4/2009 |
| WO | WO-2009/046861 A1 | 4/2009 |
| WO | WO-2009/058322 A1 | 5/2009 |
| WO | WO-2009/067639 A2 | 5/2009 |
| WO | WO-2009/086126 A2 | 7/2009 |
| WO | WO-2009/090553 A2 | 7/2009 |
| WO | WO-2009/142307 A1 | 11/2009 |
| WO | WO-2009/149161 A9 | 12/2009 |
| WO | WO-2009/156481 A1 | 12/2009 |
| WO | WO-2009/158035 A2 | 12/2009 |
| WO | WO-2010/002583 A2 | 1/2010 |
| WO | WO-2010/011096 A2 | 1/2010 |
| WO | WO-2010/048308 A2 | 4/2010 |
| WO | WO-2010/078325 A2 | 7/2010 |
| WO | WO-2010/082804 A2 | 7/2010 |
| WO | WO-2010/117760 A2 | 10/2010 |
| WO | WO-2010/129655 A2 | 11/2010 |
| WO | WO-2010/135541 A2 | 11/2010 |
| WO | WO-2011/130229 A1 | 10/2011 |
| WO | WO-2011/134084 A1 | 11/2011 |
| WO | WO-2012/088608 A1 | 7/2012 |
| WO | WO-2012/099851 A2 | 7/2012 |
| WO | WO-2013/058833 A1 | 4/2013 |
| WO | WO-2013/059491 A1 | 4/2013 |
| WO | WO-2013/071262 A1 | 5/2013 |
| WO | WO-2015/112015 A1 | 7/2015 |
| WO | WO-2015/112017 A1 | 7/2015 |
| WO | WO-2016/007873 A1 | 1/2016 |
| WO | WO-2016/090251 A1 | 6/2016 |
| WO | WO-2016/123342 A2 | 8/2016 |
| WO | WO 2016/153191 * | 9/2016 |
| WO | WO-2017/031114 A1 | 2/2017 |
| WO | WO-2017/058822 A1 | 4/2017 |
| WO | WO-2017/074466 A1 | 5/2017 |
| WO | WO-2017/155569 A1 | 9/2017 |
| WO | WO-2017/171871 A1 | 10/2017 |
| WO | WO-2017/173395 A1 | 10/2017 |
| WO | WO-2017/173413 A1 | 10/2017 |
| WO | WO-2017/214130 A1 | 12/2017 |
| WO | WO-2018/004517 A1 | 1/2018 |
| WO | WO-2018/035420 A1 | 2/2018 |

OTHER PUBLICATIONS

International Preliminary Report on Patentability for International Patent Application No. PCT/US2016/049983, dated Sep. 11, 2018 (9 pages).
"Sequence 4," Score Search Results for U.S. Appl. No. 12/599,679, retrieved Nov. 17, 2018 (2 pages).
Agochukwu et al., "Hearing loss in syndromic craniosynostoses: Introduction and consideration of mechanisms," available in PMC Aug. 13, 2014, published in final edited form as: Am J Audiol. 23(2):135-41 (2014) (13 pages).
Balasubramaniam et al., "Perinatal hypophosphatasia presenting as neonatal epileptic encephalopathy with abnormal neurotransmitter metabolism secondary to reduced co-factor pyridoxal-5'-phosphate availability," J Inherit Metab Dis. 33(Suppl 3):S25-33 (2010).
Barcia et al., "Infantile hypophosphatasia: treatment options to control hypercalcemia, hypercalciuria, and chronic bone demineralization," J Pediatr. 130(5):825-8 (1997).
Barvencik et al., "Skeletal mineralization defects in adult hypophosphatasia—a clinical and histological analysis," Osteoporosis Int. 22(10):2667-75 (2011).

(56) References Cited

OTHER PUBLICATIONS

Baumgartner-Sigl et al., "Pyridoxine-responsive seizures as the first symptom of infantile hypophosphatasia caused by two novel missense mutations (c.677T>C, p.M226T; c.1112C>T, p.T371I) of the tissue-nonspecific alkaline phosphatase gene," Bone. 40(6):1655-61 (2007).
Beck et al., "Whole-body MRI in the childhood form of hypophosphatasia," Rheumatol Int. 31(10):1315-20 (2011).
Beederman et al., "Molecular basis of cranial suture biology and disease: osteoblastic and osteoclastic perspectives," Genes Dis. 1(1):120-5 (2014).
Boulet et al., "A population-based study of craniosynostosis in metropolitan Atlanta, 1989-2003," Am J Med Genet A. 146A(8):984-91 (2008).
Chan et al., "Endoscope-assisted versus open repair of craniosynostosis: a comparison of perioperative cost and risk," J Craniofac Surg. 24(1):170-4 (2013).
Choi et al., "Craniosynostosis in growing children: pathophysiological changes and neurosurgical problems," J Korean Neurosurg Soc. 59(3):197-203 (2016).
Chong et al., "Minimally invasive suturectomy and postoperative helmet therapy: advantages and limitations," J Korean Neurosurg Soc. 59(3):227-32 (2016).
Clarke, "Normal bone anatomy and physiology," Clin J Am Soc Nephrol. 3(Suppl 3):S131-9 (2008).
Colantonio et al., "Closing the gaps in pediatric laboratory reference intervals: a CALIPER database of 40 biochemical markers in a healthy and multiethnic population of children," Clin Chem. 58(5):854-68 (2012).
Collmann et al., "Neurosurgical aspects of childhood hypophosphatasia," Childs Nerv Syst. 25(2):217-23 (2009).
Czerwinski et al., "Major morbidity and mortality rates in craniofacial surgery: an analysis of 8101 major procedures," Plast Reconstr Surg. 126(1):181-6 (2010).
Eade et al., "Pyrophosphate arthropathy in hypophosphatasia," Ann Rheum Dis. 40(2):164-70 (1981).
Esparza et al., "Complications in the surgical treatment of craniosynostosis and craniofacial syndromes: apropos of 306 transcranial procedures," Childs Nerv Syst. 24(12):1421-30 (2008).
Esparza et al., "Surgical treatment of isolated and syndromic craniosynostosis. Results and complications in 283 consecutive cases," Neurocirugía. 19(6):509-29 (2008).
Fraser, "Hypophosphatasia," Am J Med. 22(5):730-46 (1957).
Garber et al., "Comparing outcomes and cost of 3 surgical treatments for sagittal synostosis: a retrospective study including procedure-related cost analysis," Neurosurgery. 81(4):680-7 (2017).
Ginelliová et al., "Sudden death associated with syndromic craniosynostosis," Forensic Sci Med Pathol. 12(4):506-9 (2016).
Greenwood et al., "Familial incidence and associated symptoms in a population of individuals with nonsyndromic craniosynostosis," Genet Med. 16(4):302-10 (2014).
Guañabens et al., "Calcific periarthritis as the only clinical manifestation of hypophosphatasia in middle-aged sisters," J Bone Miner Res. 29(4):929-34 (2014).
Herring, "Mechanical influences on suture development and patency," Front Oral Biol. 12:41-56 (2008).
Hollis et al., "Current concepts in hypophosphatasia: case report and literature review," Int J Paediatr Dent. 23(3):153-9 (2013).
Hwang et al., "Update of diagnostic evaluation of craniosynostosis with a focus on pediatric systematic evaluation and genetic studies," J Korean Neurosurg Soc. 59(3):214-8 (2016).
Johnson et al., "Craniosynostosis," Eur J Hum Genet. 19(4):369-76 (2011).
Kabbani et al., "Craniosynostosis," Am Fam Physician. 69(12):2863-70 (2004).
Katsianou et al., "Signaling mechanisms implicated in cranial sutures pathophysiology: Craniosynostosis," BBA Clin. 6:165-76 (2016).
Khanna et al., "Pictorial essay: the many faces of craniosynostosis," Indian J Radiol J. 21(1):49-56 (2011).
Kim et al., "Craniosynostosis: Updates in radiologic diagnosis," J Korean Neurosurg Soc. 59(3):219-26 (2016).
Kozlowski et al., "Hypophosphatasia. Review of 24 Cases," Pediatr Radiol. 5(2):103-17 (1976) (15 pages).
Krakow et al., "Clinical and radiographic delineation of bent bone dysplasia-FGFR2 type or bent bone dysplasia with distinctive clavicles and angel-shaped phalanges," Am J Med Genet A. 170(10):2652-61 (2016).
Mathijssen, "Guideline for care of patients with the diagnoses of craniosynostosis: working group on craniosynostosis," J Craniofac Surg. 26(6):1735-807 (2015).
Merrill et al., "Bent bone dysplasia-FGFR2 type, a distinct skeletal disorder, has deficient canonical FGF signaling," Am J Hum Genet. 90(3):550-7 (2012).
Millán, "The role of phosphatases in the initiation of skeletal mineralization," Calcif Tissue Int. 93(4):299-306 (2013).
Miller et al., "Ultrasound diagnosis of craniosynostosis," Cleft Palate Craniofac J. 39(1):73-80 (2002).
Millichap, "Cognitive Development of Children with Craniosynostosis," Pediatr Neurol Briefs. 29(6):47 (2015).
Mohn et al., "Hypophosphatasia in a child with widened anterior fontanelle: lessons learned from late diagnosis and incorrect treatment," Acta Paediatr. 100(7):e43-6 (2011).
Mornet et al., "A molecular-based estimation of the prevalence of hypophosphatasia in the European population," Ann Hum Genet. 75(3):439-45 (2011).
Nakamura-Utsunomiya et al., "Clinical characteristics of perinatal lethal hypophosphatasia: a report of 6 cases," Clin Pediatr Endocrinol. 19(1):7-13 (2010).
Oginni et al., "Radiological and biochemical resolution of nutritional rickets with calcium," Arch Dis Child. 88(9):812-17 (2003).
Opperman, "Cranial sutures as intramembranous bone growth sites," Dev Dyn. 219(4):472-85 (2000).
Reginato et al., "Musculoskeletal manifestations of osteomalacia and rickets," Best Pract Res Clin Rheumatol. 17(6):1063-80 (2003).
Rodgers et al., "Spring-assisted cranioplasty for the correction of non-syndromic scaphocephaly: a quantitative analysis of 100 consecutive cases," Plast Reconstr Surg. 140(1):125-34 (2017).
Rottgers et al., "Outcomes of endoscopic suturectomy with postoperative helmet therapy in bilateral coronal craniosynostosis," J Neurosurg Pediatr. 18(3):281-6 (2016).
Rozovsky et al., "Cranial ultrasound as a first-line imaging examination for craniosynostosis," Pediatrics. 137(2):e20152230 (2016) (9 pages).
Sabbagh et al., "Hypophosphatemia leads to rickets by impairing caspase-mediated apoptosis of hypertrophic chondrocytes," Proc Natl Acad Sci U S A. 102(27):9637-42 (2005).
Sakamoto et al., "Physiological changes and clinical implications of syndromic craniosynostosis," J Korean Neurosurg Soc. 59(3):204-13 (2016).
Salva et al., "Signaling networks in joint development," Dev Dyn. 246(4):262-74 (2017).
Seshia et al., "Myopathy with hypophosphatasia," Arch Dis Child. 65(1):130-1 (1990).
Shah et al., "Sudden infant death in a patient with FGFR3 P250R mutation," Am J Med Genet A. 140A(24):2794-6 (2006).
Sharma et al., "Bilateral femoral neck fractures in a young patient suffering from hypophosphatasia, due to a first time epileptic seizure," J Orthop Case Rep. 5(3):66-8 (2015).
Sharma, "Craniosynostosis," Indian J Plast Surg. 46(1):18-27 (2013).
Silver et al., "Pulmonary hypoplasia in neonatal hypophosphatasia," Pediatr Pathol. 8(5):483-93 (1988) (12 pages).
Thacher et al., "Radiographic scoring method for the assessment of the severity of nutritional rickets," J Trop Pediatr. 46(3):132-9 (2000).
Thurner et al., "Osteopontin deficiency increases bone fragility but preserves bone mass," Bone. 46(6):1564-73 (2010).
Tokumaru et al., "Skull base and calvarial deformities: association with intracranial changes in craniofacial syndromes," Am J Neuroradiol. 17(4):619-30 (1996).
Watanabe et al., "Prevalence of c.1559delT in ALPL, a common mutation resulting in the perinatal (lethal) form of hypophosphatasia

(56) References Cited

OTHER PUBLICATIONS in Japanese and effects of the mutation on heterozygous carriers," J Hum Genet. 56(2):166-8 (2011).
Whyte et al., "Adult hypophosphatasia with chondrocalcinosis and arthropathy: variable penetrance of hypophosphatasemia in a large Oklahoma kindred," Am J Med. 72(4):631-41 (1982).
Whyte et al., "Adult hypophosphatasia treated with teriparatide," J Clin Endocrinol Metab. 92(4):1203-8 (2007).
Whyte et al., "Rickets and osteomalacia," Medicine. 37(9):483-8 (2009).
Zaleckas et al., "Diagnosis and treatment of craniosynostosis: Vilnius team experience," Acta Med Litu. 22(2):111-21 (2015).
Anderson, "Mechanism of Mineral Formation in Bone," *Pathology Reviews*. Emanuel Rubin and Ivan Damjanov (eds.), 13-23 (1990).
Whyte, Chapter 73: Hypophosphatasia: Nature's Window on Alkaline Phosphatase Function in Humans, *Principles of Bone Biology*, vol. 1, Third Edition. John P. Bilezikian, Lawrence G. Raisz and T. John Martin (eds.), 1573-98 (2008).
Whyte, Chapter 22: Hypophosphatasia, *Genetics of Bone Biology and Skeletal Disease*. Rajesh V. Thakker, Michael P. Whyte, John A. Eisman and Takashi Igarashi (eds.), 337-360 (2013).
Del Angel et al., "Birth prevalence estimation of severe Hypophosphatasia in European populations using large-scale protein-coding genetic variation databases," American Society of Human Genetics 66th Annual Meeting, Oct. 18-22, Vancouver, Canada. Poster abstract 1670T (2016) (2 pages).
Rockman-Greenberg et al., "Hypophosphatasia: Enzyme Replacement with ENB-0040, a Bone-Targeted Human Recombinant Tissue Nonspecific Alkaline Phosphatase (TNSALP) Fusion Protein," American College of Medical Genetics, 16th Annual Clinical Genetics Meeting, Mar. 25-29, Tampa, Florida (2009) (1 page).
Simmons, "Best Practices In: Recognizing and Diagnosing Hypophosphatasia," Clinical Endocrinology News. <https://www.mdedge.com/sites/default/files/issues/articles/Alexion_10_11_Final_Web.pdf>, published Sep. 30, 2013, retrieved on Mar. 27, 2019 (8 pages).
Weber et al., "Burden of disease in children with hypophosphatasia: results from patient-reported surveys," 7th International Conference on Children's Bone Health, Jun. 27-30, Salzburg, Austria. *Bone Abstracts*. 4: p. 119 (2015) (3 pages).
Whyte et al., "Asfotase alfa: Sustained Efficacy and Tolerability in Infants and Young Children with Life-Threatening Hypophosphatasia," 2014 Pediatric Academic Societies and Asian Society for Pediatric Research Joint Meeting, May 3-6, Vancouver, BC, Canada. Poster 69 (2014) (1 page).
Whyte et al., "Hypophosphatasia: A Retrospective Natural History Study of the Severe Perinatal and Infantile Forms," 2014 European Calcified Tissue Society Congress, May 17-20, Prague, Czech Republic. Poster P364 (2014) (1 page).
Whyte et al., "A retrospective, multi-national, non-interventional, natural history study of the childhood form of hypophosphatasia," ENDO 2015: The Endocrine Society Annual Meeting, Mar. 5-8, San Diego, California. Abstract LB-OR01-4 (2015) (2 pages).
Stoll et al., "Severe hypophosphatasia due to mutations in the tissue-nonspecific alkaline phosphatase (TNSALP) gene," Genet Couns. 13(3):289-95 (2002).
Mornet, "Hypophosphatasia," Best Pract Res Clin Rheumatol. 22(1):113-27 (2008).
Kajdic et al., "Craniosynostosis—Recognition, clinical characteristics, and treatment," Bosn J Basic Med Sci. 18(2):110-6 (2018).
Dortschy et al., "Bevölkerungsbezogene verteilungswerte ausgewählter laborparameter aus der studie zur gesundheit von kindern und jugendlichen in Deutschland (KiGGS)," Gesundheitsberichterstattung des Bundes, Robert Koch Institute (2009) (136 pages).
Communication pursuant to Rule 164(2)(b) and Article 94(3) EPC for European Application No. 16707571.2, dated Feb. 26, 2019 (12 pages).
Fong et al., "Hypocalcemia: Updates in diagnosis and management for primary care," Can Fam Physician. 58(2):158-62 (2012).

Makras et al., "Medical treatment of Hypercalcaemia," Hormones. 8(2):83-95 (2009).
Extended European Search Report for European Application No. 15907550.6, dated Jun. 4, 2019 (7 pages).
Wang et al., "The effects of tissue-non-specific alkaline phosphatase gene therapy on craniosynostosis and craniofacial morphology in the FGFR2$^{C342Y/+}$ mouse model of Crouzon craniosynostosis," Orthod Craniofac Res. 18 Suppl. 1(01):196-206 (2015).
Abrams et al. "Calcium and Vitamin D Requirements of Enterally Fed Preterm Infants," Pediatrics. 131(5): e1676-e1683 (2013) (9 pages).
Kishnani et al., "Hypophosphatasia: enzyme replacement therapy (ENB-0040) decreases TNSALP substrate accumulation and improves functional outcome in affected adolescents and adults," Endocrine Society's 15th International & 14th European Congress of Endocrinology, May 5-9, Florence, Italy. Abstract OC8.1 (2012) (4 pages).
Office Action for Japanese Application No. 2018-508754, dated Jul. 1, 2020 (4 pages).
"Highly Specialised Technology Evaluation: Asfotase alfa for treating paediatric-onset hypophosphatasia [ID 758]," Oct. 21, 2015, <https://www.nice.org.uk/guidance/hst6/documents/committee-papers-8>, (99 pages).
"View of NCT02235493 on Nov. 19, 2015," ClinicalTrials.gov archive, Nov. 19, 2015 (4 pages).
Achord et al., "Human beta-glucuronidase: in vivo clearance and in vitro uptake by a glycoprotein recognition system on reticuloendothelial cells," Cell 15(1):269-278 (1978).
Addison et al., "Pyrophosphate inhibits mineralization of osteoblast cultures by binding to mineral, up-regulating osteopontin, and inhibiting alkaline phosphatase activity," J Biol Chem. 282(21):15872-15883 (2007).
Advisory Action for U.S. Appl. No. 11/484,870, dated Dec. 20, 2007 (4 pages).
Ahn et al., "Idiopathic calcium pyrophosphate dihydrate (CPPD) crystal deposition disease in a young male patient: a case report," J Korean Med Sci. 18(6):917-20 (2003).
Alexion Pharma International, "Strensiq Product Monograph," <http://alexionpharma.ca/documents/Strensiq-PM-asfotase-alfa-14Aug2015.aspx>, Prepared Aug. 14, 2015 (32 pages).
Alexion Third Quarter 2017 Earnings Call, "http://files.shareholder.com/downloads/ALXN/5636824573x0x961197/3B361D6E-80E2-463E-B0E5-3EAD7FC5B9D0/Alexion_Q3_2017_Earnings_Slides.pdf" (43 pages).
Alexion, "Highlights of Prescribing Information" for Strensiq®, 2018 (8 pages).
Ali et al., "Isolation and characterization of calcifying matrix vesicles from epiphyseal cartilage," Proc Natl Acad Sci USA. 67(3):1513-1520 (1970).
Altarescu et al., "The efficacy of enzyme replacement therapy in patients with chronic neuronopathic Gaucher's disease," J Pediatr. 138(4):539-547 (2001).
Anderson et al., "Impaired calcification around matrix vesicles of growth plate and bone in alkaline phosphatase-deficient mice," *Am J Pathol*. 164:841-847 (2004).
Anderson et al., "Matrix vesicles in osteomalacic hypophosphatasia bone contain apatite-like mineral crystals," Am J Pathol. 151(6):1555-61 (1997).
Anderson et al., "Pyrophosphate stimulation of calcium uptake into cultured embryonic bones. Fine structure of matrix vesicles and their role in calcification," Dev Biol. 34:211-227 (1973).
Anderson et al., "Sustained osteomalacia of long bones despite major improvement in other hypophosphatasia-related mineral deficits in tissue nonspecific alkaline phosphatase/nucleotide pyrophosphatase phosphodiesterase 1 double-deficient mice," Am J Pathol. 166(6):1711-1720 (2005).
Anderson et al., "The role of matrix vesicles in growth plate development and biomineralization," Front Biosci. 10:822-837 (2005).
Appeal Brief as Filed in U.S. Appl. No. 12/638,527, dated Oct. 9, 2015 (101 pages).
Attwood, "The Babel of Bioinformatics," Genomics. 290(5491):471-3 (2000).

(56) References Cited

OTHER PUBLICATIONS

Barranger et al., "Lessons learned from the development of enzyme therapy for Gaucher disease," J Inherit Metab Dis. 24(Supp 2):89-96 (2001).
Barton et al., "Replacement therapy for inherited enzyme deficiency—macrophage-targeted glucocerebrosidase for Gaucher's disease," N Engl J Med. 324(21):1464-70 (1991) (abstract only).
Beertsen et al., "Root development in mice lacking functional tissue non-specific alkaline phosphatase gene: Inhibition of acellular cementum formation," J Dent Res. 78(6):1221-1229 (1999) (10 pages).
Belachew et al., "Infantile hypophosphatasia secondary to a novel compound heterozygous mutation presenting with pyridoxine-responsive seizures," JIMD Rep. 11:17-24 (2013).
Belkhouribchia et al., "Case Report: Osteomalacia with low alkaline phosphatase: a not so rare condition with important consequences," BMJ Case Rep. doi: 10.1136/bcr-2015-212827 (2016) (4 pages).
Bennett et al., "Extracellular domain-IgG fusion proteins for three human natriuretic peptide receptors," J Biol Chem. 266(34):23060-23067 (1991).
Berkseth et al., "Clinical spectrum of hypophosphatasia diagnosed in adults," Bone. 54(1):21-7 (2013).
Bernard, "Ultrastructural localization of alkaline phosphatase in initial intramembranous osteogenesis," Clin Orthop Relat Res. 135:218-225 (1978).
Bernardi, "Chromatography of proteins on hydroxyapatite," Methods Enzymol. 27:471-9 (1973).
Bhattacharyya et al., "Hypophosphatasia and the risk of atypical femur fractures: a case-control study," BMC Muscoloskelet Disord. 17:332 (2016) (4 pages).
Bianchi, "Hypophosphatasia: an overview of the disease and its treatment," Osteoporos Int. 26(12):2743-57; DOI 10.1007/s00198-015-3272-1 (2015) (15 pages).
Bishop et al., "Transformative therapy in hypophosphatasia," Arch Dis Child. 101(6):514-5 (2016).
Bishop, "Asfotase alfa for hypophosphatasia," Horizon Scanning Centre. National Institute for Health Research. http://www.hsric.nihr.ac.uk/topics/asfotase-alfa-for-hypophosphatasia/download, retrieved Oct. 20, 2013 (9 pages).
Bishop, "Clinical management of hypophosphatasia," Clin Cases Miner Bone Metab. 12(2):170-3 (2015).
Bloch-Zupan, "Hypophosphatasia: diagnosis and clinical signs—a dental surgeon perspective," Int J Paediatr Dent. 26(6):426-438 (2016).
Bobryshev et al., "Role of bone-type tissue-nonspecific alkaline phosphatase and PHOSPO1 in vascular calcification," Curr Pharm Des. 20(37):5821-8 (2014).
Bobyr et al., "High-resolution analysis of Zn(2+) coordination in the alkaline phosphatase superfamily by EXAFS and x-ray crystallography," J Mol Biol. 415(1):102-17 (2012).
Bobé et al., "Fas-mediated liver damage in MRL hemopoietic chimeras undergoing Ipr-mediated graft-versus-host disease," J Immunol. 159:4197-4204(1997).
Bocciardi et al., "Overexpression of the C-type natriuretic peptide (CNP) is associated with overgrowth and bone anomalies in an individual with balanced t(2;7) translocation," Hum Mutat. 28(7):724-731 (2007).
Bonilla, "Pharmacokinetics of immunoglobulin administered via intravenous or subcutaneous routes," Immunol Allergy Clin N Am. 28:803-819 (2008).
Boskey et al., "Matrix vesicles promote mineralization in a gelatin gel," Calcif Tissue Int 60(3):309-15(1997).
Boskey, "Amorphous calcium phosphate: The contention of bone," J Dent Res. 76:1433-1436 (1997).
Bowden et al., "Asfotase alfa treatment for 1 year in a 16 year-old male with severe childhood hypophosphatasia," Osteoporos Int. 29(2):511-5; DOI: 10.1007/s00198-017-4267-x (2018) (5 pages).
Braunstein, "Multiple fractures, pain, and severe disability in a patient with adult-onset hypophosphatasia," Bone Rep. 4:1-4 (2015).
Brenner et al., "Diverse biological actions of atrial natriuretic peptide," Physiol Rev. 70(3):665-699 (1990).
Briot et al., "Adult hypophosphatasia," Curr Opin Rheumatol. 28(4):448-51 (2016).
Buchet et al., "Multisystemic functions of alkaline phosphatases," Methods Mol Biol. 1053:27-51 (2013).
Byers et al., "Effect of enzyme replacement therapy on bone formation in a feline model of mucopolysaccharidosis type VI," Bone. 21(5):425-431 (1997).
Cahill et al., "Infantile hypophosphatasia: transplantation therapy trial using bone fragments and cultured osteoblasts,"J. Clin Endocrinol Metab. 92(8): 2923-30 (2007).
Cameron et al., "Minireview: Natriuretic peptides during development of the fetal heart and circulation," Endocrinology. 144(6):2191-2194 (2003).
Campbell et al., "Insulin-like growth factor (IGF)-binding protein-5-(201-218) region regulates hydroxyapatite and IGF-I binding," Am J Physiol. 273:E1005-1013 (1997).
Chen et al., "Gly369Cys mutation in mouse FGFR3 causes achondroplasia by affecting both chondrogenesis and osteogenesis," J Clin Invest. 104(11):1517-1525 (1999).
Choe et al., "Substrate profiling of cysteine proteases using a combinatorial peptide library identifies functionally unique specificities," J Biol Chem. 281(18):12824-12832 (2006).
Chusho et al., "Dwarfism and early death in mice lacking C-type natriuretic peptide," Proc Natl Acad Sci USA. 98(7):4016-4021 (2001).
Ciancaglini et al., "Contribution of matrix vesicles and alkaline phosphatase to ectopic bone formation," Braz. J Med Biol Res. 39(5):603-10 (2006).
Cleland et al., "Emerging protein delivery methods," Curr Opin Biotechnol. 12:212-219 (2001).
Clemens et al., "Pharmacokinetics and biological actions of subcutaneously administered human brain natriuretic peptide," J Pharmacol Exp Ther. 287(1):67-71 (1998).
Communication from Examining Division for European Application No. EP 05 73 9065.0, dated Jun. 11, 2010 (5 pages).
Communication from Examining Division for European Application No. EP 05 73 9065.0, dated Jun. 18, 2009 (6 pages).
Communication from Examining Division for European Application No. EP 08 757 088.3, dated Apr. 20, 2011 (4 pages).
Crawley et al., "Enzyme replacement therapy in a feline model of Maroteaux-Lamy Syndrome," J Clin Invest. 97(8):1864-73 (1996).
Daggubati et al., "Adrenomedullin, endothelin, neuropeptide Y, atrial, brain, and C-natriuretic prohormone peptides compared as early heart failure indicators," Cardiovasc Res. 36:246-255 (1997).
Data Sheet for pFUSE-SEAP-hFC "Plasmid designed for the expression of a SEAP-Fc Fusion protein," Invivogen, San Diego, CA (4 pages) (1989).
De la Croix Ndong et al., "Asfotase-alpha improves bone growth, mineralization and strength in mouse models of neurofibromatosis type-1," Nat Med. 20(8):904-10 (2014) (10 pages).
De Plater et al., "The natriuretic peptide (OVCNP-39) from platypus (*Ornithorhynchus anatinus*) venom relaxes the isolated rat uterus and promotes oedema and mast cell histamine release," Toxicon. 36(3):847-857 (1998).
De Roo et al., "Infantile hypophosphatasia without bone deformities presenting with severe pyridoxine-resistant seizures," Molecular Genetics and Metabolism 111(3):404-7 (2014).
Declaration of Dr. Philippe Crine for EP 08757088.3, executed Jan. 14, 2011 (6 pages).
Deeb et al., "Could alerting physicians for low alkaline phosphatase levels be helpful in early diagnosis of hypophosphatasia?," J Clin Res Pediatr Endocrinol. 10(1):19-24 (2018).
Di Mauro et al., "Kinetic characterization of hypophosphatasia mutations with physiological substrates," J Bone Miner Res. 17(8):1383-91 (2002).
Dumont et al., "Monomeric Fc fusions: impact on pharmacokinetic and biological activity of protein therapeutics," BioDrugs. 20(3):151-60 (2006).
Durussel et al., "Bone mineralization-dependent craniosynostosis and craniofacial shape abnormalities in the mouse model of infantile hypophosphatasia," Dev Dyn. 245(2):175-82 (2016).
EBI Blast for Accession No. ATD17216. Entered Oct. 16, 2008 (1 page).

(56) References Cited

OTHER PUBLICATIONS

Eng et al., "Safety and efficacy of recombinant human alpha-galactosidase A replacement therapy in Fabry's disease," N Engl J Med. 345(1):9-16 (2001).
Engel et al., "Characterization of the hormone binding site of natriuretic peptide receptor-C," FEBS Lett. 360:169-172 (1995).
Epps, "Application No. 125513Orig1s000 Medical Review(s)," Center for Drug Evaluation and Research, <http://www.accessdata.fda.gov/drugsatfda_docs/nda/2015/125513Orig1s000MedR.pdf>, Oct. 20, 2015 (254 pages).
European Collection of Authenticated Cell Cultures (ECACC) Accession No. 85110503. Retrieved May 2, 2018 (3 pages).
European Search Report for European Patent Application No. 12842640.0, dated Mar. 13, 2015 (7 pages).
Examiner's Answer to Appeal Brief for U.S. Appl. No. 12/638,527, dated Feb. 23, 2016 (9 pages).
Extended European Search Report for European Application No. 08757088.3, dated Jun. 21, 2010 (6 pages).
Extended European Search Report for European Application No. 11774253.6, dated Oct. 14, 2013 (8 pages).
Extended European Search Report for European Application No. 18173111.8, dated Aug. 21, 2018 (9 pages).
Extended European Search Report for European Application No. EP 08757088, date of completion Jun. 7, 2010 (5 pages).
Extended European Search Report for European Application No. EP 11 00 0196.3, dated Jun. 22, 2011 (6 pages).
Extended European Search Report for European Application No. EP 11 00 4496.3, dated Aug. 26, 2011 (7 pages).
Farley et al., "Effects of tunicamycin, mannosamine, and other inhibitors of glycoprotein processing on skeletal alkaline phosphatase in human osteoblast-like cells," Calcif Tissue Int. 76:63-74 (2005).
Farnum et al., "In vivo delivery of fluoresceinated dextrans to the murine growth plate: imaging of three vascular routes by multiphoton microscopy," available in PMC Oct. 28, 2008, published in final edited form as: Anat Rec A Discov Mol Cell Evol Biol. 288(1):91-103 (2006) (22 pages).
Fedde et al., "Alkaline phosphatase knock-out mice recapitulate the metabolic and skeletal defects of infantile hypophosphatasia," available in PMC Mar. 7, 2011, published in final edited form as: J Bone Miner Res. 14(12):2015-2026 (1999) (19 pages).
Fodor et al., "Differencial diagnosis of the low alkaline phosphatase activities," Orv Hetil. 158(26): 1003-1007 (2017) (Article in Hungarian) (English Abstract included).
Fujisaki et al., "Osteotropic Drug Delivery System (ODDS) based on bisphosphonic prodrug. IV effects of osteotropic estradiol on bone mineral density and uterine weight in ovariectomized rats," J Drug Target. 5(2):129-138 (1997) (11 pages).
Fujisawa et al., "Acidic amino acid-rich sequences as binding sites of osteonectin to hydroxyapatite crystals," Biochim Biophys Acta. 1292:53-60 (1996).
Furbish et al., "Uptake and distribution of placental glucocerebrosidase in rat hepatic cells and effects of sequential deglycosylation," Biochim Biophys Acta. 673:425-434 (1981).
Furuya et al., "Structural requirements of C-type natriuretic peptide for elevation of cyclic GMP in cultured vascular smooth muscle cells," Biochem Biophys Res Commun. 183(3):964-969 (1992).
Garg, "Investigation of the role of FcRn in the absorption, distribution, and elimination of monoclonal antibodies," Dissertation: State University of New York at Buffalo, 2007 (Abstract only) (2 pages).
Gasque et al., "Improvement of the skeletal and dental hypophosphatasia phenotype in Alpl -/- mice by administration of soluble (non-targeted) chimeric alkaline phosphatase," Available in PMC Mar. 1, 2016, published in final edited form as: Bone. 72:137-147 (2015) (25 pages).
Gates et al., "Effects of age, sex, and comorbidities on the pediatric outcomes data collection instrument (PODCI) in the general population," J Pediatr Orthop. 35(2):203-9 (2015).

Gilbert et al., "Chimeric peptides of statherin and osteopontin that bind hydroxyapatite and mediate cell adhesion," J Biol Chem. 275(21):16213-8 (2000).
Glass et al., "The infant skull: a vault of information," Radiographics. 24(2):507-22 (2004).
Graham et al., "Characteristics of a human cell line transformed by DNA from human adenovirus type 5," J Gen Virol. 36(1):59-72 (1977).
Greenberg et al., "A homoallelic Gly$^{317}$ to Asp mutation in ALPL causes the perinatal (lethal) form of hypophosphatasia in Canadian mennonites," Genomics. 17:215-217 (1993).
Guo et al., "Protein tolerance to random amino acid change," Proc Natl Acad Sci USA. 101(25):9205-9210 (2004).
Güzel Nur et al., "Pyridoxine-responsive seizures in infantile hypophosphatasia and a novel homozygous mutation in ALPL gene," J Clin Res Pediatr Endocrinol. 8(3):360-4 (2016).
Hagiwara et al., "Autocrine regulation of rat chondrocyte proliferation by natriuretic peptide C and its receptor, natriuretic peptide receptor-B," J Biol Chem. 269(14):10729-10733 (1994).
Hagiwara et al., "cGMP produced in response to ANP and CNP regulates proliferation and differentiation of osteoblastic cells," Am J Physiol. 270:C1311-C1318 (1996).
Halling Linder et al., "Glycosylation differences contribute to distinct catalytic properties among bone alkaline phosphatase isoforms," available in PMC Nov. 1, 2010, published in final edited form as: Bone. 45(5):987-993 (2009) (17 pages).
Hardy et al., "Dissection of a carboxy-terminal region of the yeast regulatory protein RAP1 with effects on both transcriptional activation and silencing," Mol Cell Biol. 12(3):1209-1217 (1992).
Harmey et al., "Concerted regulation of inorganic pyrophosphate and osteopontin by Akp2, Enpp1, and Ank" Am J Pathol. 164(4):1199-1209 (2004).
Harmey et al., "Elevated skeletal osteopontin levels contribute to the hypophosphatasia phenotype in Akp2$^{-/-}$ mice" J Bone Miner Res. 21(9):1377-1386 (2006).
Harris, "The human alkaline phosphatases: what we know and what we don't know," Clin Chim Acta. 186:133-50 (1989).
Hawrylak et al., "The solubilization of tetrameric alkaline phosphatase from human liver and its conversion into various forms by phosphatidylinositol phospholipase C or proteolysis," J Biol Chem. 263(28):14368-14373 (1988).
Henthorn et al., "Different missense mutations at the tissue-nonspecific alkaline phosphatase gene locus in autosomal recessively inherited forms of mild and severe hypophosphatasia," Proc Natl Acad Sci USA. 89:9924-9928 (1992).
Henthorn et al., "Missense mutations of the tissue-nonspecific alkaline phosphatase gene in hypophosphatasia," Clin Chem. 38(12):2501-5 (1992).
Herasse et al., "Molecular study of three cases of odontohypophosphatasia resulting from heterozygosity for mutations in the tissue non-specific alkaline phosphatase gene," J Med Genet. 40(8):605-9 (2003).
Hessle et al., "Tissue-nonspecific alkaline phosphatase and plasma cell membrane glycoprotein-1 are central antagonistic regulators of bone mineralization," Proc Natl Acad Sci USA. 99(14): 9445-9449 (2002).
Highlights of Prescribing Information for Strensiq™, Alexion Pharmaceuticals, Inc., available <http://www.alexion.com/Documents/strensiq_pi-10-2015.aspx>, 2015 (19 pages).
Hofmann et al., "Asfotase alfa: enzyme replacement for the treatment of bone disease in hypophosphatasia," Drugs Today (Barc). 52(5):271-85 (2016).
Hofmann et al., "Clinical aspects of hypophosphatasia: an update," Clinic Rev Bone Miner Metab. 11(2):60-70 (2013).
Hofmann et al., "Compound heterozygosity of two functional null mutations in the ALPL gene associated with deleterious neurological outcome in an infant with hypophosphatasia," Bone. 55:150-7 (2013).
Hofmann et al., "Improvement in bone manifestations and respiratory status in infants and young children with HPP treated with asfotase alfa: an update on the ENB-010-10 trial," 7th International Conference on Children's Bone Health, Jun. 27-30, Austria, Salzburg. Bone Abstracts. 4: OC18 (2015) (3 pages).

(56) References Cited

OTHER PUBLICATIONS

Hofmann et al., "Recombinant enzyme replacement therapy in hypophosphatasia," Subcell Biochem. 76:323-41 (2015).
Horton et al., "Achondroplasia," Lancet. 370:162-172, 2007.
Hosain et al., "Targeted delivery of antineoplastic agent to bone: biodistribution studies of technetium-99m-labeled gem-bisphosphonate conjugate of methotrexate," J Nucl Med. 37(1):105-7 (1996).
Hult et al., "Engineered enzymes for improved organic synthesis," Curr Opin Biotechnol. 14:395-400 (2003).
Hunter et al., "Modulation of crystal formation by bone phosphoproteins: structural specificity of the osteopontin-mediated inhibition of hydroxyapatite formation," Biochem J. 300:723-728 (1994).
Husain et al., "Fc site-specific labeling of immunoglobulins with calf intestinal alkaline phosphatase," Bioconjug Chem. 5(5):482-90 (1994).
Ikezawa, "Glycosylphosphatidylinositol (GPI)-anchored proteins," *Biol Pharm Bull.* 25(4):409-417 (2002).
Inoue et al., "Four functionally distinct C-type natriuretic peptides found in fish reveal evolutionary history of the natriuretic peptide system," Proc Natl Acad Sci USA. 100(17):10079-10084 (2003).
International Preliminary Report on Patentability for International Patent Application No. PCT/CA2011/050258, dated Nov. 15, 2012 (9 pages).
International Preliminary Report on Patentability for International Patent Application No. PCT/US2012/039004, dated Apr. 22, 2014 (8 pages).
International Preliminary Report on Patentability for International Patent Application No. PCT/US2012/060869, dated Apr. 22, 2014 (7 pages).
International Preliminary Report on Patentability for International Patent Application No. PCT/US2016/015366, dated Aug. 10, 2017 (10 pages).
International Search Report and Written Opinion for International Application No. PCT/US18/26868, dated Sep. 7, 2018 (30 pages).
International Search Report and Written Opinion for International Patent Application No. PCT/CA2005/000615, dated Aug. 18, 2005 (14 pages).
International Search Report and Written Opinion for International Patent Application No. PCT/CA2008/000923, dated Sep. 12, 2008 (11 pages).
International Search Report and Written Opinion for International Patent Application No. PCT/CA2011/050258, dated Jul. 29, 2011 (14 pages).
International Search Report and Written Opinion for International Patent Application No. PCT/CA2011/050807, dated Apr. 13, 2012 (18 pages).
International Search Report and Written Opinion for International Patent Application No. PCT/US2012/039004, dated Nov. 2, 2012 (22 pages).
International Search Report and Written Opinion for International Patent Application No. PCT/US2015/039973, dated Oct. 5, 2015 (12 pages).
International Search Report and Written Opinion for International Patent Application No. PCT/US2015/058498, dated Jan. 22, 2016 (12 pages).
International Search Report and Written Opinion for International Patent Application No. PCT/US2015/064003, dated Mar. 31, 2016 (13 pages).
International Search Report and Written Opinion for International Patent Application No. PCT/US2016/015366, dated Aug. 9, 2016 (14 pages).
International Search Report and Written Opinion for International Patent Application No. PCT/US2016/025721, dated Aug. 17, 2016 (18 pages).
International Search Report and Written Opinion for International Patent Application No. PCT/US2016/039595, dated Feb. 21, 2017 (16 pages).
International Search Report and Written Opinion for International Patent Application No. PCT/US2016/047166, dated Nov. 7, 2016 (15 pages).
International Search Report and Written Opinion for International Patent Application No. PCT/US2016/049983, dated Nov. 29, 2016 (12 pages).
International Search Report and Written Opinion for International Patent Application No. PCT/US2016/054013, dated Dec. 13, 2016 (19 pages).
International Search Report and Written Opinion for International Patent Application No. PCT/US2017/025590, dated Jun. 29, 2017 (18 pages).
International Search Report and Written Opinion for International Patent Application No. PCT/US2017/025618, dated Jul. 11, 2017 (22 pages).
International Search Report and Written Opinion for International Patent Application No. PCT/US2017/036133, dated Aug. 24, 2017 (10 pages).
International Search Report and Written Opinion for International Patent Application No. PCT/US2017/047527, dated Nov. 6, 2017 (10 pages).
International Search Report and Written Opinion for International Patent Application No. PCT/US2018/020859, dated Jun. 19, 2018 (14 pages).
International Search Report and Written Opinion for International Patent Application No. PCT/US2018/025206, dated Jul. 3, 2018 (25 pages).
International Search Report for International Patent Application No. PCT/US2012/060869, dated Mar. 25, 2013 (5 pages).
Invitation to Pay Additional Fees for International Patent Application No. PCT/CA2011/050807, dated Feb. 13, 2012 (2 pages).
Invitation to Pay Additional Fees for International Patent Application No. PCT/US2012/039004, dated Aug. 29, 2012 (2 pages).
Invitation to Pay Additional Fees for International Patent Application No. PCT/US2016/015366, dated Jun. 1, 2016 (7 pages).
Iqbal et al., "Recurrent Metatarsal Fractures in Postmenopausal Woman With Low Serum Alkaline Phosphatase: A Rare Diagnosis Not to Miss," J Investig Med High Impact Case Rep. 5(3):1-3 (2017).
Ishida et al., "Tissue-nonspecific alkaline phosphatase with an Asp(289)→Val mutation fails to reach the cell surface and undergoes proteasome-mediated degradation," J Biochem. 134(1):63-70 (2003).
Jansonius, "Structure, evolution and action of vitamin $B_6$-dependent enzymes," Curr Opin Struct Biol. 8:759-769 (1998).
Jin et al., "Novel analog of atrial natriuretic peptide selective for receptor-A produces increased diuresis and natriuresis in rats," J Clin Invest. 98(4):969-976 (1996).
Johnson et al., "Matrix vesicle plasma cell membrane glycoprotein-1 regulates mineralization by murine osteoblastic MC3T3 cells," J Bone Miner Res. 14(6):883-892 (1999).
Johnson et al., "Motor proficiency in children with neurofibromatosis type 1," Pediatr Phys Ther. 22(4):344-8 (2010).
Kakkis et al., "Enzyme-replacement therapy in mucopolysaccharidosis I," N Engl J Med. 344(3):182-8 (2001).
Kalra et al., "The role of C-type natriuretic peptide in cardiovascular medicine," Eur Heart J. 22:997-1007 (2001).
Kasugai et al., "Selective drug delivery system to bone: small peptide $(Asp)_6$ conjugation," J Bone Miner Res. 15(5):936-943 (2000).
Kaufmann et al., "Influence of low temperature on productivity, proteome and protein phosphorylation of CHO cells," Biotechnol Bioeng. 63(5):573-82 (1999).
Kishnani et al., "Biochemical and physical function outcomes in adolescents and adults with hypophosphatasia treated with asfotase alfa for up to 4 years: interim results from a phase II study," Endocrine Society's 98th Annual Meeting and Expo, Apr. 1-4, Boston, MA. Abstract OR26-3 (2016) (2 pages).
Kishnani et al., "Monitoring guidance for patients with hypophosphatasia treated with asfotase alfa," Mol Genet Metab. 122(1-2):4-17 (2017).
Kishnani et al., "OR26-3 Biochemical and Physical Function Outcomes in Adolescents and Adults with Hypophosphatasia Treated

(56) References Cited

OTHER PUBLICATIONS with Asfotase Alfa for up to 4 Years: Interim Results from a Phase II Study," ENDO 2016, Boston, MA, Apr. 3, 2016 (22 pages).
Kitaoka et al., "Safety and efficacy of treatment with asfotase alfa in patients with hypophosphatasia: results from a Japanese clinical trial," Clin Endocrinol (Oxf). 87(1):10-19 (epub pp. 1-10) (2017).
Kochendoerfer, "Protein & peptide drug delivery—third international conference: Minimally invasive delivery methods," Sep. 22-23, Philadelphia, PA. IDrugs. 6(11):1043-1045 (2003).
Kosnik-Infinger et al., "Enzyme replacement therapy for congenital hypophosphatasia allows for surgical treatment of related complex craniosynostosis: a case series," Neurosurg Focus. 38(5):E10 (2015) (8 pages).
Kostenuik et al., "Infrequent delivery of a long-acting PTH-Fc fusion protein has potent anabolic effects on cortical and cancellous bone," J Bone Miner Res. 22(10):1534-1547 (2007).
Kulikova et al., "Hypophosphatasia: the clinical description of 3 cases of the disease with the molecular-genetic verification of the diagnosis," Problems of Endocrinology. 61(3):37-42 (2015) (Article in Russian) (English Abstract included).
Lazdunski et al., "Structure-function relationships for some metalloalkaline phosphatases of E. coli," Eur J Biochem. 8(4):510-7 (1969).
Le Du et al., "Crystal structure of alkaline phosphatase from human placenta at 1.8 A resolution. Implication for a substrate specificity," J Biol Chem. 276(12):9158-65 (2001) (9 pages).
Lee et al., "Disturbed osteoblastic differentiation of fibrous hamartoma cell from congenital pseudarthrosis of the tibia associated with neurofibromatosis type I," Clin Orthop Surg. 3(3):230-7 (2011).
Leone et al., "Allosteric modulation of pyrophosphatase activity of rat osseous plate alkaline phosphatase by magnesium ions," Int J Biochem Cell Biol. 30:89-97 (1998).
Li et al., "Standard reference for the six-minute-walk test in healthy children aged 7 to 16 years," Am J Respir Crit Care Med. 176(2):174-80 (2007).
Linglart et al., "Hypophosphatasia," Curr Osteoporos Rep. 14(3):95-105; DOI 10.1007/s11914-016-0309-0 (2016) (11 pages).
Liu et al., "Tissue-nonspecific alkaline phosphatase deficiency causes abnormal craniofacial bone development in the Alpl(-/-) mouse model of infantile hypophosphatasia," available in PMC Oct. 1, 2015, published in final edited form as: Bone. 67:81-94 (2014) (30 pages).
Lo et al., "High level expression and secretion of Fc-X fusion proteins in mammalian cells," Protein Eng. 11(6):495-500 (1998).
López-Delgado et al., "Abnormal bone turnover in individuals with low serum alkaline phosphatase," Osteoporosis Int. 29(9):2147-2150; doi: 10.1007/s00198-018-4571-0 (Supplementary information included) (2018) (6 pages).
Madson et al., "Asfotase alfa: sustained efficacy and tolerability in children with hypophosphatasia treated for 5 years," ESPE Abstracts. 84:FC2.4 (2015) (2 pages).
Mahmood et al., "Selection of the first-time dose in humans: comparison of different approaches based on interspecies scaling of clearance," J Clin Pharmacol. 43:692-697 (2003).
Martos-Moreno et al., "Hypophosphatasia: clinical manifestations, diagnostic recommendations and therapeutic options," An Pediatr (Barc). S1695-4033(17)30223-0 (2017) (11 pages) (Article in Spanish) (English Abstract included).
Mather, "Establishment and characterization of two distinct mouse testicular epithelial cell lines," Biol Reprod. 23(1):243-52 (1980).
Matsumoto et al., "Rescue of severe infantile hypophosphatasia mice by AAV-mediated sustained expression of soluble alkaline phosphatase," Hum Gene Ther. 22(11):1355-64 (2011).
Mayer, "Microbiology and immunology on-line: Immunoglobulins: structure and function" <http://pathmicro.med.sc.edu/mayer/IgStruct2000.htm>, University of South Carolina School of Medicine, 12 pages (2009).
McKiernan et al., "Clinical and radiographic findings in adults with persistent hypophosphatasemia," J Bone Miner Res. 29(7):1651-60 (2014).

Mericq et al., "Regulation of fetal rat bone growth by C-type natriuretic peptide and cGMP," Pediatr Res. 47(2):189-193 (2000) (9 pages).
Meyer, "Can biological calcification occur in the presence of pyrophosphate?" Arch Biochem Biophys. 231:1-8(1984).
Michigami et al., "Common mutations F310L and T1559del in the tissue-nonspecific alkaline phosphatase gene are related to distinct phenotypes in Japanese patients with hypophosphatasia," Eur J Pediatr. 164:277-282 (2005).
Millan, "Mammalian Alkaline Phosphatases," Wiley-WCH Verlag GmbH & Co., Weinheim, Germany, 1-322 (2006).
Millán et al., "Alkaline phosphatase and hypophosphatasia," Calcif Tissue Int. 98(4):398-416 (2016).
Millán et al., "Enzyme replacement therapy for murine hypophosphatasia," J Bone Miner Res. 23(6): 777-87 (2008).
Millán et al., "Hypophosphatasia—pathophysiology and treatment," available in PMC Sep. 22, 2014, published in final edited form as: Actual Osteol. 8(3):164-182 (2012) (21 pages).
Miyazawa et al., "Cyclic GMP-dependent protein kinase II plays a critical role in C-type natriuretic peptide-mediated endochondral ossification," Endocrinology. 143(9):3604-3610 (2002).
Mori et al., "Case series: odontohypophosphatasia or missed diagnosis of childhood/adult-onset hypophosphatasia?—Call for a long-term follow-up of premature loss of primary teeth," Bone Rep. 5:228-232 (2016).
Mornet et al., "Hypophosphatasia," GeneReviews. https://www.ncbi.nlm.nih.gov/books/NBK1150/, retrieved Dec. 6, 2017, initially published Nov. 20, 2007, last updated Feb. 4, 2016 (25 pages).
Mornet et al., "Identification of fifteen novel mutations in the tissue-nonspecific alkaline phosphatase (TNSALP) gene in European patients with severe hypophosphatasia," Eur J Hum Genet. 6(4):308-14 (1998).
Mornet et al., "Structural evidence for a functional role of human tissue nonspecific alkaline phosphatase in bone mineralization," J Biol Chem. 276(33):31171-8 (2001).
Mornet, "Hypophosphatasia," Metabolism. 82:142-155; DOI: 10.1016/j.metabol.2017.08.013 (2018) (30 pages).
Mornet, "Hypophosphatasia," Orphanet J Rare Dis. 2:(40) (2007) (8 pages).
Mornet, "Molecular genetics of hypophosphatasia and phenotype-genotype correlations," Subcell Biochem. 76:25-43 (2015).
Morris et al., "Immunolocalization of alkaline phosphatase in osteoblasts and matrix vesicles of human fetal bone," Bone Miner. 19:287-298 (1992).
Morrow, "Expensive new biologic helps children fight hypophosphatasia," Manag Care. 24(12) (2015) (7 pages).
Moss et al., "Association of inorganic-pyrophosphatase activity with human alkaline-phosphatase preparations," Biochem J. 102:53-57 (1967).
Murray, "Lectin-specific targeting of lysosomal enzymes to reticuloendothelial cells," Methods Enzymol. 149:25-42 (1987).
Murshed et al., "Unique coexpression in osteoblasts of broadly expressed genes accounts for the spatial restriction of ECM mineralization to bone," Genes Dev. 19:1093-1104 (2005).
Nahabet et al., "Postnatal Pancraniosynostosis in a Patient With Infantile Hypophosphatasia," Cleft Palate Craniofac J. 53(6):741-4 (2016).
Nakao et al., "The pharmacokinetics of alpha-human atrial natriuretic polypeptide in healthy subjects," Eur J Clin Pharmacol. 31:101-103 (1986).
Narisawa et al., "Abnormal vitamin B6 metabolism in alkaline phosphatase knock-out mice causes multiple abnormalities, but not the impaired bone mineralization," J Pathol. 193:125-133 (2001).
Narisawa et al., "Inactivation of two mouse alkaline phosphatase genes and establishment of a model of infantile hypophosphatasia," Dev Dyn. 208:432-446 (1997).
Nasu et al., "Aberrant interchain disulfide bridge of tissue-nonspecific alkaline phosphatase with an Arg433 to Cys substitution associated with severe hypophosphatasia," FEBS Journal. 273:5612-5624 (2006).
NCBI Protein Database Accession No. AAC33858. Retrieved on Apr. 16, 2013 (1 page).

(56) References Cited

OTHER PUBLICATIONS

NCBI Protein Database Accession No. AAF64516. Retrieved on Apr. 16, 2013 (2 pages).
NCBI Protein Database Accession No. AAH21289. Retrieved on Apr. 16, 2013 (2 pages).
NCBI Protein Database Accession No. AAH66116. Retrieved on Apr. 16, 2013 (2 pages).
NCBI Protein Database Accession No. AAH90861. Retrieved on Apr. 16, 2013 (2 pages).
NCBI Protein Database Accession No. AAI10910. Retrieved on Apr. 16, 2013 (2 pages).
NCBI Protein Database Accession No. AAI18209. Retrieved on Apr. 17, 2013 (2 pages).
NCBI Protein Database Accession No. AAI26166. Retrieved on Apr. 16, 2013 (2 pages).
NCBI Protein Database Accession No. AAN64273. Retrieved on Apr. 16, 2013 (1 page).
NCBI Protein Database Accession No. NP_000469. Retrieved on Apr. 16, 2013 (3 pages).
NCBI Protein Database Accession No. NP_001036028. Retrieved on Apr. 16, 2013 (2 pages).
NCBI Protein Database Accession No. NP_001253798.1, downloaded on Apr. 17, 2013. (2 pages).
NCBI Protein Database Accession No. NP_001622. Retrieved on Apr. 16, 2013 (3 pages).
NCBI Protein Database Accession No. NP_001623. Retrieved on Apr. 16, 2013 (3 pages).
NCBI Protein Database Accession No. NP_031457. Retrieved on Apr. 16, 2013 (3 pages).
NCBI Protein Database Accession No. NP_037191. Retrieved on Apr. 16, 2013 (3 pages).
NCBI Protein Database Accession No. NP_112603. Retrieved on Apr. 16, 2013 (3 pages).
NCBI Protein Database Accession No. NP_776412. Retrieved on Apr. 17, 2013 (2 pages).
NCBI Protein Database Accession No. NP_789828. Retrieved on Apr. 16, 2013 (3 pages).
NCBI Protein Database Accession No. P01857. Retrieved on Apr. 18, 2013 (7 pages).
NCBI Protein Database Accession No. P05186. Retrieved on Apr. 16, 2013 (19 pages).
NCBI Protein Database Accession No. P05187. Retrieved on Apr. 16, 2013 (10 pages).
NCBI Protein Database Accession No. P08289. Retrieved on Apr. 16, 2013 (5 pages).
NCBI Protein Database Accession No. P09242. Retrieved on Apr. 16, 2013 (6 pages).
NCBI Protein Database Accession No. P09487. Retrieved on Apr. 16, 2013 (4 pages).
NCBI Protein Database Accession No. P09923. Retrieved on Apr. 16, 2013 (6 pages).
NCBI Protein Database Accession No. P10696. Retrieved on Apr. 16, 2013 (7 pages).
NCBI Protein Database Accession No. Q29486. Retrieved on Apr. 16, 2013 (3 pages).
NCBI Protein Database Accession No. Q6PYX1. Retrieved on Oct. 15, 2013 (2 pages).
NCBI Protein Database Accession No. Q9N0V0. Retrieved on Apr. 16, 2013 (1 page).
NCBI Protein Database Accession No. XP_001109717. Retrieved on Apr. 17, 2013 (1 page).
Ngo et al., Computational complexity, protein structure prediction, and the levinthal paradox. *The Protein Folding Problem and Tertiary Structure Prediction.* Merz et al. (ed.), 433, 492-495 (1994).
Nishioka et al., "Enhancement of drug delivery to bone: characterization of human tissue-nonspecific alkaline phosphatase tagged with an acidic oligopeptide," Mol Genet Metab. 88:244-255 (2006).
Nosjean et al., "Human tissue non-specific alkaline phosphatases: sugar-moiety-induced enzymic and antigenic modulations and genetic aspects," Biochem J. 321:297-303 (1997).

Oda et al., "A general method for rapid purification of soluble versions of glycosylphosphatidylinositol-anchored proteins expressed in insect cells: an application for human tissue-nonspecific alkaline phosphatase," J Biochem. 126(4):694-9 (1999).
Office Action for U.S. Appl. No. 11/111,664, dated Dec. 4, 2008 (7 pages).
Office Action for U.S. Appl. No. 11/111,664, dated May 14, 2008 (8 pages).
Office Action for U.S. Appl. No. 11/111,664, dated Oct. 4, 2007 (11 pages).
Office Action for U.S. Appl. No. 11/484,870, dated Aug. 11, 2009 (15 pages).
Office Action for U.S. Appl. No. 11/484,870, dated Feb. 2, 2009 (16 pages).
Office Action for U.S. Appl. No. 11/484,870, dated Jan. 25, 2007 (15 pages).
Office Action for U.S. Appl. No. 11/484,870, dated Jul. 5, 2007 (13 pages).
Office Action for U.S. Appl. No. 11/484,870, dated Jun. 25, 2008 (16 pages).
Office Action for U.S. Appl. No. 11/484,870, dated Oct. 1, 2007 (12 pages).
Office Action for U.S. Appl. No. 12/405,920, dated Aug. 9, 2010 (7 pages).
Office Action for U.S. Appl. No. 12/405,920, dated Dec. 17, 2009 (14 pages).
Office Action for U.S. Appl. No. 12/793,517, dated Aug. 16, 2010 (9 pages).
Office Action for U.S. Appl. No. 13/071,445, dated Feb. 6, 2012 (12 pages).
Office Action for U.S. Appl. No. 13/071,445, dated May 25, 2012 (14 pages).
Official Action for Japanese Application No. 2013-544989, dated Oct. 27, 2016 (3 pages).
Official Notification and Search Report for Eurasian Patent Application No. 201291138, dated May 17, 2013 (3 pages).
Oikawa et al., "Enzyme replacement therapy on hypophosphatasia mouse model," J Inherit Metab Dis. (2013) (9 pages).
Okazaki et al., "Lethal hypophosphatasia successfully treated with enzyme replacement from day 1 after birth," Eur J Pediatr. 175(3):433-7; DOI 10.1007/s00431-015-2641-2 (2016) (5 pages).
Orimo, "Pathophysiology of hypophosphatasia and the potential role of asfotase alfa," Ther Clin Risk Manag. 12:777-86 (2016).
Orimo, "The mechanism of mineralization and the role of alkaline phosphatase in health and disease," J Nippon Med Sch. 77(1):4-12 (2010).
Padidela et al., "Enzyme-replacement therapy in life-threatening perinatal hypophosphatasia in a premature infant," Endocrine Abstracts. 33:p. 9 (2013) (1 page).
Padidela et al., "p. 1-118: Management of Tracheobronchomalacia During Asfotase Alfa Treatment in Infants with Perinatal-Onset Hypophosphatasia: A Case Series," European Society for Paediatric Endocrinology (ESPE), Paris, France, Sep. 10-12, 2016 (1 page).
Panesar, "Hypophosphatasia: a rare disorder," US Pharm. 42(5) (2017) (8 pages).
Park et al., "Ex vivo assessment of contractility, fatigability and alternans in isolated skeletal muscles," J Vis Exp. 69:e4198 (2012) (8 pages).
Park et al., "First Korean case of infantile hypophosphatasia with novel mutation in ALPL and literature review," Ann Clin Lab Sci. 46(3):302-7 (2016).
Patti et al., "Critical residues in the ligand-binding site of the *Staphylococcus aureus* collagen-binding adhesin (MSCRAMM)," J Biol Chem. 270(20):12005-12011 (1995).
Pedersen et al., "Removal of N-terminal polyhistidine tags from recombinant proteins using engineered aminopeptidases," Protein Expr Purif. 15(3):389-400 (1999).
Pfeifer et al., "Intestinal secretory defects and dwarfism in mice lacking cGMP-dependent protein kinase II," Science. 274:2082-2086 (1996).
Phillips et al., "A modified performance-oriented mobility assessment tool for assessing clinically relevant gait impairments and

(56) References Cited

OTHER PUBLICATIONS change in children with hypophosphatasia: development and validation," Bone Abstracts. 4 p. 136 (2015).
Phillips et al., "FRI-224: Improved activities of daily living and physical function, with decreased pain, in children with hypophosphatasia treated for three years with asfotase alfa: results from the childhood health assessment questionnaire and the pediatric outcomes data collection instrument," The Endocrine Society's 97th Annual Meeting & Expo, San Diego, California, Mar. 5-8, 2015 (1 page).
Phillips et al., "Gait assessment in children with childhood hypophosphatasia: impairments in muscle strength and physical function," The Endocrine Society's 97th Annual Meeting & Expo, Mar. 5-8, 2015, San Diego, California (2 pages).
Phillips et al., "Physical therapy management of infants and children with hypophosphatasia," Mol Genet Metab. 119(1-2):14-9 (2016).
Phillips et al., "Significantly improved muscle strength, running speed, and agility in children with hypophosphatasia treated with asfotase alfa," Endocrine Society's 97th Annual Meeting and Expo, Mar. 5-8, 2015, San Diego, CA. Abstract OR29-4 (2015) (2 pages).
Potter et al., "Natriuretic peptides, their receptors, and cyclic guanosine monophosphate-dependent signaling functions," Endocr Rev. 27(1):47-72 (2006).
Ramachandran et al., "Treatment of an anabolic bone deficiency in neurofibromatosis with bone morphogenetic proteins and its potential application for congenital pseudarthrosis of the tibia," J Bone Joint Surg Br. 91-B (Suppl. 1), Abstract 137 (2009).
Ratner, "Alexion pays big for Synageva's rare disease drug candidate," Nat Biotechnol. 33(7):679 (2015).
Remde et al., "Successful asfotase alfa treatment in an adult dialysis patient with childhood-onset hypophosphatasia," J Endoc Soc. 1(9):1188-93 (2017).
Reply Brief as Filed in U.S. Appl. No. 12/638,527, dated Apr. 22, 2016 (4 pages).
Reply to Final Office Action for U.S. Appl. No. 13/071,445, dated Oct. 25, 2012 (14 pages).
Reply to Office Action for U.S. Appl. No. 11/111,664, dated Sep. 10, 2008 (32 pages).
Restriction Requirement for U.S. Appl. No. 12/599,679, dated Jun. 12, 2012 (5 pages).
Rezende et al., "Inorganic pyrophosphate-phosphohydrolytic activity associated with rat osseous plate alkaline phosphatase," Cell Mol Biol. 44(2):293-302 (1998).
Rockman-Greenberg, "Hypophosphatasia," Pediatr Endocrinol Rev. 10 Suppl 2:380-8 (2013) (Abstract only).
Rodriguez et al., "Respiratory mechanics in an infant with perinatal lethal hypophosphatasia treated with human recombinant enzyme replacement therapy," Pediatr Pulmonol. 47(9):917-22 (2012).
Rowe et al., "MEPE, a new gene expressed in bone marrow and tumors causing osteomalacia," Genomics. 67:54-68 (2000).
Russell et al., "Inorganic pyrophosphate in plasma in normal persons and in patients with hypophosphatasia, osteogenesis imperfecta, and other disorders of bone," J Clin Invest. 50:961-969 (1971).
Saglam et al., "Clinical and genetic findings of Turkish hypophosphatasia cases," J Clin Res Pediatr Endocrinol. 9(3):229-236 (2017).
Salih et al., "Identification of the phosphorylated sites of metabolically 32P-labeled osteopontin from cultured chicken osteoblasts," J Biol Chem. 272(21):13966-73 (1997).
Sands et al., "Enzyme replacement therapy for murine mucopolysaccharidosis type VII," J Clin Invest. 93(6):2324-31 (1994).
Saraff et al., "A diagnostic algorithm for children with low alkaline phosphatase activities: lessons learned from laboratory screening for hypophosphatasia," J Pediatr. 172:181-6 (2016) (7 pages).
Sather, "008-case study: 3 year old female with hypophosphatasia, treated with asfotase alfa replacement," Journal of Pediatric Nursing. 34:104 (2017).
Sawai et al., "Severe perinatal hypophosphatasia due to homozygous deletion of T at nucleotide 1559 in the tissue nonspecific alkaline phosphatase gene,". Prenat Diagn. 23(9):743-6 (2003).

Schindeler et al., "Modeling bone morphogenetic protein and bisphosphonate combination therapy in wild-type and Nf1 haploinsufficient mice," J Orthop Res. 26(1):65-74 (2008).
Schmidt et al., "Clinical, radiographic and biochemical characteristics of adult hypophosphatasia," Osteoporos Int. 28(9):2653-2662 (2017).
Schmidt et al., "Hypophosphatasia: What is currently available for treatment?" Internist (Berl). 57(12):1145-1154 (2016) (Article in German) (English abstract).
Scott, "Asfotase alfa in perinatal/infantile-onset and juvenile-onset hypophosphatasia: a guide to its use in the USA," BioDrugs. 30(1):41-8 (2016).
Scott, "Asfotase alfa: a review in paediatric-onset hypophosphatasia," Drugs. 76(2):255-62 (2016).
Seefried et al., "Pharmacodynamic results from a phase 2a, randomized, multicenter, open-label, dose-ranging study of asfotase alfa in adults with pediatric hypophosphatasia," 100th Annual Meeting and Expo of the Endocrine Society, Mar. 17-20, 2018, Chicago, IL. (1 page).
Sekido et al., "Novel drug delivery system to bone using acidic oligopeptide: pharmacokinetic characteristics and pharmacological potential," J Drug Target. 9(2):111-21 (2001).
Shapiro et al., "Hypophosphatasia in adults: clinical assessment and treatment considerations," J Bone Miner Res. 32(10):1977-1980 (2017).
Sharom et al., "Glycosylphosphatidylinositol-anchored proteins: structure, function, and cleavage by phosphatidylinositol-specific phospholipase C," Biochem Cell Biol. 80:535-549 (2002).
Sheikh et al., "A newborn with no bones: neonatal hypophosphatasia with respiratory distress," J Pediatr. 188:306 (2017).
Shukla et al., "RNA interference and inhibition of MEK-ERK signaling prevent abnormal skeletal phenotypes in a mouse model of craniosynostosis," Nat Genet. 39(9):1145-1150 (2007).
Shull et al., "Enzyme replacement in a canine model of Hurler syndrome," Proc Natl Acad Sci USA. 91:12937-12941 (1994).
Siller et al., "Alkaline phosphatase: discovery and naming of our favorite enzyme," J Bone Miner Res. 33(2):362-4 (2018).
Simm et al., "Successful use of enzyme replacement therapy in infantile hypophosphatasia," J Paediatr Child Health. 53(9):925-926 (2017).
Siris et al., "Paget's disease of bone," Trends Endocrinol Metab. 2(6):207-12 (1991).
Skolnick et al., "From genes to protein structure and function: novel applications of computational approaches in the genomic era," Trends Biotechnol. 18(1):34-9 (2000).
Sotillo et al., "Signs and symptoms of hypophosphatasia," Dimensions of Dental Hygiene. 15(4):44-47 (2017) (6 pages).
Spears et al., "Deoxyuridylate effects on thymidylate synthase-5-fluorodeoxyuridylate-folate ternary complex formation," Biochem Pharmacol. 38(18):2985-2993 (1989).
Spentchian et al., "Severe hypophosphatasia: characterization of fifteen novel mutations in the ALPL gene," Hum Mutat. 22(1) (2003) (5 pages).
Srinivas et al., "Assessment of dose proportionality, absolute bioavailability, and immunogenicity response of CTLA4Ig (BMS-188667), a novel immunosuppressive agent, following subcutaneous and intravenous administration to rats," Pharmaceutical Res. 14(7): 911-916 (1997).
Stahl et al., "Evidence for receptor-mediated binding of glycoproteins, glycoconjugates, and lysosomal glycosidases by alveolar macrophages," Proc Natl Acad Sci USA. 75(3):1399-1403 (1978).
Stec et al., "A revised mechanism for the alkaline phosphatase reaction involving three metal ions," J Mol Biol. 299(5):1303-11 (2000).
Sturtz et al., "A study of the delivery-targeting concept applied to antineoplasic drugs active on human osteosarcoma. I. Synthesis and biological activity in nude mice carrying human osteosarcoma xenografts of gem-bisphosphonic methotrexate analogues," Eur J Med Chemistry. 27:825-33 (1992).
Suda et al., "C-type natriuretic peptide as an autocrine/paracrine regulator of osteoblast: evidence for possible presence of bone natriuretic peptide system," Biochem Biophys Res Commun. 223:1-6 (1996).

(56) References Cited

OTHER PUBLICATIONS

Sugano et al., "Successful gene therapy in utero for lethal murine hypophosphatasia," Hum Gene Ther. 23(4):399-406 (2012).
Supplementary European Search Report for European Application No. EP 05 73 9065 (date of completion of search Nov. 7, 2008, dated Dec. 2, 2008) (3 pages).
Supplementary European Search Report for European Patent Application No. 11853820.6, dated Mar. 25, 2014 (3 pages).
Symersky et al., "Structure of the collagen-binding domain from a *Staphylococcus aureus* adhesin," Nat Struct Biol. 4(10):833-838 (1997).
Takahashi et al., "Parental serum alkaline phosphatase activity as an auxiliary tool for prenatal diagnosis of hypophosphatasia," Prenat Diagn. 37(5):491-6 (2017).
Takano et al., "Molecular evolution of shark C-type natriuretic peptides," Zoolog Sci. 11:451-454 (1994).
Taketani et al., "Clinical and genetic aspects of hypophosphatasia in Japanese patients," Arch Dis Child. 99(3):211-5 (2014) (6 pages).
Taketani et al., "Ex vivo expanded allogeneic mesenchymal stem cells with bone marrow transplantation improved osteogenesis in infants with severe hypophosphatasia," Cell Transplant. 24(10):1931-43 (2015).
Takinami et al., "The mutant (F310L and V365I) tissue-nonspecific alkaline phosphatase gene from hypophosphatasia," J Med Dent Sci. 51(1):67-74 (2004).
Tamura et al., "Critical roles of the guanylyl cyclase B receptor in endochondral ossification and development of female reproductive organs," Proc Natl Acad Sci USA. 101(49):17300-17305 (2004).
Teixeira et al., "Nitric oxide, C-type natriuretic peptide and cGMP as regulators of endochondral ossification," Dev Biol. 319:171-178 (2008).
Tenorio et al., "Molecular and clinical analysis of ALPL in a cohort of patients with suspicion of hypophosphatasia," Am J Med Genet A. 173(3):601-10 (2017).
Tomatsu, Declaration Under 37 C.F.R. § 1.132 for U.S. Appl. No. 11/484,870, dated Jun. 1, 2009 (3 pages).
Tomatsu, Declaration Under 37 C.F.R. § 1.132 for U.S. Appl. No. 11/484,870, dated Nov. 27, 2007 (2 pages).
Tomazos et al., "Determination of the Minimal Clinically Important Difference in the Six-Minute Walk Test for Patients with Hypophosphatasia," European Society for Paediatric Endocrinology, 55th Annual ESPE, Paris, France, Sep. 10-12, 2016, <http://abstracts.eurospe.org/hrp/0086/hrp0086FC2.5.htm>, (4 pages).
Tsiantouli et al., "Hypophosphatasia," Rev Med Suisse. 13(559):855-8 (2017) (Article in French) (English Abstract Included).
Tsuji et al., "A loss-of-function mutation in natriuretic peptide receptor 2 (Npr2) gene is responsible for disproportionate dwarfism in cn/cn mouse," J Biol Chem. 280(14):14288-14292 (2005).
Tye et al., "Delineation of the hydroxyapatite-nucleating domains of bone sialoprotein," J Biol Chem. 278(10):7949-7955 (2003).
Uludag et al., "Bone affinity of a bisphosphonate-conjugated protein in vivo," Biotechnol Prog. 16(6):1115-8 (2000).
UniProtKB Accession No. P01857. Retrieved May 2, 2018 (13 pages).
UniProtKB Accession No. P05186. Retrieved May 2, 2018 (19 pages).
Urlaub et al., "Deletion of the diploid dihydrofolate reductase locus from cultured mammalian cells," Cell. 33:405-412 (1983).
Urlaub et al., "Isolation of Chinese hamster cell mutants deficient in dihydrofolate reductase activity," Proc Natl Acad Sci U S A. 77(7):4216-20 (1980).
Wang et al., "A mouse model for achondroplasia produced by targeting fibroblast growth factor receptor 3," Proc Natl Acad Sci USA. 96:4455-4460 (1999).
Wang et al., "Current concepts in odontohypophosphatasia form of hypophosphatasia and report of two cases," BMC Oral Health. 16(1):70 (2016) (8 pages).
Wang et al., "Mice lacking Nf1 in osteochondroprogenitor cells display skeletal dysplasia similar to patients with neurofibromatosis type 1," Hum Mol Genet. 20(20):3910-3924 (2011).
Wang et al., "Structure-based chemical modification strategy for enzyme replacement treatment of phenylketonuria," Mol Genet Metab. 86:134-140 (2005).
Waymire et al., "Mice lacking tissue non-specific alkaline phosphatase die from seizures due to defective metabolism of vitamin B-6," Nat Genet. 11(1):45-51 (1995).
Weber et al., "Burden of disease in adult patients with hypophosphatasia: Results from two patient-reported surveys," Metabolism. 65(10):1522-30 (2016).
Weinberg, "An overview of infliximab, etanercept, efalizumab, and alefacept as biologic therapy for psoriasis," Clin Ther. 25(10):2487-505 (2003).
Weiss et al., "A missense mutation in the human liver/bone/kidney alkaline phosphatase gene causing a lethal form of hypophosphatasia," Proc Natl Acad Sci USA. 85:7666-7669 (1988).
Weiss et al., "Isolation and characterization of a cDNA encoding a human liver/bone/kidney-type alkaline phosphatase," Proc Natl Acad Sci USA. 83(19):7182-6 (1986) (6 pages).
Weiss et al., "Structure of the human liver/bone/kidney alkaline phosphatase gene," J Biol Chem. 263(24):12002-10 (1988).
Weninger et al., "Biochemical and morphological effects of human hepatic alkaline phosphatase in a neonate with hypophosphatasia," Acta Paediatr Scand. Suppl. 360:154-160 (1989).
Whyte et al., "Alkaline phosphatase: placental and tissue-nonspecific isoenzymes hydrolyze phosphoethanolamine, inorganic pyrophosphate, and pyridoxal 5'-phosphate. Substrate accumulation in carriers of hypophosphatasia corrects during pregnancy," J Clin Invest. 95(4):1440-5 (1995).
Whyte et al., "Asfotase alfa therapy for children with hypophosphatasia," JCI Insight. 1(9):e85971 (2016) (11 pages).
Whyte et al., "Asfotase alfa treatment improves survival for perinatal and infantile hypophosphatasia," J Clin Endocrinol Metab. 101(1):334-42 (2016) (17 pages).
Whyte et al., "Enzyme replacement therapy for infantile hypophosphatasia attempted by intravenous infusions of alkaline phosphatase-rich Paget plasma: results in three additional patients," J Pediatr. 105(6):926-33 (1984).
Whyte et al., "Enzyme-replacement therapy in life-threatening hypophosphatasia," N Engl J Med. 366(10):904-13 (2012).
Whyte et al., "Hypophosphatasia: Enzyme replacement therapy (asfotase alfa) decreases TNSALP substrate accumulation and improves functional outcomes in affected adolescents and adults," Bull Group Int Rech Sci Stomatol Odontol. 51(1):35 (2012).
Whyte et al., "Hypophosphatasia: natural history study of 101 affected children investigated at one research center," Bone. 93:125-138 (2016).
Whyte et al., "Hypophosphatasia: validation and expansion of the clinical nosology for children from 25 years experience with 173 pediatric patients," Bone. 75:229-39 (2015).
Whyte et al., "Infantile hypophosphatasia: enzyme replacement therapy by intravenous infusion of alkaline phosphatase-rich plasma from patients with Paget bone disease," J Pediatr. 101(3):379-86 (1982).
Whyte et al., "Infantile hypophosphatasia: normalization of circulating bone alkaline phosphatase activity followed by skeletal remineralization. Evidence for an intact structural gene for tissue nonspecific alkaline phosphatase," J Pediatr. 108(1):82-8 (1986).
Whyte et al., "Markedly increased circulating pyridoxal-5'-phosphate levels in hypophosphatasia," J Clin Invest. 76:752-756 (1985).
Whyte et al., "Marrow cell transplantation for infantile hypophosphatasia," J Bone Miner Res. 18(4):624-36 (2003).
Whyte, "Heritable Forms of Rickets and Osteomalacia," in Connective Tissues and Its Heritable Disorders, pp. 765-787, 2002 (eds. R.M. Royce and B. Steinmann, Wiley-Liss, Inc. Hoboken).
Whyte, "Hypophosphatasia—aetiology, nosology, pathogenesis, diagnosis and treatment," Nat Rev Endocrinol. 12(4):233-46 (2016).
Whyte, "Hypophosphatasia and the role of alkaline phosphatase in skeletal mineralization," Endocr Rev. 15(4):439-461 (1994).
Whyte, "Hypophosphatasia," in The Metabolic and Molecular Bases of Inherited Disease (8th ed.), pp. 5313-5329, 2001 (McGraw-Hill Book Company) (epub pp. 1-41).

(56) References Cited

OTHER PUBLICATIONS

Whyte, "Hypophosphatasia: an overview for 2017," Bone. 102:15-25 (2017).
Whyte, "Hypophosphatasia: enzyme replacement therapy brings new opportunities and new challenges," J Bone Miner Res. 32(4):667-675 (2017).
Whyte, "Hypophosphatasia: Nature's window on alkaline phosphatase function in man," *Principles of Bone Biology*, 2nd ed., Bilezikian, Raisz, and Rodan. 2:1229-1248 (2002).
Whyte, "Physiological role of alkaline phosphatase explored in hypophosphatasia," Ann N Y Acad Sci. 1192:190-200 (2010).
Wickramasinghe et al., "A case of hypophosphatasia," Ceylon Med J. 48(3):94-5 (2003).
Williams et al., "Solute transport in growth plate cartilage: In vitro and in vivo," Biophys J. 93(3):1039-1050 (2007).
Wroblewski et al., "Pharmacokinetics, metabolic stability, and subcutaneous bioavailability of a genetically engineered analog of DcR3, flint [DcR3(R218Q)], in cynomolgus monkeys and mice," Drug Metab Dispos. 31(4):502-507 (2003).
Yadav et al., "Dose response of bone-targeted enzyme replacement for murine hypophosphatasia," available in PMC Aug. 1, 2012, published in final edited form as: Bone. 49(2):250-6 (2011) (20 pages).
Yamamoto et al., "A successful treatment with pyridoxal phosphate for West syndrome in hypophosphatasia," Pediatr Neurol. 30(3):216-8 (2004).
Yamamoto et al., "Long term phenotypic correction of severe infantile hypophosphatasia in a mouse model by neonatal injection of lentiviral vector," Mol Ther. 17:S67-S68, Abstract 171 (2009).
Yamamoto et al., "Prolonged survival and phenotypic correction of Akp2(-/-) hypophosphatasia mice by lentiviral gene therapy," J Bone Miner Res. 26(1):135-42 (2011).
Yasoda et al., "Natriuretic peptide regulation of endochondral ossification. Evidence for possible roles of the C-type natriuretic peptide/guanylyl cyclase-B pathway," J Biol Chem. 273(19):11695-11700 (1998).
Yasoda et al., "Overexpression of CNP in chondrocytes rescues achondroplasia through a MAPK-dependent pathway," Nat Med. 10(1):80-86 (2004).
Yasoda et al., "Systemic administration of C-type natriuretic peptide as a novel therapeutic strategy for skeletal dysplasias," Endocrinology. 150(7):3138-3144 (2009).
Yoder et al., "Reduced ability of C-type natriuretic peptide (CNP) to activate natriuretic peptide receptor B (NPR-B) causes dwarfism in Ibab -/- mice," Peptides. 29(9):1575-1581 (2008).
Yokogawa et al., "Selective delivery of estradiol to bone by aspartic acid oligopeptide and its effects on ovariectomized mice," Endocrinology. 142(3):1228-1233 (2001).
Young et al., "Structure, expression, and regulation of the major noncollagenous matrix proteins of bone," Clin Orthop Relat Res. 281:275-294 (1992).
Zierhut et al., "Population PK-PD model for Fc-osteoprotegerin in healthy postmenopausal women," J Pharmacokinet Pharmacodyn. 35:379-399 (2008).
Zurutuza et al., "Correlations of genotype and phenotype in hypophosphatasia," Hum Mol Genet. 8(6):1039-1046 (1999).
Carden et al., "Tracheomalacia and tracheobronchomalacia in children and adults: an in-depth review," Chest. 127(3):984-1005 (2005).
Di Rocco et al., "Craniosynostosis and hypophosphatasia," Arch Pediatr. 24(5S2):5S89-5S92 (2017).
Hancarova et al., "Hypophosphatasia due to uniparental disomy," Bone. 81:765-766 (2015).
International Search Report and Written Opinion for International Application No. PCT/US2019/045963, dated Jan. 30, 2020 (26 pages).
Leung et al., "Outcome of perinatal hypophosphatasia in Manitoba Mennonites: a retrospective cohort analysis," JIMD Rep. 11:73-78 (2013).
Li et al., "Timing of the initiation of bisphosphonates after surgery for fracture healing: a systematic review and meta-analysis of randomized controlled trials," Osteoporos Int. 26(2):431-41 (2015).
Murgu et al., "Tracheobronchomalacia and excessive dynamic airway collapse," Respirology. 11(4):388-406 (2006).
Park et al., "The effect of alendronate loaded biphasic calcium phosphate scaffolds on bone regeneration in a rat tibial defect model," Int J Mol Sci. 16(11):26738-53 (2015) (17 pages).
Mornet, "The tissue nonspecific alkaline phosphatase gene mutations database," <www.sesep.uvsq.fr/03_hypo_mutations.php>, last updated Nov. 28, 2019 (14 pages).
Morrison et al., "Mitigation of tracheobronchomalacia with 3D-printed personalized medical devices in pediatric patients," available in PMC Apr. 29, 2016, published in final edited form as: Sci Transl Med. 7(285):285ra264 (2015) (23 pages).
Official Action and Translation for Japanese Application No. 2017-539393, dated Sep. 17, 2019 (14 pages).
Official Action for Russian Patent Application No. 2017123540, dated Jul. 8, 2019 (15 pages).
Rodionova et al., "Hypophosphatasia in adults: clinical cases and literature review," Osteoporosis and Bone Diseases. 18(2):25-7 (2015) (4 pages).
Taketani et al., Chapter 9: Hypophosphatasia. *Human Pathobiochemistry.* T. Oohashi et al. (eds.), 91-100 (2019).
Whyte et al., "Asfotase alfa for infants and young children with hypophosphatasia: 7 year outcomes of a single-arm, open-label, phase 2 extension trial," Lancet Diabetes Endocrinol. 7(2):93-105 (2019) (52 pages).
Whyte et al., "Hypophosphatasia (HPP) in children: enzyme replacement therapy (EzRT) using bone-targeted, tissue-nonspecific alkaline phosphatase (TNSALP)," Ann Neurol. 68(Suppl 14):S70 Abstract WIP-28 (2010) (1 page).
Whyte et al., "Natural history of perinatal and infantile hypophosphatasia: a retrospective study," J Pediatr. 209:116-124.e4 (2019) (13 pages).
Pradhan et al., "Exposure-Response Modeling and Simulation to Support Evaluation of Efficacious and Safe Exposure and Dose Range for Asfotase alfa in Patients with Hypophosphatasia," ASBMR 2015 Annual Meeting Abstracts. J Bone and Med Res. SU0380:S316 (2015) (1 page).
Abbruzzese, "The Tinetti Performance-Oriented Mobility Assessment Tool," Am J Nursing. 98(12):16J-16L (1998) (3 pages).
International Search Report and Written Opinion for International Patent Application No. PCT/US20/64140, dated Apr. 23, 2021 (70 pages).
Kishnani et al., "Five-year efficacy and safety of asfotase alfa therapy for adults and adolescents with hypophosphatasia," Bone. 121:149-162 (2019).
Alexion Pharmaceuticals, "Safety Study of Human Recombinant Tissue Non-Specific Alkaline Phosphatase Fusion Protein Asfotase Alfa in Adults With Hypophosphatasia (HPP)," ClinicalTrials.gov. NCT00739505, last updated Mar. 29, 2019 (8 pages).
Alexion Pharmaceuticals, "Safety and Efficacy Study of Asfotase Alfa in Adolescents and Adults With Hypophosphatasia (HPP)," ClinicalTrials.gov. NCT01163149, last updated Mar. 13, 2019 (9 pages).
Alexion Pharmaceuticals, "Strensiq (asfotase alfa) for injection," retrieved from <globalgenes.org/2015/11/05/alexion-announces-fda-approval-for--strensiq/?gclid=CjwKCAjwwqaGBhBKEiwAMk-FtFQOKvuVN-WmNcDVyu9Q9X3f6QB-V0Two0x216TR2H4_Qc6jSlhvxoCiLMQAvD_BwE>, dated Nov. 5, 2015 (1 page).
European Medicines Agency, "Strensiq: Asfotase Alfa," <www.ema.europa.eu/en/medicines/human/EPAR/strensiq>, dated Mar. 25, 2021 (8 pages).
Hofmann et al. "Efficacy and safety of asfotase alfa in infants and young children with hypophosphatasia: a phase 2 open-label study," J Clin Endocrinol Metab. 104(7): 2735-2747 (2019) (14 pages).
Examination Report No. 1 for Australian Patent Application No. 2016308624, dated Aug. 27, 2021 (6 pages).
Kim et al., "CHO cells in biotechnology for production of recombinant proteins: current state and further potential," Appl Microbiol Biotechnol. 93(3): 917-30 (2012).
Office Action for Chinese Patent Application No. 201780021666.7, dated Jul. 21, 2021 (34 pages).

(56) References Cited

OTHER PUBLICATIONS

McCormack et al., "Is bigger better? An argument for very low starting doses," CMAJ. 183(1):65-9 (2011).
Rush, "Childhood hypophosphatasia: to treat or not to treat," Orphanet J Rare Dis. 13(1):116 (2018) (5 pages).
Phillips et al., "Clinical Outcome Assessments: Use of Normative Data in a Pediatric Rare Disease," Value Health. 21(5):508-514 (2018).
Office Action for Japanese Patent Application No. 2018-551309, dated Nov. 2, 2021 (11 pages).

\* cited by examiner

MANUFACTURING OF ALKALINE PHOSPHATASES

SEQUENCE LISTING

The amino acid sequences listed in the accompanying sequence listing are shown using standard three-letter code for amino acids, as defined in 37 C.F.R. 1.822. The Sequence Listing is submitted as an ASCII text file, created on Aug. 16, 2016, named 0351 WO_SL.txt and 6,604 bytes in size, which is incorporated by reference herein.

FIELD OF THE INVENTION

The disclosure is directed to a method for producing a recombinant polypeptide, comprising: (a) providing a 100 L to 25,000 L fed-batch bioreactor comprising (i) cells capable of expressing the recombinant polypeptide asfotase alfa (SEQ ID NO: 1), and (ii) a culture medium suitable for conducting such expression, the culture medium comprising about 25 µM to about 300 µM zinc; (b) culturing the cells under conditions suitable to express the recombinant asfotase alfa; wherein the pH of the culture medium is about 6.7 to about 7.1, and wherein zinc is added into said culture medium such that the zinc concentration in the culture medium is maintained at a concentration of about 25 µM to about 300 µM of zinc.

BACKGROUND

Hypophosphatasia (HPP) is a life-threatening, genetic and ultra-rare metabolic disorder that results in a failure to produce functional tissue nonspecific alkaline phosphatase (TNSALP). It leads to the accumulation of unmineralized bone matrix (e.g. rickets, osteomalacia), characterized by hypo-mineralization of bones and teeth. When growing bone does not mineralize properly, an impairment of growth is a result that disfigures joints and bones. This result in turn impacts motor performance, respiratory function, and may even lead to death. Different forms of HPP were discovered to include perinatal, infantile, juvenile, and adult HPP. Recently, six clinical forms have been defined, most based upon age at symptom onset, to include perinatal, benign prenatal, infantile, juvenile, adult, and odonto-HPP. Asfotase alfa is an approved first-in-class targeted enzyme replacement therapy designed to address defective endogenous TNSALP levels. For treating HPP with TNSALP, see Whyte et al., 2012 *N Engl J Med.* 366:904-13.

Asfotase alfa (STRENSIQ®, Alexion Pharmaceuticals, Inc.) is a soluble fusion glycoprotein comprised of the catalytic domain of human TNSALP, a human immunoglobulin G1 Fc domain and a deca aspartate peptide (i.e., D10) used as a bone-targeting domain. In vitro, asfotase alfa binds with a greater affinity to hydroxyapatite than does soluble TNSALP lacking the deca-aspartate peptide, thus allowing the TNSALP moiety of asfotase alfa to efficiently degrade excess local inorganic pyrophosphate (PPi) and restore normal mineralization. Pyrophosphate hydrolysis promotes bone mineralization, and its effects are similar among the species evaluated in nonclinical studies. Initial efficacy studies were conducted in a mouse model of HPP (Akp2$^{-/-}$ mice). The Akp2$^{-/-}$ mouse model, created by inactivating the TNSALP gene (Narisawa et al. 1997 *Dev Dyn.* 208:432-46), shares many common features of the human condition including accumulation of unmineralized bone matrix.

BRIEF SUMMARY

Disclosed herein are compositions of alkaline phosphatases (e.g., asfotase alfa) which have specific characteristics (e.g., particular glycan structures, particular total sialic acid content (TSAC) values, etc.) and manufacturing processes utilized to produce the alkaline phosphatases (e.g., asfotase alfa) having such specific characteristics. Such alkaline phosphatases (e.g., asfotase alfa) are suited for use in therapy, for example, for treatment of conditions associated with decreased alkaline phosphatase protein levels and/or functions (e.g., insufficient cleavage of inorganic pyrophosphate (PPi)) in a subject, for example, a human subject.

In one aspect, the present disclosure provides a method for producing a recombinant polypeptide having alkaline phosphatase function. In various embodiments, the alkaline phosphatase function may include any functions of alkaline phosphatase known in the art, such as enzymatic activity toward natural substrates including phosphoethanolamine (PEA), inorganic pyrophosphate (PPi) and pyridoxal 5'-phosphate (PLP). Such recombinant polypeptide can comprise asfotase alpha (SEQ ID NO: 1).

In some embodiments, the method disclosed herein further comprises adding zinc into said culture medium for producing the recombinant polypeptide. Zinc may help improving the activity and/or stability of the recombinant polypeptide. In some embodiments, zinc may be added to provide a zinc concentration of from about 1 to about 300 µM in said culture medium. In one embodiment, zinc may be added to provide a zinc concentration of from about 10 to about 150 µM (e.g., 10, 20, 30, 40, 50, 60, 70, 80, 90, 100, 110, 120, 130, 140, or 150 µM) in the culture medium. In some embodiments, zince is added to provide a zinc concentration in the culture medium of from about 25 µM to about 150 µM, or about 60 µM to about 150 µM. In one particular embodiment, zinc is added to provide a zinc concentration in the culture medium of from about 30, 60, or 90 µM of zinc. In one particular embodiment, zinc is added to provide a zinc concentration in the culture medium of about 28 µM. In some embodiments, the zinc is added into said culture medium in a bolus, continuously, or semi-continuously.

In some embodiments, the method disclosed herein further comprises controlling the pH of said culture medium for producing the recombinant polypeptide. For example, the pH may be set at about 6.8 to about 7.0. In one particular embodiment, the pH is set at about 6.9.

In some embodiments, the method disclosed herein further comprises adding at least one extra fresh culture medium bolus feed to the original cell-containing culture medium during culturing and/or polypeptide production. Such addition of fresh culture medium may improve activity (e.g., specific activity) of the produced recombinant polypeptide. In one embodiment, at least one, two, three, or four feed bolus(es) are added to the culture medium during culturing. In one particular embodiment, at least four feed boluses are added. In some embodiments, the feed bolus addition(s) improves specific activity of the recombinant polypeptide. The cells disclosed herein for producing the recombinant polypeptide may be any cells (e.g., mammalian cells) known in the art. In some embodiments, the cells are selected from the group comprising CHO, NSO/1, PER.C6, COS-7, human embryonic kidney line (293 or 293 cells subcloned for growth in suspension culture), BHK, TM4, CVI, VERO-76, HeLa, MDCK, BRL 3A, W138, Hep G2, MMT 060562, TRI, MRC 5, FS4 cells, and Hep G2 cells. In some embodiments, the cells are CHO cells.

In some embodiments, the cells the cells are grown at a first temperature for certain of time for cell growth and then shifted to a second temperature for polypeptide expression. For example, in some embodiments, it is disclosed the method further comprises culturing the cells at a first temperature until reaching a cell density of at least about $2.5 \times 10^6$ viable cells, and then shifting to a second temperature which is lower than the first temperature for recombinant polypeptide expression. For example, in some embodiments, the first temperature is about 35° C. to about 37.5° C. In some embodiments, the second temperature is about 29° C. to about 35° C. In some embodiments, the first temperature is about 37° C. and the second temperature is about 30° C. In some embodiments, the first temperature is about 36.5° C. and the second temperature is about 33° C.

In another aspect, the present disclosure provides a recombinant polypeptide produced by any one of methods disclosed herein. Such produced recombinant polypeptide may have at least one of specific characteristics originated from the producing methods disclosed herein. Such characteristics may include at least one selected from the group comprising: (a) a total sialic acid content (TSAC) between about 0.9 to about 3.5 mol sialic acid/mol protein monomer; (b) an isoelectric focusing (IEF) between about 5.2 to about 6.7; (c) a major glycan structure as shown in FIG. 41 or FIG. 42; (d) a 2-AB labeled oligosaccharide chromatogram profile as shown in FIG. 38 or 39; (e) a MALDI-ToF glycopeptide finger printing profile as shown in FIG. 40, or 44-49; (f) a major band on a reduced SDS-PAGE having a molecular weight of about 88-108 kDa and no less than about 85% of the total amount of the produced recombinant polypeptide; (g) a major band on a non-reduced SDS-PAGE having a molecular weight of about 194 to about 273 kDa and no less than about 85% of the total amount produced recombinant polypeptide; (h) no less than about 95.0% for dimers of the recombinant polypeptide and no more than about 5.0%0 for aggregates by size exclusion high pressure liquid chromatography (HPLC); (i) no less than about 95.0% purity via reverse-phase high pressure liquid chromatography (RP-HPLC); (j) no less than about 90.0% for main peak, no more than about 6.0% for acidic peaks, and no more than about 4.0% for basic peaks via Anion Exchange Chromatography (AEX); (k) a hydroxyapatite (HA) binding percentage of about 75 to about 125%; (l) a product specific activity (pNPP) of about 620 to about 1250 units/mg; (m) a $K_m$ of about 13 to about 69 CpM in an inorganic pyrophosphate (PPi) hydrolysis assay; (n) a $K_{cat}$ of about 65 to about 165 s$^{-1}$ in an inorganic pyrophosphate (PPi) hydrolysis assay; (o) a pI range of about 6.45 to about 6.95 for all peaks on capillary electrophoresis; (p) peaks on a MALDI-ToF mass spectrum as shown in FIG. 34A after deglycosylation; (q) peaks on a MALDI-ToF mass spectrum as shown in FIG. 34B after reduction and deglycosylation; (r) peaks on a MALDI-ToF mass spectrum as shown in FIG. 35; (s) a phosphorylation profile as shown in FIG. 36; (t) a sialyated glycans profile on a negative MALDI-ToF mass spectrum as shown in FIG. 37A; (u) a neutral glycans profile on a positive MALDI-ToF mass spectrum as shown in FIG. 37B; (v) a molar ratio of magnesium per mole of recombinant polypeptide of from about 0.03 to about 0.15; (w) a molar ratio of calcium per mole of recombinant polypeptide of from about 0.5 to about 1.5; and (x) molar ratio of zinc per mole of recombinant polypeptide of from about 0.5 to about 3.0.

In one embodiment, the produced recombinant protein has from about 0.7 to about 1.19 free cysteine per half molecule.

In one embodiment, the produced recombinant protein has phosphorylation at Ser 93 at a percentage of from about 13.5% to about 35.7%.

In one embodiment, the produced recombinant protein has no less than 90.0% main peak, no more than 6.0% for acidic peaks, and no more than 4.0% for basic peaks on an AEX chromatogram. In one particular embodiment, the produced recombinant protein has no less than 93.7% main peak, no more than 4.9% for acidic peaks, and no more than 3.4% for basic peaks on an AEX chromatogram.

In some embodiments, the produced recombinant protein has a total sialic acid content (TSAC) between about 0.9 to about 3.5 mol sialic acid/mol protein monomer. In one embodiment, the produced recombinant protein has a mean Total Sialic Acid Content (TSAC) value from about 1.2 to about 3.0 mol sialic acid/mol per monomer. In one embodiment, the produced recombinant protein has a mean Total Sialic Acid Content value from about 1.9 to about 2.7 mol sialic acid/mol per monomer. In one particular embodiment, the produced recombinant protein has a mean Total Sialic Acid Content value from about 1.85 to about 2.28 mol sialic acid/mol per monomer.

In one embodiment, the produced recombinant protein has a binding molar ratio of magnesium ion of less than about 0.15. In some embodiments, the produced recombinant protein has a molar ratio of magnesium of about 0.05 to about 0.10. In one particular embodiment, the produced recombinant protein has a binding molar ratio of magnesium ion of about 0.12.

In some embodiments, the produced recombinant protein comprises at least about 95.0% for dimers of the recombinant polypeptide about 5.0% or less polypeptide aggregates, i.e., as measured by size exclusion HPLC. In one embodiment, the produced recombinant protein comprises at least about 96.8% dimers of the recombinant polypeptide and about 3.2% or less polypeptide aggregates, i.e., as measured by a size exclusion HPLC. In one particular embodiment, the produced recombinant protein comprises at least about 97.6% dimers of the recombinant polypeptide and about 2.4% or less aggregates, i.e., as measured by size exclusion HPLC.

In one embodiment, the produced recombinant protein has no less than 95.0% purity as measured by RP-HPLC. In one particular embodiment, the produced recombinant protein has no less than 97.6% purity as measured by RP-HPLC.

In some embodiments, the produced recombinant protein has a Hydroxyapatite (HA) binding percentage of about 75 to about 125%. In one embodiment, the produced recombinant protein has a mean % hydroxyapatite binding of from about 85% to about 97%. In one particular embodiment, the produced recombinant protein has a mean % hydroxyapatite binding of from about 90% to about 91%.

In one embodiment, the produced recombinant protein has a specific activity (pNPP) of about 620 to about 1250 units/mg. In one particular embodiment, the produced recombinant protein has a mean specific activity (pNPP) of about 904.0 to about 907.7 U/mg.

In some embodiments, the recombinant polypeptide is encoded by a polynucleotide encoding a polypeptide comprising the sequence as set forth in SEQ ID NO: 1, or a sequence completely complementary to SEQ ID NO: 1.

The recombinant polypeptide disclosed herein may be produced under an industrial or a commercial scale. For example, in some embodiments, the fed-batch reactor is 200 L to 20,000 L. In some embodiments, the fed-batch reactor is 2,000 L to 20,000 L.

In another aspect, the present disclosure provides a pharmaceutical formulation comprising a composition comprising the recombinant polypeptide disclosed herein, in combination with a pharmaceutically acceptable carrier, diluent or excipient.

In another aspect, the present disclosure provides a method of using the recombinant polypeptide, or the pharmaceutical formulation discussed herein to increase cleavage of inorganic pyrophosphate (PPi) in a subject.

In another aspect, the present disclosure provides a method of treating a subject, comprising administering to the subject suffering from a condition associated with alkaline phosphatase deficiency a therapeutically effective amount of the recombinant polypeptide, or the pharmaceutical formulation discussed herein. Such condition associated with alkaline phosphatase deficiency includes, for example, hypophosphatasia (HPP) and neurofibromatosis type I (NF1). Such hypophosphatasia (HPP) may be any one of perinatal, infantile, juvenile, or adult HPP. Such condition may be characterized with unmineralized bone matrix and/or hypo-mineralization of bones and teeth. For example, such unmineralized bone matrix may lead to rickets and/or osteomalacia.

In some embodiments, such subject is a mammal. In some embodiment, such subject is a human.

BRIEF DESCRIPTION OF THE DRAWINGS

In the appended drawings:

FIG. 35 discloses "TYNT-NAQVPDSAGTATAYLCGVK" as residues 83-105 of SEQ ID NO: 1, "SAGTA" as residues 93-97 of SEQ ID NO: 1 and "AYLCGV" as residues 99-104 of SEQ ID NO: 1, respectively, in order of appearance.

DETAILED DESCRIPTION

Definitions

Figure 1:
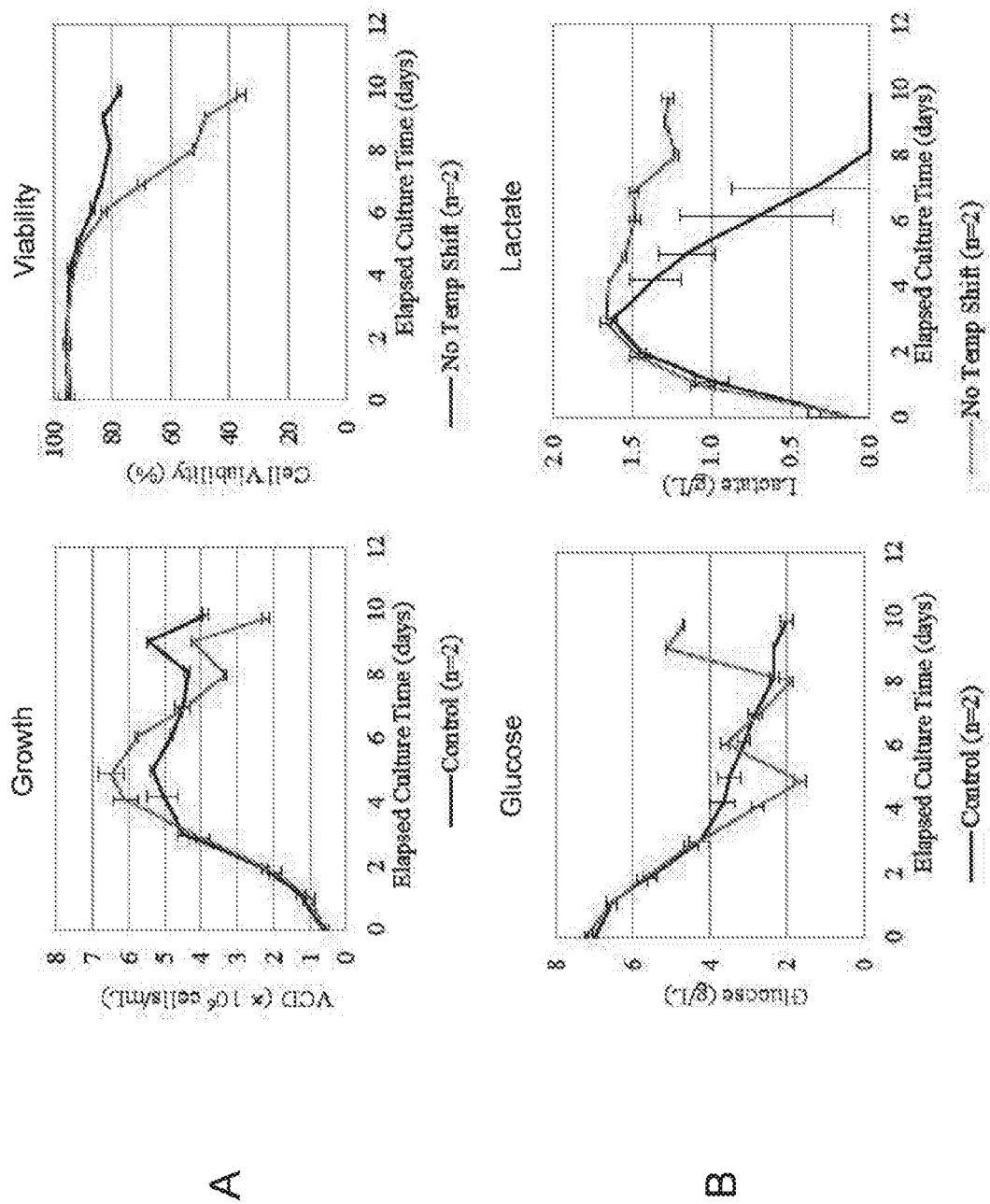
FIG. 1 are graphs showing the comparisons of cell growth (panel A, left) and viability (panel A, right) and overall glucose (panel B, left) and lactate (panel B, right) concentrations between an exemplary production process (#1) with or without temperature shifting for protein production. Control represents the average result of two runs with temperature shifting.

"About", "Approximately": As used herein, the terms "about" and "approximately", as applied to one or more particular cell culture conditions, refer to a range of values that are similar to the stated reference value for that culture condition or conditions. In certain embodiments, the term "about" refers to a range of values that fall within 25, 20, 19, 18, 17, 16, 15, 14, 13, 12, 11, 10, 9, 8, 7, 6, 5, 4, 3, 2, 1 percent or less of the stated reference value for that culture condition or conditions.

"Amino acid": The term "amino acid," as used herein, refers to any of the twenty naturally occurring amino acids that are normally used in the formation of polypeptides, or analogs or derivatives of those amino acids. Amino acids of the present disclosure can be provided in medium to cell cultures. The amino acids provided in the medium may be provided as salts or in hydrate form.

"Batch culture": The term "batch culture," as used herein, refers to a method of culturing cells in which all of the components that will ultimately be used in culturing the cells, including the medium (see definition of "medium" below) as well as the cells themselves, are provided at the beginning of the culturing process. A batch culture is typically stopped at some point and the cells and/or components in the medium are harvested and optionally purified.

"Bioreactor": The term "bioreactor" as used herein refers to any vessel used for the growth of a cell culture (e.g., a mammalian cell culture). The bioreactor can be of any size so long as it is useful for the culturing of cells. Typically, the bioreactor will be at least 1 liter and may be 10, 100, 250, 500, 1000, 2500, 5000, 8000, 10,000, 12,0000, 20,000 liters or more, or any volume in between. The internal conditions of the bioreactor, including, but not limited to pH and temperature, are typically controlled during the culturing period. The bioreactor can be composed of any material that is suitable for holding mammalian or other cell cultures suspended in media under the culture conditions of the present disclosure, including glass, plastic or metal. The term "production bioreactor" as used herein refers to the final bioreactor used in the production of the polypeptide or protein of interest. The volume of the large-scale cell culture production bioreactor is typically at least 500 liters and may be 1000, 2500, 5000, 8000, 10,000, 12,0000, 20,000 liters or more, or any volume in between. One of ordinary skill in the art will be aware of and will be able to choose suitable bioreactors for use in practicing the present disclosure.

"Cell density": The term "cell density," as used herein, refers to the number of cells present in a given volume of medium.

"Cell viability": The term "cell viability," as used herein, refers to the ability of cells in culture to survive under a given set of culture conditions or experimental variations. The term as used herein also refers to that portion of cells which are alive at a particular time in relation to the total number of cells, living and dead, in the culture at that time.

"Culture" and "cell culture": These terms, as used herein, refer to a cell population that is suspended in a medium (see definition of "medium" below) under conditions suitable for survival and/or growth of the cell population. As will be clear to those of ordinary skill in the art, these terms as used herein may refer to the combination comprising the cell population and the medium in which the population is suspended.

"Fed-batch culture": The term "fed-batch culture," as used herein, refers to a method of culturing cells in which additional components are provided to the culture at some time subsequent to the beginning of the culture process. The provided components typically comprise nutritional supplements for the cells, which have been depleted during the culturing process. A fed-batch culture is typically stopped at some point and the cells and/or components in the medium are harvested and optionally purified. Fed-batch culture may be performed in the corresponding fed-batch bioreactor.

"Fragment": The term "fragment," as used herein, refers to a polypeptide and is defined as any discrete portion of a given polypeptide that is unique to or characteristic of that polypeptide. The term as used herein also refers to any discrete portion of a given polypeptide that retains at least a fraction of the activity of the full-length polypeptide. In some embodiments the fraction of activity retained is at least 10% of the activity of the full-length polypeptide. In various embodiments the fraction of activity retained is at least 20%, 30%, 40%, 50%, 60%, 700/%, 80%0 or 90% of the activity of the full-length polypeptide. In other embodiments the fraction of activity retained is at least 95%, 96%, 97%, 98% or 99% of the activity of the full-length polypeptide. In one embodiment, the fraction of activity retained is 100% of the activity of the full-length polypeptide. The term as used herein also refers to any portion of a given polypeptide that includes at least an established sequence element found in the full-length polypeptide. In some embodiments, the sequence element spans at least 4-5 amino acids of the full-length polypeptide. In some embodiments, the sequence element spans at least about 10, 15, 20, 25, 30, 35, 40, 45, 50 or more amino acids of the full-length polypeptide.

"Integrated Viable Cell Density": The term "integrated viable cell density," as used herein, refers to the average density of viable cells over the course of the culture multiplied by the amount of time the culture has run. Assuming the amount of polypeptide and/or protein produced is proportional to the number of viable cells present over the course of the culture, integrated viable cell density is a useful tool for estimating the amount of polypeptide and/or protein produced over the course of the culture.

"Medium", "cell culture medium", and "culture medium": These terms, as used herein, refer to a solution containing nutrients which nourish growing mammalian cells. Typically, these solutions provide essential and non-essential amino acids, vitamins, energy sources, lipids, and trace elements required by the cell for minimal growth and/or survival. The solution may also contain components that enhance growth and/or survival above the minimal rate, including hormones and growth factors. The solution is, e.g., formulated to a pH and salt concentration optimal for cell survival and proliferation. The medium may also be a "defined media"—a serum-free media that contains no proteins, hydrolysates or components of unknown composition. Defined media are free of animal-derived components and all components have a known chemical structure.

"Metabolic waste product": The term "metabolic waste product," as used herein, refers to compound produced by the cell culture as a result of normal or non-normal metabolic processes that are in some way detrimental to the cell culture, particularly in relation to the expression or activity of a desired recombinant polypeptide or protein. For example, the metabolic waste products may be detrimental to the growth or viability of the cell culture, may decrease the amount of recombinant polypeptide or protein produced, may alter the folding, stability, glycosylation or other post-translational modification of the expressed polypeptide or protein, or may be detrimental to the cells and/or expression or activity of the recombinant polypeptide or protein in any number of other ways. Exemplary metabolic waste products include lactate, which is produced as a result of glucose metabolism, and ammonium, which is produced as a result of glutamine metabolism. In one embodiment, methods are taken to slow production of, reduce or even eliminate metabolic waste products in cell cultures.

"Osmolality" and "osmolarity": Osmolality is a measure of the osmotic pressure of dissolved solute particles in an aqueous solution. The solute particles include both ions and non-ionized molecules. Osmolality is expressed as the concentration of osmotically active particles (i.e., osmoles) dissolved in 1 kg of solution (1 mOsm/kg $H_2O$ at 38° C. is equivalent to an osmotic pressure of 19 mm Hg). "Osmolarity," by contrast, refers to the number of solute particles dissolved in 1 liter of solution. When used herein the abbreviation "mOsm" means "milliosmoles/kg solution".

"Perfusion culture": The term "perfusion culture," as used herein, refers to a method of culturing cells in which additional components are provided continuously or semi-continuously to the culture subsequent to the beginning of the culture process. The provided components typically comprise nutritional supplements for the cells, which have been depleted during the culturing process. A portion of the cells and/or components in the medium are typically harvested on a continuous or semi-continuous basis and are optionally purified.

"Polypeptide": The term "polypeptide," as used herein, refers a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond.

"Protein": The term "protein," as used herein, refers to one or more polypeptides that function as a discrete unit. If a single polypeptide is the discrete functioning unit and does not require permanent physical association with other polypeptides in order to form the discrete functioning unit, the terms "polypeptide" and "protein" as used herein are used interchangeably.

"Recombinantly-expressed polypeptide" and "recombinant polypeptide": These terms, as used herein, refer to a polypeptide expressed from a host cell that has been genetically engineered to express that polypeptide. The recombinantly-expressed polypeptide can be identical or similar to a polypeptide that is normally expressed in the mammalian host cell. The recombinantly-expressed polypeptide can also be foreign to the host cell, i.e., heterologous to peptides normally expressed in the host cell. Alternatively, the recombinantly-expressed polypeptide can be chimeric in that portions of the polypeptide contain amino acid sequences that are identical or similar to polypeptides normally expressed in the mammalian host cell, while other portions are foreign to the host cell.

"Seeding": The term "seeding," as used herein, refers to the process of providing a cell culture to a bioreactor or another vessel. The cells may have been propagated previously in another bioreactor or vessel. Alternatively, the cells may have been frozen and thawed immediately prior to providing them to the bioreactor or vessel. The term refers to any number of cells, including a single cell.

"Titer": The term "titer," as used herein, refers to the total amount of recombinantly-expressed polypeptide or protein produced by a cell culture divided by a given amount of medium volume. Titer is typically expressed in units of milligrams of polypeptide or protein per milliliter of medium.

Acronyms used herein include, e.g., VCD: Viable Cell Density; IVCC: Integral of Viable Cell Concentration; TSAC: Total Sialic Acid Content; HPAE-PAD: High-Performance Anion Exchange Chromatography with Pulsed Amperometric Detection; SEC: Size Exclusion Chromatography; AEX: Anion Exchange Chromatography; LoC: Lab-on-Chip; and MALDI-TOF: Matrix Assisted Laser Desorption/Ionization-Time of Flight.

The present disclosure provides a method of culturing cells (e.g., mammalian cells including but not limited to Chinese Hamster Ovary (CHO) cells) expressing a recombinant protein. The present disclosure provides manufacturing systems for the production of an alkaline phosphatase (e.g., asfotase alfa) by cell culture. In certain embodiments, systems are provided that minimize production of one or more metabolic products that are detrimental to cell growth, viability, and/or protein production or quality. In particular embodiments, the cell culture is a batch culture, a fed-batch culture, a culture or a continuous culture. Other embodiments of the disclosure are discussed in detail below. Those of ordinary skill in the art will understand, however, that various modifications to these embodiments are encompassed within the scope of the disclosure.

Proteins

The present disclosure relates to expression of an alkaline phosphatase, asfotase alpha, protein in cell culture. In certain embodiments, such asfotase alpha, after being manufactured by the methods disclosed herein, can be used to treat or prevent alkaline phosphatase-related diseases or disorders. For example, such asfotase alpha may be administered to a subject having decreased and/or malfunctioned endogenous alkaline phosphatase, or having overexpressed (e.g., above normal level) alkaline phosphatase substrates. In some embodiments, the asfotase alpha in this disclosure is a recombinant protein. In some embodiments, the asfotase alpha is a fusion protein. In some embodiments, the asfotase alpha in this disclosure specifically targets a cell type, tissue (e.g., connective, muscle, nervous, or epithelial tissues), or organ (e.g., liver, heart, kidney, muscles, bones, cartilage, ligaments, tendons, etc.). Asfotase alfa is a soluble Fc fusion protein consisting of two sTNALP-Fc-$D_{10}$ polypeptides each with 726 amino acids as shown in SEQ ID NO:1. Underlined asparagine (N) residues correspond to potential glycosylation sites (i.e., N 123, 213, 254, 286, 413 & 564). Bold underlined amino acid residues ($L_{486}$-$K_{487}$ & $D_{715}$-$I_{716}$) correspond to linkers between sALP and Fc, and Fc and $D_{10}$ domains, respectively.

```
                                                         (SEQ ID NO: 1)
            10         20         30         40         50         60
     LVPEKEKDPK YWRDQAQETL KYALELQKLN TNVAKNVIMF LGDGMGVSTV TAARILKGQL 70         80         90        100        110        120
     HHNPGEETRL EMDKEPFVAL SKTYNTNAQV PDSAGTATAY LCGVKANEGT VGVSAATERS 130        140        150        160        170        180
     RCNTTQGNEV TSILRWAKDA GKSVGIVTTT RVNHATPSAA YAHSADRDWY SDNEMPPEAL 190        200        210        220        230        240
     SQGCKDIAYQ LMHNIRDIDV IMGGGRKYMY PKNKTDVEYE SDEKARGTRL DGLDLVDTWK 250        260        270        280        290        300
     SFKPRYKHSH FIWNRTELLT LDPHNVDYLL GLFEPGDMQY ELNRNNVTDP SLSEMVVVAI 310        320        330        340        350        360
     QILRKNPKGF FLLVEGGRID HGHHEGKAKQ ALHEAVEMDR AIGQAGSLTS SEDTLTVVTA 370        380        390        400        410        420
     DHSHVFTFGG YTPRGNSIFG LAPMLSDTDK KPFTAILYGN GPGYKVVGGE RENVSMVDYA 430        440        450        460        470        480
     HNNYQAQSAV PLRHETHGGE DVAVFSKGPM AHLLHGVHEQ NYVPHVMAYA ACIGANLGHC 490        500        510        520        530        540
     APASSLKDKT HTCPPCPAPE LLGGPSVFLF PPKPKDTLMI SRTPEVTCVV VDVSHEDPTV 550        560        570        580        590        600
     KFNWYVDGVE VHNAKTKPRE EQYNSTYRVV SVLTVLHQDW LNGKEYKCKV SNKALPAPIE 610        620        630        640        650        660
     KTISKAKGQP REPQVYTLPP SREEMTKNQV SLTCLVKGFY PSDIAVEWES NGQPENNYKT 670        680        690        700        710        720
     TPPVLDSDGS FFLYSKLTVD KSRWQQGNVF SCSVMHEALH NHYTQKSLSL SPGKDIDDDD

DDDDDD
```

Each polypeptide or monomer is composed of five portions. The first portion (sALP) containing amino acids L1-S485 is the soluble part of the human tissue non-specific alkaline phosphatase enzyme, which contains the catalytic function. The second portion contains amino acids L486-K487 as a linker. The third portion (Fc) containing amino acids D488-K714 is the Fc part of the human Immunoglobulin gamma 1 (IgG1) containing hinge, $CH_2$ and $CH_3$ domains. The fourth portion contains D715-I716 as a linker. The fifth portion contains amino acids D717-D726 (D10), which is a bone targeting moiety that allows asfotase alfa to bind to the mineral phase of bone. In addition, each polypeptide chain contains six potential glycosylation sites and eleven cysteine (Cys) residues. Cys102 exists as free cysteine. Each polypeptide chain contains four intra-chain disulfide bonds between Cys122 and Cys184, Cys472 and Cys480, Cys528 and Cys588, and Cys634 and Cys692. The two polypeptide chains are connected by two inter-chain disulfide bonds between Cys493 on both chains and between Cys496 on both chains. In addition to these covalent structural features, mammalian alkaline phosphatases are thought to have four metal-binding sites on each polypeptide chain, including two sites for zinc, one site for magnesium and one site for calcium.

Asfotase Alfa

In one embodiment, the alkaline phosphatase protein (e.g., the bone-targeted sALP fusion protein) is asfotase alfa (i.e., sTNALP-Fc-$D_{10}$; SEQ ID NO:1). Specifically, asfotase alfa is a complex soluble glycoprotein with a polypeptide length of 726 amino acids. Asfotase alfa is an Fc-fusion protein composed of 3 domains. From the N-terminus to the C terminus, asfotase alfa comprises: (1) the soluble catalytic domain of human tissue non-specific alkaline phosphatase (TNSALP) (UniProtKB/Swiss-Prot Accession No. P05186), (2) the human immunoglobulin G1 Fc domain (UniProtKB/Swiss-Prot Accession No. P01857) and (3) a deca aspartate peptide ($D_{10}$) used as a bone-targeting domain (Nishioka et al. 2006 *Mol Genet Metab* 88:244-255). The protein associates into a homo-dimer from two primary protein sequences. This fusion protein contains 6 confirmed complex N-glycosylation sites. Five of these N-glycosylation sites are located on the sALP domain and one on the Fc domain. Another important post-translational modification present on asfotase alfa is the presence of disulfide bridges stabilizing the enzyme and the Fc-domain structure. A total of 4 intra-molecular disulfide bridges are present per monomer and 2 inter-molecular disulfide bridges are present in the dimer. One cysteine of the alkaline phosphatase domain is free.

Asfotase alfa may be used as an enzyme-replacement therapy for the treatment of hypophosphatasia (HPP). In patients with HPP, loss-of-function mutation(s) in the gene encoding TNSALP causes a deficiency in TNSALP enzymatic activity, which leads to elevated circulating levels of substrates, such as inorganic pyrophosphate (PPi) and pyridoxal-5'-phosphate (PLP). Administration of asfotase alfa to patients with HPP cleaves PPi, releasing inorganic phosphate for combination with calcium, thereby promoting hydroxyapatite crystal formation and bone mineralization, and restoring a normal skeletal phenotype. For more details on asfotase alfa and its uses in treatment, see PCT Publication Nos. WO2005103263 and WO2008138131, the teachings of which are incorporated herein by reference in their entirety. In another embodiment, asfotase alfa may be used as an enzyme-replacement therapy for the treatment of Neurofibromatosis type I (NF1). For more details on asfotase alfa and its uses (together with the uses of other alkaline phosphatases) in treatment of NF1, see PCT Publication No. WO 2013/058833, which is incorporated herein by reference in its entirety.

Manufacturing Process

The alkaline phosphatase protein (e.g., asfotase alfa) may be produced by mammalian or other cells using standard methods known in the art. Such cells may be grown in culture dishes, flask glasses, or bioreactors. Specific processes for cell culture and producing recombinant proteins are known in the art, such as described in Nelson and Geyer, 1991 *Bioprocess Technol.* 13:112-143 and Rea et al., *Supplement to BioPharm International* March 2008, 20-25. Exemplary bioreactors include batch, fed-batch, and continuous reactors. In some embodiments, the alkaline phosphatase protein is produced in a fed-batch bioreactor.

Potential variability in the cell culture process physicochemical environment includes, for example, changes in pH, temperature, cell culture media composition, raw material lot-to-lot variation, medium filtration material, bioreactor scale difference, gassing strategy (air, oxygen, and carbon dioxide), etc. As disclosed herein, the glycosylation profiles of manufactured alkaline phosphatase protein may be affected by alterations in one or more parameters.

Development for Cell Culture Processes

For recombinant protein production in cell culture, the recombinant gene with the necessary transcriptional regulatory elements is first transferred to a host cell. Usually, a second gene is transferred that confers to recipient cells a selective advantage. In the presence of the selection agent, which is typically applied a few days after gene transfer, only those cells that express the selector gene survive. Two popular genes for selection are dihydrofolate reductase (DHFR), an enzyme involved in nucleotide metabolism, and glutamine synthetase (GS). In both cases, selection occurs in the absence of the appropriate metabolite (hypoxanthine and thymidine, in the case of DHFR, glutamine in the case of GS), preventing growth of nontransformed cells. In general, for efficient expression of the recombinant protein, it is not important whether the biopharmaceutical-encoding gene and selector genes are on the same plasmid or not.

Following selection, surviving cells may be transferred as single cells to a second cultivation vessel, and the cultures are expanded to produce clonal populations. Eventually, individual clones are evaluated for recombinant protein expression, with the highest producers being retained for further cultivation and analysis. From these candidates, one cell line with the appropriate growth and productivity characteristics is chosen for production of the recombinant protein. A cultivation process is then established that is determined by the production needs.

Cells

Any mammalian cell or non-mammalian cell type, which can be cultured to produce a polypeptide, may be utilized in accordance with the present disclosure. Non-limiting examples of mammalian cells that may be used include, e.g., Chinese hamster ovary cells +/−DHFR (CHO, Urlaub and Chasin, 1980 *Proc. Natl. Acad. Sci. USA*, 77:4216); BALB/c mouse myeloma line (NSO/1, ECACC Accession No: 85110503); human retinoblasts (PER.C6 (CruCell, Leiden, The Netherlands)); monkey kidney CVI line transformed by SV40 (COS-7, ATCC CRL 1651); human embryonic kidney line (293 or 293 cells subcloned for growth in suspension culture, Graham et al., 1977 *J. Gen Virol.*, 36:59); baby hamster kidney cells (BHK, ATCC CCL 10); mouse Sertoli cells (TM4, *Mather, Biol. Reprod.*, 23:243-251 (1980)); monkey kidney cells (CVI ATCC CCL 70); African green monkey kidney cells (VERO-76, ATCC CRL-I 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., 1982, *Annals N.Y. Acad. Sci.* 383:44-68); MRC 5 cells; FS4 cells; and a human hepatoma line (Hep G2). In a particular embodiment, culturing and expression of polypeptides and proteins occurs from a Chinese Hamster Ovary (CHO) cell line.

Additionally, any number of commercially and non-commercially available recombinant cell lines that express polypeptides or proteins may be utilized in accordance with the present disclosure. One skilled in the art will appreciate that recombinant cell lines might have different nutrition requirements and/or might require different culture conditions for optimal growth and polypeptide or protein expression, and will be able to modify conditions as needed.

As noted above, in many instances the cells will be selected or engineered to produce high levels of protein or polypeptide. Often, cells are genetically engineered to produce high levels of protein, for example by introduction of a gene encoding the protein or polypeptide of interest and/or by introduction of control elements that regulate expression of the gene (whether endogenous or introduced) encoding the polypeptide of interest.

Temperature Shifting

Run times of cell culture processes, especially non-continuous processes (e.g., fed-batch processes in bioreactors), are usually limited by the remaining viability of the cells, which typically declines over the course of the run. Therefore, extending the length of time for cell viability is desired for improving recombination protein production. Product quality concerns also offer a motivation for minimizing decreases in viable cell density and maintaining high cell viability, as cell death can release sialidases to the culture supernatant, which may reduce the sialic acid content of the protein expressed. Protein purification concerns offer yet another motivation for minimizing decreases in viable cell density and maintaining high cell viability. Cell debris and the contents of dead cells in the culture can negatively impact one's ability to isolate and/or purify the protein product at the end of the culturing run. Thus, by keeping cells viable for a longer period of time in culture, there is a reduction in the contamination of the culture medium by cellular proteins and enzymes (e.g., cellular proteases and sialidases) that may cause degradation and ultimate reduction in the quality of the desired glycoprotein produced by the cells.

Many methods may be applied to achieve high cell viability in cell cultures. One involves lowering culture temperature following initial culturing at a normal temperature. For example, see Ressler et al., 1996, *Enzyme and Microbial Technology* 18:423-427). Generally, the mammalian or other types of cells capable of expressing a protein of interest are first grown under a normal temperature to increase cell numbers. Such "normal" temperatures for each cell type are generally around 37° C. (e.g., from about 35° C. to about 39° C., including, for example, 35.0° C., 35.5° C., 36.0° C., 36.5° C., 37.0° C., 37.5° C., 38.0° C., 38.5° C., and/or 39.0° C.). In one particular embodiment, the temperature for producing asfotase alfa is first set at about 37° C. When a reasonably high cell density is reached, the culturing temperature for the whole cell culture is then shifted (e.g., decreased) to promote protein production. In most cases lowering temperature shifts the cells towards the non-growth G1 portion of the cell cycle, which may increase cell density and viability, as compared to the previous higher-temperature environment. In addition, a lower temperature may also promote recombinant protein production by increasing the cellular protein production rate, facilitating protein post-translational modification (e.g., glycosylation), decreasing fragmentation or aggregation of newly-produced proteins, facilitating protein folding and formation of 3D structure (thus maintaining activity), and/or decreasing degradation of newly produced proteins. In some embodiments, the lower temperature is from about 30° C. to about 35° C. (e.g., 30.0° C., 30.5° C., 31.0° C., 31.5° C., 32.0° C., 32.5° C., 33.0° C., 33.5° C., 34.0° C., 34.5° C., and/or 35.0° C.). In other embodiments, the temperature for producing asfotase alfa is first set to from about 35.0° C. to about 39.0° C. and then shifted to from about 30.0° C. to about 35.0° C. In one embodiment, the temperature for producing asfotase alfa is first set at about 37.0° C. and then shifted to about 30° C. In another embodiment, the temperature for producing asfotase alfa is first set at about 36.5° C. and then shifted to about 33° C. In yet another embodiment, the temperature for producing asfotase alfa is first set at about 37.0° C. and then shifted to about 33° C. In yet a further embodiment, the temperature for producing asfotase alfa is first set at about 36.5° C. and then shifted to about 30° C. In other embodiments, multiple (e.g., more than one) steps of temperature shifting may be applied. For example, the temperature may be lowered from 37° C. first to 33° C. and then further to 30° C.

The time for maintaining the culture at a particular temperature prior to shifting to a different temperature may be determined to achieve a sufficient (or desired) cell density while maintaining cell viability and an ability to produce the protein of interest. In some embodiments, the cell culture is grown under the first temperature until the viable cell density reaches about $10^5$ cells/mL to about $10^7$ cells/mL (e.g., $1\times10^5$, $1.5\times10^5$, $2.0\times10^5$, $2.5\times10^5$, $3.0\times10^5$, $3.5\times10^5$, $4.0\times10^5$, $4.5\times10^5$, $5.0\times10^5$, $5.5\times10^5$, $6.0\times10^5$, $6.5\times10^5$, $7.0\times10^5$, $7.5\times10^5$, $8.0\times10^5$, $8.5\times10^5$, $9.0\times10^5$, $9.5\times10^6$, $1.0\times10^6$, $1.5\times10^6$, $2.0\times10^6$, $2.5\times10^6$, $3.0\times10^6$, $3.5\times10^6$, $4.0\times10^6$, $4.5\times10^6$, $5.0\times10^6$, $5.5\times10^6$, $6.0\times10^6$, $6.5\times10^6$, $7.0\times10^6$, $7.5\times10^6$, $8.0\times10^6$, $8.5\times10^6$, $9.0\times10^6$, $9.5\times10^6$, $1\times10^7$ cell/mL, or more) before shifting to a different temperature. In one embodiment, the cell culture is grown under the first temperature until the viable cell density reaches about 2.5 to about $3.4\times10^6$ cells/mL before shifting to a different temperature. In another embodiment, the cell culture is grown under the first temperature until the viable cell density reaches about 2.5 to about $3.2\times10^6$ cells/mL before shifting to a different temperature. In yet another embodiment, the cell culture is grown under the first temperature until the viable cell density reaches about 2.5 to about $2.8\times10^6$ cells/mL before shifting to a different temperature.

In some embodiments, the cell culture is grown under 37° C. until the viable cell density reaches about $2.5-2.8\times10^6$ cells/mL before shifting to 30° C. for protein production. In other embodiments, the cell culture is grown under 37° C. until the viable cell density reaches about $2.5-3.4\times10^6$ cells/mL before shifting to 30° C. for protein production.

pH

Alteration of the pH of the growth medium in cell culture may affect cellular proteolytic activity, secretion, and protein production levels. Most of the cell lines grow well at about pH 7-8. Although optimum pH for cell growth varies relatively little among different cell strains, some normal fibroblast cell lines perform best at a pH 7.0-7.7 and transformed cells typically perform best at a pH of 7.0-7.4 (Eagle, 1973 The effect of environmental pH on the growth of normal and malignant cells. *J Cell Physiol* 82:1-8). In some embodiments, the pH of the culture medium for producing asfotase alfa is about pH 6.5-7.7 (e.g., 6.50, 6.55, 6.60, 6.65, 6.70, 6.75, 6.80, 6.85, 6.90, 6.95, 7.00, 7.05, 7.10, 7.15, 7.20, 7.25, 7.30, 7.35, 7.39, 7.40, 7.45, 7.50, 7.55, 7.60, 7.65, and 7.70). In some embodiments, the pH of the culture medium for producing asfotase alfa is about pH 7.20-7.60. In other embodiments, the pH of the culture medium for producing asfotase alfa is about pH 6.9-7.1. In one particular embodiment, the pH of the culture medium for producing asfotase alfa is about pH 6.9. In another embodiment, the pH of the culture medium for producing asfotase alfa is about pH 7.30. In yet another embodiment, the pH of the culture medium for producing asfotase alfa is about pH 7.39.

All references cited herein are incorporated by reference in their entirety.

Although this disclosure has been described in some detail by way of illustration and example for purposes of clarity of understanding, it is apparent to those skilled in the art that certain minor changes and modifications will be practiced. Therefore, the description and examples should not be construed as limiting the scope of the disclosure.

EXAMPLES

Example 1. General Manufacturing Process for Asfotase Alfa

As described herein, a manufacturing process to produce alkaline phosphatases (e.g., asfotase alfa (sTNALP-Fc-D10)) has been developed.

TABLE 1

Differences between exemplary manufacturing processes (upstream)

|  | Process X | Process Y | Process Z |
|---|---|---|---|
| Parental Cell line | CHO | CHO | CHO |
| Production medium | HyClone SFM4CHO | HyClone SFM4CHO | HyClone SFM4CHO + BD select |
| Feed | CHO Feed (0.5%) | CHO Feed (2%, i.e., 4 × medium feed) | CHO Feed (2%) + Cell Boost 2 + 5 (9%) |
| pH set point | 6.90 | 6.90 | 6.90 |
| Temperature | 37.0° C. then shifted to 30° C. | 37.0° C. then shifted to 30° C. | 37.0° C. then shifted to 30° C. |
| DO | 40% | 40% | 40% |
| Supplement | N/A | N/A | ZnSO4 |
| Harvest time | 240 ± 12 hr | 240 ± 12 hr | 240 ± 12 hr |

Stable CHO cell lines expressing asfotase alfa were developed using the GS gene expression system. Secondary clones were derived from high producing primary clones in a single round of limited dilution cloning and a final cell line was selected.

An exemplary manufacturing process, Process X, is described herein. A vial of the Master Cell Bank was thawed and the entire volume of the vial was re-suspended. The entire volume was transferred to a 250 mL shake flask for growth. Samples were taken daily for counts and viability tests (also for all following expansion steps). Cells were expanded through several steps and inoculated into a 1,000 L seed bioreactor (N−3 low level), a 1,000 L seed bioreactor (N−2 high level), and a 4,000 L seed bioreactor (N−1) and then a 20,000 L production bioreactor. After production of asfotase alfa, the harvest clarification process was employed to remove intact cells and cell debris by sterile filtration. The harvest was then ultrafiltered (Post Harvest UF) for concentration and buffer dilution. Further processes included, for example, viral inactivation (to chemically inactivate viral particles), MabSelect SuRe chromatography, hydrophobic interaction chromatography (HIC), post HIC UF/DF (UF/DF2), capto adhere mixed-mode chromatography, virus filtration (by size exclusion), formulation (UF/DF3) and bulk fill. Multiple manufacturing processes were performed including, for example, 2,000 L-scale processes and the following scale-up to the 20,000 L production scale. Exemplary differences between the 2,000 L (2K) and the 20,000 L (20K) processes are summarized in Tables 2 and 3. The 2,000 L (2K) scale process had a more pronounced lag-phase and more varied late stage viability (data not shown).

TABLE 2

Inoculum Expansion Parameter Comparison between Exemplary 2,000 L Process and 20,000 L Process

| Parameter | 2,000 L Process | 20,000 L Process |
| --- | --- | --- |
| Culturing Vessels | Shake flasks, cell bags | Shake flasks, roller bottles, cell bags, expansion bioreactors |
| Temperature | 37° C. | 36.5-37.5° C. |
| Medium | HyQSFM4CHO with 4 mM Glutamine and 100 nM Methotrexate | HyQSFM4CHO with 4 mM Glutamine and 100 nM Methotrexate |
| Seed density target | Thaw: $0.50 \times 10^6$ viable cells/mL Passaging: $0.40 \times 10^6$ viable cells/mL | Thaw: $0.50 \times 10^6$ viable cells/ML Passaging: $0.35 \times 10^6$ viable cells/mL |
| Passage length | 3-4 days | 3-4 days |
| Time to production bioreactor | Fixed (7 passages, 21-28 days) | Varies (11 Passages, with ability to maintain at 100 L high volume stage) |
| Cell density at time of passage | $\geq 1.00 \times 10^6$ viable cells/mL | $\geq 1.40 \times 10^6$ viable cells/mL |

TABLE 3

Production Bioreactor Parameter Comparison between Exemplary 2,000 L Process and 20,000 L Process

| Parameter | 2,000 L Process | 20,000 L Process |
| --- | --- | --- |
| Temperature | 37° C. at inoculation; 30° C. once cell density is $2.5\text{-}2.8 \times 10^6$ viable cells/mL | 37° C. at inoculation 30° C. once cell density is $2.5\text{-}3.4 \times 10^6$ viable cells/mL |
| pH | pH allowed to drift to 7.10 on day 1, to 7.00 on day 2 and then controlled at 6.90 from day 3 - harvest | $6.90 \pm 0.10$ |
| Dissolved oxygen | 40% | 40% |
| Seed density | $0.50 \times 10^6$ viable cells/mL | $0.55 \times 10^6$ viable cells/mL |
| Feed timing | Single bolus feed prior to temperature shift | Single bolus feed prior to temperature shift |
| Foam control | Foam-away foam | Antifoam-C as required |
| Culture duration | Day 10 or when viability <50% | Day 10 or when viability<60% |

The overall yields of 2K processes and 20K processes as well as the qualities of the corresponding produced asfotase alfa were compared. Analytical methods used to compare the product characterization include, e.g., SEC-HPLC, RP-HPLC, and other methods to measure specific activity, protein concentration, pH, and total sialic acid content (TSAC) of produced asfotase alfa. In addition, impurities and safety tests were also performed to measure, e.g., residual DNA, residual Protein A, host cell proteins, bioburden and endotoxin in asfotase alfa produced from different processes. Three additional tests, i.e., isoelectric focusing (IEF), sodium dodecyl sulfate polyacrylamide gel electrophoresis (SDS-PAGE), and oligosaccharide mapping, were also performed to compare drug substances from 2K and 20K scale batches. Results of these three tests showed comparable profiles for these batches. In conclusion, the asfotase alfa quality between the 2,000 L and 20,000 L scales was comparable across all batches.

Example 2. Impact of Temperature Shifting on Asfotase Alfa Productivity and Quality Among different manufacturing processes adopted and practiced for producing sTNALP-Fc-$D_{10}$, temperature shifting is generally found to affect the productivity and final asfotase alfa quality. Temperature shift from growth temperature (comparatively high temperature) to production temperature (comparatively low temperature) was implemented in all processes.

To compare the effects of temperature shifting versus no shifting, duplicate sTNALP-Fc-$D_{10}$ production bioreactor runs were conducted, wherein there was or was not a temperature shift. Sartorius 2 L and 10 L bioreactors were used for different production processes. In this exemplary process, raw materials used in the production bioreactors included, e.g., production medium, 10% Sodium carbonate, CHO feed, and glutamine stock solution, as summarized in Table 4. SFM4CHO refers to serum free medium for CHO.

TABLE 4

Process Parameter in An Exemplary Process

| Process Parameter | Process #1 |
| --- | --- |
| Cell line | Cell line X (derived from CHO) |
| Production medium | CM70 (SFM4CHO + Pluronic + Sodium bicarbonate) + Glutamine |
| Seeding density | $5.5e^5$ cells/mL |
| pH | 6.90 w/o dead band |
| DO | 40% (Air 0.0016 VVM + $O_2$ as needed) |
| Temperature | 37.0° C. -> 30° C. (when VCD is 25-32$e^5$ cells/mL) |
| Feed | 5 mL/L CHO feed when VCD is 25-32$e^5$ cells/mL |
| Other supplements | If [gln] <0.18 g/L (1.2 mM), increase [gln] to 0.29 g/L (2.0 mM) prior to temperature shift. |
| Harvest criteria | 240 ± 12 h (within 30 hrs of viability <60%) |

Methods
Cell Culture Experiment Design

Two blocks of experiments were implemented to evaluate the impact of temperature shift on asfotase alfa productivity and quality attributes for an exemplary process. As shown in Table 5, two bioreactor runs (i.e., #1 and #2) were conducted with temperature shifting (37° C. to 30° C.) and two other runs (i.e., #3 and #4) were conducted without temperature shifting from 37° C.

TABLE 5

Bioreactor conditions for Process #1

| Bioreactor ID | Condition |
| --- | --- |
| #1 | Temp Shift 1 |
| #2 | Temp Shift 2 |
| #3 | No Temp Shift 1 |
| #4 | No Temp Shift 2 |

Cell density and viability were counted using a cell counter (i.e., ViCell VR, Beckman Coulter). pH and off-line gas was measured using pHOx, and major metabolites including glucose and lactate were measured using a sensor (Nova Profile 100, Nova Biomedical, Waltham, Mass.). Enzymatic activity was measured using a standard method with the modification that each sample was diluted only once, instead of three times, prior to enzymatic activity measurement.

Harvest and Purification Methods

Fifty microliters of day 10 (240±4 hours) samples were harvested from all bioreactors using syringes. Post cell removal by centrifugation (3000×g, 5 min), supernatants were clarified using 0.22 μm bottle-top filters, and stored at −80° C. prior to purification. A single step of high throughput protein A purification was applied in this study. Samples were buffer exchanged to low salt buffer (5 mM $Na_3PO_4$, pH 7.4) prior to analytical and protein characterization analysis.

Analytical and Protein Characterization Methods

Quality attributes analyzed in this study included asfotase alfa aggregation, fragmentation, charge distribution, total sialic acid content (TSAC), and neutral glycan species levels. The aggregate level was estimated by the percentage of aggregate peaks to the total protein quantified in SEC. The fragment level was estimated by the percentage of fragment to the total protein quantified in LoC. The charge distribution was estimated by the percentage of the basic peaks, main peak and acid peak to the total protein, respectively, quantified in AEX. The total sialic acid content (TSAC) was quantified by HPAE-PAD. Detection of neutral glycan species was performed by MALDI-TOF mass spectrometry.

Results
Cell Culture Performance

In Process #1, the temperature set point was shifted from 37° C. to 30° C. within 5 hours after the viable cell density (VCD) reached 25-32×$10^5$ cells/mL. Without the temperature shift, the cell culture reached a higher peak VCD but experienced a more rapid viability decline (FIG. 1A). Higher overall glucose consumption was observed under the no-temperature-shift condition as well (FIG. 1B). A glucose bolus addition was applied on day 5 and day 8 under the no-temperature-shift condition according to the process description. Interestingly, lactate was still consumed, but at a considerably lower rate under the no-temperature-shift condition than the temperature-shift condition (FIG. 1B).

Figure 2:
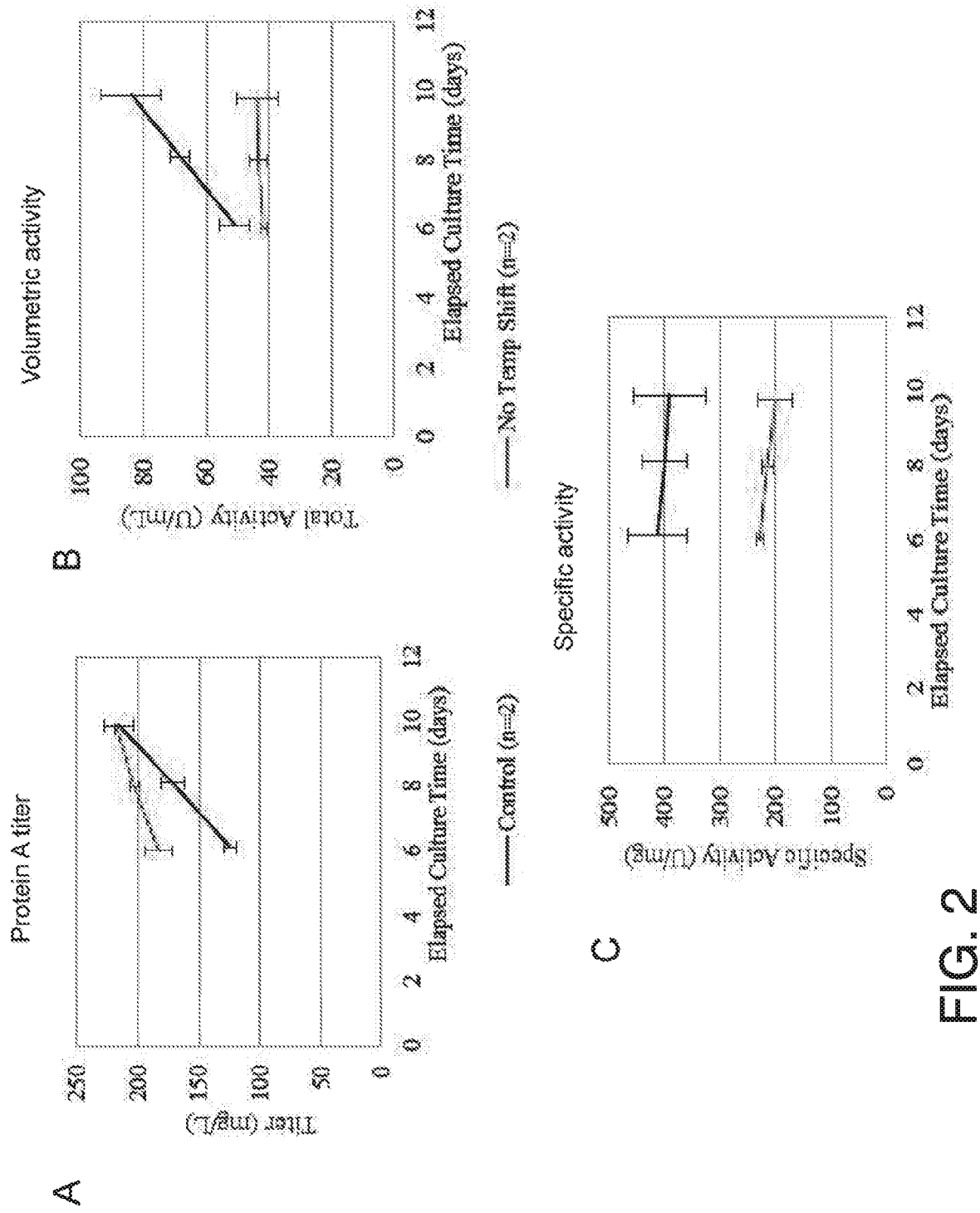
FIG. 2 are graphs showing the comparisons of Protein A bindable titer (panel A), volumetric activity (panel B) and specific activity (panel C) of asfotase alfa produced using an exemplary production process (#1) with or without temperature shifting. Control represents the average result of two runs with temperature shifting.

A higher peak VCD under the no-temperature-shift condition led to early production of protein A bindable titer (FIG. 2A). With the more rapid viability decline under the no-temperature-shift condition, similar protein A bindable titers were achieved on day 10 under both conditions. The overall specific protein A bindable productivities were 6.4 pg/cell/day for the temperature-shift condition, and 6.7 pg/cell/day for the no-temperature-shift condition. Interestingly, though similar protein A bindable titer was observed under both conditions, the volumetric activity under the no-temperature-shift condition was considerably lower than the temperature-shift condition (FIG. 2B). In addition, the specific activity under the no-temperature-shift condition was significantly lower than the temperature-shift condition throughout the culture duration (FIG. 2C). This data indicates that a temperature shift from 37° C. to 33° C. is optimal for maintaining the specific activity for Process #1. All quality attributes quantified in Process #1 are summarized in Table 6.

TABLE 6

Quantified Quality Attributes for Process #1

| Sample ID | Condition | AEX (% Basic) | AEX (% Main) | AEX (% Acidic) | LoC (% Main, NR) | LoC (% Main, R) | SEC (% Agg) | SEC (% Dimer) | SEC (% Fragment) | TSAC |
|---|---|---|---|---|---|---|---|---|---|---|
| #1 | Temp shift | 0.6 | 98.5 | 0.9 | 95.9 | 100.0 | 10.3 | 89.6 | 0.0 | 1.9 |
| #2 | Temp shift | 0.2 | 98.8 | 1.1 | 97.1 | 100.0 | 10.9 | 89.1 | 0.0 | 2.0 |
| #3 | No Temp Shift | 0.6 | 99.1 | 0.2 | 100.0 | 96.8 | 24.0 | 76.0 | 0.0 | 3.9 |
| #4 | No Temp Shift | 0.6 | 99.2 | 0.2 | 100.0 | 98.3 | 25.6 | 74.4 | 0.0 | 3.9 |

Figure 3:
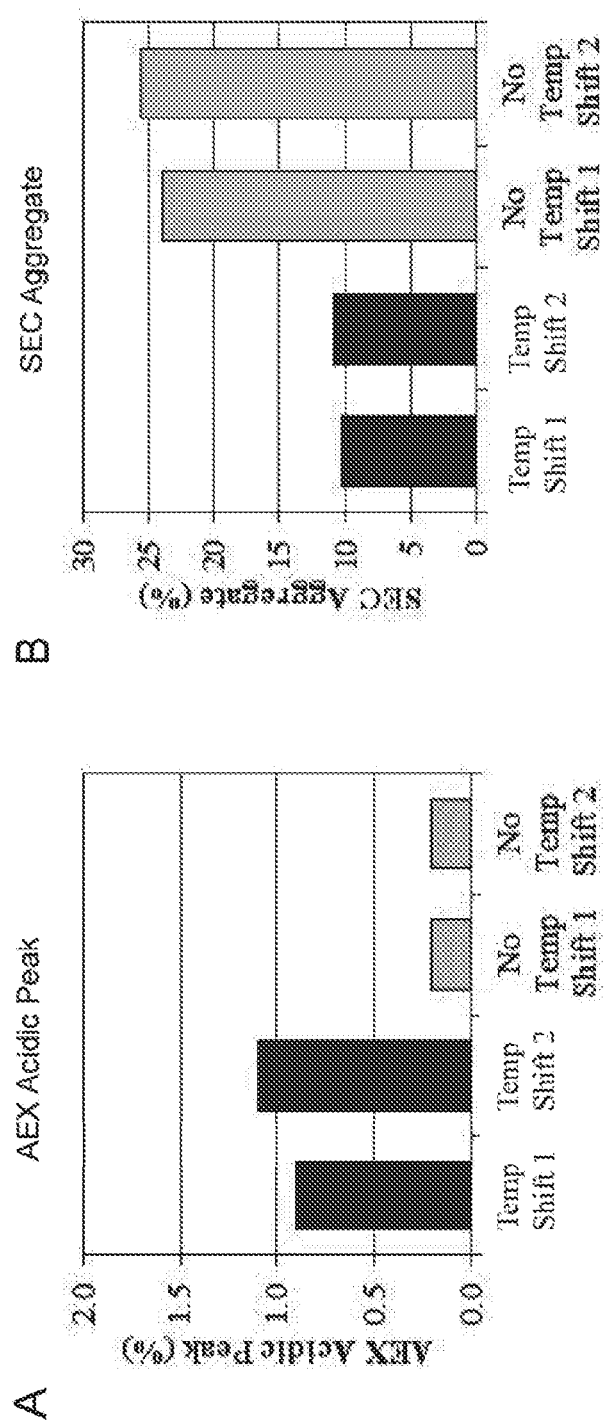
FIG. 3 are graphs showing the comparisons of AEX (Anion Exchange Chromatography) acidic peak (%) (panel A) and SEC (Size Exclusion Chromatography) aggregate (%) (panel B) measurements of asfotase alfa produced using an exemplary production process (#1) with or without temperature shifting.

AEX results indicated that fewer acidic species were generated from the no-temperature-shift condition in comparison to the temperature-shift condition (FIG. 3A). However, significantly higher aggregates were quantified by SEC results under the no-temperature-shift condition (FIG. 3B). Under the no-temperature-shift condition, the non-reduced LoC mean peak percentage was higher (FIG. 4A, also in the "LoC (% Main, NR)" column in Table 6), while the reduced LoC mean peak percentage was lower (FIG. 4B, also in the "LoC (% Main, R)" column in Table 6).

Figure 4:
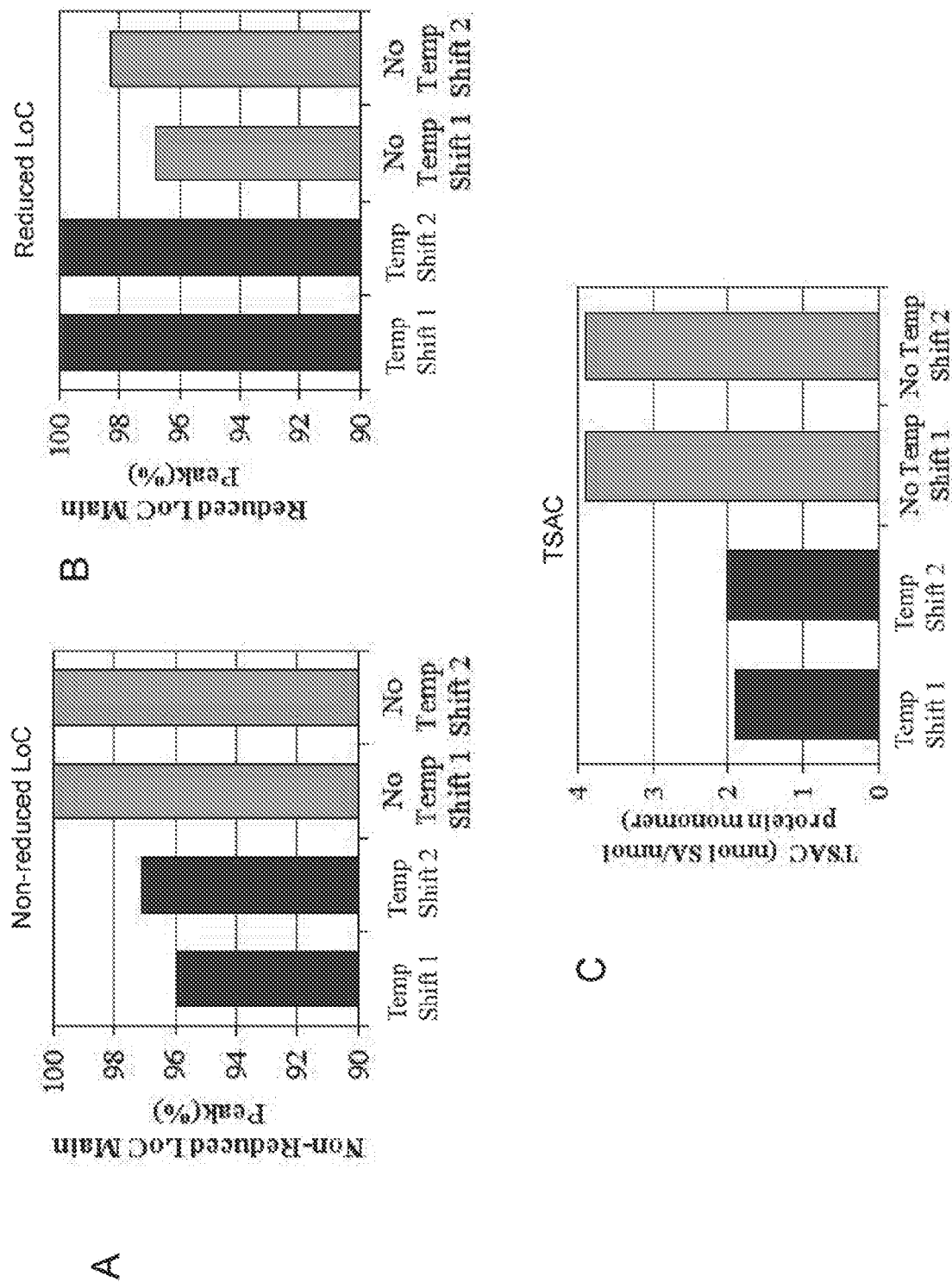
FIG. 4 are graphs showing the comparisons of non-reduced LoC (Lab-on-Chip; panel A), reduced LoC (panel B), and TSAC (total sialic acid content; panel C) of asfotase alfa produced using an exemplary production process (#1) with or without temperature shifting.

Sialylation was significantly increased by approximately one fold under the no-temperature-shift condition (FIG. 4C).

Figure 5:
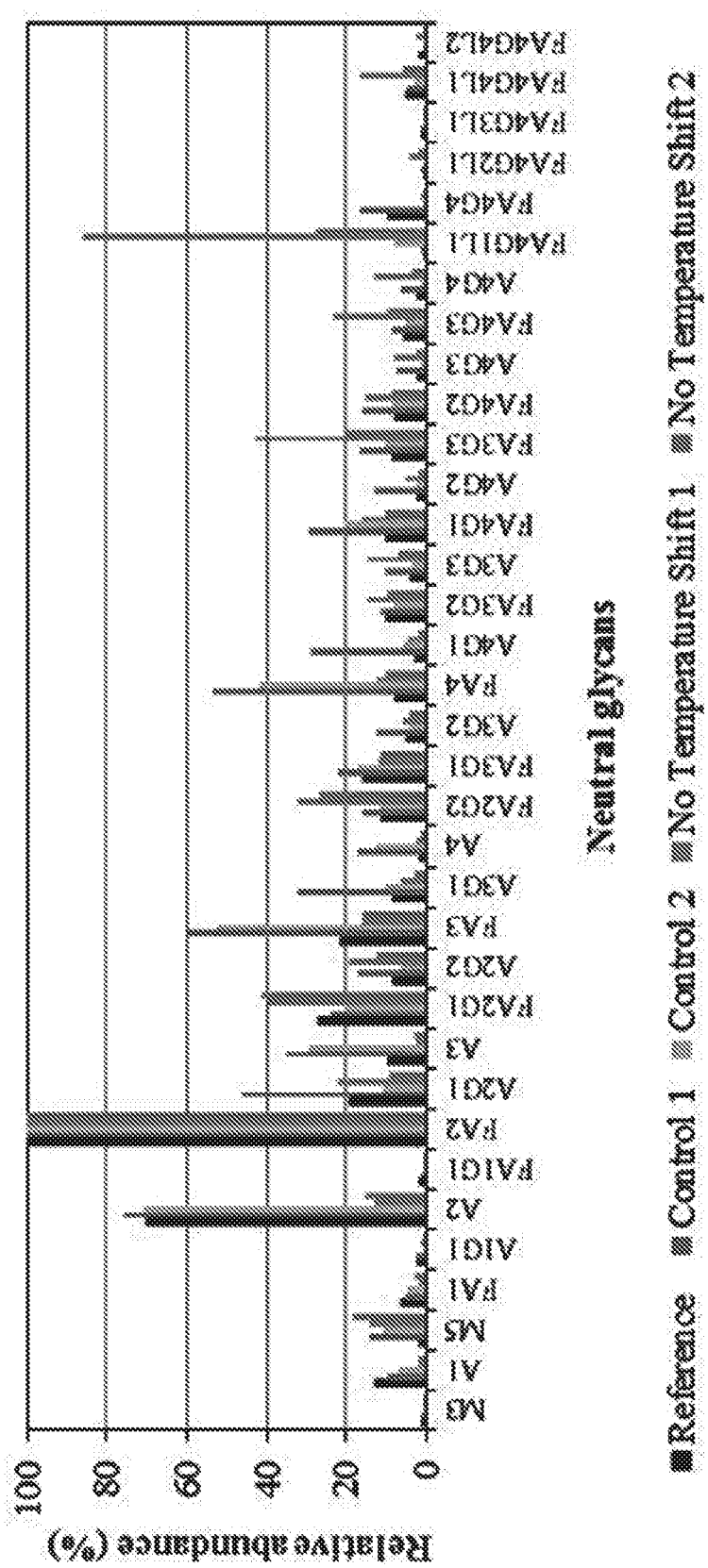
FIG. 5 is a graph showing the neural glycan profiles (by matrix assisted laser desorption/ionization-time of flight, or MALDI-TOF) of asfotase alfa produced by an exemplary production process (#1) with or without temperature shifting. Reference represents a standard asfotase alfa produced by a previous 20K process.

Analysis of neutral glycans by MALDI-TOF exhibited no higher-order mannose species or atypical glycan species detected under the no-temperature-shift condition (FIG. 5). However, the no-temperature-shift condition resulted in less amount of A2 (the predominant afucosylated glycan species under the control condition with temperature shifting), higher fucosylation (higher ratio of FA2 to A2), and an increase in higher-order glycans including FA3G3, FA4G3, FA4G1L1, and FA4G4L1 (FIG. 5).

The impact of not shifting temperature on asfotase alfa productivity and quality in Process #1 is summarized in Table 7. Without the temperature shift, the produced asfotase alfa had a much lower specific activity. Meanwhile, the higher production temperature under the no-temperature-shift condition led to higher sialylation and higher fucosylation.

TABLE 7

Impact of Not Shifting Temperature on
Asfotase Alfa Productivity and Quality

| Parameters | Process #1 - No Temp Shift |
|---|---|
| Protein A titer | No impact |
| Volumetric activity | Significantly lower volumetric activity |
| Specific activity | Significantly lower specific activity |
| AEX acidic peak | Less acidic peak |
| SEC aggregate | Further evaluation needed |
| LoC Fragment | Further evaluation needed |
| TSAC | Significantly higher TSAC |
| Neutral glycan | Higher fucosylation and more higher order glycans |

Example 3. Initial Upstream Process Parameter Assessment for Exemplary Process #2

This example summarizes the initial assessment of upstream manufacturing process parameters for an exemplary asfotase alfa manufacturing process #2 and their potential to impact critical quality attributes of produced asfotase alfa. Some upstream process parameters include % aggregation, % fragmentation, sialylation, glycosylation, charge distribution, and specific activity.

Cell Culture

All production processes referenced in this study were conducted either in shake flasks or bioreactors. Post thaw, cells were expanded through a series of shake flasks and spinner flasks prior to the inoculation of the production bioreactor. The production bioreactor (2 L, 5 L, 10 L, or 200 L) was scaled using consistent power per volume and sparge gas volume per liquid volume per minute (VVM), unless otherwise specified. The temperature of the production bioreactor was controlled at 36.5° C. from 0 to approximately 120 hours, and shifted to 33.0° C. at approximately 120 hours, unless otherwise specified. The dissolved oxygen set point was maintained at 30%. Approximately 2.7% (v/v) of CPN feed per bolus was added at the 96 hour (hr), the 144 hour, and the 192 hour when the culture was harvested on day 10 (240 hr±6 hr), while an additional bolus feed was given at 240 hr when the culture was harvested later than day 10.

Harvest and Purification

Samples harvested from production bioreactors were clarified by 0.22 μm filtration post centrifugation at 3000×g for 5 minutes. Purification of the clarified filtered harvest was performed and the extent of the purification was dictated by the study and sample test requirements. Either one chromatography step (protein A) or two sequential chromatography steps (protein A followed by hydrophobic interaction chromatography (HIC)) purification were implemented for most samples tested. Additionally, samples were buffer exchanged into a low salt buffer (5 mM $Na_3PO_4$, pH7.4) prior to analytical testing.

Analytical Characterization

Quality attributes referenced in this study were identified as subsets of broader quality metrics such as purity, potency, and structure. The quality subsets described include % aggregation, % fragmentation, charge distribution, total sialic acid content (TSAC), neutral glycan profile, and specific activity. Both the aggregate and fragment levels were determined by relative peak areas quantified using gel permeation HPLC (GP-HPLC). In addition, the fragment level was determined using either SDS-PAGE or Lab-on-Chip (LoC) capillary electrophoresis. The charge distribution was estimated using anion-exchange (AEX) chromatography. TSAC was quantified by high-performance anion exchange chromatography with pulsed amperometric detection (HPAE-PAD). Detection of neutral glycan species was performed by matrix-assisted laser desorption/ionization (MALDI) mass spectrometry. Specific activity was measured following the paranitrophenylphosphate (pNPP)-based alkaline phosphatase enzymatic assay.

Results

1. Growth and Production Temperature

The impact of temperature on product fragmentation has been discussed. For asfotase alfa produced by the chosen cell clone grown at 36.5° C., the main asfotase alfa band was calculated to be 95.9%, with approximately 4% as fragments, measured by SDS-PAGE. When temperature was shifted from 36.5° C. to 33.0° C. on day 5, the same clone produced nearly no asfotase alfa fragments (main band calculated to be >990%). Other secondary clones showed very similar trends in the reduction of fragments via temperature shifting from 36.5° C. to 33.0° C., though not all secondary clones were able to reduce the fragment level to be below 1%. Therefore, the growth temperature and production temperature can impact fragmentation. In addition, the timing associated with conducting the temperature shift could also impact asfotase alfa quality.

Figure 6:
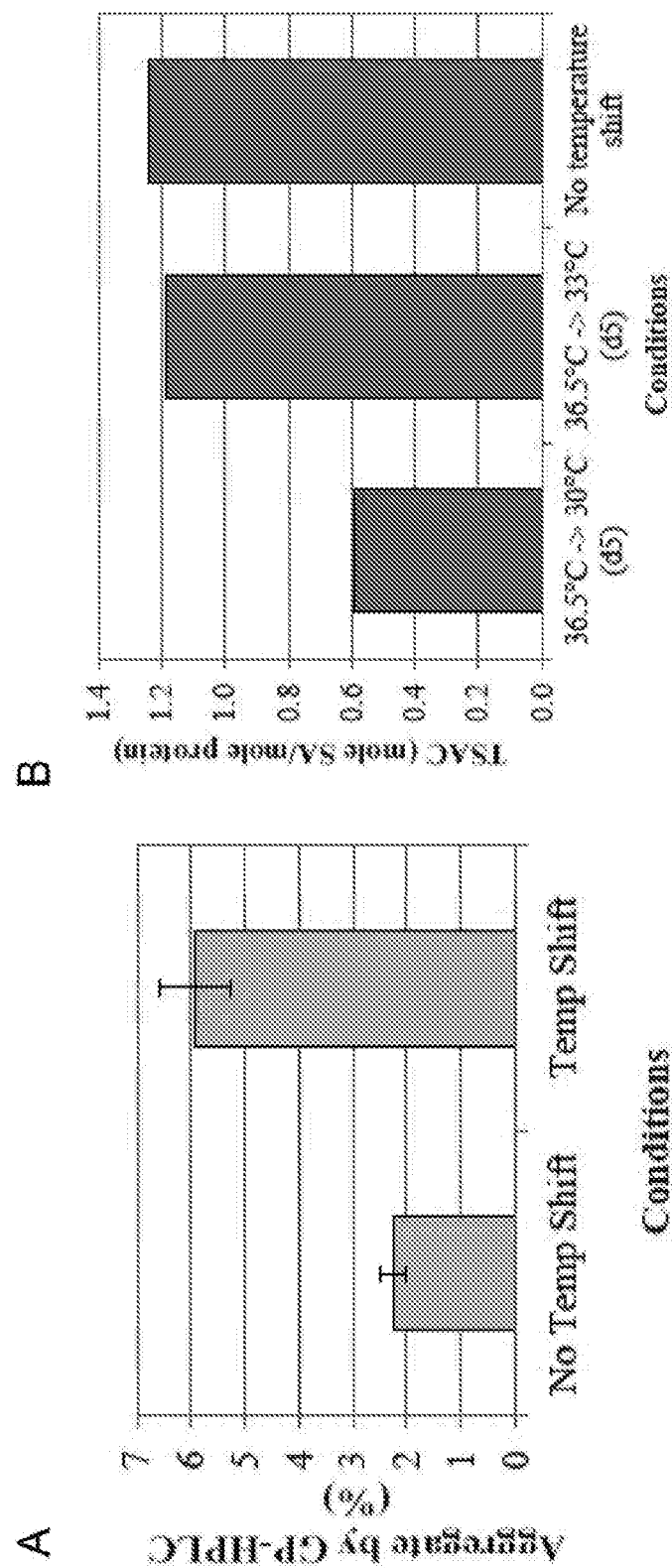
FIG. 6 are graphs showing the impact of shifting production temperature on the aggregate levels (panel A) and TSAC (panel B) of produced asfotase alfa. The error bars represent standard deviation under each condition.

Higher aggregate levels detected by GP-HPLC were observed under lower production temperatures during secondary clone screening in 2 L bioreactors. FIG. 6A showed the aggregate level of asfotase alfa produced by 6 secondary clones when the temperature was shifted to 33° C. compared to material produced by 10 secondary clones when the temperature was not shifted (i.e., maintained at 36.5° C.). These data suggest temperature shifting from 36.5° C. to 33.0° C. can cause an increase in aggregate level.

In addition, the impact of temperature shifting on TSAC was investigated during primary clone selection and initial process development (FIG. 6B). A primary clone was used to investigate the impact of production temperature (day 5 onwards) on sialylation, or TSAC in 2 L bioreactors. In this study, the production temperature was shifted from 36.5° C. to 30.0° C. on day 5 under condition 1, from 36.5° C. to 33.0° C. on day 5 under condition 2, and the control was run without a temperature shift. Samples were harvested when viability was between 60% and 80%, and those cultures were run for 11 to 18 days prior to harvest depending on viability. As shown in FIG. 6B, implementing a temperature shift resulted in lower TSAC as compared to the control under constant temperature under similar viability, and shifting to a lower temperature corresponded to a lower TSAC. The desired minimum TSAC value herein is 1.8. As sialylation (or TSAC) will change the charge profile of the product, and convert neutral glycans to negatively charged glycans, these three quality attributes (production temperature, aggregation, and TSAC) are considered to be closely related.

2. pH

Figure 7:
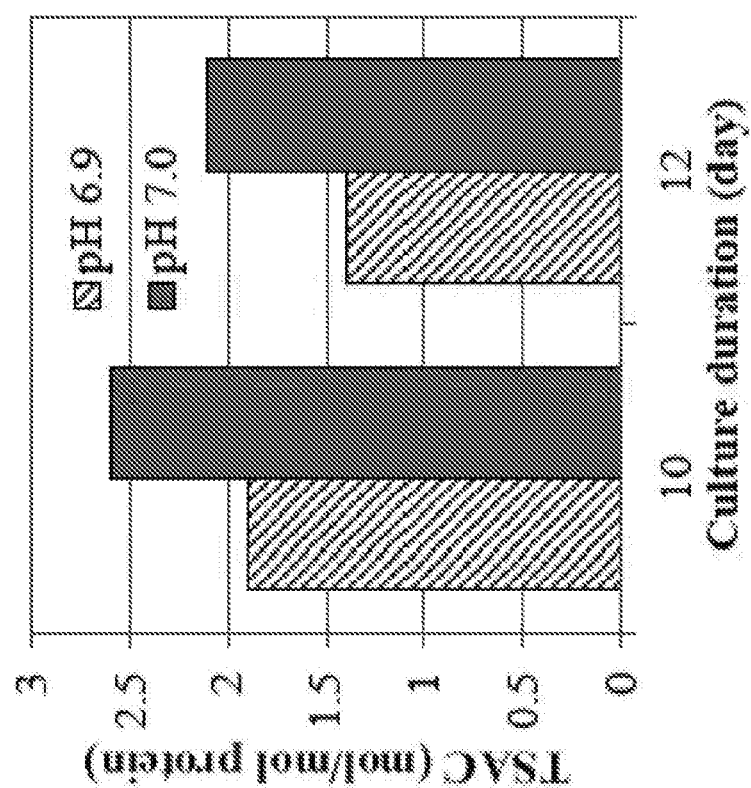
FIG. 7 is a graph showing the impact of culture pH on the TSAC values of asfotase alfa produced by exemplary Process #2 after 10 or 12 days of culturing.

Preliminary results indicated that changing the pH set point from 6.90 to 7.00 led to increased TSAC (FIG. 7). Using the chosen secondary clone, two 2 L bioreactors with pH set point 6.90 and 7.00, respectively, were used to investigate the impact of pH on asfotase alfa sialylation. Samples were harvested from bioreactors on day 10 and day 12, respectively. It was observed that the TSAC dropped from 1.9 on day 10 to 1.4 on day 12 under pH 6.90 condition. Though the same trend in declining TSAC values was observed under pH 7.00 conditions, the TSAC values under pH 7.00 on both days (2.6 on day 10, and 2.1 on day 12) were higher than those under the lower pH condition. These data suggested that TSAC declines with culture duration and a lower pH set point results in a lower TSAC value.

3. Medium Feed Addition

Figure 8:
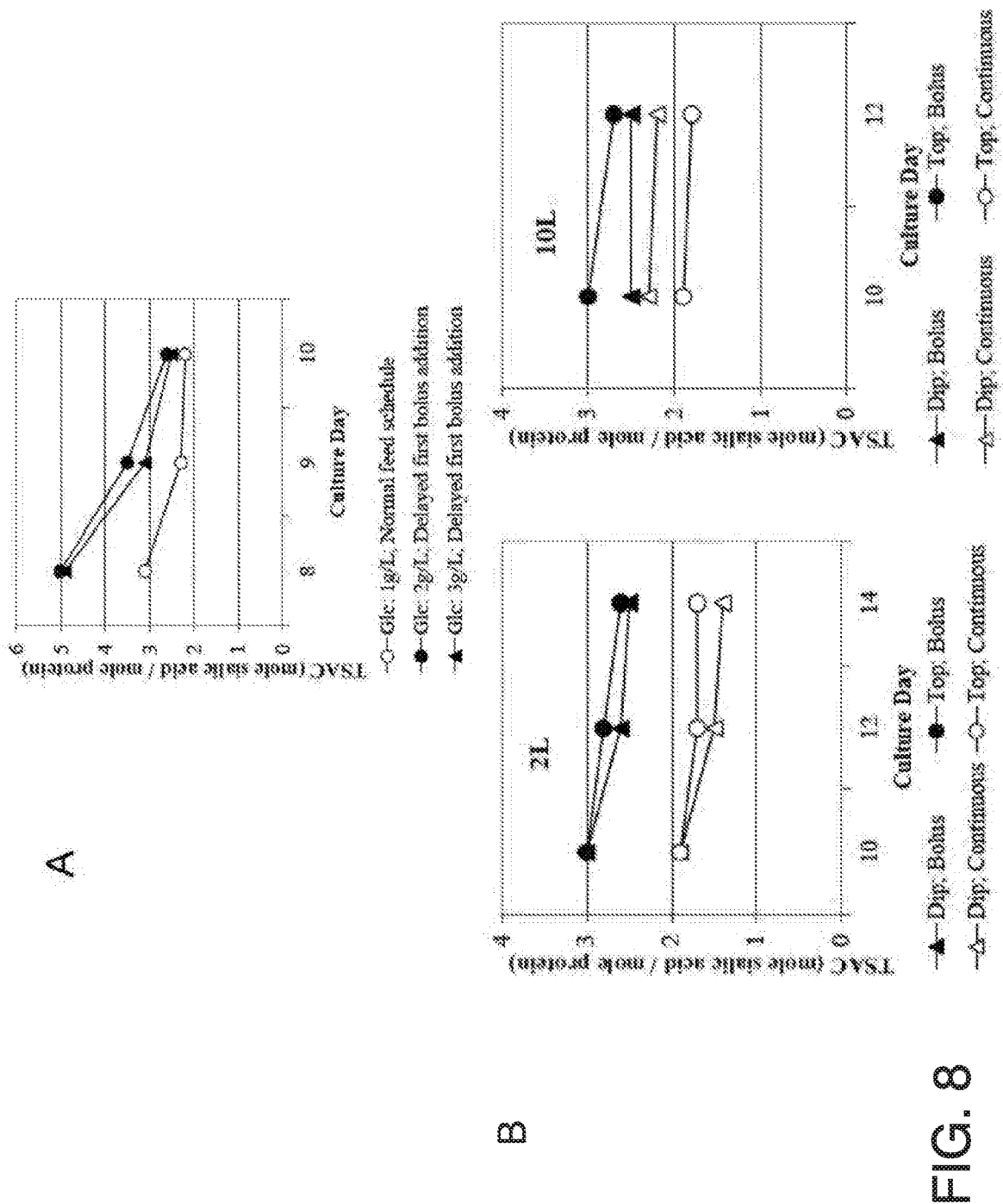
FIG. 8 are graphs showing the impacts of medium feed addition (represented by different concentrations of glycose (glc); panel A) and feed addition mode (panel B) on asfotase alfa TSAC in exemplary Process #2.

Preliminary data indicated that delaying the first bolus addition or increasing the glucose concentration in the medium may lead to significantly higher TSAC in comparison to the control condition (FIG. 8A).

In addition, how the medium feed is delivered (either continuously or by bolus addition) also had an impact on TSAC. Data from both 2 L and 10 L scales indicated significantly higher TSAC was observed when the feed was added in bolus mode, in comparison to the continuous addition mode (FIG. 8B). Therefore, the CPN feed is determined to be supplemented as bolus. In addition, no impact on TSAC was observed when the feed was delivered through top port drop addition or by subsurface (dip) addition.

4. Zinc Sulfate Addition

Zinc ions are known to be essential for alkaline phosphatase (e.g., asfotase alfa) stability as it helps to maintain their structure and activity. For example, two zinc atoms associate with one placental alkaline phosphatase molecule (Helene Le Du et al. 2001 *J. Biol. Chem.* 276:9158-9165). Based on this ratio, for the titer of 1 g/L asfotase alfa produced by the exemplary manufacturing process developed in small-scale models, approximately 20 μM zinc is needed for asfotase alfa activity.

Figure 9:
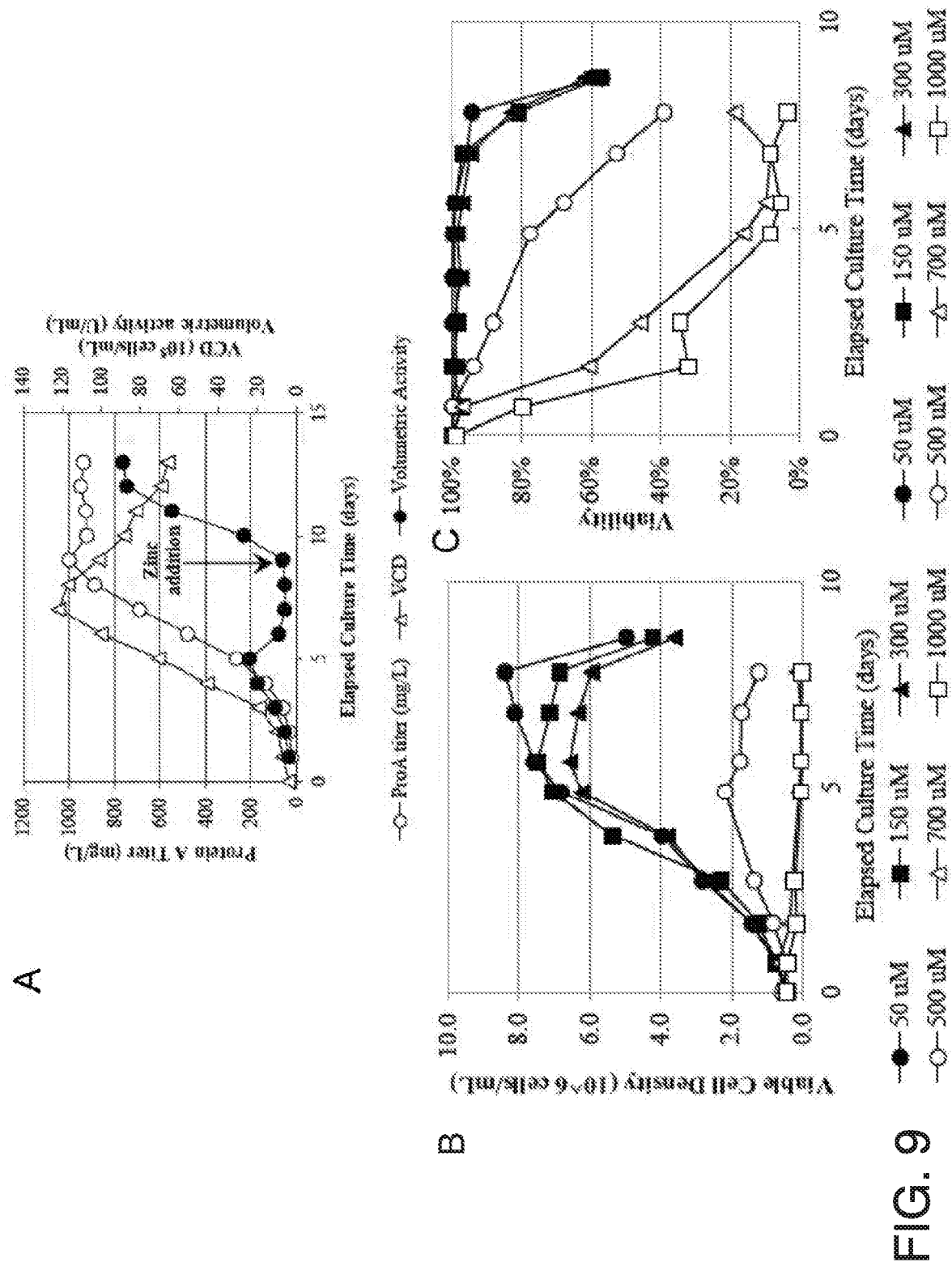
FIG. 9 are graphs showing the impact of zinc supplementation on asfotase alfa activity (panel A; zinc supplemented at Day 9) and the impact of zinc concentration on cell growth (panel B) and viability (panel C) in exemplary Process #2.

It was observed that as cell culture progressed, protein A-bindable asfotase alfa was being produced continuously, but the corresponding volumetric activity did not synchronize with the protein A titer, which indicated that the protein being produced was inactive (FIG. 9A). Furthermore, while the volumetric activity decreased from day 5 to day 9, the protein activity was immediately restored upon zinc sulfate supplementation on day 9. This data suggested that zinc needs to be supplemented into the production medium. In this study, the zinc sulfate concentration was increased by 25 μM through bolus addition on day 9. Given that protein A titer was approximately 1000 mg/L on day 9, this zinc bolus addition increased the ratio of zinc ion to asfotase alfa by at least 2:1.

Figure 17:
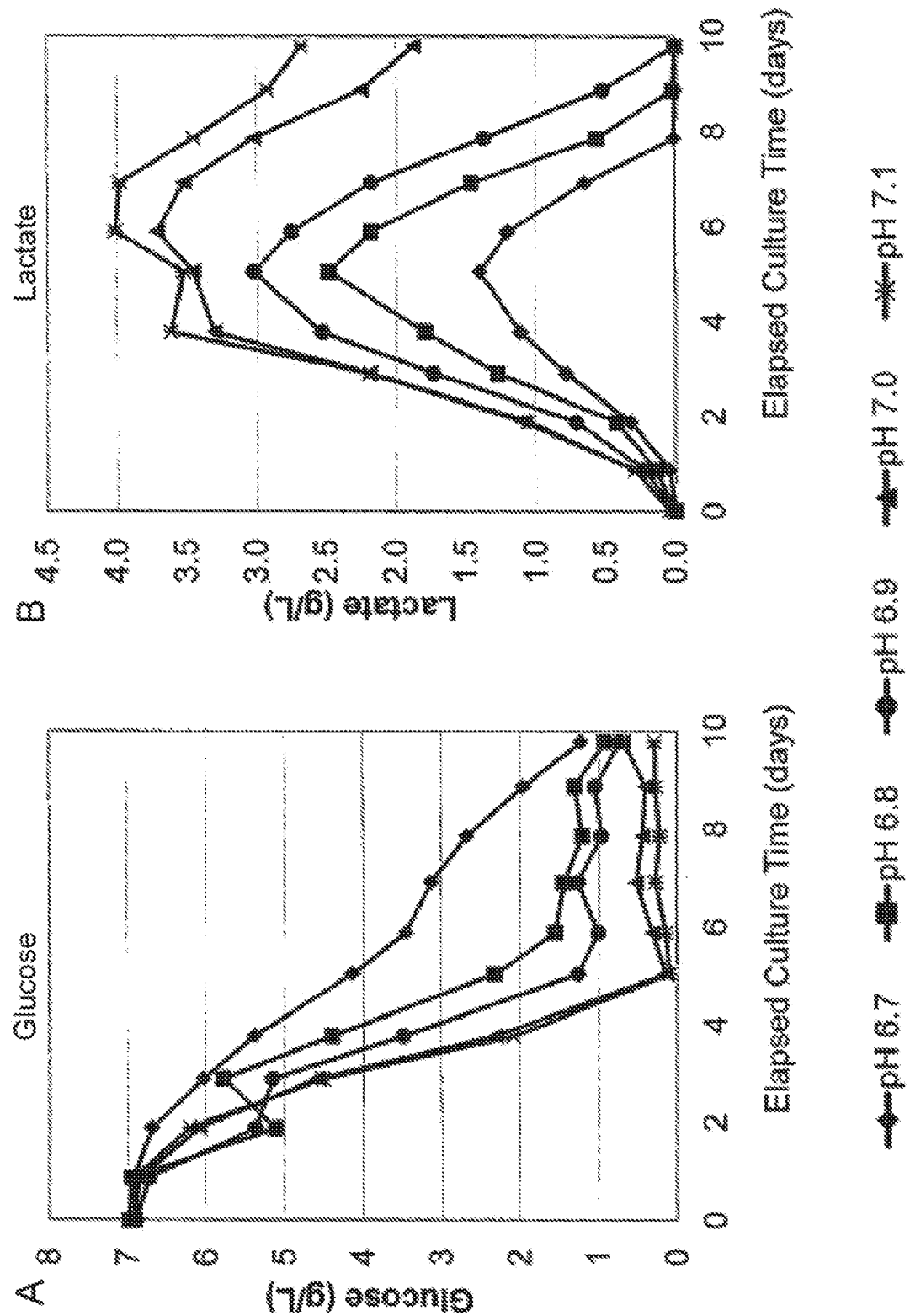
FIG. 17 are graphs showing the impact of culture medium pH on glucose (panel A) and lactate (panel B) concentrations in the culture medium up to ten days in exemplary Process #4.

In the following study, the cytotoxicity level of zinc sulfate on cell growth and viability was investigated using a mini-bioreactor system in batch mode, in which zinc sulfate in different concentrations was added into the culture medium at day 0. When zinc sulfate concentration was below 300 μM, little impact on growth or viability was observed (FIGS. 9B and 17C). However, in conditions where the zinc concentration was greater than or equal to 500 μM, both the growth and the viability were dramatically affected. Therefore, the optimal concentration of total zinc supplementation was under 500 μM. Thus, it was estimated that the optimal zinc concentration to be supplemented at day 0 may be between about 25 μM and about 300 μM (considering both cell growth/viability and protein function issues). In fact, zinc concentration at 150 μM may be even better than 300 μM since the former resulted in less cell growth inhibition after day 5 (FIG. 9A). It is also surprising that although 20 μM zinc is theoretically sufficient for producing functional asfotase alfa (i.e., 2 zinc ions per active enzyme), the actual zinc supplementation may require significantly higher zinc concentrations (e.g., 150 μM) in alkaline phosphates (e.g., asfotase alfa, TNALP, PALP, GCALP, IAP, or fusion/variant proteins thereof) manufacturing processes.

5. Seeding Density

Generally, higher seeding density leads to a higher peak viable cell density, which is primarily due to certain nutrient component constraints in the production medium. As feeding and temperature shift is based on culture duration, seeding density in conjunction with other upstream process parameters, especially temperature shift timing, could potentially impact asfotase alfa quality.

6. Harvest Timing

The harvest timing in this exemplary process was 240±6 hr. The impact of harvest timing on TSAC has been demonstrated (see, e.g., FIG. 7). In addition, harvest timing is also considered to be associated with viability (see, e.g., FIG. 14), and the viability decline toward the end of the culture indicates that harvest timing could potentially impact asfotase alfa quality.

Various upstream process parameters were assessed, including control of seeding density, temperature, pH, DO, gassing strategy, agitation, CPN feed, glucose addition, galactose addition, zinc addition, and harvest timing. More upstream process parameters, including % aggregation, % fragmentation, sialylation, glycosylation, charge distribution, and specific activity, were evaluated, e.g., as discussed below.

Temperature had a strong impact on aggregation, fragmentation, and sialylation. pH also impacted asfotase alfa sialylation. Gassing strategy or/and agitation seemed to impact viability. CPN feed addition seemed to have an impact on sialylation. Zinc addition was shown to be essential for maintaining enzymatic activity, and the amount of zinc addition (150 μM) was determined based on the studies presented. Harvest timing was shown to be associated with viability and TSAC decline towards the end of the culture.

Example 4. Further Upstream Process Parameter Assessment for Exemplary Process #3

This example summarizes further characterization of upstream processes that were performed for the purpose of screening production bioreactor process parameters. For initial assessments, a list of upstream process parameters were tested in this exemplary process, include production culture pH, temperature, seeding density, gassing strategy, agitation, CPN feed, glucose addition, galactose addition, and harvest timing.

Acronyms

CPP: critical process parameter, a process parameter (process input) that has an impact on a critical quality attribute and therefore will be monitored and controlled to ensure the process produces the desired quality.
CQA: critical quality attribute
HPLC: High Performance Liquid Chromatography
LoQ: Limit of Quantification
P/V: Power per Volume Materials and Methods Process parameters that were shown in initial experiments to have a potential impact were further investigated. Six blocks of bioreactors were conducted in the following process characterization study (Table 8). Three levels for each process parameter were tested with the median level as the current set point (the control) in consideration of the controlling capability at manufacturing and process parameter range testing. In block 1 to 5, three-level full factorial design with two replicate controls was implemented. In block 6, four combinations of extreme P/V and sparge VVM plus two controls were conducted.

TABLE 8

Investigated Process Parameters and Levels

| Block | Process Parameter | Investgated Levels | | |
|---|---|---|---|---|
| | | Low | Median | High |
| 1 | Gluscose addition threshold (g/L) | 1.5 | 2.0 | 3.0 |
| | Galactose addition (g/L) | 7 | 10 | 15 |
| 2 | pH set point | 6.75 | 6.90 | 7.10 |
| | Production temperature (° C.) | 30.0 | 33.0 | 35.0 |
| 3 | Growth temperature | 35.0 | 36.5 | 37.5 |
| | DO set point (%) | 15 | 30 | 60 |
| 4 | Feed amount (%) | 67 | 100 | 133 |
| | Feed initiation (day) | 3 | 4 | 5 |
| 5 | Seeding density (105 cells/mL) | 4.0 | 5.5 | 8.0 |
| | Temp shift timing (hr) | 108 | 120 | 132 |
| 6 | P/V (W/m3) | 9->41 | 17->81 | 26->121 |
| | Maximum sparge | 0.015 | 0.020 | 0.025 |

Cell Culture

All production processes referenced in this study were conducted either in 2 L or 10 L bioreactors. Post thaw cells were expanded through a series of shake flasks and spinner flasks prior to the inoculation of the production bioreactor. The production bioreactor (2 L or 10 L) was scaled using P/V and sparge VVM, unless otherwise specified. Under the control condition, the cell culture process parameters were as follows. Culture pH set point was 6.90 with 0.05 dead band. The temperature was controlled at 36.5° C. from 0 to 120 hours, and shifted to 33° C. at 120 hours. The dissolved oxygen set point was maintained at 30%. The initial PN was 17 W/m$^3$ (0-96 hr) and shifted to 81 W/m3 prior to the first bolus feed addition at 96 hr. 2.67% (v/v) of CPN feed per bolus was added at 96 hr, 168 hr, and 192 hr. Glucose was maintained at ≤2 g/L. If glucose was below 2 g/L, daily bolus addition was applied to increase glucose concentration to be in the range of 1.8 to 2.0 g/L. Galactose was supplemented throughout the culture: 2.0 g/L on day 0 an day 4, and 1.0 g/L daily from day 5 to day 9. A portion of the culture was harvested on day 10 (240±4 hr) and day 11 (264±4 hr).

Harvest and Purification

Samples harvested from production bioreactors were clarified by 0.22 μm filter post centrifugation at 3000×g for 5 minutes. Purification of the clarified filtered harvest was performed. The extent of the purification was dictated by the study and sample test requirements. Either one step (protein A) or two sequential steps (protein A and HIC) purification were implemented. Additionally, samples were buffer exchanged into a low-salt containing buffer (5 mM Na$_3$PO$_4$, pH7.4) prior to analytical testing.

Analytical Characterization

Quality attributes referenced in this study include % aggregation, % fragmentation, charge distribution, total sialic acid content (TSAC), and neutral glycan profile. Both the aggregate and fragment levels were determined by relative peak areas quantified using size exclusion chromatography (SEC). In addition, the asfotase alfa purity (main peak) was also determined using Lab-on-Chip (LoC) capillary electrophoresis. The charge distribution was estimated using anion-exchange chromatography (AEX). TSAC was quantified by High-Performance Anion Exchange Chromatography with Pulsed Amperometric Detection (HPAE-PAD). Detection of neutral glycan species was performed by Matrix Assisted Laser Desorption/Ionization-Time of Flight (MALDI-TOF) mass spectrometry. Volumetric activity was measured following the paranitrophenylphosphate (pNPP)-based alkaline phosphatase enzymatic assay.

Statistical Analysis and Data Visualization

The potential of tested process parameters to impact productivity and each quality attribute were evaluated using the statistical software package JMP (Cary, N.C.). Three continuous parameters (three levels for two tested process parameter, respectively, and two levels for harvest) were analyzed. Individual p-values calculated by two sided t-test were reported, and 0.05 was chosen as the significance threshold. Contour plots generated by JMP were used to visualize the potential impact of tested parameters on each quality attribute.

Results

As the acceptable range for each CQA in this exemplary process was still under investigation, an exemplary experimental range was generated and used for comparison purposes (Table 9). The data source stemmed from all of the day 10 results obtained in this study. For the impurity measurement including fragment and aggregate by SEC and basic and acidic peak by AEX, the average plus two fold of standard deviation was used as the upper threshold. As the calculated upper threshold for fragment measured by SEC and basic peak measured by AEX is lower than the LoQ (1%) of SEC and AEX assay, the upper threshold was set to be 1% for both attributes. As for TSAC, the average, minus and plus two fold of standard deviation, was used as the experimental range.

TABLE 9

Small Scale Experimental Ranges for CQA

| | | Critical Quality Attributes | | | |
|---|---|---|---|---|---|
| | TSAC | Aggregate SEC (%) | Fragment SEC (%) | Basic peak AEX (%) | Acidic peak AEX (%) |
| Average (Avg) | 2.2 | 8.0 | 0.5 | 0.4 | 8.6 |
| Standard deviation (stdev) | 0.4 | 0.8 | 0.2 | 0.1 | 0.8 |
| Avg − 1 × stdev | 1.8 | 7.3 | 0.3 | 0.3 | 7.8 |
| Avg − 2 × stdev | 1.5 | 6.5 | 0.1 | 0.2 | 7.0 |
| Avg + 1 × stdev | 2.5 | 8.8 | 0.7 | 0.5 | 9.4 |
| Avg + 1 × stdev | 2.9 | 9.6 | 0.8 | 0.6 | 10.2 |
| Experimental range | 1.5 to 2.9 | ≤9.6 | ≤1.0 | ≤1.0 | ≤10.2 |

The significance of the direct impact of each process parameter on each CQA is summarized in Table 10. The p-value of P/V and sparge VVM impact was not calculated due to lack of statistical power. The p-values less than or equal to 0.05 are considered as statistically significant.

TABLE 10

Significance of Direct Impact of Each Process Parameter on CQA Analyzed by JMP

| | | SEC | | AEX | |
|---|---|---|---|---|---|
| p-value | TSAC | Aggregate | Fragment | Basic | Acidic |
| Glucose | 0.41 | 0.63 | — | 0.98 | 0.67 |
| Galactose | 0.04 | 0.37 | — | 0.14 | 0.44 |
| pH | 0.00 | 0.63 | 0.00 | 0.05 | 0.29 |
| Production temp | 0.00 | 0.00 | 0.00 | 0.64 | 0.00 |
| DO | 0.72 | 0.73 | 0.72 | 0.64 | 0.79 |
| Growth temp | 0.16 | 0.47 | 0.01 | 0.26 | 0.04 |
| Feed amount | 0.03 | 0.00 | 0.14 | 0.70 | 0.00 |
| Feed timing | 0.37 | 0.00 | 0.71 | 0.03 | 0.00 |
| Seeding density | 0.81 | 0.34 | 0.00 | 0.31 | 0.49 |
| Temp shift timing | 0.06 | 0.64 | 0.00 | 0.70 | 0.26 |

Table 11 summarizes the average quality attribute value obtained at the minimum and maximum tested process parameter level. For instance, in the glucose and galactose addition study, three bioreactors used 1.5 g/L as the glucose addition threshold, and each of them had a different galactose addition level. The CQA value at 1.5 g/L of glucose threshold condition was then calculated using the average from those three bioreactor. In the following sections, day 10 data is used for quality discussion unless otherwise mentioned.

TABLE 11

Averaged Quality Attribute Values under Tested Conditions

| | | | | Critical Quality Attributes | | | |
|---|---|---|---|---|---|---|---|
| Process Parameters and Tested Ranges | | | TSAC | Aggregate, SEC (%) | Fragment, SEC (%) | Basic peak, AEX (%) | Acidic peak, AEX (%) |
| Glucose threshold (g/L) | Min | 1.5 | 2.5 | 5.9 | 0.0 | 0.3 | 5.9 |
| | Max | 3.0 | 2.4 | 5.5 | 0.0 | 0.4 | 5.5 |
| Total galactose addition (g/L) | Min | 7 | 2.3 | 5.5 | 0.0 | 0.3 | 5.6 |
| | Max | 15 | 2.4 | 6.3 | 0.0 | 0.5* | 5.7* |
| pH | Min | 6.75 | 1.9 | 5.7 | 0.0 | 0.5 | 5.7 |
| | Max | 7.10 | 2.7 | 5.7 | 0.1 | 0.3 | 6.1 |
| Production Temp (° C.) | Min | 30.0 | 1.6 | 8.2 | 0.0 | 0.3 | 8.5 |
| | Max | 35.0 | 2.7 | 3.8 | 0.1 | 0.6 | 3.7 |
| Dissolved Oxygen (%) | Min | 15 | 2.3 | 7.8 | 0.5 | 0.4 | 8.7 |
| | Max | 60 | 2.3 | 7.6 | 0.6 | 0.4 | 8.9 |
| Growth Temp (° C.) | Min | 35.0 | 2.2 | 7.7 | 0.4 | 0.3 | 8.5 |
| | Max | 37.5 | 2.4 | 7.6 | 0.8 | 0.4 | 9.2 |
| Feed amount (%) | Min | 67 | 2.1 | 8.5 | 0.4 | 0.3 | 8.9 |
| | Max | 133 | 1.9 | 8.8 | 0.4 | 0.3 | 9.4 |
| Feed initiation (day) | Min | 3 | 2.1 | 8.9 | 0.4 | 0.4 | 9.3 |
| | Max | 5 | 2.0 | 8.2 | 0.4 | 0.3 | 8.6 |

TABLE 11-continued

Averaged Quality Attribute Values under Tested Conditions

| Process Parameters and Tested Ranges | | | TSAC | Aggregate, SEC (%) | Fragment, SEC (%) | Basic peak, AEX (%) | Acidic peak, AEX (%) |
|---|---|---|---|---|---|---|---|
| Seeding ($10^3$ cells/mL) | Min | 4.0 | 2.4 | 9.0 | 0.6 | 0.5 | 8.3 |
| | Max | 8.0 | 2.4 | 8.3 | 0.8 | 0.6 | 8.9 |
| Temp Shift Timing (h) | Min | 108 | 2.5 | 8.6 | 0.6 | 0.5 | 8.5 |
| | Max | 132 | 2.3 | 8.8 | 0.8 | 0.5 | 9.2 |
| Harvest (day) | Min | 10 | 2.1 | 8.2 | 0.4 | 0.3 | 8.4 |
| | Max | 11 | 1.8 | 8.1 | 0.5 | 0.4 | 8.9 |
| Generation No. | Min | 38 | 1.9 | 8.8 | 0.4 | 0.4 | 8.6 |
| | Max | 48 | 2.1 | 7.7 | 0.5 | 0.4 | 8.7 |
| P/V (W/m$^3$) | Min | 9 (0-96 hr); 41 (96-240 hr) | 2.2 | 6.5 | 0.3 | 0.5 | 6.8 |
| | Max | 26 (0-96 hr); 121 (96-240 hr) | 1.9 | 6.9 | 0.3 | 0.2 | 7.3 |
| Maximum Sparge VVM | Min | 0.015 | 2.0 | 6.7 | 0.3 | 0.4 | 7.1 |
| | Max | 0.025 | 2.1 | 6.8 | 0.3 | 0.3 | 7.0 |

Note:
When the average percentage of basic peak and acidic peak measured by AEX was calculated for the condition 15 g/L of total galactose addition, an outlier sample was excluded due to its low peak response in the assay. Its biological replicate sample from another bioreactor remained for the calculation purpose.

1. pH

Prior results indicated pH impacted TSAC of produced asfotase alfa. The potential impact of culture pH and production temperature on asfotase alfa productivity and quality was further investigated in 2 L bioreactors. A full factorial design comprising three culture pH levels (6.75, 6.90, and 7.10) and three production temperature levels (30.0° C., 33.0° C., and 35.0° C.) was implemented, and samples from all conditions were harvested at 240±4 hour, and 264±4 hours, respectively. Two-step purification (ProA+HIC) was applied prior to analytical analysis.

Figure 10:
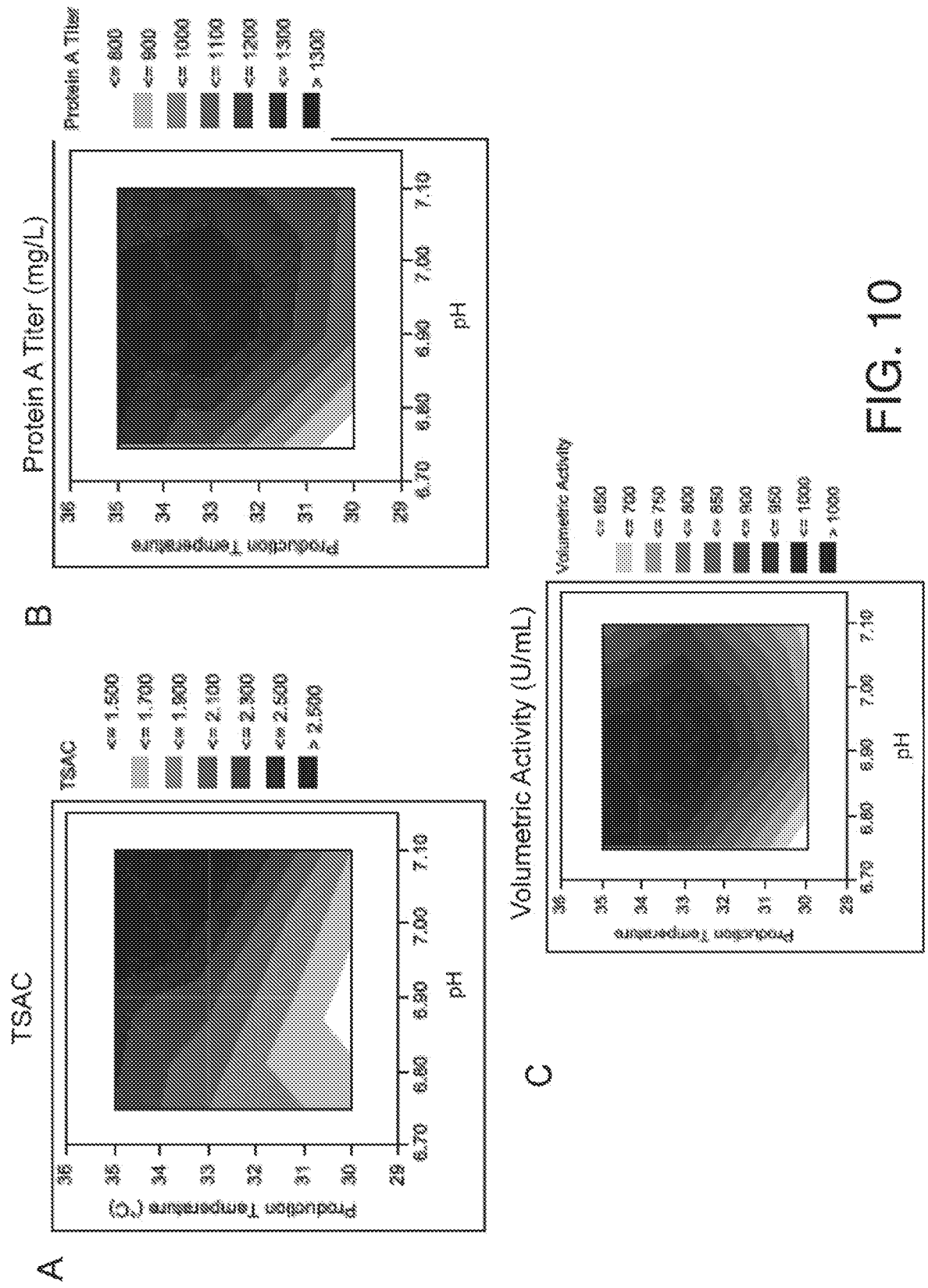
FIG. 10 are graphs showing the impact of pH and production temperature on asfotase alfa TSAC (panel A), protein A titer (panel B), and volumetric activity (panel C) in exemplary Process #3.

Culture pH set point in the tested range 6.75 to 7.10 was not considered to be a critical process parameter (CPP) in that all CQAs tested were within the small scale experimental range specified in Table 9. However, pH was shown to significantly affect several tested quality attributes. Elevating the pH set point from 6.75 to 7.10 led to TSAC increasing from 1.9 to 2.7 at the post-shift control production temperature of 33° C. (FIG. 10A). pH also had significant impact on fragmentation measured by SEC and basic peak measured by AEX (Table 10), but the impact was less than or equal to 0.2% (Table 11) which was below the HPLC-based assay variation of 0.5%. Furthermore, under the control condition (pH 6.90 and production temperature 33.0° C.), the highest productivity in terms of both protein A titer and volumetric activity was achieved (FIGS. 10B and 10C).

The data indicated that the impact of a pH set point ranging from 6.75 to 7.10 on CQA was all within the experimental range, suggesting production culture pH was unlikely to be a CPP. In various embodiments, alkaline phosphatase (e.g., asfotase alfa) is produced at a pH set point of 6.65, 6.70, 6.75, 6.80, 6.85, 6.90, 6.95, 7.00, 7.05, 7.10, 7.15, 7.2, or higher.

2. Temperature

Prior results indicated that temperature had a strong impact on several parameters including aggregation, fragmentation, and TSAC. As previous processes employ a temperature shift from 36.5° C. to 33.0° C. at 120 hours, the investigation of the temperature impact was dissected into three parameters: growth temperature (0 to 120 hours), production temperature (120 hours to harvest), and temperature shift timing. These three temperature-related parameters were further investigated separately and summarized below.

2.1 Growth Temperature

The impact of growth temperature was investigated together with the DO set point in 2 L bioreactors. Three levels of growth temperature (35.0° C., 36.5° C. and 37.5° C.) were maintained from 0 to 120 hour under different test conditions, followed by a temperature shift to 33.0° C. at 120 hours. Samples from all conditions were harvested at 240±4 hours, and 264±4 hours. One-step purification (ProA) was applied prior to analytical analysis. Growth temperature impacts growth rate and viability. A higher growth temperature correlated to a faster growth rate in the early stages, followed by a rapid growth-rate decline post temperature shift, which resulted in lower peak VCD. In addition, cultures with a higher growth temperature also had 2-4% lower final viability on the day of harvest. Interestingly, growth temperature impacts productivity significantly, and the volumetric activity achieved a peak value at a growth temperature of 36.5° C. (FIG. 11A).

Figure 11:
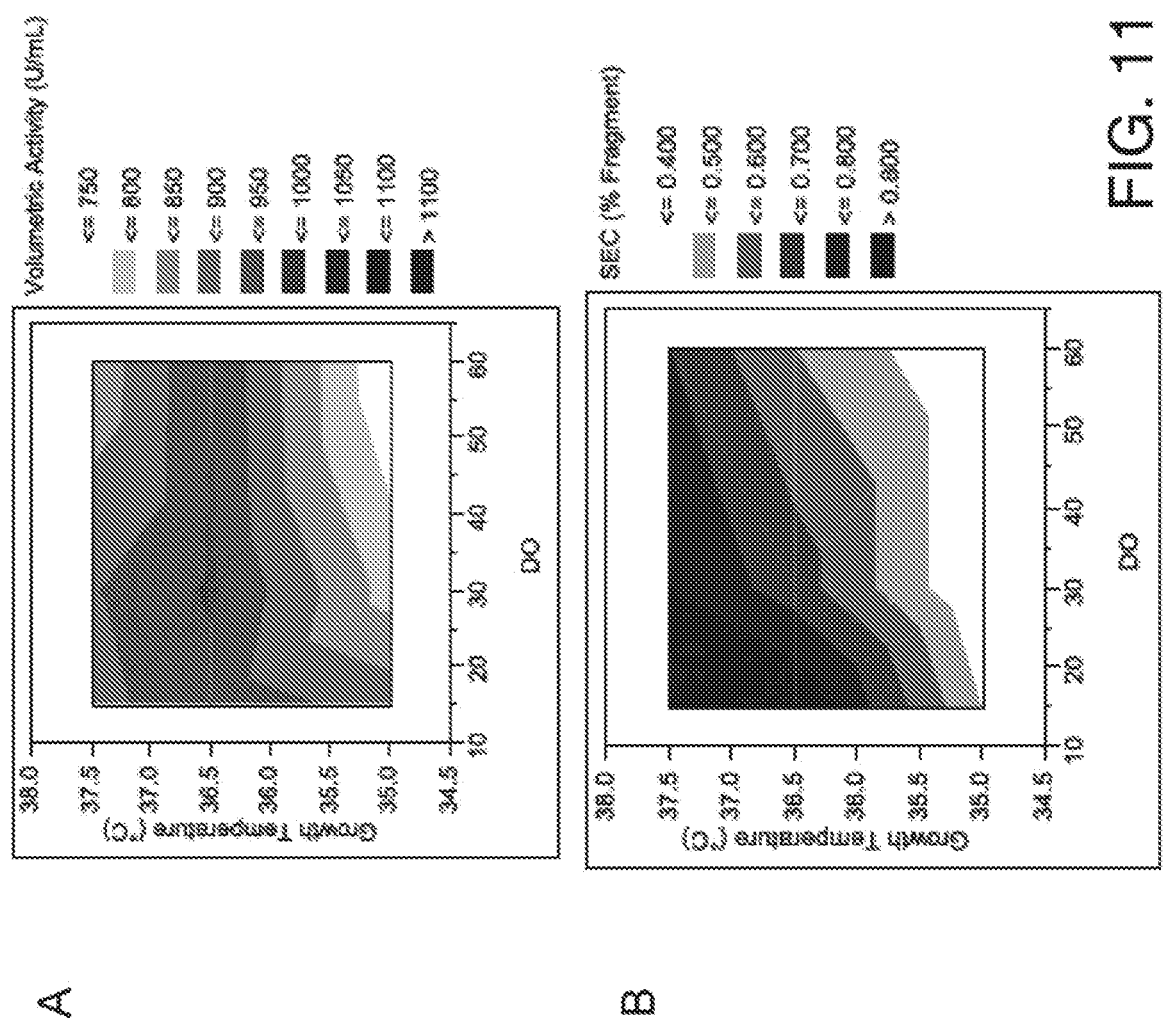
FIG. 11 are graphs showing the impact of growth temperature on volumetric activity (panel A) and asfotase alfa fragmentation (panel B, measured by SEC) in exemplary Process #3.

As for the impact on asfotase alfa quality, the growth temperature was shown to have a significant impact only on fragmentation as measured by SEC (FIG. 11B). Increasing the growth temperature from 35.0° C. to 37.5° C. resulted in a fragment level that was elevated from 0.3% to 0.8%. It is noted that those measured values were all below the LoQ (1%) of SEC assay.

As the impact on CQAs by growth temperature were all within the experimental range (Table 9 and Table 11), a growth temperature ranging from 35.0° C. to 37.5° C. is unlikely to be a CPP. In various embodiments, alkaline phosphatase (e.g., asfotase alfa) is produced at a growth temperature of 33.0° C., 33.5° C., 34.0° C., 34.5° C., 35.0° C., 35.5° C., 36.0° C., 36.5° C., 37.0° C., 37.5° C., 38.0° C., or 38.5° C. In one particular embodiment, alkaline phosphatase (e.g., asfotase alfa) is produced at a growth temperature of 35.0° C., 36.5° C., 37.0° C. or 37.5° C.

2.2 Production Temperature

The impact of production temperature (30.0° C., 33.0° C., and 35.0° C.) on CQA was investigated together with a culture pH set point in 2 L bioreactors. One-step purification (ProA) was applied prior to analytical analysis.

Figure 12:
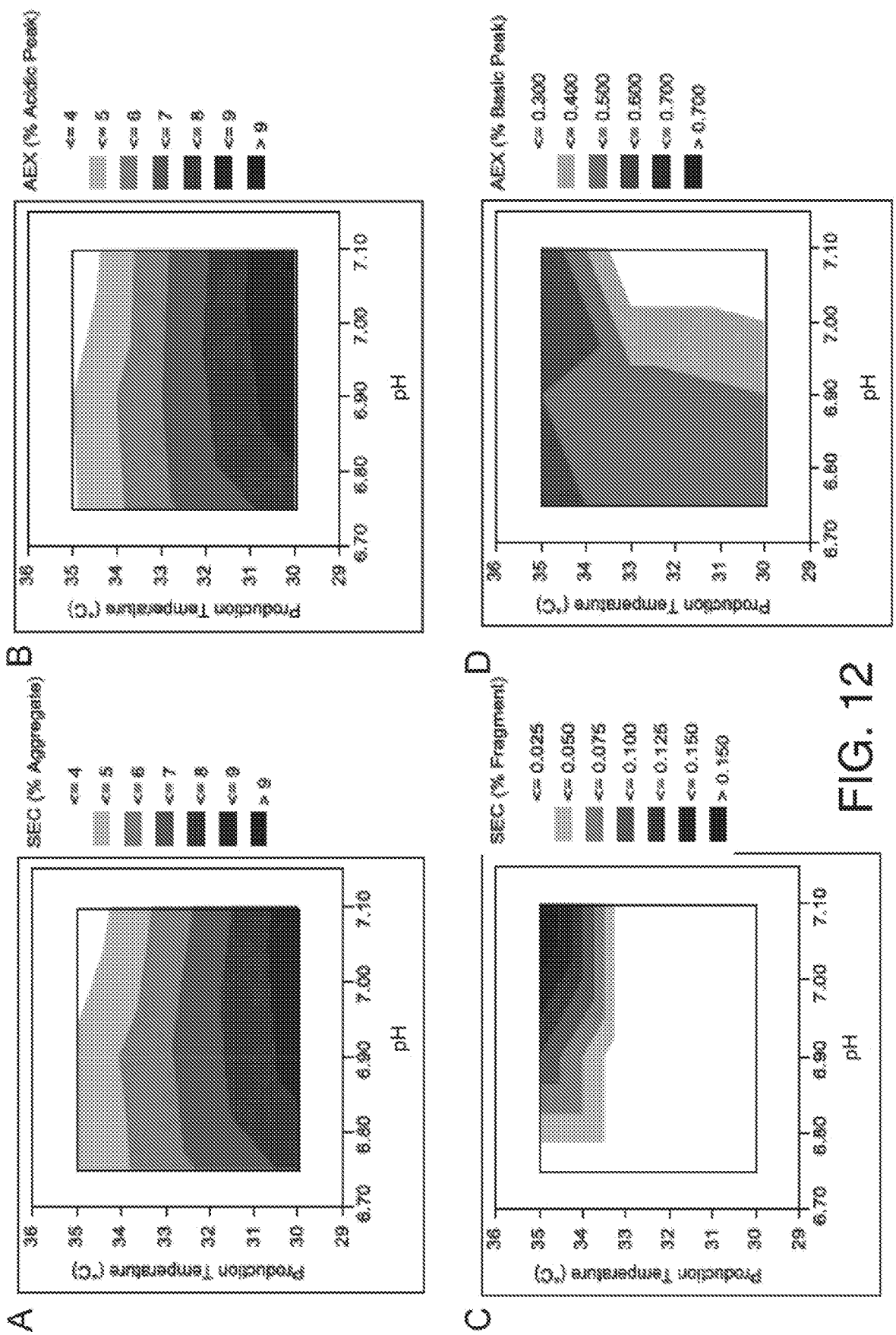
FIG. 12 are graphs showing the impact of production temperature and pH on asfotase alfa aggregation (panel A, measured by SEC), % acidic peak (panel B, measured by AEX), asfotase alfa fragmentation (panel C, measured by SEC), and % basic peak (panel D, measured by AEX) in exemplary Process #3.

Production temperature significantly impacts CQAs especially TSAC, aggregation and fragmentation, as measured by SEC, and acidic peak measured by AEX (Table 10 and Table 11). Elevating the production temperature from 30.0° C. to 35.0° C. led to an average TSAC increase from 1.6 to 2.7 (FIG. 10A), while lowering production temperature from 35.0° C. to 30.0° C. resulted in a large increase in aggregates as measured by SEC, from 3.8% to 8.2% (FIG. 12A). In addition, the acidic peak measured by AEX increased from 3.7% to 8.5% with lowering the production temperature (FIG. 12B). This data suggested that a production temperature higher than 30.0° C. is probably beneficial to reduce the risk of low TSAC and prevent increased aggregation/acidic peak. Meanwhile, there seems to be a very subtle positive correlation between production temperature and fragmentation, as measured by SEC (FIG. 12C), and the basic peak, measured by AEX (FIG. 12D). This data suggested a production temperature lower than 35° C. might be preferred to reduce the risk of asfotase alfa fragmentation.

In terms of the impact on productivity, production temperature appears to have the largest impact on protein A titer and volumetric activity (FIGS. 10B and 10C). In the range of 30.0° C. to 35.0° C., increasing production temperature correlates with increasing productivity. However, under pH 7.10, production temperature interacts with pH to impact productivity, with the highest volumetric productivity occurring at a production temperature of 33.0° C. Peak productivity in regards to both volumetric activity and protein A titer was observed at pH 6.90 under production temperature that is greater than or equal to 33.0° C. Though the production temperature was shown to have a significant impact on several CQAs (Table 10), the impact was still within the experimental range (Table 9 and Table 11). Therefore, production temperature in the range of 30.0° C. to 35.0° C. is unlikely to be a CPP.

In various embodiments, alkaline phosphatase (e.g., asfotase alfa) is produced at a production temperature of 29.0° C., 29.5° C., 30.0° C., 30.5° C., 31.0° C., 31.5° C., 32.0° C., 32.5° C., 33.0° C., 33.5° C., 34.0° C., 34.5° C., 35.0° C., 35.5° C., 36° C., or a higher temperature. In one particular embodiment, alkaline phosphatase (e.g., asfotase alfa) is produced at a production temperature of 30.0° C., 30.5° C., or 35.0° C.

3. Temperature Shift Timing

The impact of temperature shift timing on CQA was investigated together with seeding density in 2 L bioreactors. Three temperature shift times (108 hr, 120 hr and 132 hr) were tested, and samples from all conditions were harvested at 240±4 hour and 264±4 hour. One-step purification (Protein A) was applied prior to analytical analysis.

Figure 13:
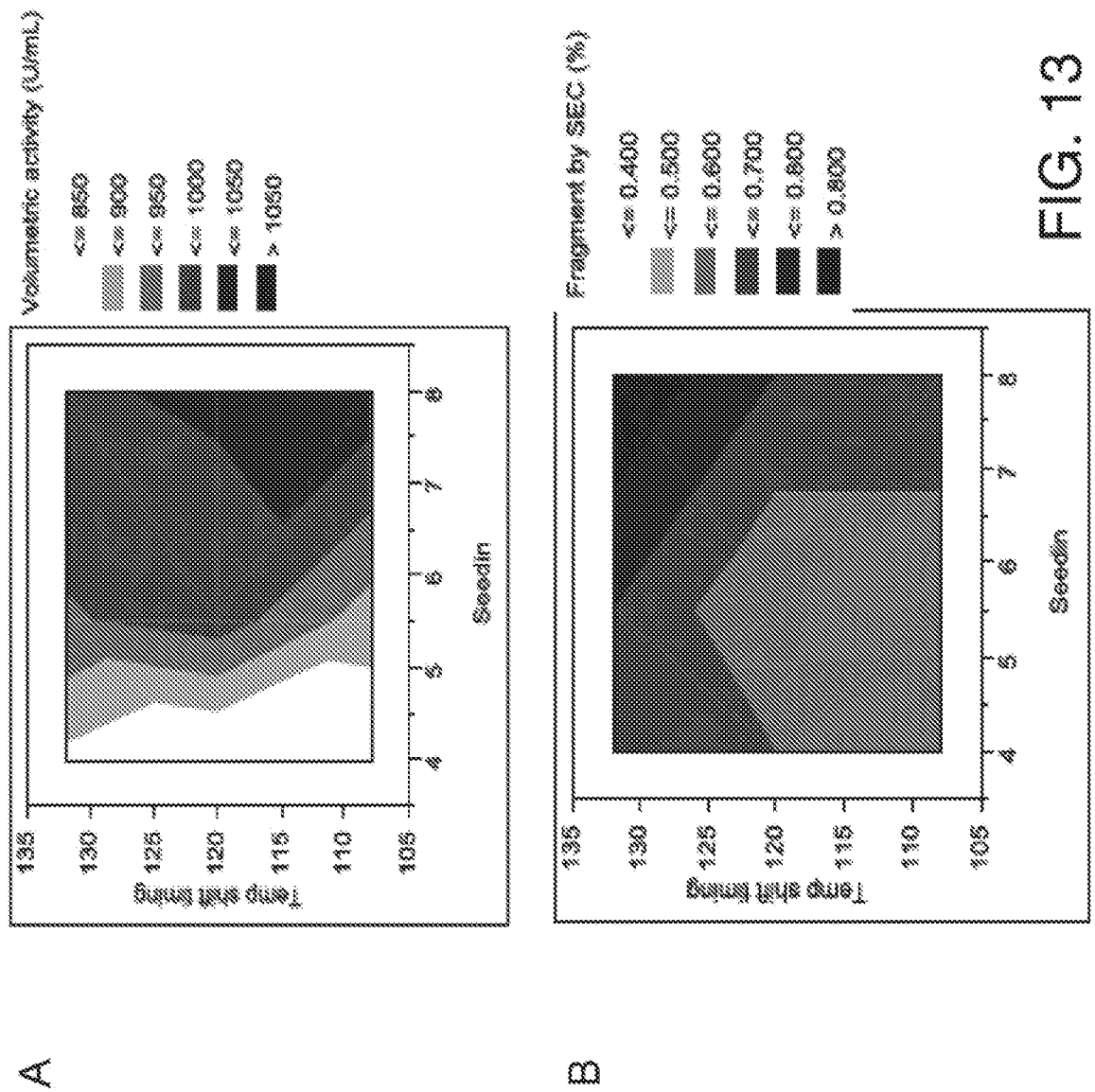
FIG. 13 are graphs showing the impact of seeding density and temperature shift timing on volumetric activity (panel A) and asfotase alfa fragmentation (panel B, measured by SEC). Seeding stands for seeding density in exemplary Process #3.

Temperature shift timing has a subtle impact on volumetric activity (FIG. 13A). At high seeding density, delaying temperature shift timing from 108 hr to 132 hr seems to decrease the volumetric activity. However, at lower seeding density, maximum volumetric activity is observed under the later temperature shift condition.

In terms of asfotase alfa quality, temperature shift timing was shown to only significantly impact fragmentation, as measured by SEC (FIG. 13B). Under the latest temperature shift condition (132 hr), the average fragment level was 0.8%, close to the small scale experimental range for fragmentation (<1.0%). Therefore, a narrower temperature shift time window is probably beneficial to reduce the risk of fragmentation.

As the impact on CQAs by temperature shift timing was all within the experimental range (Table 9 and Table 11), temperature shift timing ranging from 108 hr to 132 hr is unlikely to be a CPP.

In various embodiments, alkaline phosphatase (e.g., asfotase alfa) is produced by a process in which a temperature shifting occurs at about 100 hr, 105 hr, 108 hr, 110 hr, 115 hr, 120 hr, 125 hr, 130 hr, 132 hr, 135 hr, 140 hr, 145 hr, or 150 hr post the starting point of growth (e.g., inoculation). In one particular embodiment, alkaline phosphatase (e.g., asfotase alfa) is produced by a process in which a temperature shifting occurs at about 108 hr, 120 hr or 132 hr. In various embodiments, alkaline phosphatase (e.g., asfotase alfa) is harvested at a time point of about 200 hr, 210 hr, 220 hr, 230 hr, 240 hr, 250 hr, 260 hr, 264 hr, 270 hr, 280 hr, 288 hr (i.e., 12 days), or more than 12 days. In one particular embodiment, alkaline phosphatase (e.g., asfotase alfa) is harvested at a time point of about 240, 264, or 288 hr.

4. Medium Feed

Previous results indicated that medium feed addition impacts sialylation. As a control for this exemplary process, three boluses of medium were added to the production bioreactor on day 4, day 6, and day 8, and the total amount was equivalent to 8% (v/v) of the initial culture volume. With the number of boluses unchanged, three feed amounts were tested: 67%, 100% (the control), and 133%. In terms of bolus addition timing, three strategies were investigated: (1) day 3, day 5, and day 7; (2) day 4, day 6, and day 8 (the control); (3) day 5, day 7, and day 9. All bioreactors were conducted in 2 L bioreactors, and samples from all conditions were harvested at 240±4 hours and 264±4 hours. One-step purification (Protein A) was applied prior to analytical analysis.

Figures 14A, 14B:
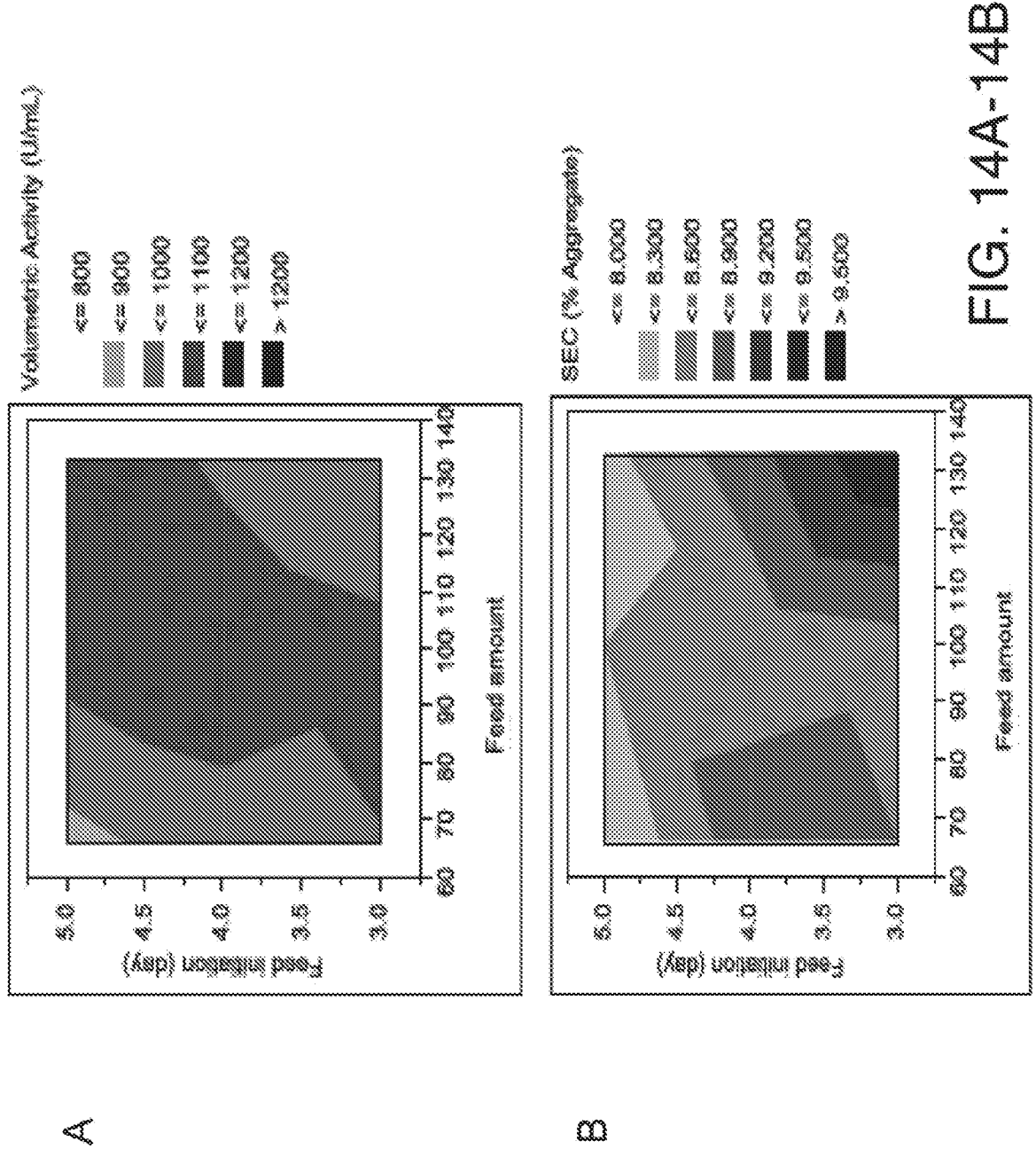
FIG. 14 are graphs showing the impact of medium feed (amount and timing) on asfotase alfa volumetric activity (panel A), aggregation (panel B, measured by SEC), % acidic peak (panel C, measured by AEX), % basic peak (panel D, measured by AEX), and TSAC (panel E) in exemplary Process #3.
Figures 14C, 14D, 14E:
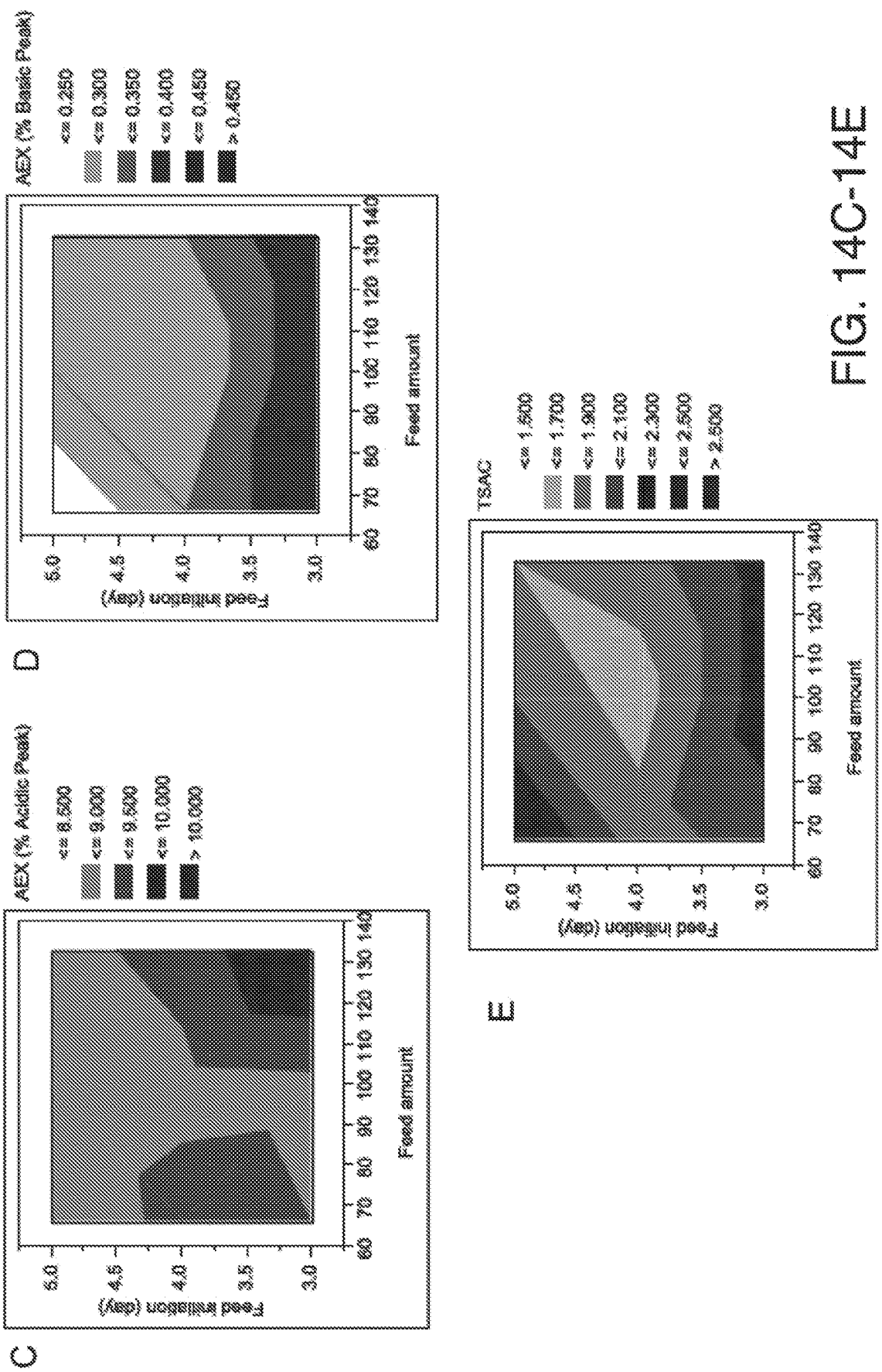

Though medium feed amount and initiation timing did not directly impact productivity, their interaction seemed to have a subtle impact on volumetric activity (FIG. 14A). Under the control condition, maximum volumetric activity was achieved. When 33% less feed was provided, delaying feed initiation resulted in lower volumetric activity.

The elevated acidic peak (10.1%) and aggregation (9.5%) observed under more (133%) and earlier (first bolus on day 3) feed condition is close to the small scale experimental range (10.2% for acidic peak, and 9.6% for aggregation, Table 9), indicating that at least one parameter needs to be controlled tighter at scales, e.g., 15% variation of the medium feed amount per bolus, and/or relatively short addition time window (96±3 hr, 144±3 hr, and 192±3 hr). As the impact on CQAs by medium feed addition was all within the experimental range (Table 9 and Table 11), medium feed amount ranging from 67% to 133% and feed timing (96±24 hr, 144±24 hr, and 192±24 hr) is unlikely to be a CPP.

In various embodiments, alkaline phosphatase (e.g., asfotase alfa) is produced by a process in which extra boluses of culture medium are added to the production bioreactor. For example, one, two, three, four, five, six, or more boluses of culture medium may be added. In one particular embodiment, three boluses of culture medium are added. In various embodiments, such extra boluses of culture medium may be added in various amounts. For example, such boluses of culture medium may be added in an amount of about 20%, 25%, 30%, 33%, 40%, 45%, 50%, 60%, 67%, 70%, 75%, 80%, 90%, 100%, 110%, 120%, 125%, 130%, 133%, 140%, 150%, 160%, 167%, 170%, 175%, 180%, 190%, 200%, or more, of the original volume of culture medium in the production bioreactor. In one particular embodiment, such boluses of culture medium may be added in an amount of about 33%, 67%, 100%, or 133% of the original volume. In various embodiments, such addition of extra boluses may occur at various times during the cell growth or protein production period. For example, boluses may be added at day 1, day 2, day 3, day 4, day 5, day 6, day 7, day 8, day 9, day 10, day 11, day 12, or later in the process. In one particular embodiment, such boluses of culture medium may be added in every other day (e.g., at (1) day 3, day 5, and day 7; (2) day 4, day 6, and day 8; or (3) day 5, day 7, and day 9. In practice, the frequency, amount, time point, and other parameters of bolus supplements of culture medium may be combined freely according to the above limitation and determined by experimental practice.

5. Seeding Density

In this study, the impact of seeding density on CQA was investigated together with temperature shift timing in 2 L bioreactors. Three seeding densities ($4.0 \times 10^5$ cells/mL, $5.5 \times 10^5$ cells/mL and $8.0 \times 10^5$ cells/mL) were tested, and samples from all conditions were harvested at 240±4 hour, and 264±4 hour. One-step purification (Protein A) was applied prior to analytical analysis.

Temperature shift timing has a very strong impact on productivity. As shown in FIG. 13A, increasing the seeding density from $4.0 \times 10^5$ cells/mL to $8.0 \times 10^5$ cells/mL led to a volumetric activity increase from 806 U/mL to 1012 U/mL on average.

In terms of asfotase alfa quality, seeding density was only shown to significantly impact fragmentation, as measured by SEC (FIG. 13B). Under the highest seeding density condition ($8.0 \times 10^5$ cells/mL), the average fragment level was 0.8%, close to the small-scale experimental range for fragmentation (<1.0%). Therefore, a tighter seeding density range may be beneficial in order to reduce the risk of fragment generation at scales.

As the impact on CQAs by seeding density was all within the experimental range (Table 9 and Table 11), a seeding density ranging from $4.0 \times 10^5$ cells/mL to $8.0 \times 10^5$ cells/mL is unlikely to be a CPP. In various embodiments, alkaline phosphatase (e.g., asfotase alfa) is produced by a process in which cells are seeded in a density of about $1.0 \times 10^5$ cells/mL, $1.5 \times 10^5$ cells/mL, $2.0 \times 10^5$ cells/mL, $2.5 \times 10^5$ cells/mL, $3.0 \times 10^5$ cells/mL, $3.5 \times 10^5$ cells/mL, $4.0 \times 10^5$ cells/mL, $4.5 \times 10^5$ cells/mL, $5.0 \times 10^5$ cells/mL, $5.5 \times 10^5$ cells/mL, $6.0 \times 10^5$ cells/mL, $6.5 \times 10^5$ cells/mL, $7.0 \times 10^5$ cells/mL, $7.5 \times 10^5$ cells/mL, $8.0 \times 10^5$ cells/mL, $8.5 \times 10^5$ cells/mL, $9.0 \times 10^5$ cells/mL, $9.5 \times 10^5$ cells/mL, $1.0 \times 10^6$ cells/mL, $1.5 \times 10^6$ cells/mL, $2.0 \times 10^6$ cells/mL, or a higher density. In one particular embodiment, in such process cells are seeded in a density of about $4.0 \times 10^5$ cells/mL, $5.5 \times 10^5$ cells/mL or $8.0 \times 10^5$ cells/mL.

6. Harvest Timing

Prior data indicated that delaying harvest timing was associated with a viability and TSAC decline, so harvest timing can have a potential impact on other CQAs. In all process characterization studies, samples were harvested from day 10 (240±4 hr) and day 11 (264±4 hr) from all bioreactors. Ten 2 L bioreactors served as the control condition in multiple blocks of the process characterization study. As all were performed under the same conditions with current process parameter settings, they allowed for the investigation of harvest timing on asfotase alfa productivity and quality. The analytical result from those ten 2 L bioreactors is listed in Table 12. It is noted that samples from two bioreactors (#18 and #19) were purified by a two-step purification (ProA+HIC), while those from the other eight bioreactors (#10-#17) were purified only by ProA. It should be noted that HIC is able to increase sample purity without impacting TSAC.

TABLE 12

Analytical Result from Exemplary 2 L Bioreactor Batches

| # | Harvest (Day) | AEX (%) Basic | Main | Acidic | SEC (%) Aggregate | Main | Fragment | TSAC | Purification |
|---|---|---|---|---|---|---|---|---|---|
| 10 | 10 | 0.2 | 90.8 | 9.1 | 8.0 | 91.6 | 0.4 | 2.1 | ProA |
| 10 | 11 | 0.4 | 90.1 | 9.5 | 8.4 | 91.2 | 0.5 | 1.7 | |
| 11 | 10 | 0.3 | 90.7 | 9.0 | 7.5 | 92.0 | 0.6 | 2.3 | |
| 11 | 11 | 0.3 | 90.4 | 9.3 | 7.7 | 91.5 | 0.8 | 1.8 | |
| 12 | 10 | 0.2 | 90.9 | 8.9 | 8.5 | 91.2 | 0.3 | 1.7 | |
| 12 | 11 | 0.4 | 90.4 | 9.3 | 8.8 | 90.8 | 0.4 | 1.4 | |
| 13 | 10 | 0.3 | 90.9 | 8.8 | 8.3 | 91.2 | 0.5 | 1.5 | |
| 13 | 11 | 0.4 | 90.3 | 9.3 | 8.6 | 90.8 | 0.6 | 1.4 | |
| 14 | 10 | 0.5 | 91.0 | 8.6 | 8.0 | 91.5 | 0.5 | 2.2 | |
| 14 | 11 | 0.4 | 91.6 | 8.0 | 7.2 | 92.3 | 0.5 | 2.1 | |
| 15 | 10 | 0.5 | 91.0 | 8.5 | 7.9 | 91.6 | 0.5 | 2.5 | |
| 15 | 11 | 0.5 | 92.1 | 7.4 | 6.6 | 92.9 | 0.5 | 2.4 | |
| 16 | 10 | 0.3 | 94.3 | 5.4 | 9.1 | 90.7 | 0.2 | 2.1 | |
| 16 | 11 | 0.4 | 90.3 | 9.3 | 9.2 | 90.6 | 0.3 | 2.0 | |
| 17 | 10 | 0.4 | 91.0 | 8.7 | 8.9 | 90.8 | 0.3 | 2.3 | |
| 17 | 11 | 0.4 | 90.3 | 9.4 | 8.9 | 90.8 | 0.4 | 2.4 | |
| 18 | 10 | 0.5 | 93.4 | 6.1 | 5.9 | 94.1 | 0.0 | 2.5 | ProA + HIC |
| 18 | 11 | 0.5 | 92.8 | 6.6 | 6.3 | 93.6 | 0.0 | 1.5 | |
| 19 | 10 | 0.4 | 93.7 | 5.9 | 5.8 | 94.2 | 0.0 | 1.8 | |
| 19 | 11 | 0.5 | 92.5 | 7.1 | 6.7 | 93.3 | 0.0 | 1.6 | |

In each individual study, harvest timing was treated as the third parameter for statistical analysis. As shown in each individual study, delaying harvest from day 10 to day 11 led to approximately 10-15% increased protein A titer and volumetric activity.

A significant impact of harvesting timing on TSAC was observed in all five individual studies. Delaying harvest by one day resulted in a TSAC drop of approximately 0.3-0.4 moles of sialic acid per mole of protein on average, although TSAC on both conditions were still within the small-scale experimental range (1.5-2.9) as specified in Table 9. Due to the significant impact of harvest timing on TSAC, early harvest could be performed to increase TSAC.

As for aggregation, as measured by SEC, and acidic peak, as measured by AEX, harvest timing was shown to have statistically significant impact in three out of five studies (Table 13).

However, the magnitude of the impact on either CQA was marginal, less than 1% as compared to the control conditions in each individual study. In addition, all values fell in the small-scale experimental ranges that are specified in Table 9 (≤9.6% for aggregates and ≤10.2% for acidic peak).

The fragment level was impacted by harvest timing in one out of five studies (shown in Table 13). However, delaying harvest by one day resulted in elevated fragment by only 0.1-0.2% under two control conditions, and the fragment level on day 11 was still below the LoQ (1%) of SEC assay. Similarly, the basic peak level was elevated from 0.2-0.3% on day 10 to 0.4% on day 11 with a p-value of 0.03 (Table 13). However, both values were still far below the LoQ (1%) of the AEX assay. Therefore, harvest timing, ranging from day 10 (240±4 hr) to day 11 (264±4 hr), is unlikely to be a CPP.

TABLE 13

Impact of Harvest Timing on CQA from Individual Studies

| p-value for harvest timing | TSAC | SEC | | AEX | |
| --- | --- | --- | --- | --- | --- |
| | | Aggregate | Fragment | Basic | Acidic |
| Reference 1 | 0.00 | 0.84 | — | 0.55 | 0.61 |
| Reference 2 | 0.02 | 0.00 | 0.37 | 0.13 | 0.01 |
| Reference 3 | 0.02 | 0.21 | 0.34 | 0.64 | 0.00 |
| Reference 4 | 0.00 | 0.00 | 0.21 | 0.03 | 0.00 |
| Reference 5 | 0.01 | 0.01 | 0.00 | 0.33 | 0.43 |

Conclusion

Tested process parameters in this study include the culture pH set point, temperature, seeding density, medium feed amount and timing, glucose addition, galactose addition, and harvest timing. Table 14 summarizes each used process parameters.

TABLE 14

Summary of Process Parameters

| Process parameter | Tested ranges |
| --- | --- |
| pH set point | 6.75-7.10 |
| Growth temperature (° C.) | 35.0-37.5 |
| Production temperature (° C.) | 30.0-35.0 |
| Temperature shift timing (hr) | 108-132 |
| Medium feed amount (%) | 67-133 |
| Medium feed initiation | day 3-day 5 |
| Seeding density (cells/mL) | 4.0-8.0 × $10^5$ |
| Harvest timing (day) | day 10-day 11 |

Example 5. Higher Resolution Investigation of the Impact of pH and Production Temperature on Asfotase Alfa Quality Attributes for Exemplary Process #4

Further to previous assessments, this study provides a higher-resolution examination of the impact of culture pH and production temperature (≥120 hr) on asfotase alfa productivity and quality attributes in an exemplary manufacturing process. Tested scenarios include: 1) different pH levels (i.e., 6.70, 6.80, 6.90, 7.00, and 7.10) and a same production temperature of 33.0° C.; and 2) different production temperature levels (i.e., 31.0° C., 32.0° C., 33.0° C., 34.0° C., and 35.0° C.) and a same pH set point of 6.90. Samples from all conditions were harvested at 240±4 hours, and protein A-purified materials were tested for several quality attributes (e.g., percent fragmentation, percent aggregation, charge distribution, total sialic acid content (TSAC), and neutral glycan coverage. This study confirmed that the process run at a pH set point ranging from 6.70 to 7.10 and a production temperature ranging from 31.0° C. to 35.0° C. maintained all CQAs.

Cell Culture

All experiments conducted in this study used the Mobius 3 L disposable bioreactors (CR0003L200; EMD Millipore). A list of process parameters used in this study in presented in Table 15. Further, four additional culture pH conditions were examined with the control production temperature (33.0° C.) and four additional temperatures were examined with the control culture pH (6.90) (Table 16).

TABLE 15

Cell Culture Process Parameters for the Exemplary Process #4

| Process Condition | Set point |
| --- | --- |
| Initial Working Volume | 1.6 L |
| Temperature | 36.5° C. (0-120 hr); 33.0° C. (120-240 hr) |
| pH | 6.90 ± 0.05 |
| DO | 30% |
| Glucose Addition | If [glc] ≤1.8 g/L, bolus addition daily to increase glucose concentration to 1.8-2.0 g/L |
| Medium with galactose | 2.7% (v/v) bolus addition at 96, 144, 192 hr |
| $CuSO_4$ addition | 20 µM at 24 hr |

TABLE 16

Tested conditions

| No. | Culture pH | Production Temperature |
| --- | --- | --- |
| 1 | 6.70 | 33.0° C. |
| 2 | 6.80 | 33.0° C. |
| 3 | 6.90 | 33.0° C. |
| 4 | 7.00 | 33.0° C. |
| 5 | 7.10 | 33.0° C. |
| 6 | 6.90 | 31.0° C. |
| 7 | 6.90 | 32.0° C. |
| 8 | 6.90 | 35.0° C. |
| 9 | 6.90 | 34.0° C. |
| 10 | 6.90 | 33.0° C. |

Cell density and viability were counted using a ViCell VR. pH and off-line gases were measured using a pHOx, and major metabolites including glucose and lactate were measured using a Nova Profile 100 (Nova Biomedical, Waltham, Mass.). Enzymatic activity was measured using standard methods with the modification that each sample was diluted only once, instead of three times, prior to enzymatic activity measurement.

Harvest and Purification

Fifty microliters of day 10 (240±4 hours) samples were harvested from all bioreactors using syringes. Post cell removal by centrifugation (3000×g, 5 min), supernatants were clarified using 0.22 µM bottle-top filters, and stored at −80° C. prior to purification. A single step of high-throughput plate-based purification (protein A) was applied in this study. Samples were buffer exchanged to a low salt buffer (5 mM $Na_3PO_4$, pH 7.4) prior to analytical and protein characterization analysis.

Analytical and Protein Characterization

Critical quality attributes analyzed in this study included percent aggregate, percent fragment, charge distribution, TSAC, and neutral glycan distribution. The aggregate level was estimated by the percentage of aggregate peaks to the total protein quantified in SEC. The fragment level was estimated by the percentage of fragment to the total protein quantified in SEC, as well as in LoC. The charge distribution was estimated by the percentage of the basic peaks, main peak and acid peak to the total protein, respectively, quantified by AEX. Sialylation level (or TSAC) was quantified by HPAE-PAD. Detection of neutral glycan species was performed by MALDI-TOF mass spectrometry. Isoelectric focusing was performed using an iCE280 system.

Results

Cell Culture Performance

Figure 15:
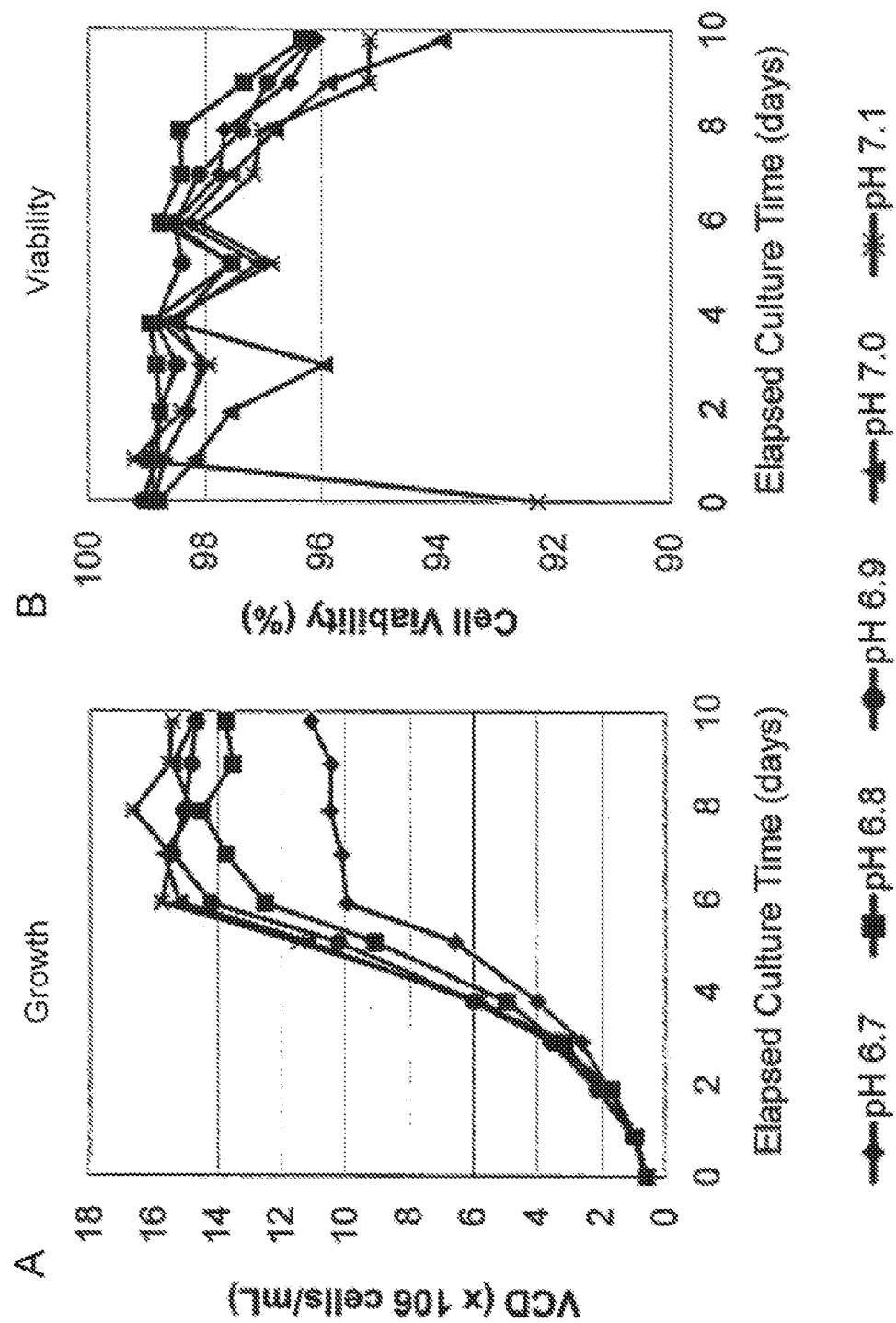
FIG. 15 are graphs showing the impact of culture medium pH on cell growth (panel A) and viability (panel B) up to ten days in exemplary Process #4.

As noted, both culture pH and production temperature have an impact on cell culture performance. The low pH condition (pH=6.70) resulted in the lowest growth rate and lowest maximum VCD, reaching a maximum density of $11.1 \times 10^6$ cells/mL (FIG. 15A) on the day of harvest (day 10). Higher pH conditions (pH=7.00 and 7.10) resulted in 1-2% lower viability than the other conditions on day 10 (FIG. 15B).

Figure 16:
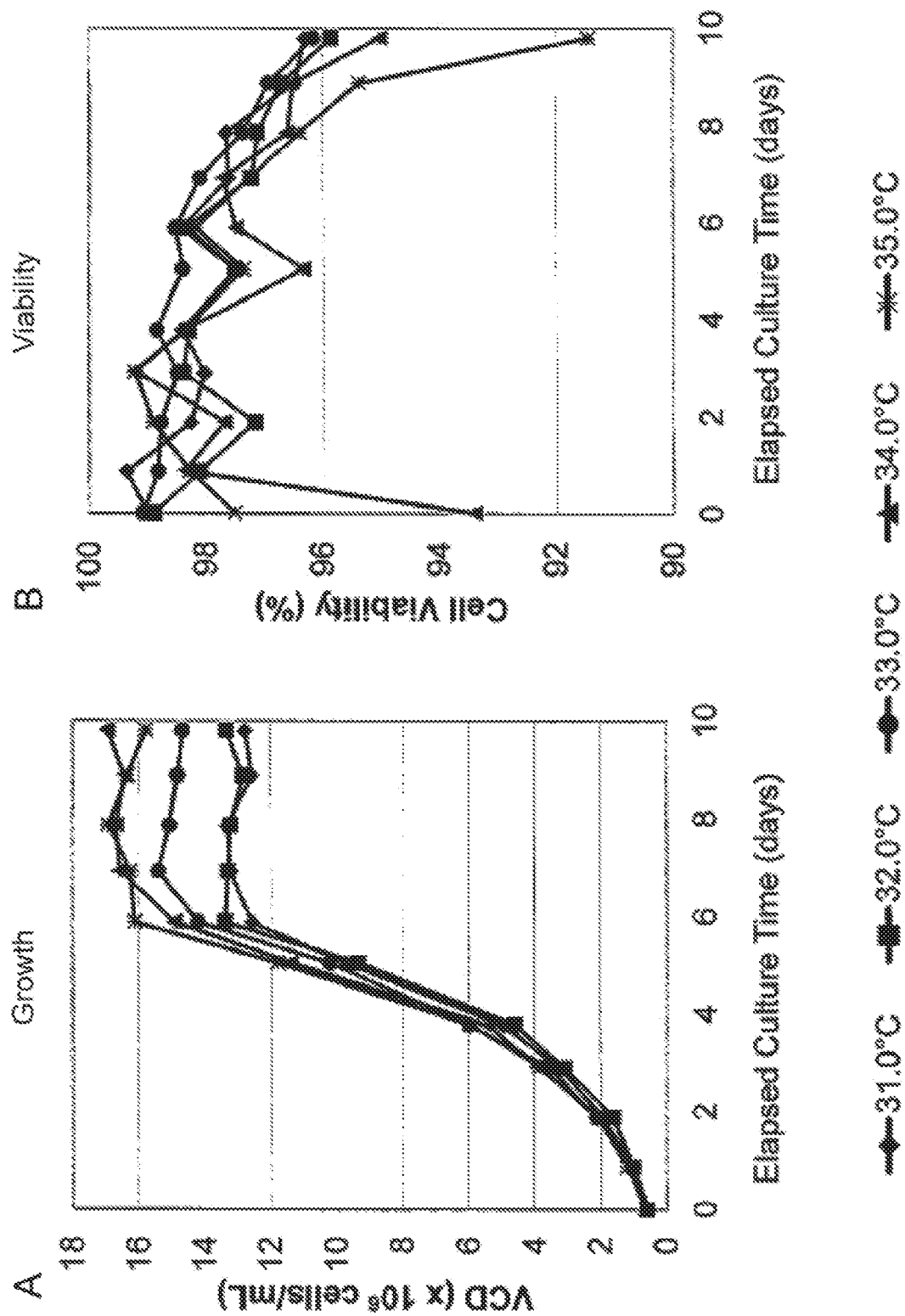
FIG. 16 are graphs showing the impact of production temperature on cell growth (panel A) and viability (panel B) up to ten days in exemplary Process #4.

Higher production temperatures were also associated with increased growth (FIG. 16A) and more rapid declines in viability towards the end of the culture (FIG. 16B). Lower production temperature produced a lower peak VCD but produced comparable viability to the control set point of 33.0° C.

Increasing the culture pH also caused much more rapid consumption of glucose (FIG. 17A) and caused both a greater production of lactate during the early stages of the culture (prior to the temperature shift) and a greater overall accumulation of lactate throughout the culture duration (FIG. 17B).

Figure 18:
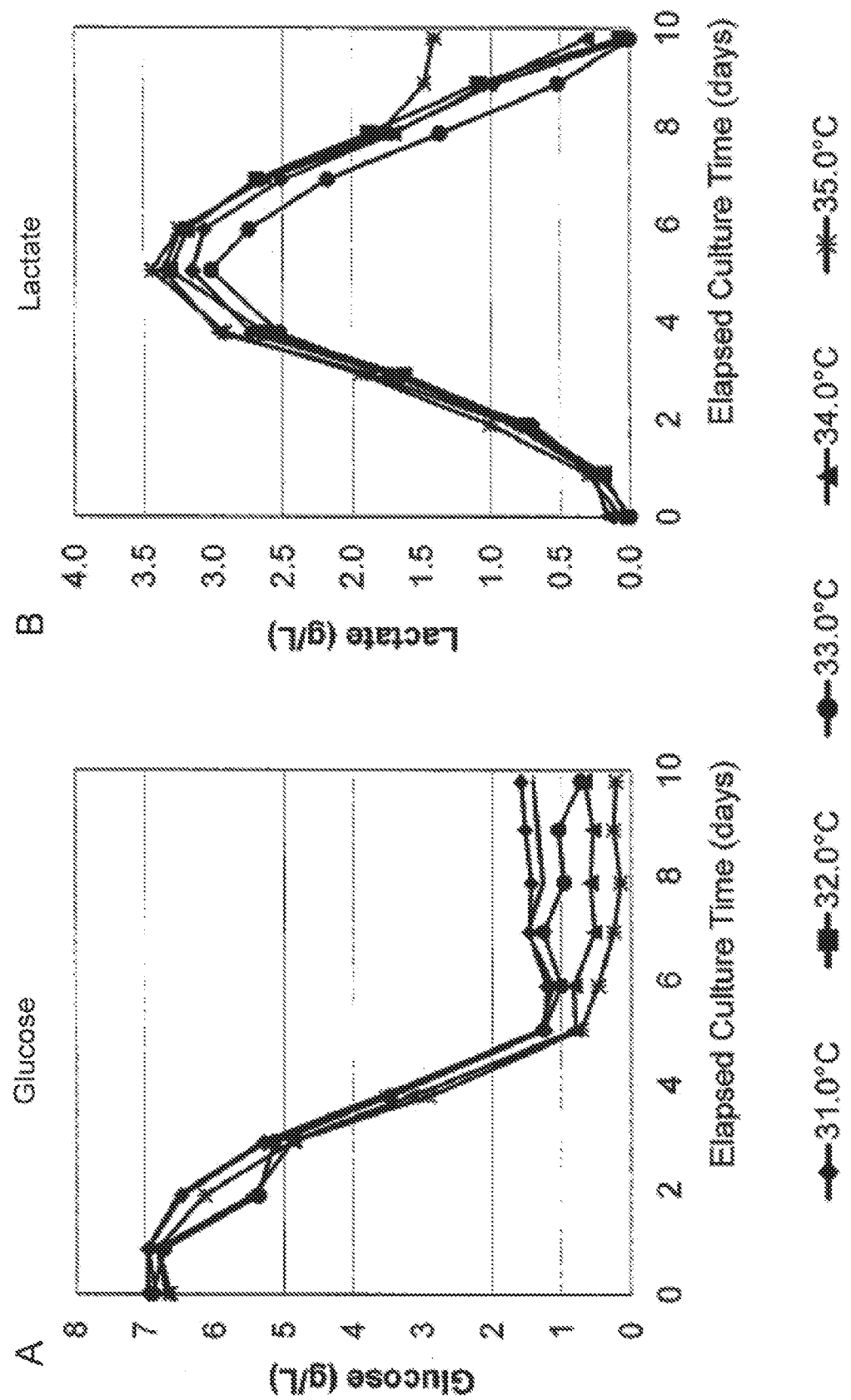
FIG. 18 are graphs showing the impact of production temperature on glucose (panel A) and lactate (panel B) concentrations in culture medium up to ten days in exemplary Process #4.

Culture cells were grown for five days (120 hr) prior to shifting grown temperature to production temperature. Both the glucose and lactate profiles were very consistent between day 0 and day 5 (FIG. 18A and FIG. 18B). After the temperature shift, higher production temperatures were associated with higher consumption of glucose. A slight decrease in the maximum concentration of lactate was observed for the 33.0° C. production temperature condition, as compared to the other conditions. Additionally, a 35.0° C. production temperature showed significantly decreased lactate consumption during days 9 and 10 of the culture, as compared to all other conditions.

Figure 19:
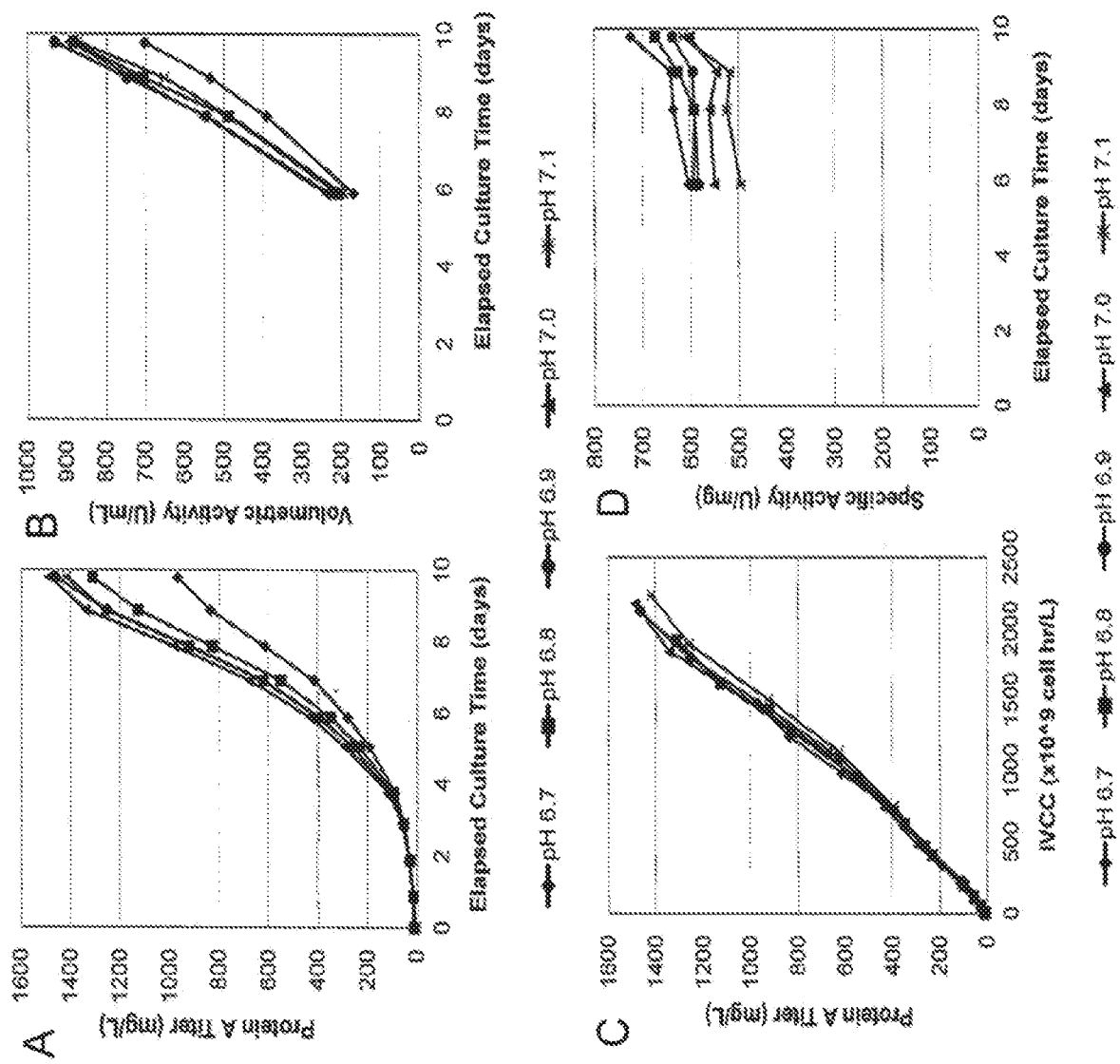
FIG. 19 are graphs showing the impact of culture medium pH on protein A titer (panel A), volumetric activity (panel B), specific protein A productivity (panel C), and specific activity (panel D) up to ten days in exemplary Process #4.

It was previously observed that production temperature had a more dramatic effect than culture pH on both protein A titer and specific activity for the range of production temperatures between 30.0° C. and 35.0° C. and a culture pH between 6.75 and 7.10. However, the low pH condition in this study (6.70) appeared to have had a dramatic impact on the protein A titer producing a 35% decline as compared to the control condition (pH=6.90) (FIG. 19A) and a much lower volumetric activity as compared to all other examined pH conditions (FIG. 19B). Culture pH did not appear to have an impact on specific protein A productivity (FIG. 19C). However, the low pH condition generated the highest specific activity (FIG. 19D), and a general trend between decreasing culture pH and increasing specific activity was observed.

Figure 20:
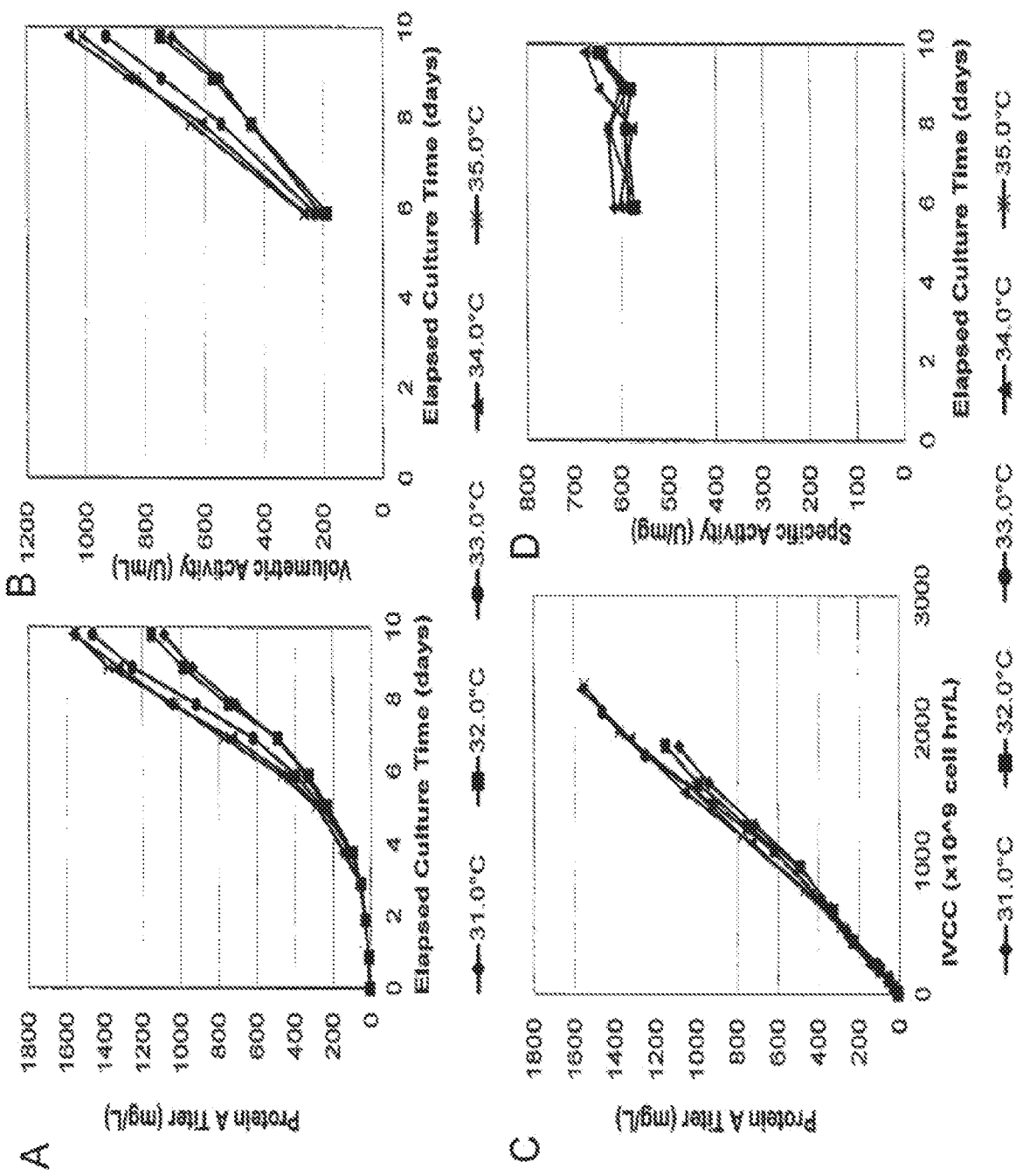
FIG. 20 are graphs showing the different impact of production temperature on protein A titer (panel A), volumetric activity (panel B), specific protein A productivity (panel C), and specific activity (panel D) in exemplary Process #4.

The low production temperature conditions (31.0° C. and 32.0° C.) caused a large decline (26% and 21% respectively) in protein A titer, as compared to the control conditions (FIG. 20A). Additionally, increased production temperature was associated with higher volumetric activity (FIG. 20B) and slightly increased specific protein A productivity (FIG. 20C). No impact was observed on specific activity from changing production temperatures (FIG. 20D).

All quality attributes from this study and the previous work examining the impact of culture pH and production temperature are summarized in Table 17.

TABLE 17

Quantified Quality Attributes for Varying pH and Production Temperature

| # | pH | Production Temp (° C.) | AEX (%) Basic | AEX (%) Main | AEX (%) Acidic | LoC (% Main, NR) | LoC (% Main, R) | SEC (%) Aggregate | SEC (%) Main | SEC (%) Frag | TSAC |
|---|------|------|-----|------|-----|------|-------|-----|------|-----|-----|
| 20 | 6.70 | 33.0 | 0.2 | 93.2 | 6.5 | 98.6 | 100.0 | 6.2 | 93.8 | 0 | 1.5 |
| 21 | 6.80 | 33.0 | 0.1 | 93.4 | 6.4 | 98.7 | 100.0 | 6.1 | 93.9 | 0 | 1.9 |
| 22 | 6.90 | 33.0 | 0.1 | 93.1 | 6.7 | 97.2 | 100.0 | 6.2 | 93.8 | 0 | 1.9 |
| 23 | 7.00 | 33.0 | 0.1 | 94.4 | 5.4 | 96.8 | 100.0 | 5.6 | 94.4 | 0 | 2.4 |
| 24 | 7.10 | 33.0 | 0.1 | 94.4 | 5.5 | 97.1 | 100.0 | 5.8 | 94.2 | 0 | 2.6 |
| 25 | 6.90 | 31.0 | 0.1 | 92.3 | 7.6 | 97.0 | 100.0 | 7.0 | 93.0 | 0 | 1.8 |
| 26 | 6.90 | 32.0 | 0.1 | 92.4 | 7.5 | 97.2 | 100.0 | 6.7 | 93.3 | 0 | 1.9 |
| 27 | 6.90 | 35.0 | 0.1 | 95.2 | 4.6 | 98.5 | 100.0 | 5.0 | 94.8 | 0.2 | 2.8 |
| 28 | 6.90 | 34.0 | 0.1 | 93.2 | 6.6 | 98.2 | 100.0 | 6.6 | 93.2 | 0.2 | 2.6 |
| 29 | 6.75 | 33.0 | 0.4 | 93.8 | 5.8 | 97.0 | 100.0 | 5.6 | 94.4 | 0 | 1.9 |
| 30 | 6.90 | 30.0 | 0.4 | 90.8 | 8.8 | 97.1 | 100.0 | 8.5 | 91.4 | 0 | 1.4 |
| 31 | 6.90 | 33.0 | 0.5 | 93.4 | 6.1 | 100.0 | 100.0 | 5.9 | 94.1 | 0 | 2.5 |
| 32 | 6.90 | 35.0 | 0.5 | 95.4 | 4.0 | 100.0 | 100.0 | 4.2 | 95.7 | 0.1 | 2.4 |
| 33 | 7.10 | 33.0 | 0.2 | 94.0 | 5.8 | 100.0 | 100.0 | 5.3 | 94.7 | 0 | 2.8 |

Figure 21:
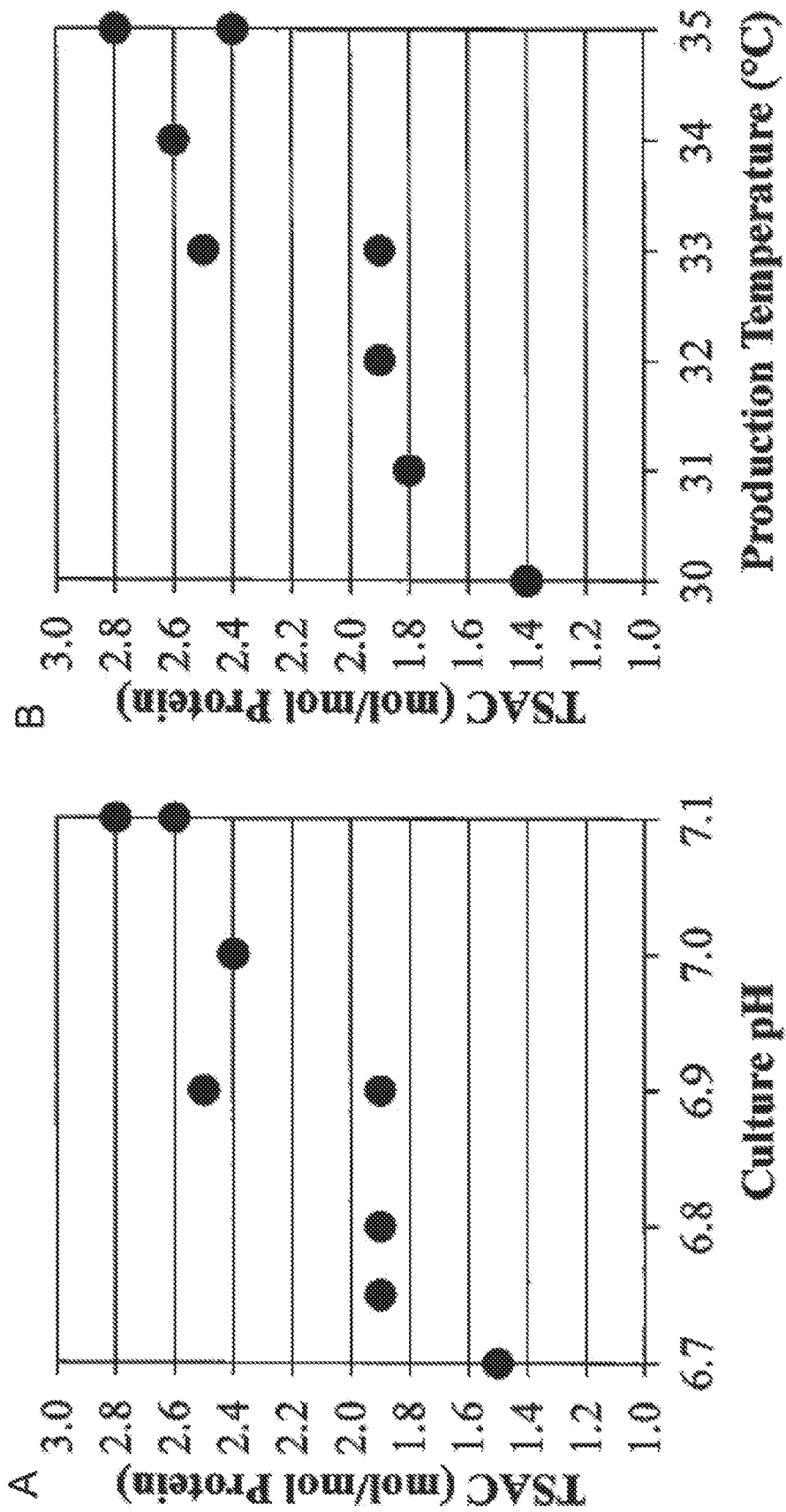
FIG. 21 are graphs showing the impact of culture medium pH (panel A) and production temperature (panel B) on asfotase alfa TSAC in exemplary Process #4.

As in previous studies, TSAC was affected by both culture pH and production temperature (FIG. 21). The small-scale experimental range for TSAC was 1.5-2.9, and higher TSAC was more desirable within this range. Increasing either culture pH or production temperature was shown to increase TSAC of the product. On one hand, increasing the culture pH set point from 6.70 to 7.10 led to a TSAC increase approximately from 1.5 to 2.6-2.8, which was in the small-scale experimental range. On the other hand, increasing production temperature from 30.0° C. to 35.0° C. led to a TSAC increase approximately from 1.4 to 2.6-2.8. As the TSAC value (1.4) under a production temperature of 30.0° C. was lower than the lower limit (1.5) of the small-scale experimental range, a production temperature of 30.0° C. should probably be avoided in the production bioreactor.

This data indicates that TSAC may be increased by increasing culture pH or production temperature, or both.

Figure 22:
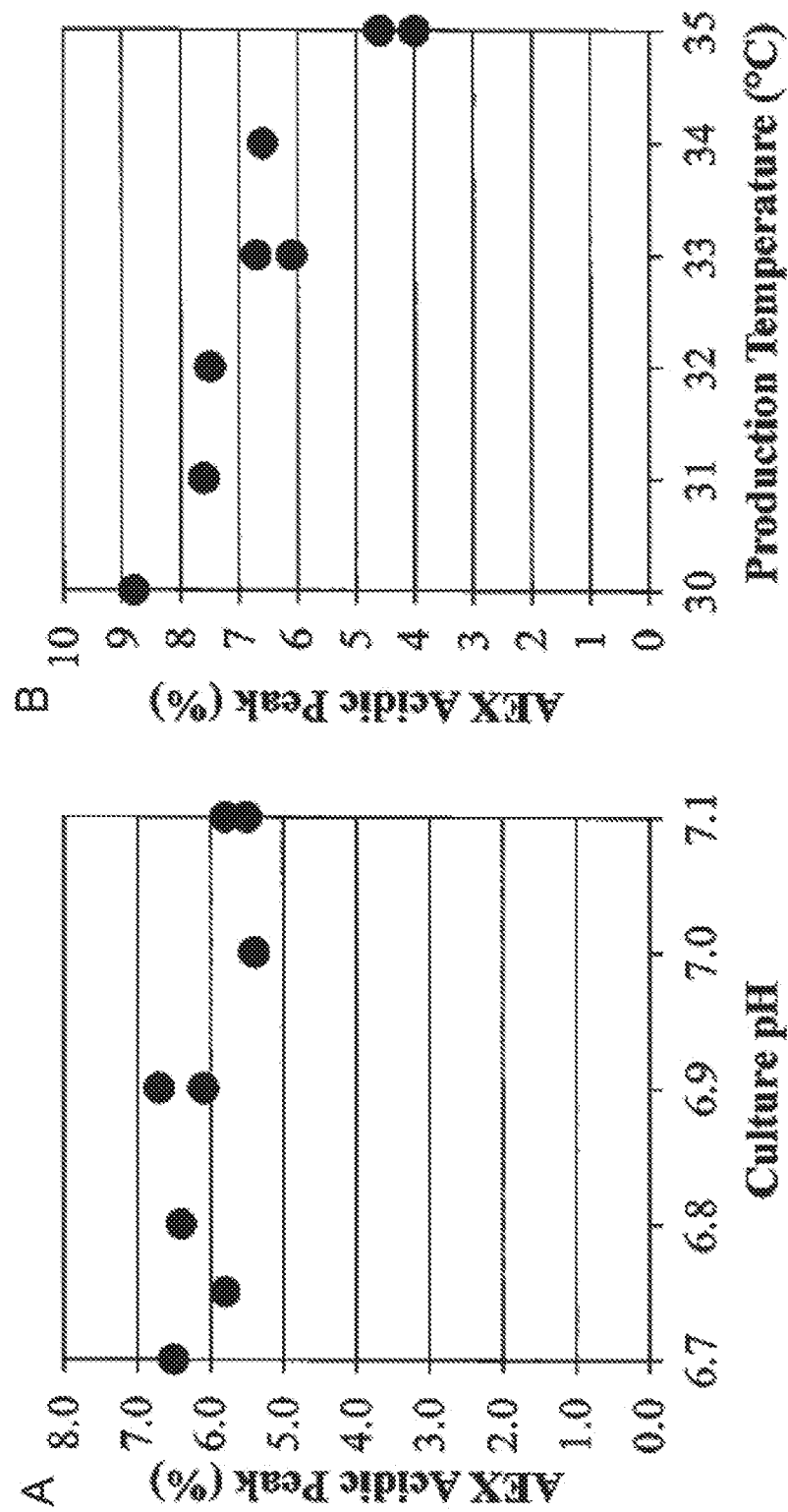
FIG. 22 are graphs showing the impact of culture medium pH (panel A) and production temperature (panel B) on AEX acidic peak of the produced asfotase alfa in exemplary Process #4.

The impurity level, as presently measured by the acidic peak percentage using AEX, is presented in FIG. 22. Increasing production temperature decreased the acidic peak percentage in the product. Culture pH did not appear to have any correlation with the impurity measured by AEX acidic peak. Although production temperature demonstrated an impact on AEX acidic peak percentage, all values were within acceptable limits for purification (≤10.2%). The AEX basic peak was consistently below 1%, the LoQ for the assay, for all conditions examined.

Figure 23:
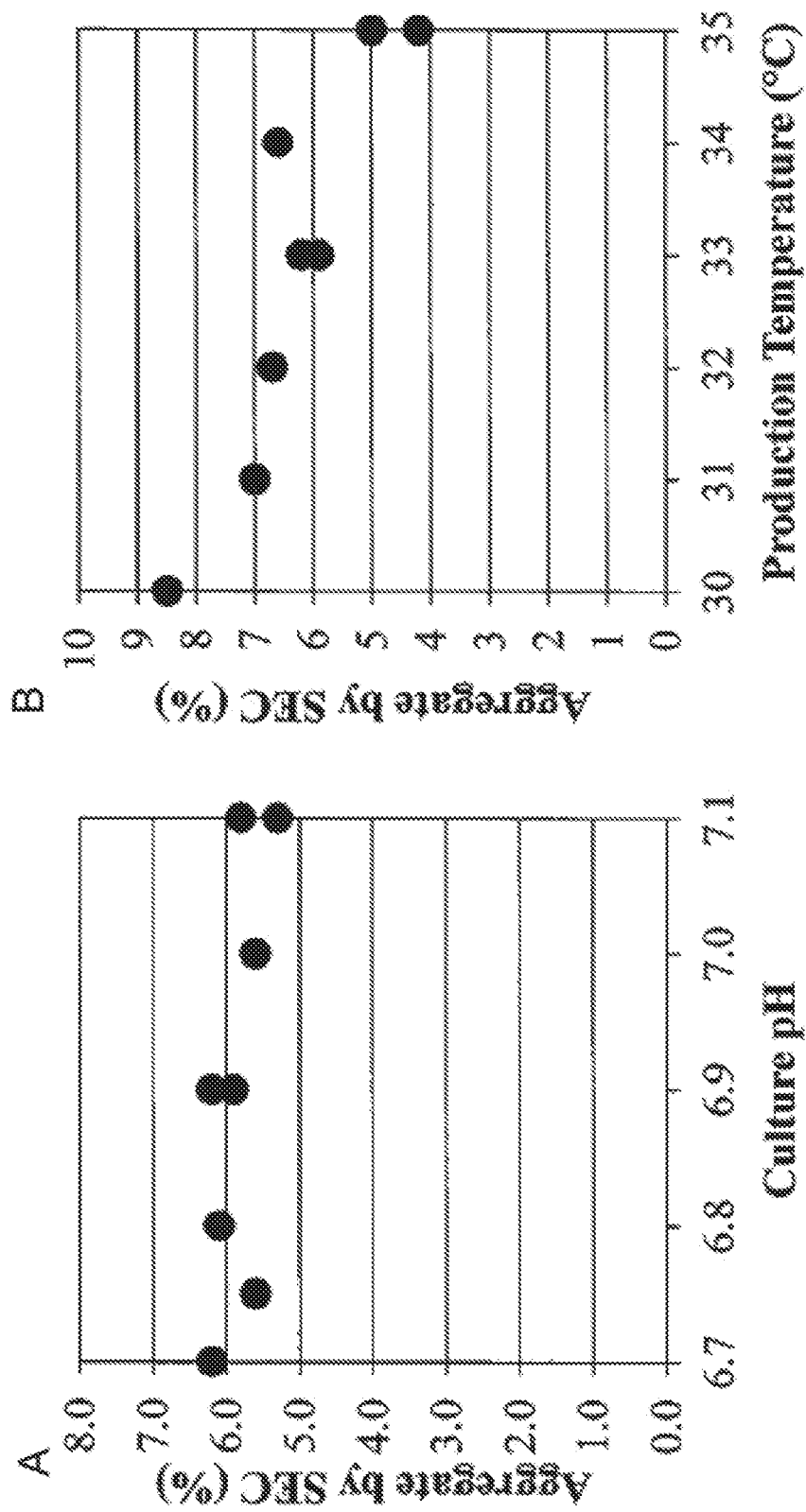
FIG. 23 are graphs showing the impact of culture medium pH (panel A) and production temperature (panel B) on asfotase alfa aggregation (measured by SEC) in exemplary Process #4.

A previous study showed a strong correlation between AEX acidic peak and aggregate percentage, as measured by SEC. This trend was maintained for this study, as shown in FIG. 23. Higher production temperature led to a lower aggregate percentage. All aggregate percentages were within the small-scale experimental range (≤9.6%). Culture pH does not have a strong effect on the aggregate percentage. Asfotase alfa fragments as measured by SEC were below 1%, the LoQ for the assay, for all conditions.

Figure 24:
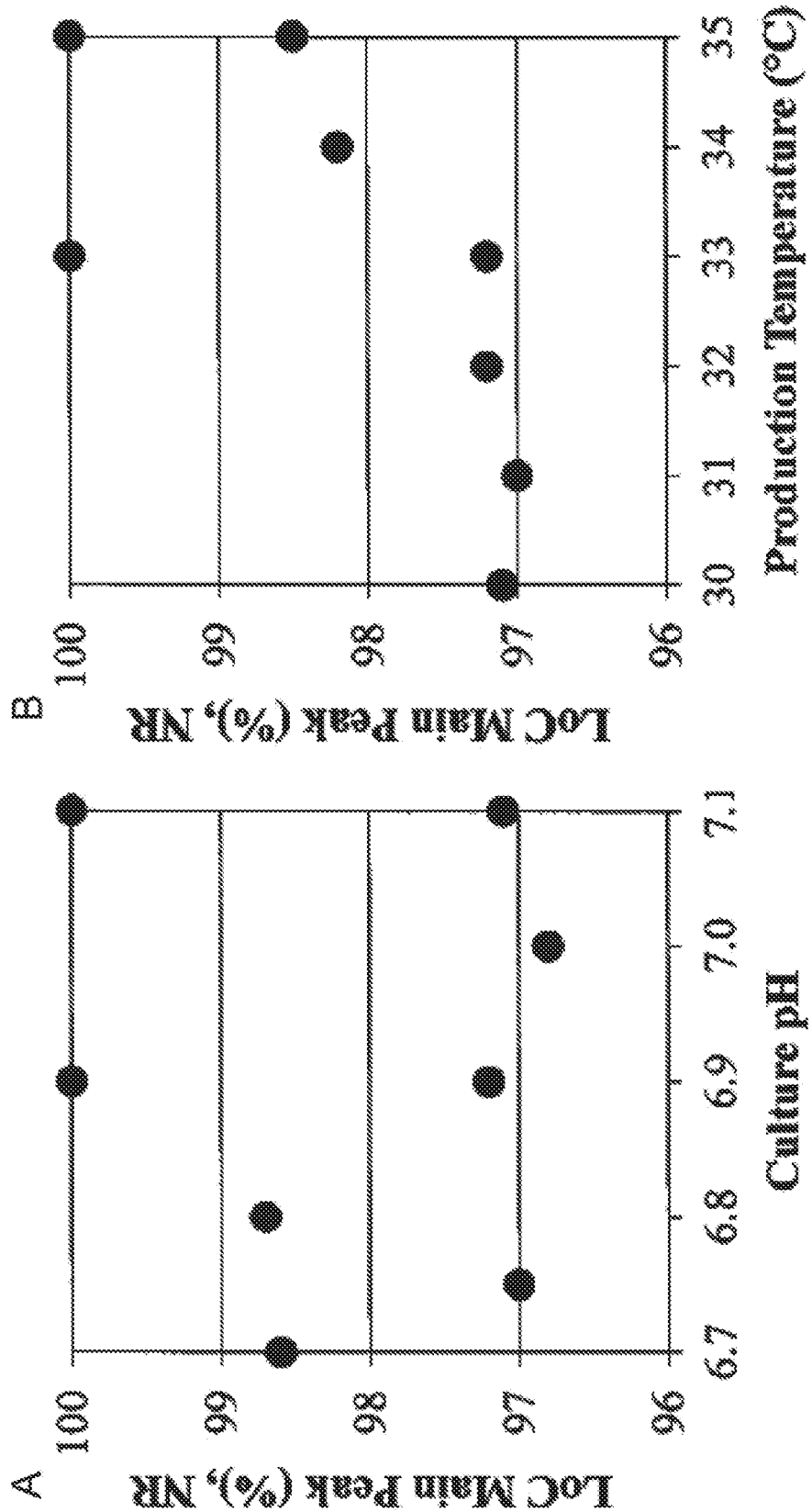
FIG. 24 are graphs showing the different impact of culture medium pH (panel A) and production temperature (panel B) on LoC main Peak (%, non-reduced condition) measurement of produced asfotase alfa in exemplary Process #4.

The main peak percentage measured by LoC was previously identified to be significantly impacted by production temperature. A positive correlation between increasing production temperature and non-reduced main peak percentage was discovered (FIG. 24B). No clear impact of culture pH on LoC main peak percentage (non-reduced) was found (FIG. 24A). The reduced LoC analysis identified 100% main peak for all conditions.

Figure 25:
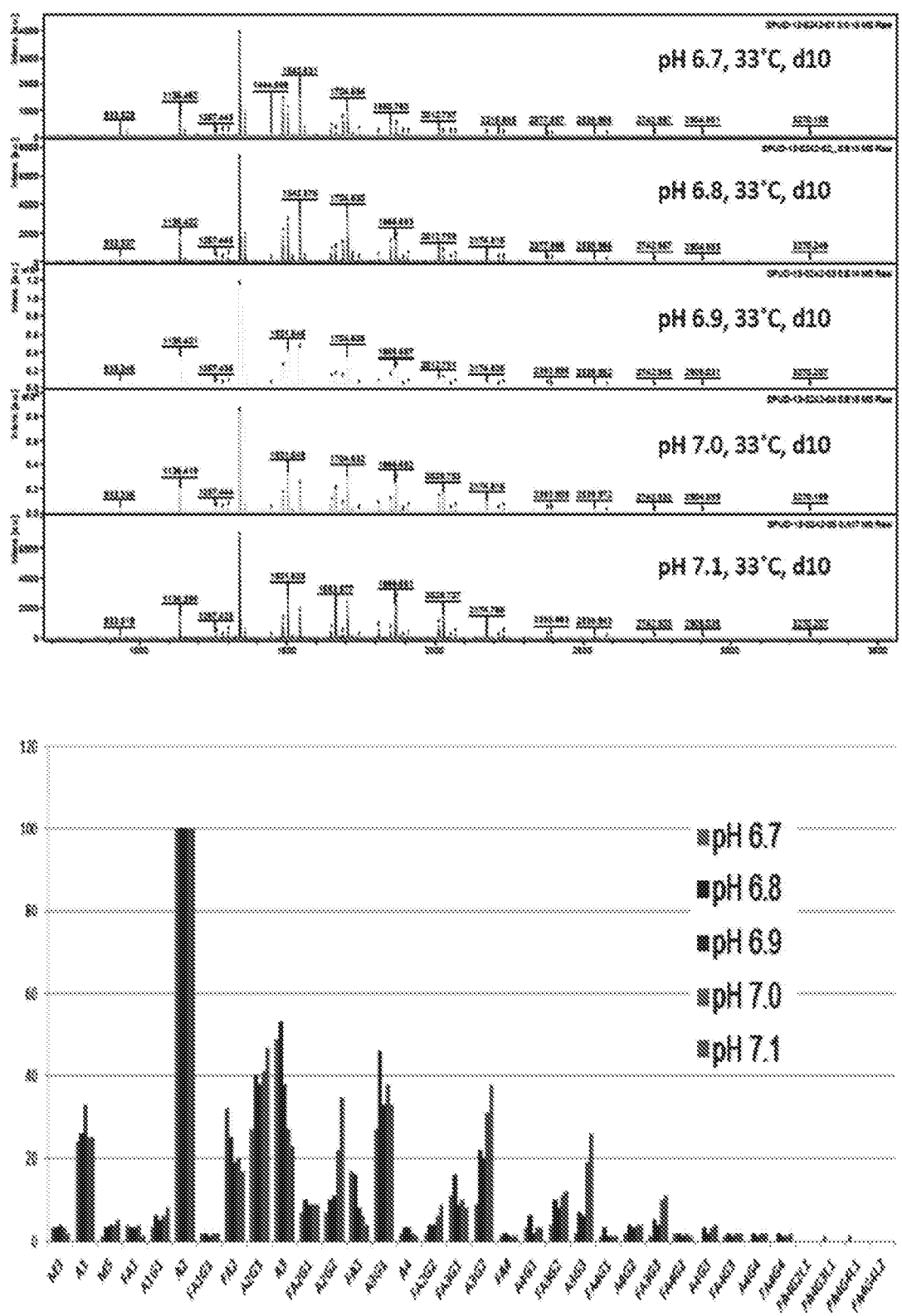
FIG. 25 are graphs showing the impact of culture medium pH on neutral glycan profiles of produced asfotase alfa (measured by MALDI-ToF) in exemplary Process #4. The top panel shows all MALDI-ToF peaks for asfotase alfa produced at 33° C. for 10 days but under different culture medium pH. The value of each peak was calculated and compared in the bottom panel.
Figure 26:
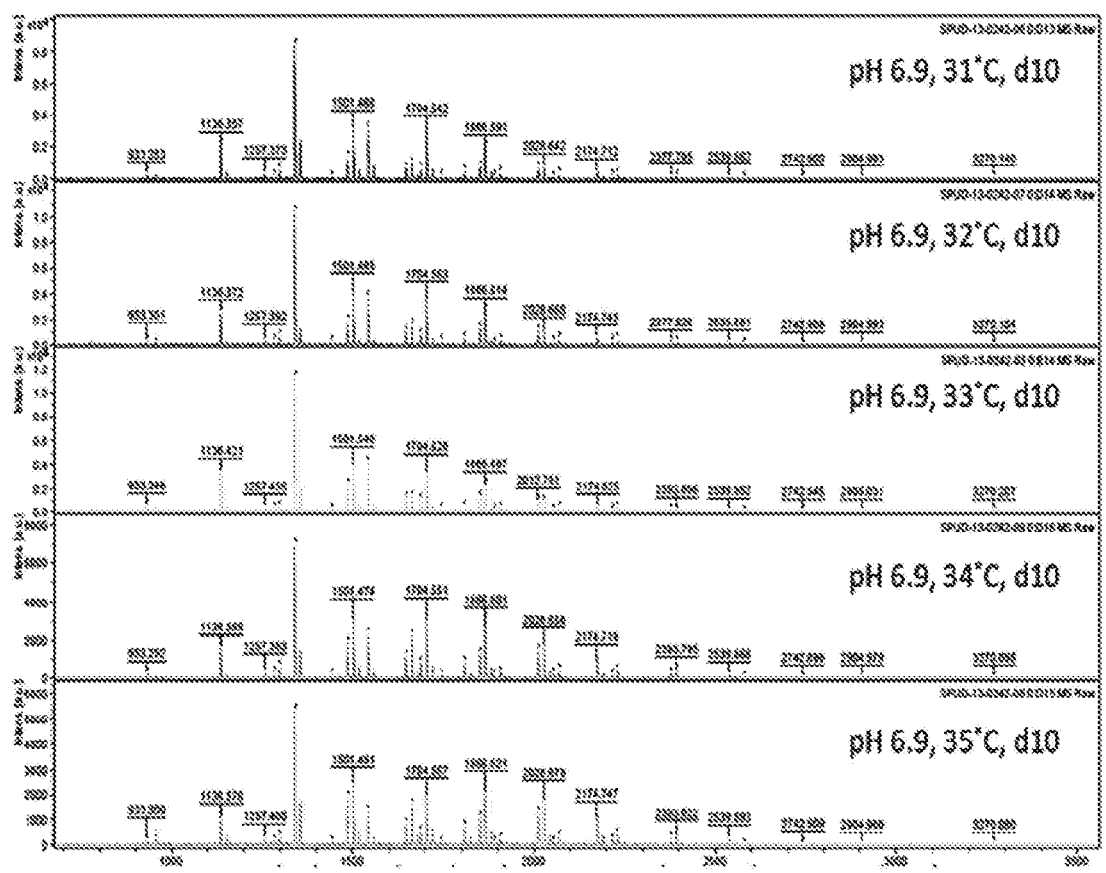
FIG. 26 are graphs showing the impact of production temperature on neutral glycan profiles of produced asfotase alfa (measured by MALDI-ToF) in exemplary Process #4. The top panel shows all MALDI-ToF peaks for asfotase alfa produced under different production temperature at pH 6.9 for 10 days. The value of each peak was calculated and compared in the bottom panel.
Figure 26:
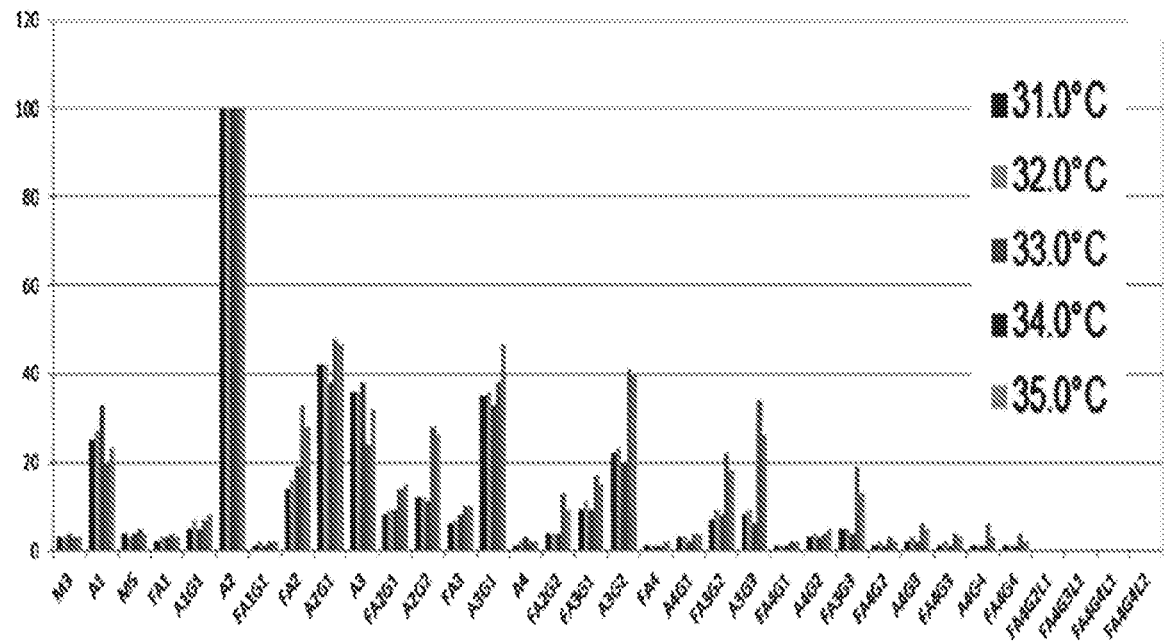

No new neutral species were observed for any of the conditions, as compared to the BDS materials described in the exemplary process in Example 2. However, a profile shift was seen between the low pH condition and higher pH, in which more higher-order glycoforms were observed from the material produced at a higher culture pH (FIG. 25). A similar trend was observed for production temperature with more higher order glycoforms present in the material produced at the higher production temperature (34.0° C. and 35.0° C.) (FIG. 26).

Figure 27:
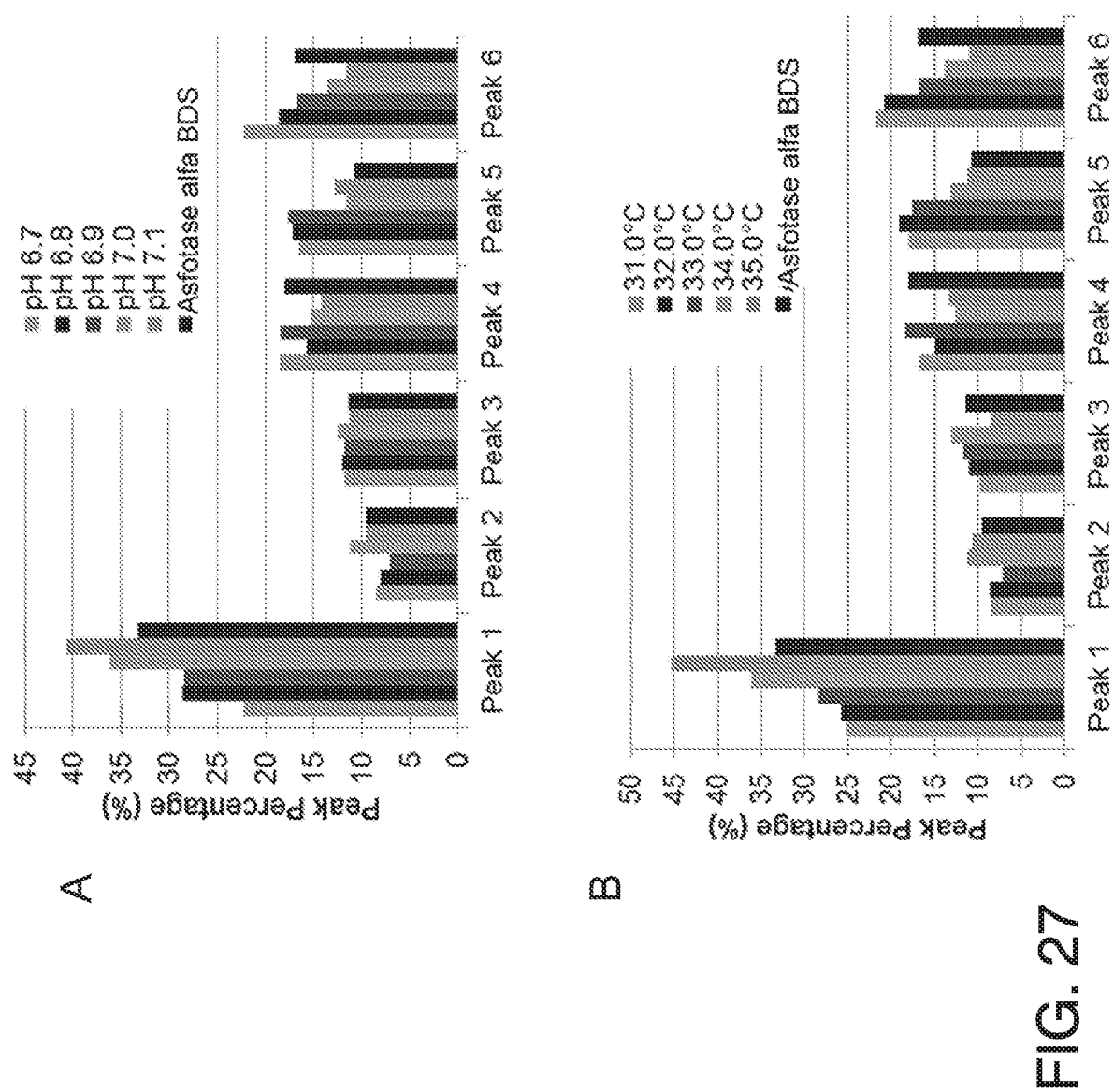
FIG. 27 are graphs showing the impact of culture medium pH (panel A) and production temperature (panel B) on capillary isoelectric focusing peak percentages for iCE280 analysis of asfotase alfa quality in exemplary Process #4.
Figure 28:
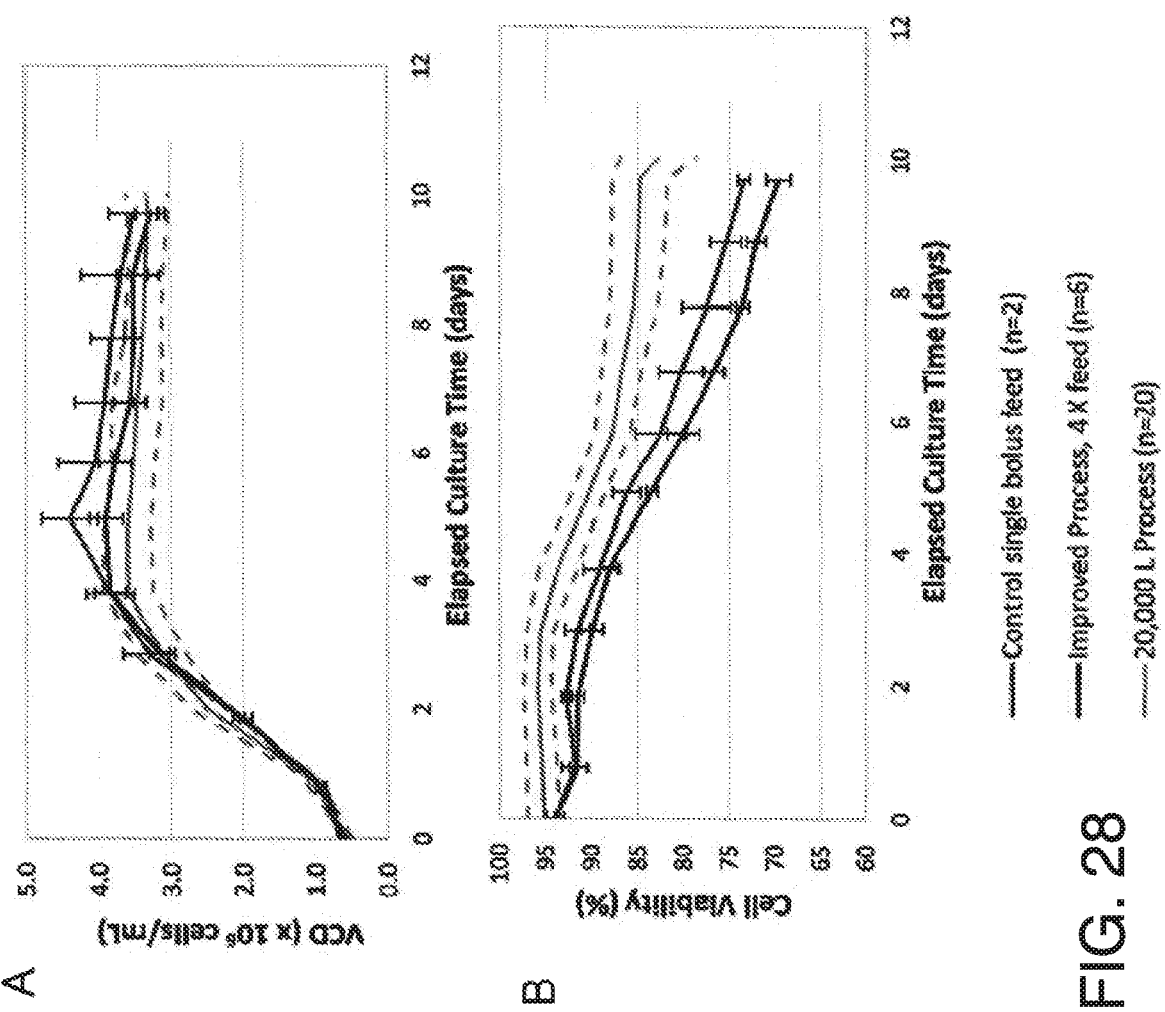
FIG. 28 are graphs comparing cell growth (panel A) and viability (panel B) for different processes (blue line: a control process (performed for two bioreactor tanks) with single bolus medium feed); red line: an improved process (performed for six bioreactor tanks) with four times of medium feeds; gray line: previous 20K processes (performed for twenty bioreactor tanks) as a standard. The solid gray line represents the average of 20K processes, while the dotted lines represent average ±1× standard deviation.

Peak determination from iCE280 chromatograms was performed by identifying the most basic peak as Peak 6 and identifying the next four peaks as Peak 5 through 2 in reverse numerical order. Peak 1 then consisted of all peak percentages identified below the pI of the next peak after Peak 2. The resulting pI values for the identified peaks are listed in Table 18. Both culture medium pH and production temperature appear to have an impact upon capillary isoelectric focusing results (FIG. 27). Increasing either culture pH or production temperature produced an increase in the percentage of the low pI peaks, identified as Peak 1. Additionally, the related percentage of the high pI peaks, Peak 5 and 6, was decreased with increasing culture pH or production temperature. These factors indicated a general shift towards more acidic species associated with increasing pH or production temperature. This shift may be related to increased sialylation associated with both increased pH and production temperature, which would produce a greater percentage of acidic species.

TABLE 18

| pI ranges for identified iCE280 peaks | |
| --- | --- |
| Peak ID | pI range |
| Peak 1 | ≤6.63 |
| Peak 2 | 6.62-6.67 |
| Peak 3 | 6.67-6.72 |
| Peak 4 | 6.71-6.77 |
| Peak 5 | 6.77-6.82 |
| Peak 6 | ≥6.83 |

Conclusions

This study confirms previous results indicating that culture pH (6.70-7.10) and production temperature (31.0-35.0° C.) are unlikely to be CPPs in that the measured CQAs were all within the small scale range as previously specified. Both culture pH and production temperature impact many cell culture performance parameters and quality attributes. Notably, increasing either the culture pH or production temperature leads to an increased maximum VCD but also causes a rapid decline in viability in the late stages of the culture.

Both culture pH and production temperature can impact productivity in terms of protein A titer and volumetric activity. A culture pH of 6.70 resulted in lower protein A titer and volumetric activity. Increasing the culture pH set point resulted in decreased specific activity. Therefore, though culture pH has a positive impact on protein A titer, there was almost no difference in terms of volumetric activity under a pH ranging from 6.80 to 7.10. In addition, increasing the production temperature led to an increased protein A titer and volumetric activity, but did not impact specific activity.

Increasing the culture pH or production temperature also led to higher TSAC values. Increasing the latter parameter also decreased aggregate and acidic peak formation. Finally, culture pH and production temperature both appear to shift the isoelectric focusing profile of the product. These results indicate that a pH ranging from 6.70 to 7.10 and a production temperature ranging from 31.0° C. to 35.0° C. are acceptable, and tight controls of both process parameters are recommended to maintain process robustness and consistency in scaling up (e.g., to a 10,000 L scale-up process).

Example 6. Improving Active Asfotase Alfa Titer by Extra Feed Supplementation

The previous exemplary processes for producing asfotase alfa (sTNALP-Fc-$D_{10}$), as described in previous Examples, were low-producing processes with an active asfotase alfa titer of approximately 0.1 g/L at harvest. An alternative manufacturing process is exemplified herein for process improvement. Both upstream and downstream processes were evaluated.

The potential impact of upstream cell culture process parameters on asfotase alfa quality and productivity were evaluated in a previous study. Cell culture parameters including metal supplementation ($Zn^{2+}/Mg^{2+}/Ca^{2+}$), temperature shift timing, CHO feed amount and harvest timing were evaluated, in order to improve titer and/or volumetric activity without impacting any other critical quality attributes (CQAs). The data from the previous study indicated that metal supplementation resulted in significantly lower TSAC than the control condition, and therefore was excluded in further evaluation. Delaying the temperature shift timing from 54 hours to 78 hours resulted in lower specific activity and higher protein A titer. As a result, the overall volumetric activity under the later temperature shift conditions remained the same. Increasing the CHO feed bolus amount from 1× (5 ml/L on day 2) to 4× (5 ml/L on day 2, 4, 6, and 8) led to a significant increase in volumetric activity without adverse impact on other tested quality attributes (e.g., TSAC, charge distribution, and neutral glycan distribution). Delaying the harvest day from day 10 to day 12 was associated with higher productivities (e.g., volumetric activity, protein A titer, and specific activity) and marginally lower TSAC. Based on this data, an increase in CHO feed amount was chosen in this study for further evaluation at the 10 L scale.

Materials and Methods

An upstream process for asfotase alfa (sTNALP-Fc-$D_{10}$) production was run with the following seed train and cell culture process: inoculum thaw of cells with target seeding density at 5×$10^5$ cells/mL; inoculum expansion (flask/roller stage) with target seeding density at 3.5×$10^5$ cells/mL; inoculum expansion (cell bag stage) with target seeding density at 3.5×$10^5$ cells/mL; inoculum expansion (100 L—low level) with target seeding density at 3.5×$10^5$ cells/mL; inoculum expansion (100 L—high level) with target seeding density at 3.5×$10^5$ cells/mL; 1000 L seed bioreactor (N3—low level) with target seeding density at 3.5×$10^5$ cells/mL; 1000 L seed bioreactor (N2—high level) with target seeding density at 3.5×$10^5$ cells/mL; 4000 L seed bioreactor (N1) with target seeding density at 3.5×$10^5$ cells/mL; 20000 L production bioreactor with target seeding density at 5.5×$10^5$ cells/mL. For this study, the small-scale seed train process used as inoculum for the bioreactors for both control and improved bioreactor processes included: inoculum thaw; Passage 1 (1×100 mL shake flask, target seed at 5×$10^5$ cells/mL); Passage 2 (2×100 mL shake flask, target seed at 3.5×$10^5$ cells/mL); Passage 3 (2×1 L spinner, target seed at 3.5×$10^5$ cells/mL); Passage 4 (2×15 L spinner, target seed at 3.5×$10^5$ cells/mL); 8×10 L bioreactor, target seed at 5.5×$10^5$ cells/mL. The 10 L bioreactors used in this study was the Sartorius BIOSTAT® B-DCU II bioreactor system (Sartorius Stedim Biotech) and MFCS/win 3.0 Module Shell 3.0 (level 32) data acquisition software (Sartorius Stedim Biotech). A list of raw materials used in the production bioreactors includes: CM69 growth medium, 100 μM MTX (methotrexate), 200 mM L-Glutamine, CM70 growth medium, Sigma CHO Feed, 10% Sodium carbonate, and FoamAway AOF (Gibco).

A cell vial from a development working cell bank of asfotase alfa (sTNALP-Fc-$D_{10}$) clone (cell line X) was thawed and passaged through the seed train through the N–1 stage (equivalent to the 4000 L seed bioreactor in the 20,000 L process previously used). The N–1 culture was conducted in two 15 L spinners with a working volume of 15 L. Both N–1 cultures were used for inoculation. Agitation was set at 200 rpm with a total gas flow of 20 L/hr. Oxygen and carbon dioxide gassing were adjusted according to measured dissolved oxygen and pH. Eight 10 L bioreactors were inoculated and harvested on day 10. Two bioreactors were fed using the control feeding strategy (one feeding), while six others were fed using the improved feeding strategy (multiple feedings at day 2, 4, 6, and 8). Table 19 summarizes the cell culture process parameters used for these bioreactors.

TABLE 19

Cell Culture Process Parameters

| Process Parameters | Control | Improved Process |
|---|---|---|
| Initial Working Volume (media and inoculum) | 10 L (Sartorius 10 L bioreactor) | |

TABLE 19-continued

Cell Culture Process Parameters

| Process Parameters | Control | Improved Process |
|---|---|---|
| Target Seeding Density | 5.5 × $10^5$ cells/mL | |
| pH | 6.90 (without dead band) | |
| Temperature | 37.0° C., then shift to 30.0° C. when viable cell density is 25-32 × $10^5$ cells/mL (58 hr post inoculation) | |
| DO | 40% | |
| Agitation | 309 rpm (P/V = 81 W/$m^3$) | |
| Gassing strategy | Air flow 20 mL/min + Oxygen as needed | |
| Overlay | 450 mL/min air | |
| CHO feed | 5 mL/L bolus (50 mL) on day 2 based on initial working volume | 50 mL bolus* (50 mL) on day 2, 4, 6, and 8 |
| Glucose addition | If [glucose] is below 2 g/L, increase to 3 g/L via bolus addition | |
| Glutamine addition | If [glutamine] is below 0.18 g/L (1.2 mM), increase to 0.29 g/L (2.0 mM) via bolus addition prior to temperature shift | |
| Base (10% w/w $Na_2CO_3$) | Add if needed | |
| Antifoam | 5 mL on day 0, then 1 mL as needed throughout culture | |

*each bolus feed contains 1.2 mM zinc chloride, comparing to the basal medium containing only about 9 μM zinc chloride. Thus, each bolus feed increases about 6 μM of zinc concentration (0.5 v/v).

The manufacturing process at 20,000 L scale employs a VCD based feeding strategy (single bolus at VCD about 25.0-32.0×$10^5$ cells/mL, usually around day 2 of culture). In this study, temperature shift timing was programmed to occur at 58 hours post inoculation to meet the VCD criteria (25.0-32.0×$10^5$ cells/mL) based on averaged doubling time 24.5 hours calculated from manufacturing data at 20K bioreactor. This change was implemented to simplify the process and to allow tighter control of the timing of feeding.

Results

Cell culture performance of all bioreactors is summarized in FIG. 28 through FIG. 31.

Growth dynamics and viability of the currently improved process were compared to the control and previous 20,000 L processes. The VCD over the course of the culture were similar to the control and 20,000 L processes (FIG. 28A, error bars represent ±1× standard deviation). Cell viability under the control processes and the improved Process #4 declined in similar rates, which is faster than the rate under the previous 20,000 L-scale processes (FIG. 28B). Final viability was 73% and 70%, respectively, for the control and the improved processes, while the 20,000 L process typically remains about 80%. This appears to be a scaling issue with the 10 L system, possibly due to agitation rate. This was tested in a second material generation block and data from that run indicated that the viability drop was likely due to a combination of the agitation rate and the ViCell cell counter settings being set to a generic CHO cell type, which had a broader acceptable cell diameter range (5-50 μM) than that for the cell type (11-30 μM) in previous processes.

Figure 29:
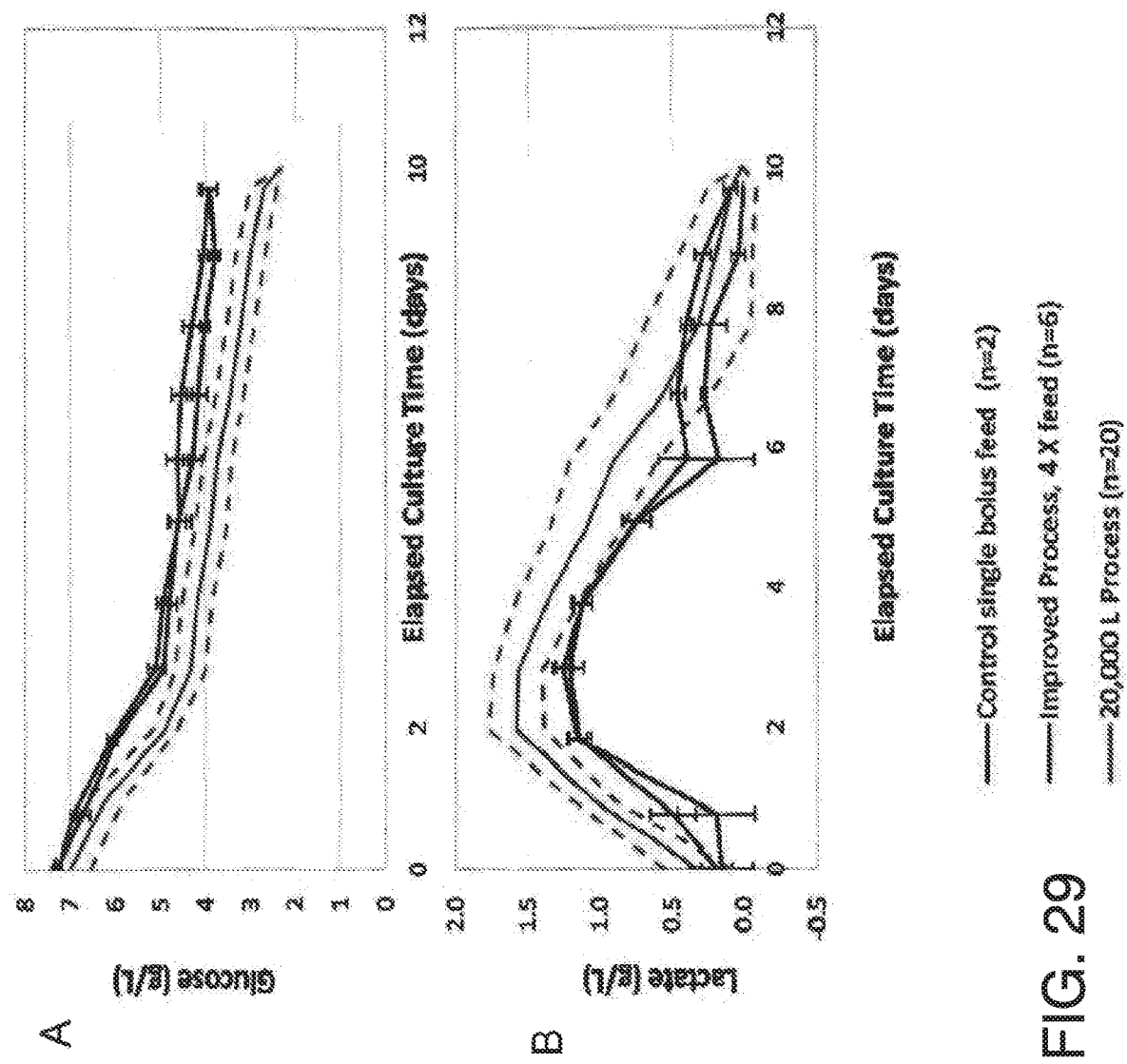
FIG. 29 are graphs comparing glucose utilization (panel A) and lactate production (panel B) for different processes (blue line: a control process (performed for two bioreactor tanks) with single bolus medium feed); red line: an improved process (performed for six bioreactor tanks) with four times of medium feeds; gray line: previous 20K processes (performed for twenty bioreactor tanks) as a standard. The solid gray line represents the average of 20K processes, while the dotted lines represent average ±1× standard deviation.

Glucose utilization and lactate consumption profiles are shown in FIG. 29. The improved process showed similar glucose utilization and lactate profiles to that of the control.

Figure 30:
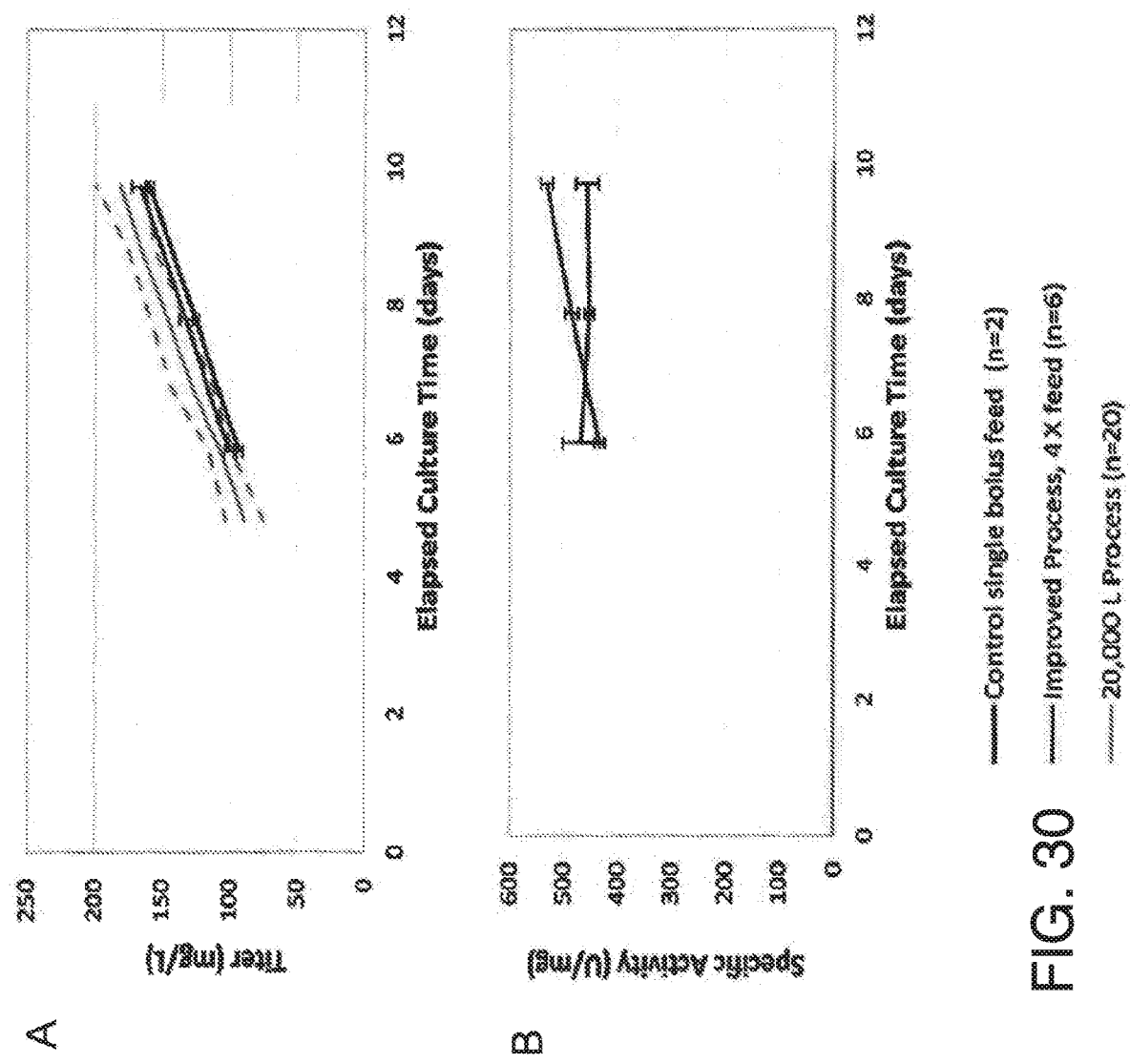
FIG. 30 are graphs comparing protein A titer (panel A) and specific activity (panel B) of asfotase alfa produced by different processes (blue line: a control process performed for two bioreactor tanks with single bolus medium feed); red line: an improved process (performed for six bioreactor tanks) with four times of medium feeds; gray line: previous 20K processes (performed for twenty bioreactor tanks) as a standard). The solid gray line represents the average of 20K processes, while the dotted lines represent average ±1× standard deviation.
Figure 31:
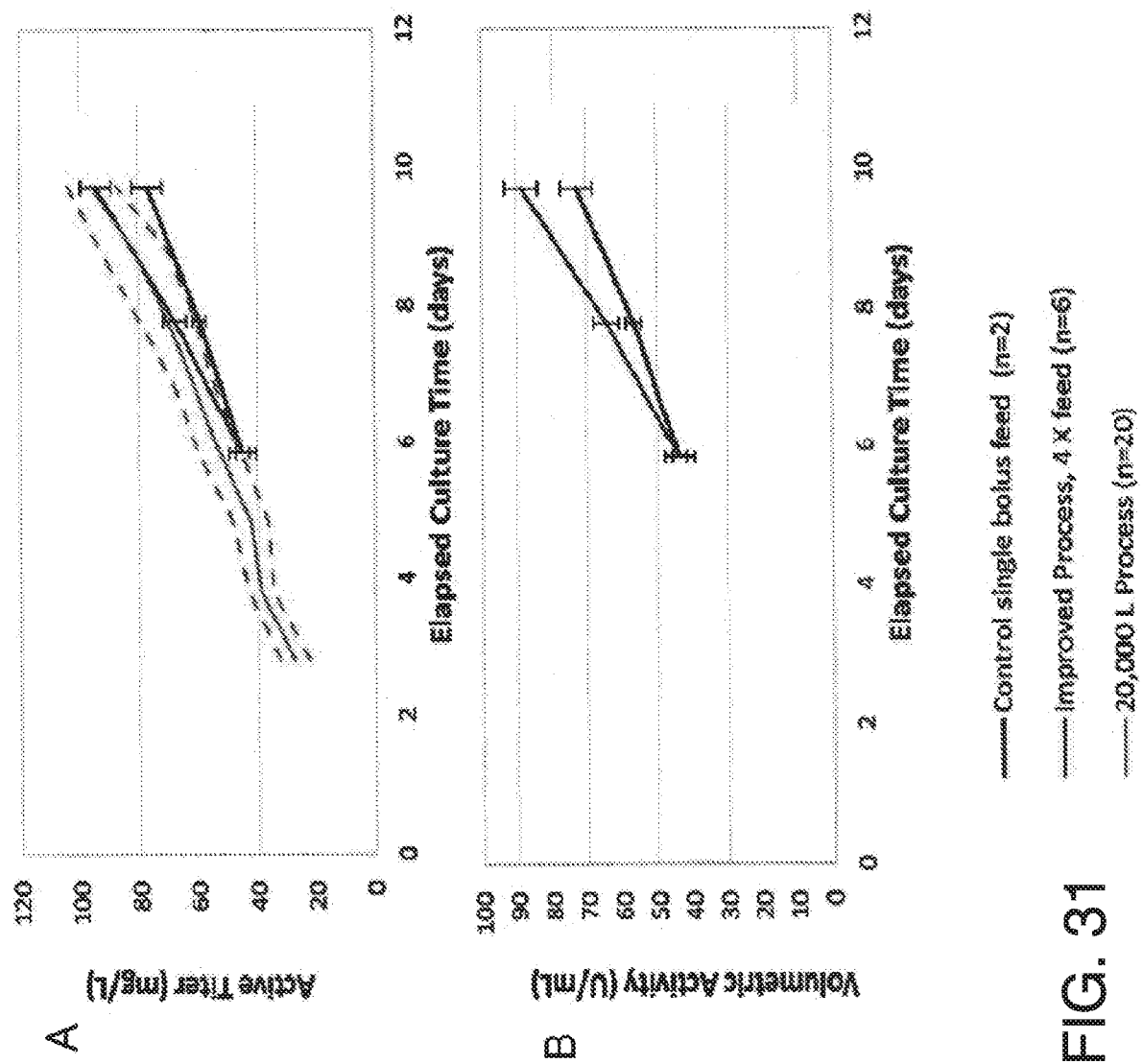
FIG. 31 are graphs comparing active titer (panel A) and total volumetric activity (panel B) for different processes (blue line: a control process (performed for two bioreactor tanks) with single bolus medium feed); red line: an improved process (performed for six bioreactor tanks) with four times of medium feeds; gray line: previous 20K processes (performed for twenty bioreactor tanks) as a standard). The solid gray line represents the average of 20K processes, while the dotted lines represent average ±1× standard deviation.

Protein A titer of asfotase alfa and specific activity throughout the culture are shown in FIG. 30. Protein A titer for both the control and improved process were comparable. However, they were both lower than the titers typically seen at the 20,000 L process. This may be partially attributable to the scale differences seen with the viability, since the power to volume ratio used in this study was found to be 30% higher than that used at manufacturing (confirmed by subsequence receipt of the PN ratio used at manufacturing scale). Specific activity (units/mg protein) for the improved process was on average 17% higher (532 U/mg vs. 456 U/mg) than control. These data, taken with the protein A titer data, indicate that while the same amount of protein is produced with each process, the protein produced was more active when the culture is fed more.

Active titer and total volumetric activity (shown in FIG. 31) indicate that the improved process generates approximately 22-24% more activity than the control process at the 10 L scale. The improved process generated approximately the same active titer as seen at the 20,000 L scale, while the control process was about 19% lower.

Conclusion

Figure 32:
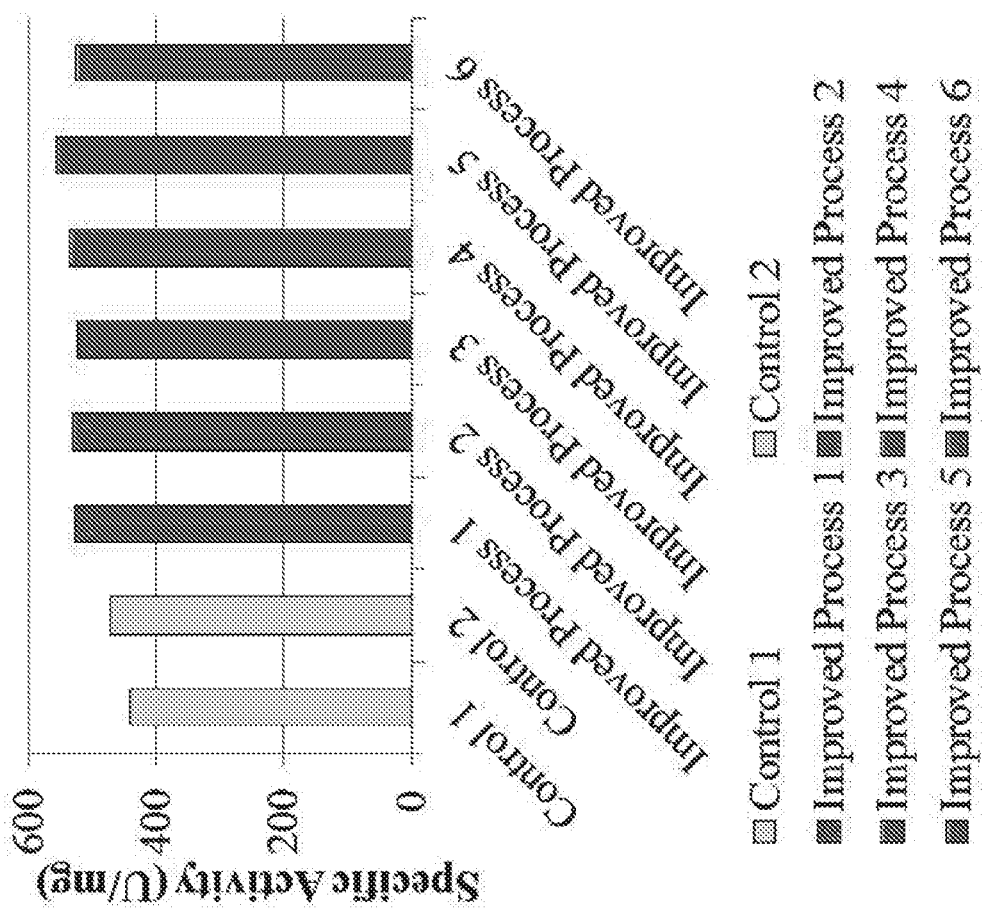
FIG. 32 is a graph comparing asfotase alfa specific activity from control processes (gray; single bolus medium feed) and improved processes (dark gray; four times of medium feeds).

This study documents the cell culture performance of an improved manufacturing process (10 L scale), which utilizes an increased feed amount that led to an approximately 22-24% increase in active titer, while maintaining the protein A titer of the product. The comparison of asfotase alfa specific activity between control and improved processes is shown in FIG. 32. Clearly, all six replicate improved process conditions (each with three extra feed additions) showed higher specific activity than the controls.

Each bolus feed contained 1.2 mM zinc chloride, as compared to the basal medium that contains only about 9 µM zinc chloride. Thus, each bolus feed resulted in an increase of about 6 µM of zinc concentration (0.5 v/v) in the whole culture. Without being limited to any particular theory, it is postulated that the increase in specific activity by extra feed supplementation is at least partly due to the zinc supplementation.

Example 7. Further Improving Asfotase Alfa Activity by Zinc Supplementation

Figure 33:
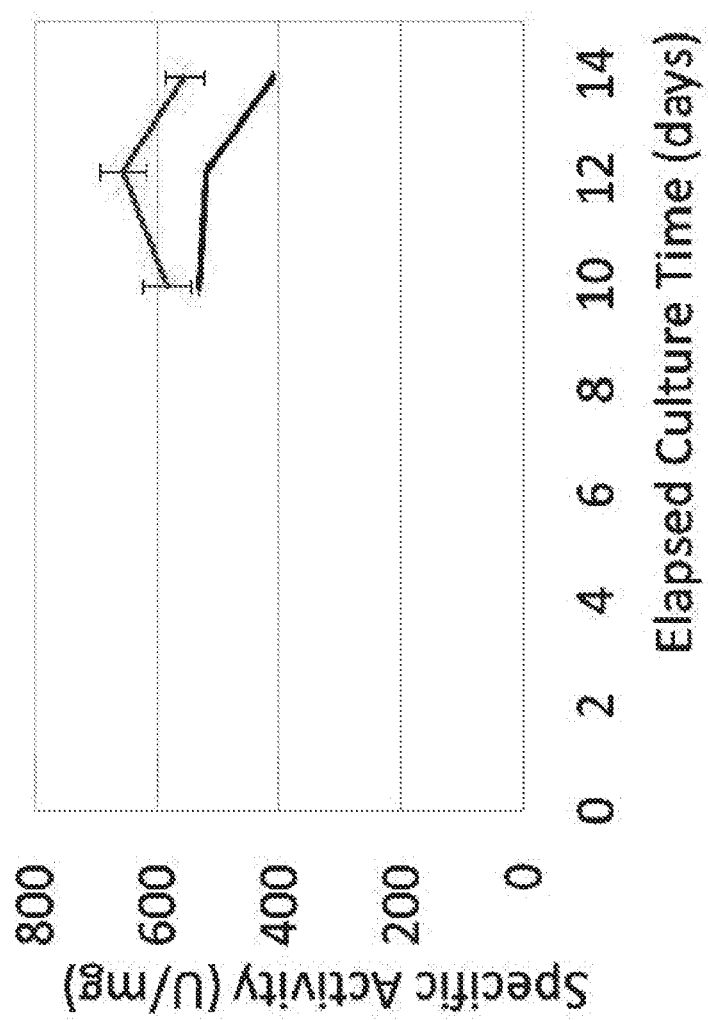
FIG. 33 is a graph comparing asfotase alfa specific activity from a previous Process Y (lower line; without further zinc supplement) and a further improved process (upper line; showing the average of 30-90 μM zinc supplement conditions and the culture time extended to 14 days).

Based on manufacturing processes disclosed in previous Examples, new studies were carried out to further optimize upstream process parameters. Exemplary Processes Z and Z' are summarized and compared in Table 20.

respectively). The 30 µM supplementation was done by front-loading into the culture medium. The 60 and 90 µM supplementations involved supplementing zinc in two equal boluses on day 2 and 6 (for 60 µM condition), or three equal boluses on day 2, 6, and 10 (for 90 µM condition). As shown in FIG. 33, zinc supplementation (red line; showing the average of three experiments with different zinc concentrations) effectively improved asfotase alfa specific activity, as compared to the control Process Y (blue line). This increase reached its peak around the 288-hour (i.e., 12 days) time slot and decreased afterwards.

Example 8. Characterization of Manufactured Asfotase Alfa

An exemplary characterization of manufactured asfotase alfa with multiple orthogonal analytical methods is illustrated herein. These methods were employed to evaluate identity, purity, size, structure, glycosylation, and charge profiles of produced asfotase alfa. Some methods were also used to ensure lot-to-lot consistency. Additionally, product-related substances and product-related impurities were also characterized.

Structural Elucidation of Asfotase Alfa

Matrix-Assisted-Laser-Desorption-Ionization Time-of-Flight (MALDI-TOF) Analysis of Molecular Weights after Removal of Oligosaccharides MALDI-TOF mass spectrometry analysis of asfotase alfa after removal of oligosaccharides was used to establish the identity of asfotase alfa. In addition, the presence of any significant levels of posttranslational modifications with molecular weights substantially different from the theoretical molecular weight of asfotase alfa would also be detected by this method. Removal of oligosaccharides was achieved by digestion of asfotase alfa using PNGaseF with or without reduction of disulfide bonds. The samples were desalted and mixed with a 90:10 mixture of 2,5-dihydroxybenzoic acid and 2-hydroxy-5-methoxybenzoic acid in acetonitrile and trifluoreacetic acid. The samples were air-dried and then analyzed using a MALDI-TOF mass spectrometer. Mass

TABLE 20

Differences between Exemplary Manufacturing Processes (upstream)

| | Process X | Process Y | Process Z | Process Z' |
|---|---|---|---|---|
| Parental Cell line | CHO | CHO | CHO | CHO |
| Production medium | HyClone SFM4CHO | HyClone SFM4CHO | HyClone SFM4CHO + BD select | HyClone SFM4CHO + BD select |
| Feed | CHO Feed (0.5%) | CHO Feed (2%, i.e., 4 × medium feed) | CHO Feed (2%) + Cell Boost 2 + 5 (9%) | CHO Feed (2%) + Cell Boost 2 + 5 (9%) |
| pH set point | 6.90 | 6.90 | 6.90 | 6.90 |
| Temperature | 37.0° C. then shifted to 30° C. | 37.0° C. then shifted to 30° C. | 37.0° C. then shifted to 30° C. | 37.0° C. then shifted to 30° C. |
| DO | 40% | 40% | 40% | 40% |
| Supplement | N/A | N/A | ZnSO$_4$ | ZnSO$_4$ (30-90 µM) |
| Harvest time | 240 ± 12 hr | 240 ± 12 hr | 240 ± 12 hr | 288 ± 48 hr |

Figure 34:
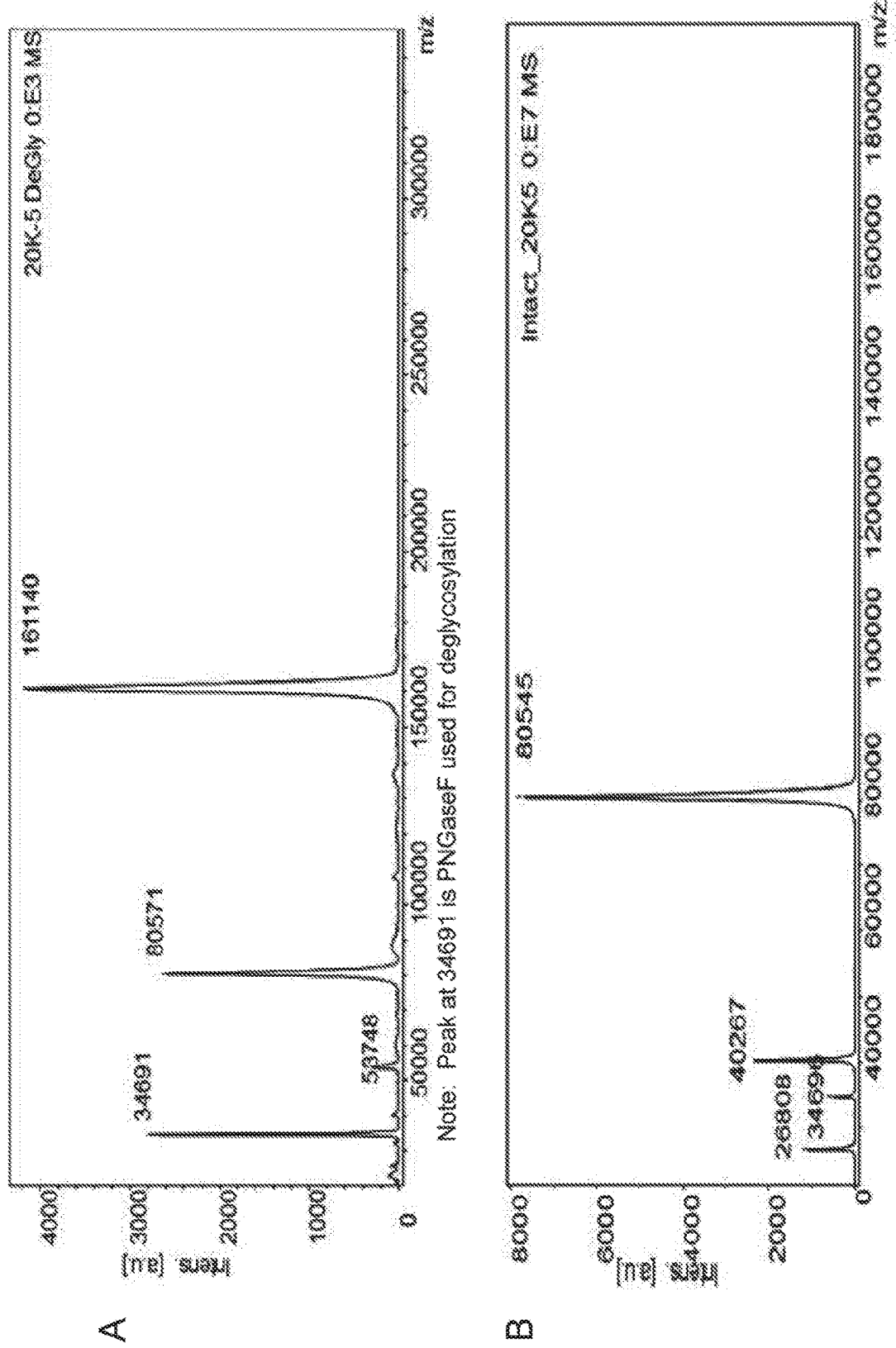
FIG. 34 are graphs showing MALDI-ToF mass spectrum data for produced asfotase alfa after deglycosylation (panel A) and for produced asfotase alfa which was reduced and deglycosylated (panel B).

Further optimizations have been carried out based on previous Process Y. For example, new Process Z' included supplementing about 30-90 µM zinc sulfate into the culture medium and increasing total culture time from about 240 hours (i.e., 10 days) to about 288 hours (i.e., 12 days). A small scale shake flask study was carried out to test three variants of Process Z' (supplementing 30, 60, or 90 µM zinc, spectra were acquired in positive mode. The instrument was externally calibrated using bovine serum albumin (BSA). Mass spectrum of asfotase alfa after deglycosylation is shown in FIG. 34A. Peaks with m/z of 161,140, 80,571 and 53,748 correspond to the molecule that is singly, doubly or triply charged, respectively. The measured molecular weight of 161,140 Da was in agreement with the calculated molecular weight (161,135.2 Da) within the 1% accuracy limit of the instrument. A mass spectrum of asfotase alfa after reduction and removal of oligosaccharide is shown in FIG. 34B. Peaks with m/z of 80,545, 40,267, and 26,808 correspond to the molecule that is singly, doubly or triply charged, respectively. The measured molecular weight of 80,545 Da is in agreement with the calculated molecular weight of 80,577.7 Da within the 1% accuracy limit of the instrument. The results confirmed the identity of asfotase alfa and demonstrated the lack of significant levels of posttranslational modifications other than glycosylation.

Analytical Ultracentrifugation (AUC)

AUC was used to determine the percentage of aggregates, dimer and fragments if present and thus the purity of asfotase alfa. In addition, it determines the molecular weight of asfotase alfa dimer, which is a characteristic of the molecule because of the unique amino acid sequence and posttranslational modifications. It is considered to be an orthogonal method to size exclusion chromatography (SEC). Asfotase alfa samples were diluted to approximately 1 mg/mL using 25 mM phosphate, 150 mM NaCl, pH 7.4. An analytical ultracentrifuge was used to carry out sedimentation velocity analysis. Double sector cells equipped with quartz windows were used. The rotor was equilibrated under vacuum at 20° C. and after approximately 1 hour the rotor was accelerated to 36,000 RPM. Absorption scans at 280 nm were acquired at 4.5 minute intervals for approximately 6 hours. The data was first analyzed using DCDT to determine the apparent molecular weight and then using the c(s) method (SEDFIT software) to determine the percentage of dimer, high molecular weight and low molecular weight species. The molecular weight of asfotase alfa was 211 kDa and the purity was 96.8% for the representative batch.

MALDI-TOF of Intact Molecular Weight

Figure 35:
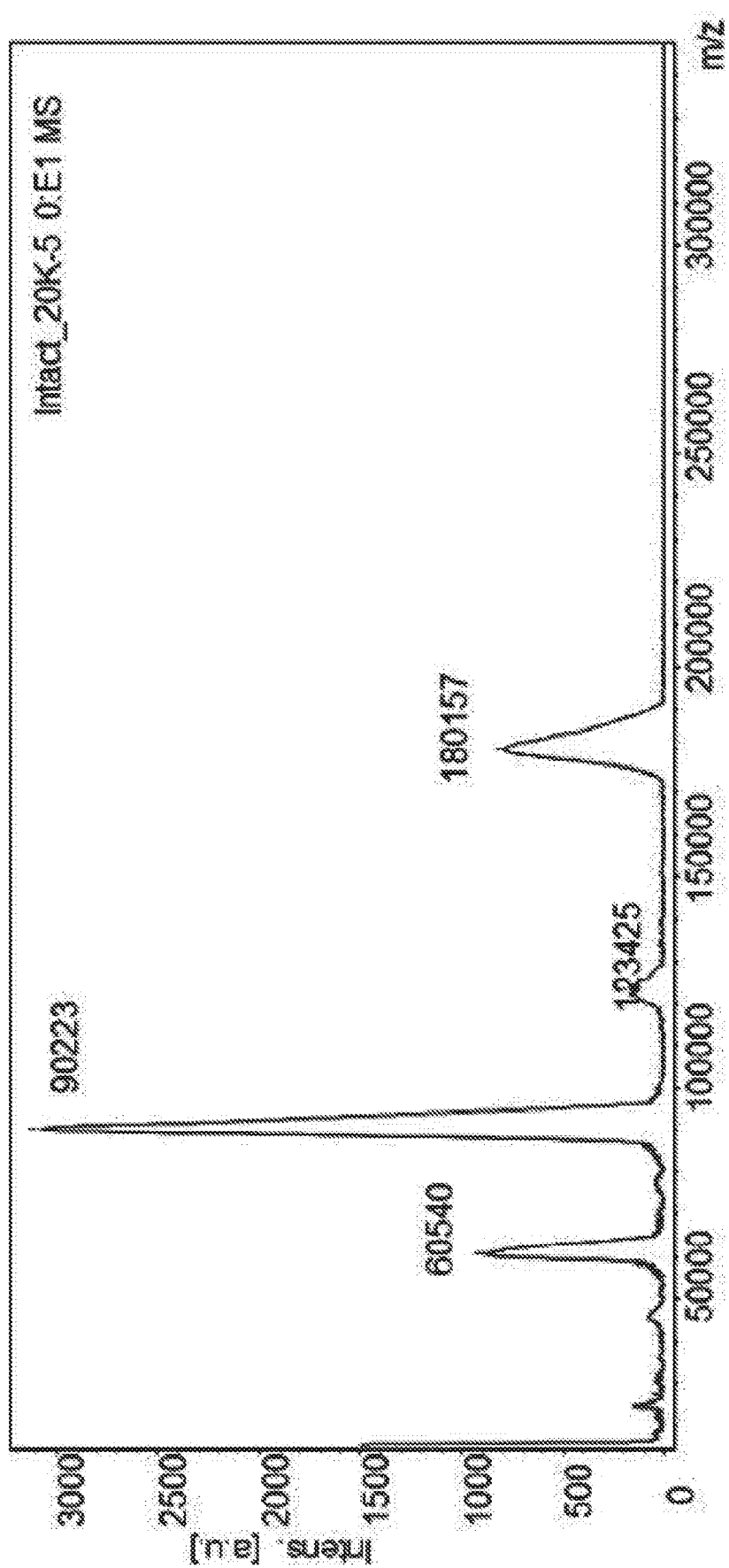
FIG. 35 is a graph showing the MALDI-ToF mass spectrum of produced asfotase alfa.

MALDI-TOF measurement of the molecular weight of asfotase alfa determines the size of the molecule including all posttranslational modifications, mainly, glycosylation. Asfotase alfa samples were desalted and mixed with matrix made from a 90:10 mixture of 2,5-dihydroxybenzoic acid and 2-hydroxy-5-methoxybenzoic acid. The samples were air-dried and then analyzed using an MALDI-TOF mass spectrometer. Mass spectra were acquired in positive mode. The instrument was externally calibrated using bovine serum albumin (BSA). A mass spectrum of asfotase alfa is shown in FIG. 35. Peaks with m/z of 180,157, 90,223 and 60,540 correspond to the molecule that is singly, doubly or triply charged, respectively. Other low abundant peaks were formed due to fragmentation caused by the harsh instrument settings. The measured molecular weight of 180,157 Da is significantly higher than the calculated molecular weight of 161,135.2 Da based on the known amino acid sequence. This result indicates extensive posttranslational modifications of asfotase alfa, mainly glycosylation, since MALDI-TOF and ESI-TOF analyses of deglycosylated asfotase alfa did not detect significant levels of modifications.

Size Exclusion Chromatography Multiple-Angle Light Scattering (SEC-MALS)

SEC-MALS is used to separate proteins based on sizes and then determine the molecular weight of each peak. Asfotase alfa was analyzed by SEC-MALS (data not shown). The calculated molecular weight of the peak in the retention time window of 7.0-8.2 minutes is 194.1 Da, which is in good agreement with the calculated molecular weight of asfotase alfa based on the known amino acid sequence and extensive glycosylation and also in agreement with the molecular weight observed by MALDI-TOF.

Metal Analysis

Inductively coupled plasma-mass spectrometry (ICP-MS) was used to determine the content of zinc and magnesium and inductively coupled plasma-atomic emission spectrometry (ICP-AES) was used to determine the level of calcium. Asfotase alfa samples were digested using microwave digestion with heat with the addition of concentrated nitric acid first and then with the addition of hydrogen peroxide. The samples were then analyzed using an ICP-MS instrument for zinc and magnesium and an ICP-AES instrument for calcium. The determined molar ratios (mole of ions/mole of asfotase alfa monomer) were 2.27 for zinc, 0.97 for calcium and 0.12 for magnesium. The ratios of zinc and calcium were in good agreement with the reported ratios in literature (Stec et al. 2000 *J Mol Biol* 299:1303-1311 and Mornet et al., 2001 *J. Biol Chem* 276:31171-31178). Mornet et al. (2001) teaches that calcium may occupy the magnesium binding site on TNALP and thus suggests that the ratio of magnesium in the asfotase alfa molecule may be less than one (1). However, the tested ratio of magnesium as 0.12 is still surprisingly low.

Determination of the Phosphorylation Site

Figure 36:
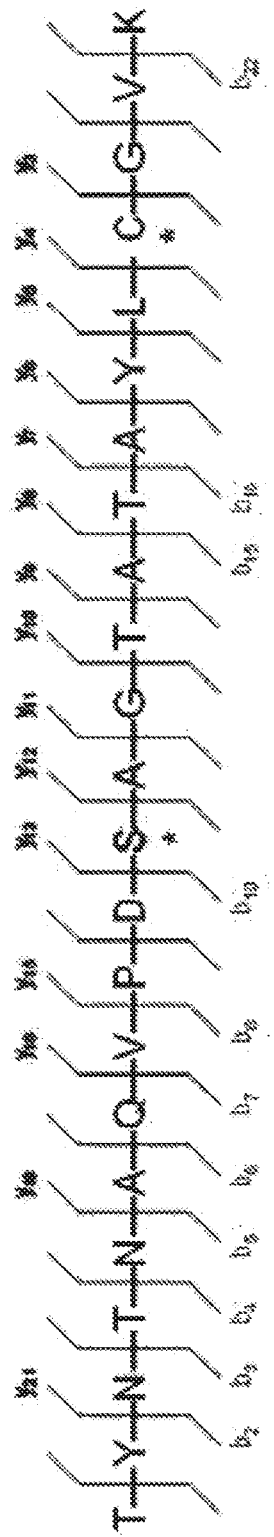
FIG. 36 are graphs showing the MS/MS determination of the phosphorylation site on asfotase alfa.
Figure 36:
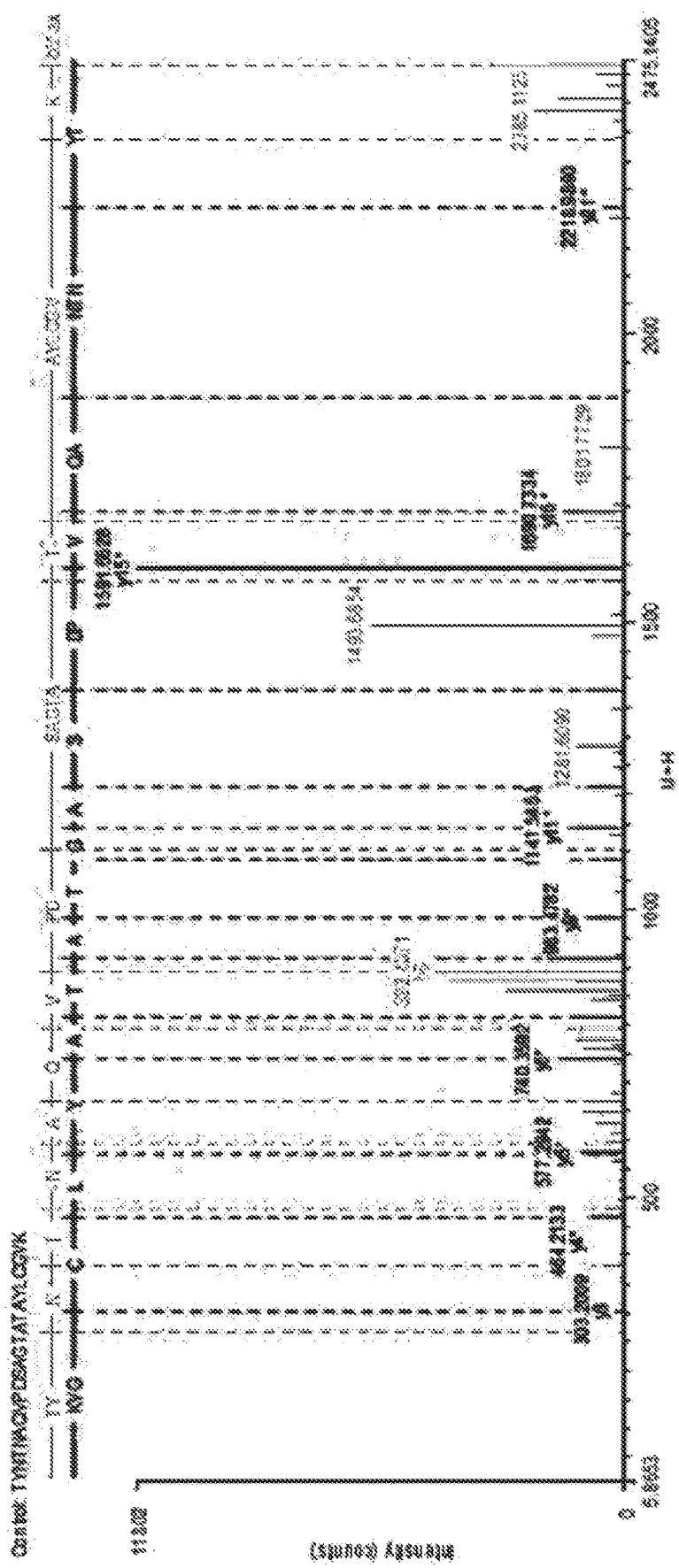

UPLC-MS$^e$ was used to determine the site and the percentage of phosphorylation. Asfotase alfa at a final concentration of 0.5 mg/mL was denatured and reduced in the presence of 6M guanidine hydrochloride in 0.2 M Tris, pH, 8.6, using 40 mM DTT at 37° C. for 1 hour. The reduced sample was alkylated by the addition of iodoacetic acid to a final concentration of 50 mM and incubation at room temperature for 30 minutes. The sample was then buffer-exchanged into 50 mM ammonium bicarbonate using dialysis tubing with molecular weight cut-off of 10 kDa. The sample was digested using trypsin at a final ratio (w:w) of 1:50 trypsin; protein at 37° C. for 24 hours. A UPLC system equipped with a reversed-phase C18 column and a Q-TOF mass spectrometer were used to analyze the digested samples. Tryptic peptide containing Ser93 was identified as both phosphorylated and non-phosphorylated. As shown in FIG. 36, the MS/MS spectrum demonstrated that S93 is shifted by +80 Da, the mass of a phosphate added by phosphorylation, as observed by the y12 and y13 ions. The relative percentage of phosphorylation was determined using extracted ion chromatograms (EIC's) peak areas as 33.9%.

MALDI Analysis of Free Glycans

Figure 37:
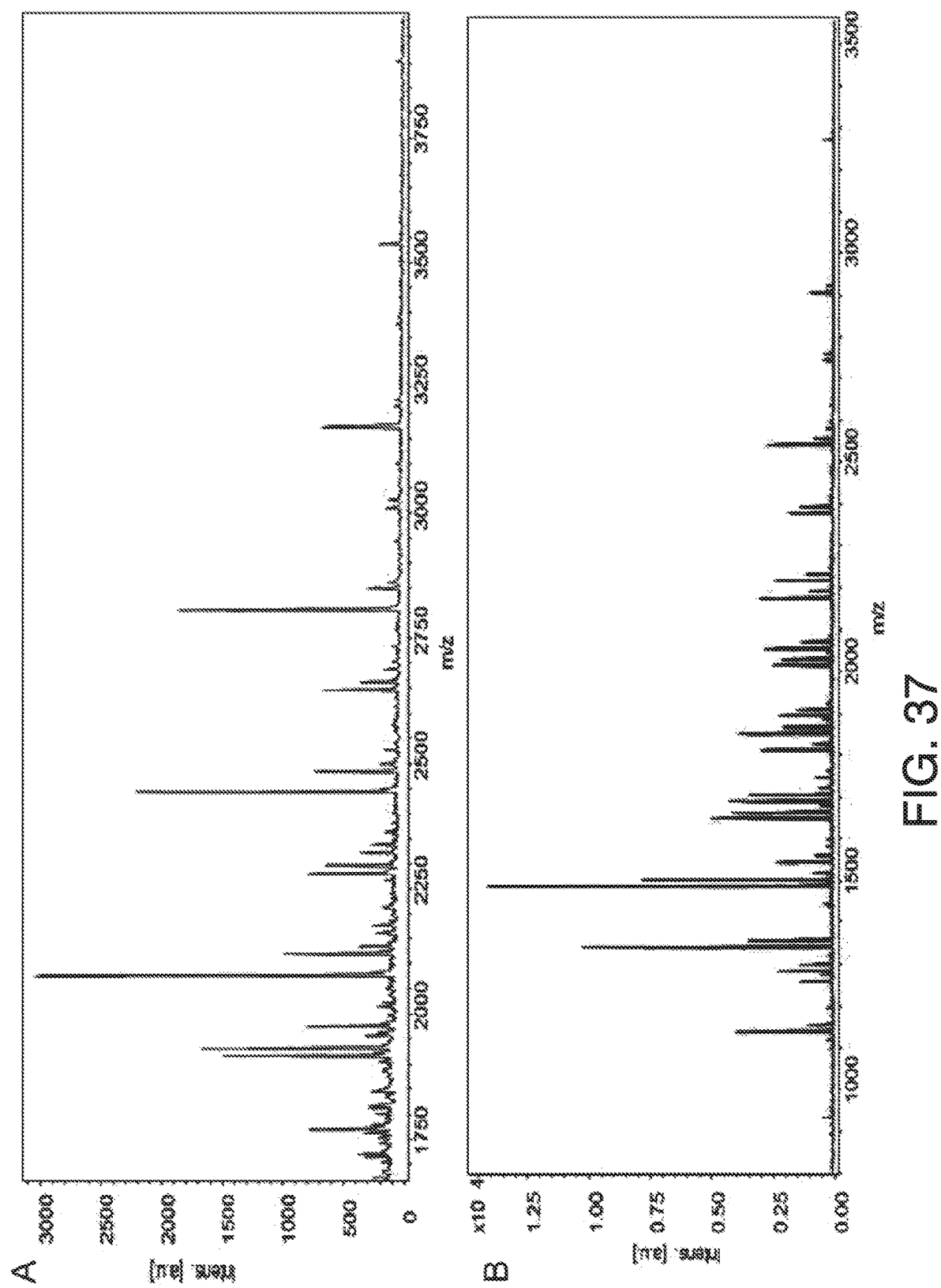
FIG. 37 are graphs showing the negative MALDI-ToF mass spectrum of sialyated glycans (panel A) and the positive MALDI-ToF mass spectrum of neutral glycans (panel B) on produced asfotase alfa.

MALDI-TOF analysis of free glycans was used to determine oligosaccharide species and their relative percentage. Oligosaccharides were released from asfotase alfa reference standard by PNGaseF digestion. The released glycans were purified using Top tip carbon reversed phase columns. The released glycans were mixed 1:1 with sDHB matrix and then analyzed by MALDI-TOF. Analyses were performed in negative mode for glycans with sialic acid and then in positive mode for neutral glycans. A mass spectrum acquired using the negative mode is shown in FIG. 37A. A mass spectrum acquired using the positive mode is shown in FIG. 37B. Oligosaccharide species are determined by matching the observed molecular weights with the theoretical molecular weights of commonly-known oligosaccharides. The relative percentage was determined by dividing the individual peak intensity by the total peak intensities of all glycans. The major oligosaccharides are summarized in Table 21 and Table 22. Based on the molecular weights, the structure of the sialic acid was determined to be N-acetylneuraminic acid (Neu5Ac or NANA).

TABLE 21

Theoretical and Observed Molecular Weights of Sialyated Glycans (M − H)⁻

| Theoretical m/z | Glycoforms | Observed m/z | Error (ppm) | Intensity | Relative Intensity |
|---|---|---|---|---|---|
| 1768.628 | A2G1 + NANA | 1768.581 | 46.923 | 619.000 | 44 |
| 1914.685 | FA2G1 + NANA | 1914.682 | 3.816 | 646.122 | 46 |
| 1930.680 | A2G2 + NANA | 1930.677 | 3.596 | 774.051 | 55 |
| 1971.707 | A3G1 + NANA | 1971.649 | 57.426 | 195.000 | 14 |
| 2076.738 | FA2G2 + NANA | 2076.733 | 5.538 | 1402.453 | 100 |
| 2117.765 | FA3G1 + NANA | 2117.755 | 9.504 | 359.057 | 26 |
| 2133.760 | A3G2 + NANA | 2133.729 | 31.127 | 245.000 | 17 |
| 2279.818 | FA3G2 + NANA | 2279.823 | −5.668 | 421.152 | 30 |
| 2295.813 | A3G3 + NANA | 2295.825 | −12.668 | 333.253 | 24 |
| 2320.844 | FA4G1 + NANA | 2320.75 | 94.536 | 155.000 | 11 |
| 2336.839 | A4G2 + NANA | 2336.793 | 46.579 | 103.000 | 7 |
| 2441.870 | FA3G3 + NANA | 2441.863 | 7.559 | 995.507 | 71 |
| 2482.897 | FA4G2 + NANA | 2482.904 | −7.393 | 296.679 | 21 |
| 2498.899 | A4G3 + NANA | 2498.827 | 71.854 | 158.291 | 11 |
| 2644.950 | FA4G3 + NANA | 2644.952 | −2.229 | 289.645 | 21 |
| 2660.945 | A4G4 + NANA | 2660.97 | −25.771 | 165.363 | 12 |
| 2685.976 | FA4G2 + GN + NANA | 2685.915 | 61.386 | 52.974 | 4 |
| 2807.003 | FA4G4 + NANA | 2807.003 | −0.322 | 849.240 | 61 |
| 2848.029 | FA4G3 + GN + NANA | 2848.034 | −4.806 | 67.026 | 5 |
| 3010.082 | FA4G4 + GN + NANA | 3010.022 | 59.538 | 85.000 | 6 |
| 3026.077 | A4G4L1 + NANA | 3025.985 | 91.732 | 80.000 | 6 |
| 3172.137 | FA4G4L1 + NANA | 3172.11 | 26.443 | 277.854 | 20 |
| 3213.161 | FA4G3L1 + GN + NANA | 3213.175 | −13.611 | 15.000 | 1 |
| 3537.267 | FA4G4L2 + NANA | 3537.181 | 86.085 | 72.238 | 5 |
| 3902.399 | FA4G4L3 + NANA | 3902.451 | −51.951 | 21.992 | 2 |

TABLE 22

Theoretical and Observed Molecular Weights of Neutral Glycans (M + Na)⁺

| Theoretical (m/z) | Glycoforms | m/z | Error (ppm) | Intensity | Relative Intensity |
|---|---|---|---|---|---|
| 933.317 | M3 | 933.301 | 16 | 383.81 | 4 |
| 1136.401 | A1 | 1136.4 | 0.6 | 2765.27 | 31 |
| 1257.427 | M5 | 1257.435 | −8.2 | 792.57 | 9 |
| 1282.454 | FA1 | 1282.465 | −10.7 | 1580.16 | 18 |
| 1298.453 | A1G1 | 1298.454 | −0.6 | 840.8 | 9 |
| 1339.48 | A2 | 1339.484 | −4 | 6704.09 | 75 |
| 1444.507 | FA1G1 | 1444.522 | −14.9 | 386.39 | 4 |
| 1485.538 | FA2 | 1485.545 | −7.1 | 8939.36 | 100 |
| 1501.533 | A2G1 | 1501.53 | 2.8 | 4852.75 | 54 |
| 1542.559 | A3 | 1542.556 | 3.4 | 1570.78 | 18 |
| 1647.591 | FA2G1 | 1647.599 | −8.3 | 3217.43 | 36 |
| 1663.586 | A2G2 | 1663.582 | 3.6 | 2328 | 26 |
| 1688.617 | FA3 | 1688.624 | −6.7 | 2752.37 | 31 |
| 1704.612 | A3G1 | 1704.609 | 3.2 | 1998.15 | 22 |
| 1745.639 | A4 | 1745.624 | 14.8 | 803 | 9 |
| 1809.644 | FA2G2 | 1809.647 | −3.5 | 1704.05 | 19 |
| 1850.67 | FA3G1 | 1850.675 | −4.9 | 2024.14 | 23 |
| 1866.665 | A3G2 | 1866.656 | 9 | 1263.32 | 14 |
| 1891.697 | FA4 | 1891.7 | −3.3 | 1384.76 | 15 |
| 1907.692 | A4G1 | 1907.692 | −0.4 | 937.19 | 10 |
| 2012.723 | FA3G2 | 2012.728 | −5.1 | 1352.46 | 15 |
| 2028.718 | A3G3 | 2028.719 | −1.2 | 992.03 | 11 |
| 2053.75 | FA4G1 | 2053.761 | −11.5 | 1404.04 | 16 |
| 2069.744 | A4G2 | 2069.742 | 2.4 | 771.77 | 9 |
| 2174.776 | FA3G3 | 2174.779 | −3.3 | 1463.26 | 16 |
| 2215.793 | FA4G2 | 2215.814 | −20.7 | 1180.8 | 13 |
| 2231.797 | A4G3 | 2231.791 | 6.2 | 572.1 | 6 |
| 2377.855 | FA4G3 | 2377.864 | −8.9 | 853.1 | 10 |
| 2393.85 | A4G4 | 2393.849 | 1 | 529.86 | 6 |
| 2418.877 | FA4G1L1 | 2418.954 | −76.6 | 202 | 2 |
| 2539.904 | FA4G4 | 2539.918 | −14.3 | 1009.29 | 11 |
| 2580.93 | FA4G2L1 | 2580.949 | −18.8 | 188.9 | 2 |
| 2742.983 | FA4G3L1 | 2742.985 | −1.9 | 255 | 3 |
| 2905.036 | FA4G4L1 | 2905.048 | −12.1 | 301.29 | 3 |
| 3270.168 | FA4G4L2 | 3270.102 | 66.1 | 204.96 | 2 |

2-Aminobenzamide (2-AB) Labeled Oligosaccharides Profiling

Figure 38:
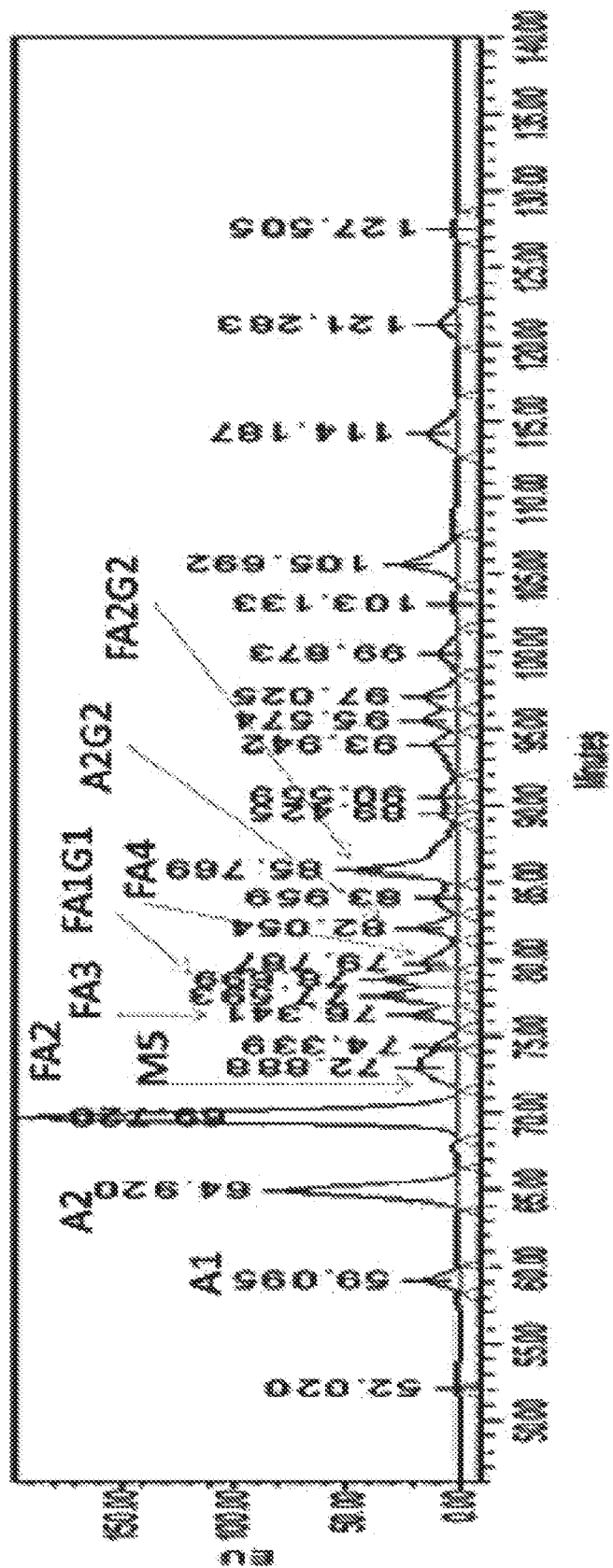
FIG. 38 is a graph showing the fluorescence chromatogram of oligosaccharides of asfotase alfa.
Figure 39:
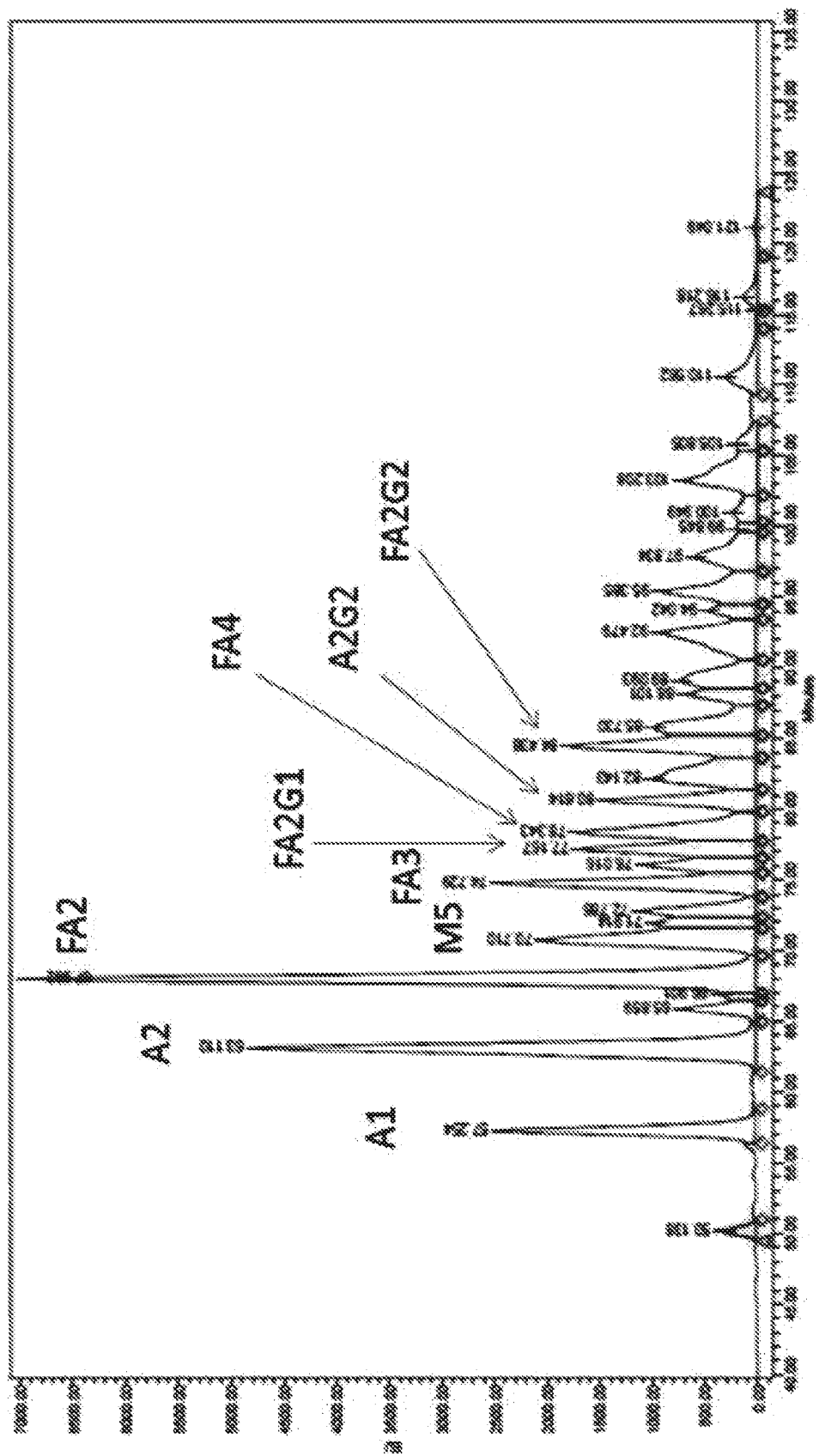
FIG. 39 is a graph showing the fluorescence chromatogram of the asfotase alfa reference standard.

Released oligosaccharides from asfotase alfa were labeled by 2-aminobenzamide (2-AB) and then analyzed by normal phase HPLC with fluorescence detection to determine the types and the relative percentage of various oligosaccharides. Asfotase alfa samples were reduced using dithiothreitol (DTT) at 37° C. for 1 hour and then digested using PNGaseF at 37° C. overnight to release N-linked oligosaccharides. Protein from the digested sample was precipitated and separated from the released glycans by cold ethanol and centrifugation. Supernatants containing the released glycans were dried using a vacuum centrifuge, reconstituted using 1% formic acid and incubated at room temperature for 40 minutes and then dried again. The samples were then labeled using 2-AB labeling reagents by following the manufacturer's instruction (Ludger, Oxfordshire, UK). The labeled glycans were cleaned up using glycan S cartridges (Prozyme, Hayward, Calif.) and then analyzed using HPLC with fluorescence detection with an excitation wavelength of 330 nm and emission wavelength of 420 nm. A fluorescence chromatogram from the analysis of asfotase alfa is shown in FIG. 38. Identities of peaks were established by fraction collection, mass spectrometry analysis of molecular weights and matching the molecular weights to the molecular weights of commonly-known oligosaccharide structures. Oligosaccharides identified by 2-AB labeling are summarized in Table 23. A chromatogram obtained from analysis of an asfotase alfa reference standard is shown in FIG. 39.

TABLE 23

Glycoforms and Their Relative Percentage by 2-AB Labeling

| Glycoforms | Relative % |
|---|---|
| M3 | 0.02 |
| A1 | 1.90 |

TABLE 23-continued

Glycoforms and Their Relative Percentage by 2-AB Labeling

| Glycoforms | Relative % |
|---|---|
| FA1 | 11.58 |
| A2 | 0.26 |
| FA2 | 25.55 |
| M5/A3 | 5.18 |
| A2G1 | 1.25 |
| FA3 | 2.67 |
| FA2G1 | 4.58 |
| FA2G1 | 4.59 |
| FA4 | 2.68 |
| A2G2 | 2.46 |
| FA3G1 | 2.25 |
| FA2G2 | 7.03 |
| FA4G1 | 3.42 |
| FA3G3 | 1.71 |
| A3G3/A4G2 | 3.00 |
| FA3G3 | 2.49 |
| FA3G3 | 3.01 |
| FA4G3 | 2.13 |
| FA4G3 | 0.89 |
| FA4G4 | 5.35 |
| FA4G4L1 | 3.54 |
| FA4G4L2 | 1.87 |
| UNKNOWN | 0.61 |

Glycopeptide Profiling

Figure 40:
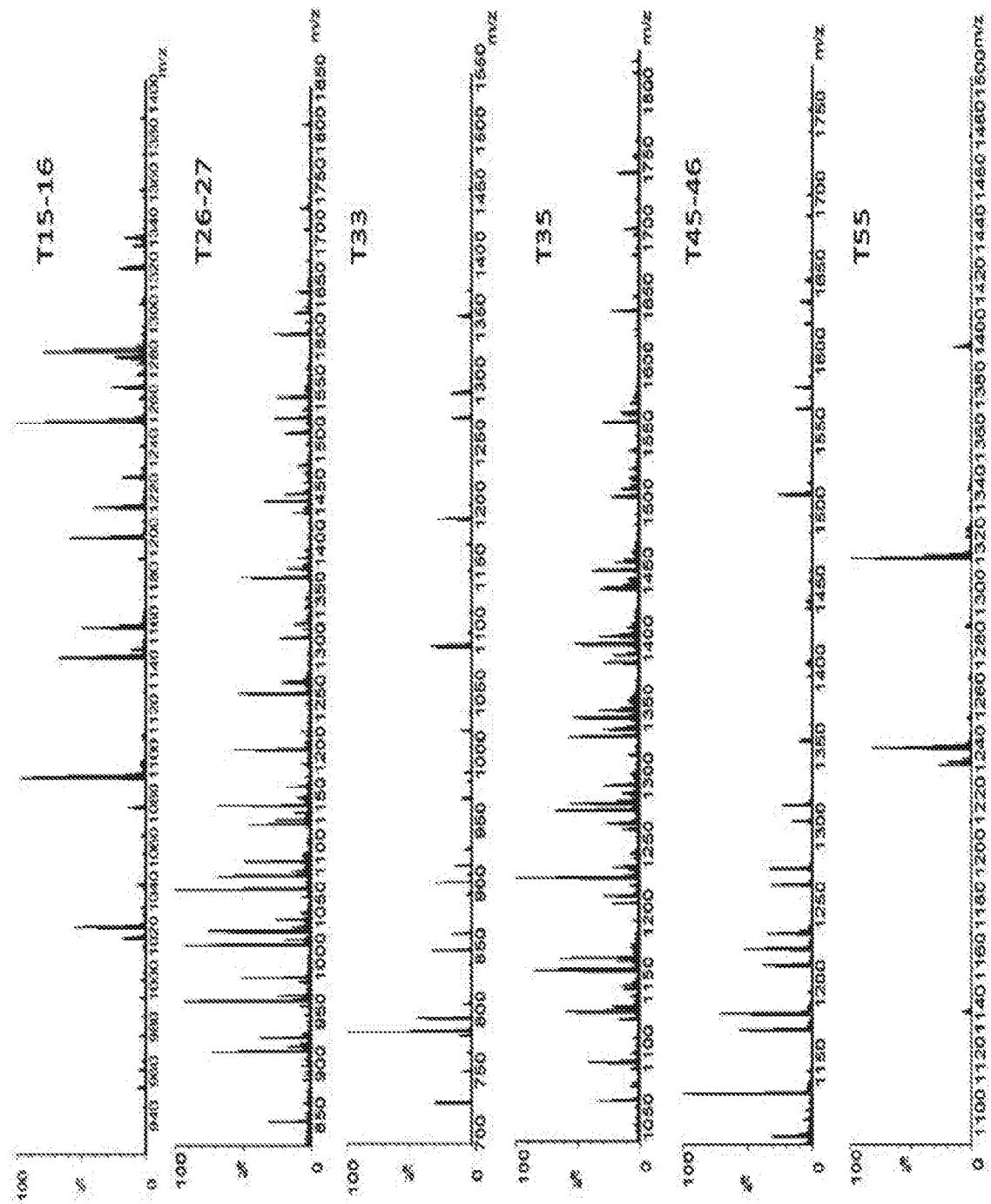
FIG. 40 are graphs showing mass spectrum of glycopeptides generated from asfotase alfa.

A glycopeptide profile was used to determine the site-specific oligosaccharide distribution. Asfotase alfa samples at a final concentration of 0.5 mg/mL were denatured and reduced in the presence of 6M guanidine hydrochloride in 0.2 M Tris, pH, 8.6, using 40 mM DTT at 37° C. for 1 hour. The reduced samples were alkylated by the addition of iodoacetic acid to a final concentration of 50 mM and incubation at room temperature for 30 minutes. The samples were then buffer-exchanged into 50 mM ammonium bicarbonate using dialysis tubing with a molecular weight cut-off of 10 kDa. The samples were digested using trypsin at a final ratio (w:w) of 1:50 trypsin; protein at 37° C. for 24 hours. An UPLC system equipped with a reversed-phase C18 column and a Q-TOF mass spectrometer were used to analyze the digested samples. Data were acquired in the positive mode. Mass spectra across the elution time widows were averaged for each glycopeptide. Six glycopeptides were generated from trypsin digestion of asfotase alfa, corresponding to six glycosylation sites per monomer of asfotase alfa. Because the peptide moiety is the primary factor determining the retention times, glycopeptides are separated based on their unique amino acid sequence; therefore, site-specific oligosaccharide distribution can be obtained. Mass spectra of glycopeptides are shown in FIG. 40. Oligosaccharide species associated with each glycosylation site are summarized in Table 24.

TABLE 24

Oligosaccharide Species Associated with Each Glycopeptide

| Tryptic Peptides | Retention Times | Glycoforms | Theoretical Molecular Weights | Observed Molecular Weights |
|---|---|---|---|---|
| T15-16 | 39.7-40.7 | FA1 | 3078.34 | 3078.32 |
| | | FA2 | 3281.42 | 3281.40 |
| | | FA2G1 | 3443.47 | 3443.45 |
| | | FA3 | 3484.50 | 3484.48 |
| | | FA2G2 | 3605.53 | 3605.51 |
| | | FA3G1 | 3646.55 | 3646.54 |
| | | FA4 | 3687.58 | 3687.57 |
| | | FA3G2 | 3808.61 | 3808.60 |
| | | FA4G1 | 3849.63 | 3849.62 |
| | | FA3G3 | 3970.66 | 3970.65 |
| T76-27 | 17.4-17.9 | A2 | 2755.12 | 2755.11 |
| | | FA2 | 2901.18 | 2901.16 |
| | | FA2G1 | 3063.23 | 3063.21 |
| | | FA3 | 3104.76 | 3104.25 |
| | | FA2G2 | 3225.28 | 3225.27 |
| | | FA3G1 | 3266.31 | 3266.29 |
| | | FA4 | 3307.34 | 3307.32 |
| | | FA4G1 | 3469.39 | 3469.38 |
| | | FA4G2 | 3631.43 | 3631.43 |
| | | FA4G3 | 3793.49 | 3793.47 |
| T33 | 28.6-29.9 | A1 | 2191.92 | 2191.93 |
| | | A2 | 2394.99 | 2395.01 |
| | | A2G1 | 2557.05 | 2557.06 |
| | | A3 | 2598.07 | 2598.07 |
| | | A2G2 | 2719.10 | 2719.11 |
| | | A3G1 | 2760.13 | 2760.14 |
| | | A4 | 2801.15 | 2801.16 |
| T35 | 99.5-102.8 | A2 | 3496.66 | 3496.65 |
| | | A3 | 3699.74 | 3699.73 |
| | | FA3 | 3845.80 | 3845.79 |
| | | A4 | 3902.82 | 3902.80 |
| | | FA3G1 | 4007.85 | 4007.85 |
| | | FA4 | 4048.88 | 4048.87 |
| | | FA4G1 | 4210.93 | 4210.93 |
| T45-46 | 46.3-47.0 | FA2 | 4548.04 | 4547.99 |
| | | FA2G1 | 4710.09 | 4710.05 |
| | | FA3 | 4751.11 | 4751.08 |
| | | FA2G2 | 4872.14 | 4872.10 |
| | | FA3G1 | 4913.17 | 4913.13 |
| | | FA4 | 4954.19 | 4954.21 |
| | | FA3G2 | 5075.22 | 5075.18 |
| | | FA4G1 | 5116.25 | 5116.21 |
| | | FA4G2 | 5278.29 | 5278.26 |
| T55 | 19.6-20.0 | A1 | 2284.91 | 2284.92 |
| | | A2 | 2487.99 | 2488.00 |
| | | FA2 | 2634.05 | 2634.06 |
| | | FA2G1 | 2796.10 | 2796.12 |

Figure 41:
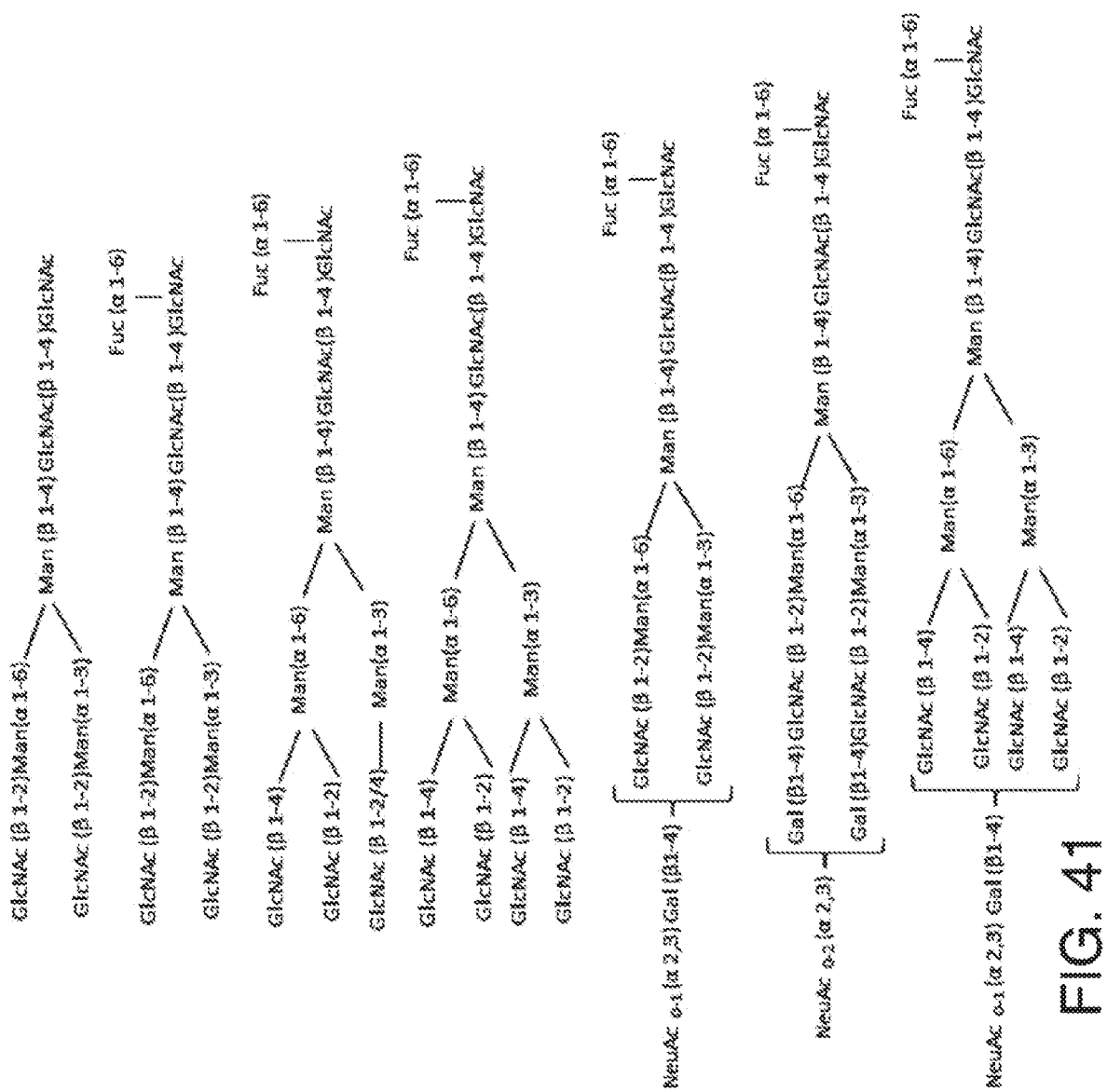
FIG. 41 are representations of the proposed structures of major glycans of asfotase alfa ($C_{7108}H_{11008}O_{2206}S_{56}$ (Protein Part dimer); or $C_{3554}H_{5506}O_{1103}S_{28}$ (Monomer)). The number of NeuAc per glycan (FA2G2, FA2G1 and A2G2) is an estimated number.
Figure 42:
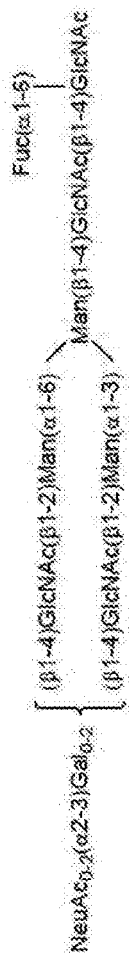
FIG. 42 are representations of the estimated glycan structure on glycosylation sites of asfotase alfa.
Figure 42:
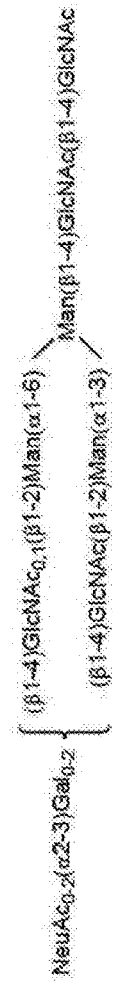
Figure 42:
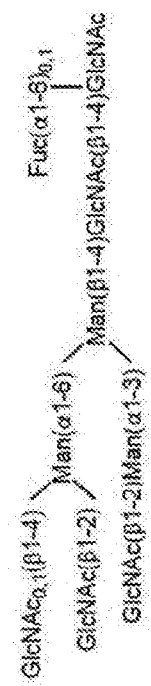
Figure 42:
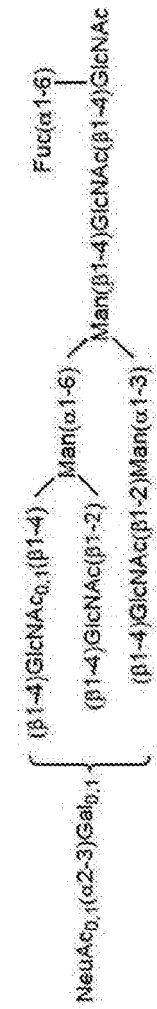
Figure 42:
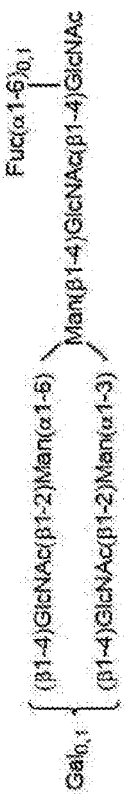

Based on observed molecular weights and other analysis results (e.g., mass spectrum data and 2-aminobenzamide (2-AB) labeled oligosaccharides profiling data), structures of major glycans (≥4% relative abundance) of asfotase alfa were determined in FIG. 41 and FIG. 42.

Figure 43:
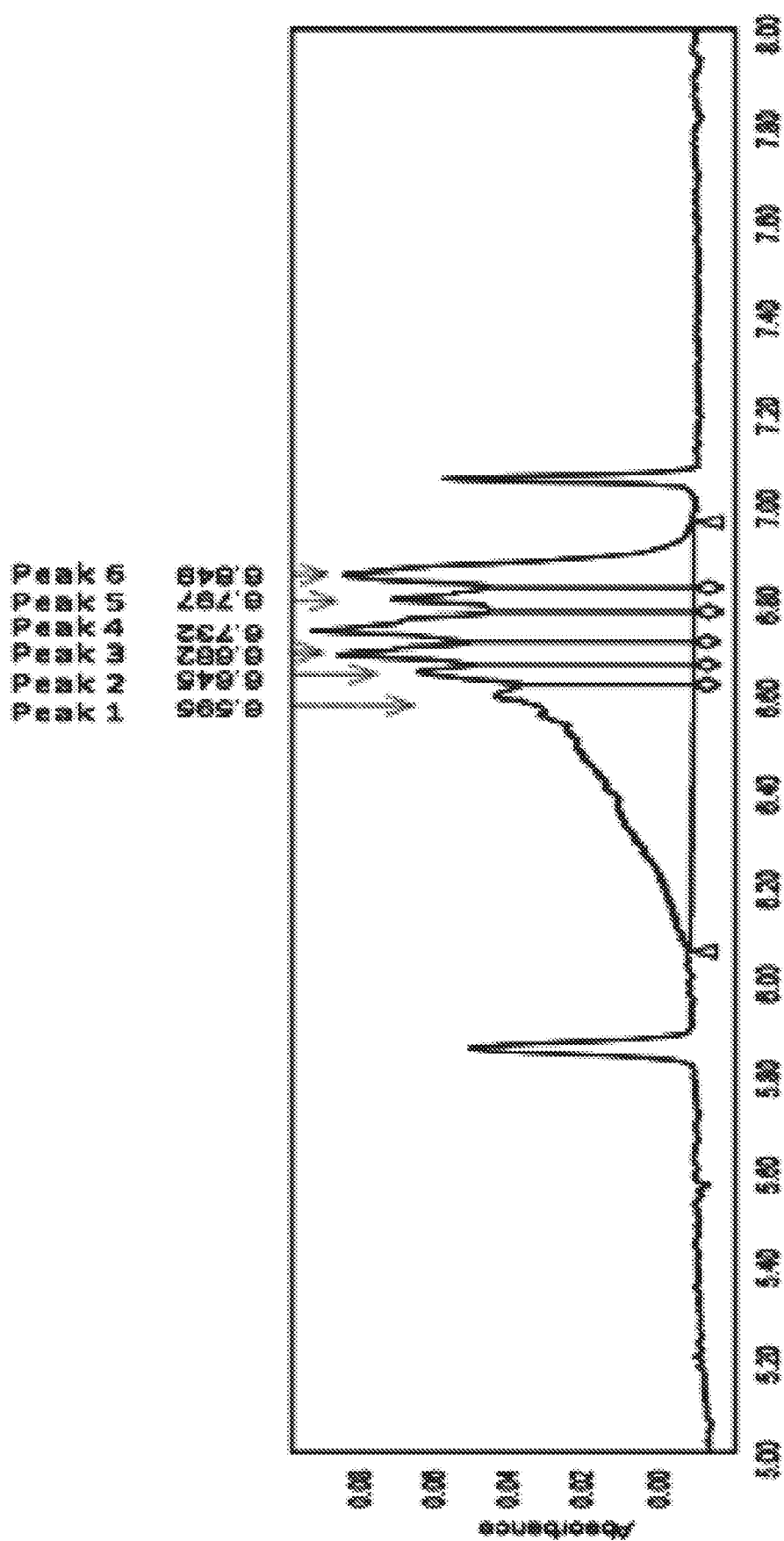
FIG. 43 is a graph showing the representative electropherogram of asfotase alfa.
Figure 44:
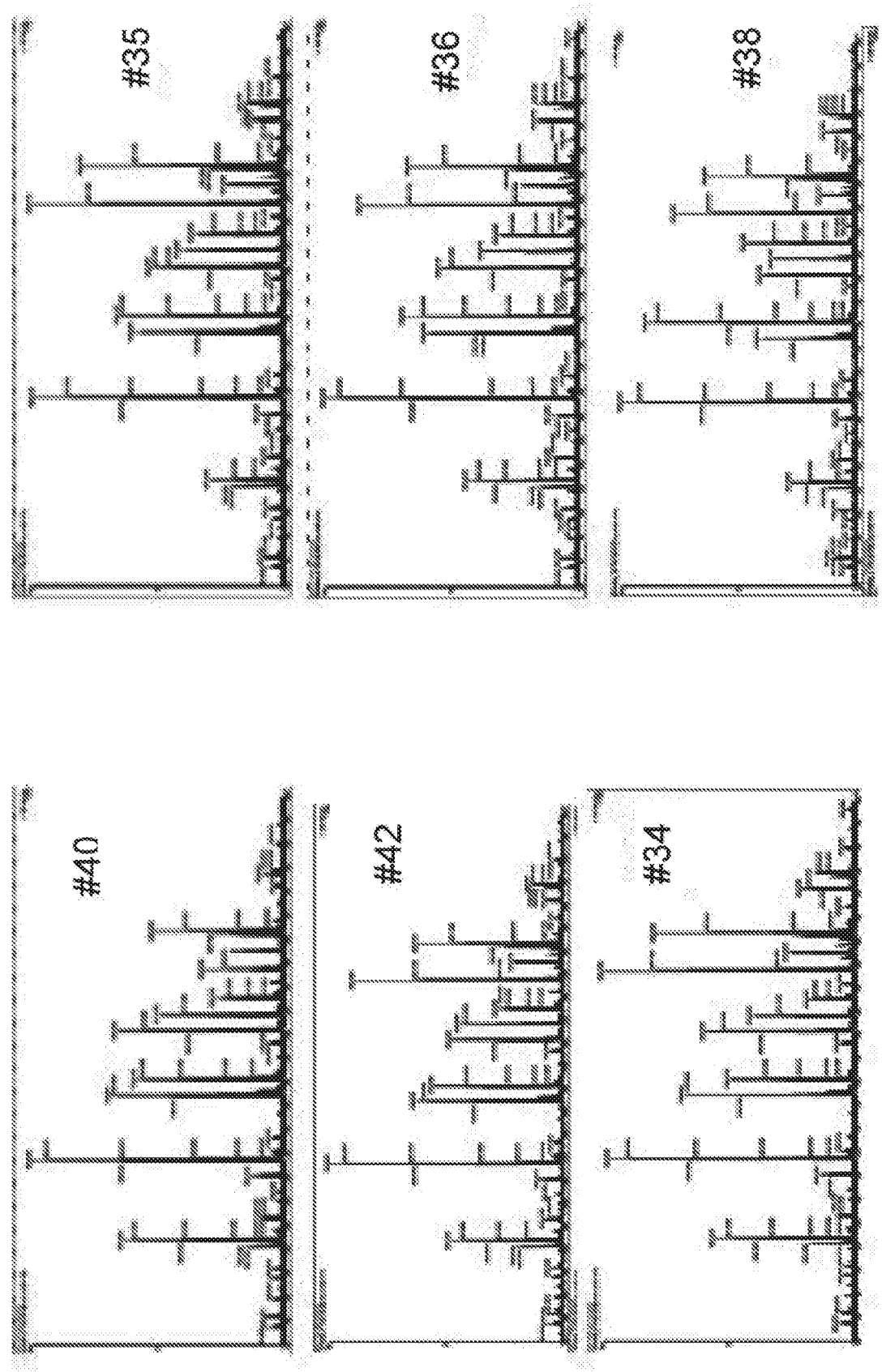
FIG. 44 are graphs showing glycopeptide mass fingerprints for asfotase alfa produced from 20K and 2K batches (N123 in T15-16). 2K Batch Numbers: #35, #36 and #38; 20K Batch Numbers: #40, #42 and #34.
Figure 45:
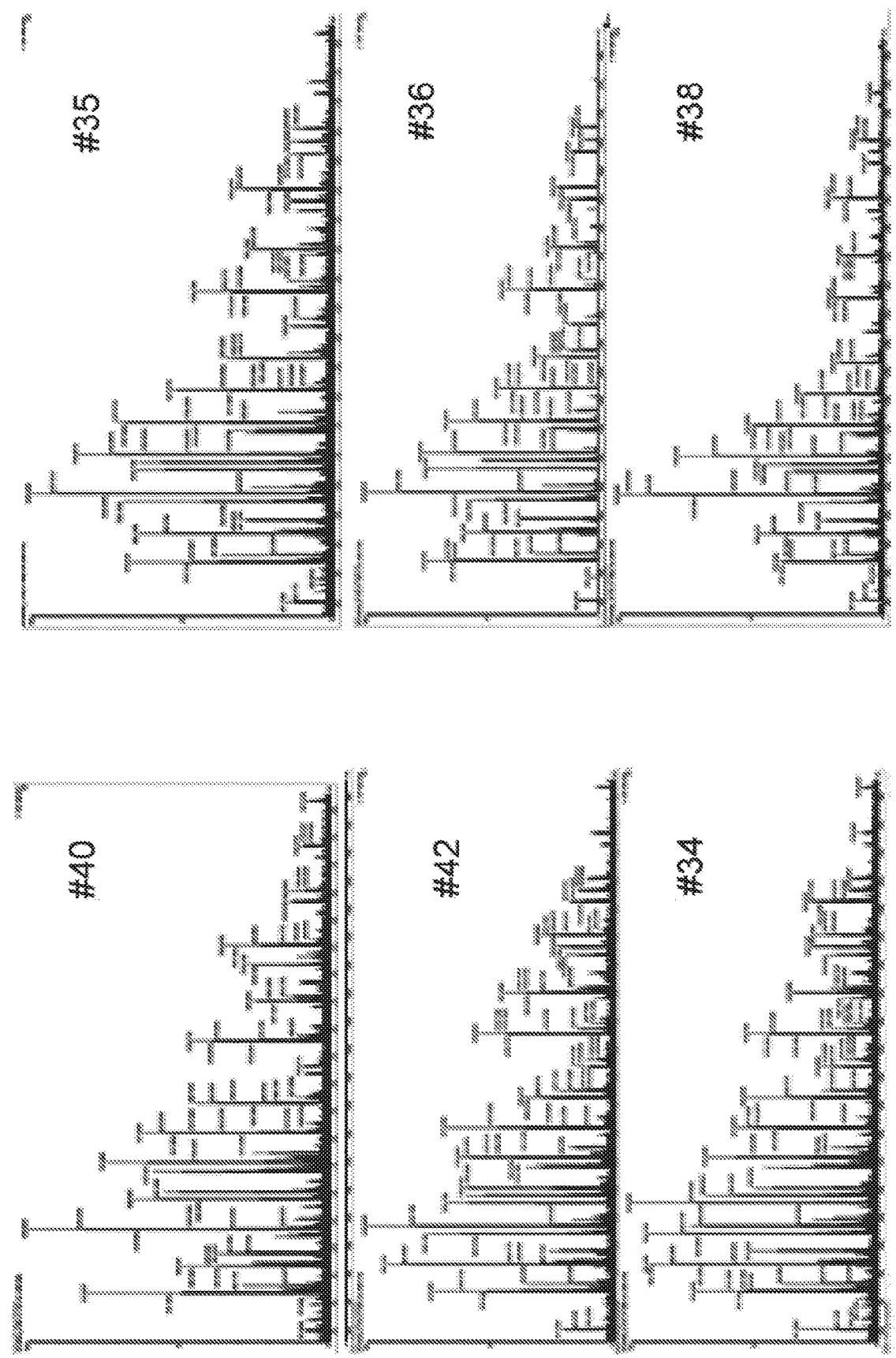
FIG. 45 are graphs showing glycopeptide mass fingerprints for asfotase alfa produced from 20K and 2K batches (N213 in T26-27). 2K Batch Numbers: #35, #36 and #38; 20K Batch Numbers: #40, #42 and #34.
Figure 46:
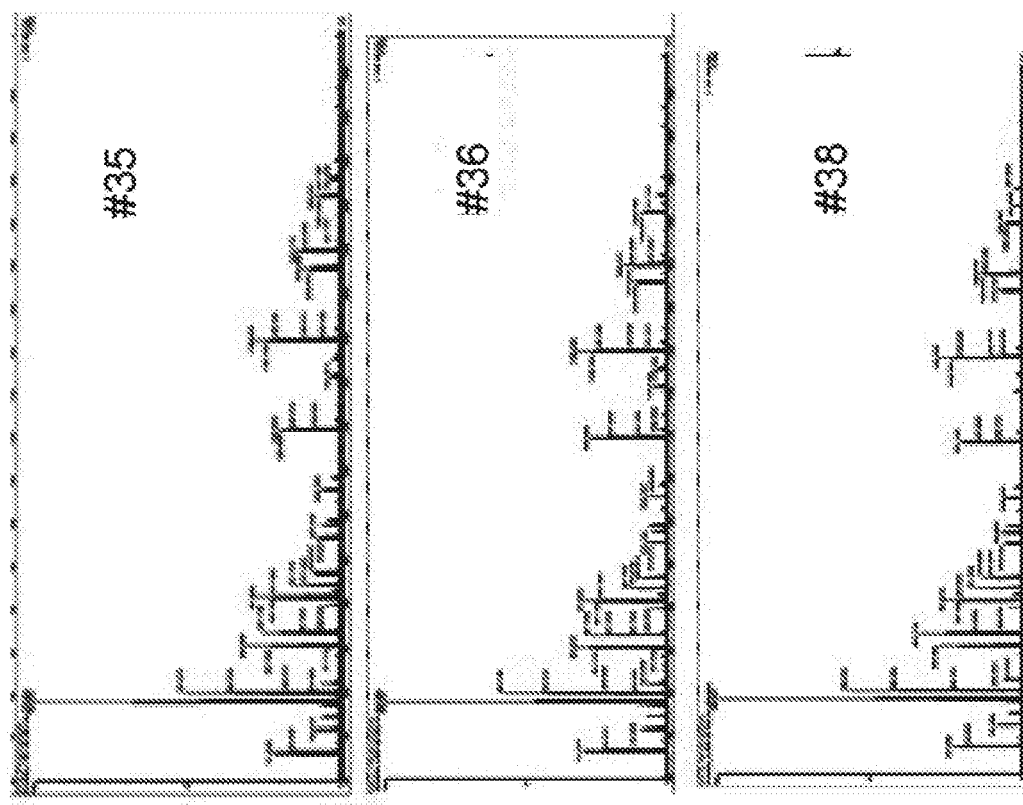
FIG. 46 are graphs showing glycopeptide mass fingerprints for asfotase alfa produced from 20K and 2K batches (N254 in T33). 2K Batch Numbers: #35, #36 and #38; 20K Batch Numbers: #40, #42 and #34.
Figure 46:
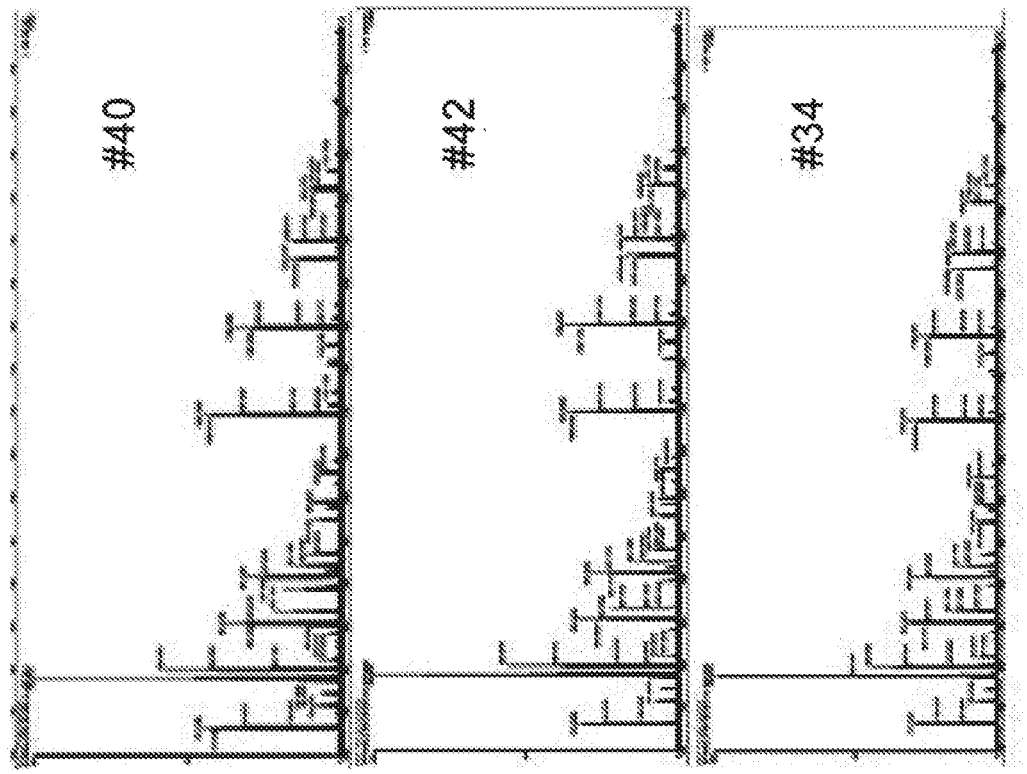
Figure 47:
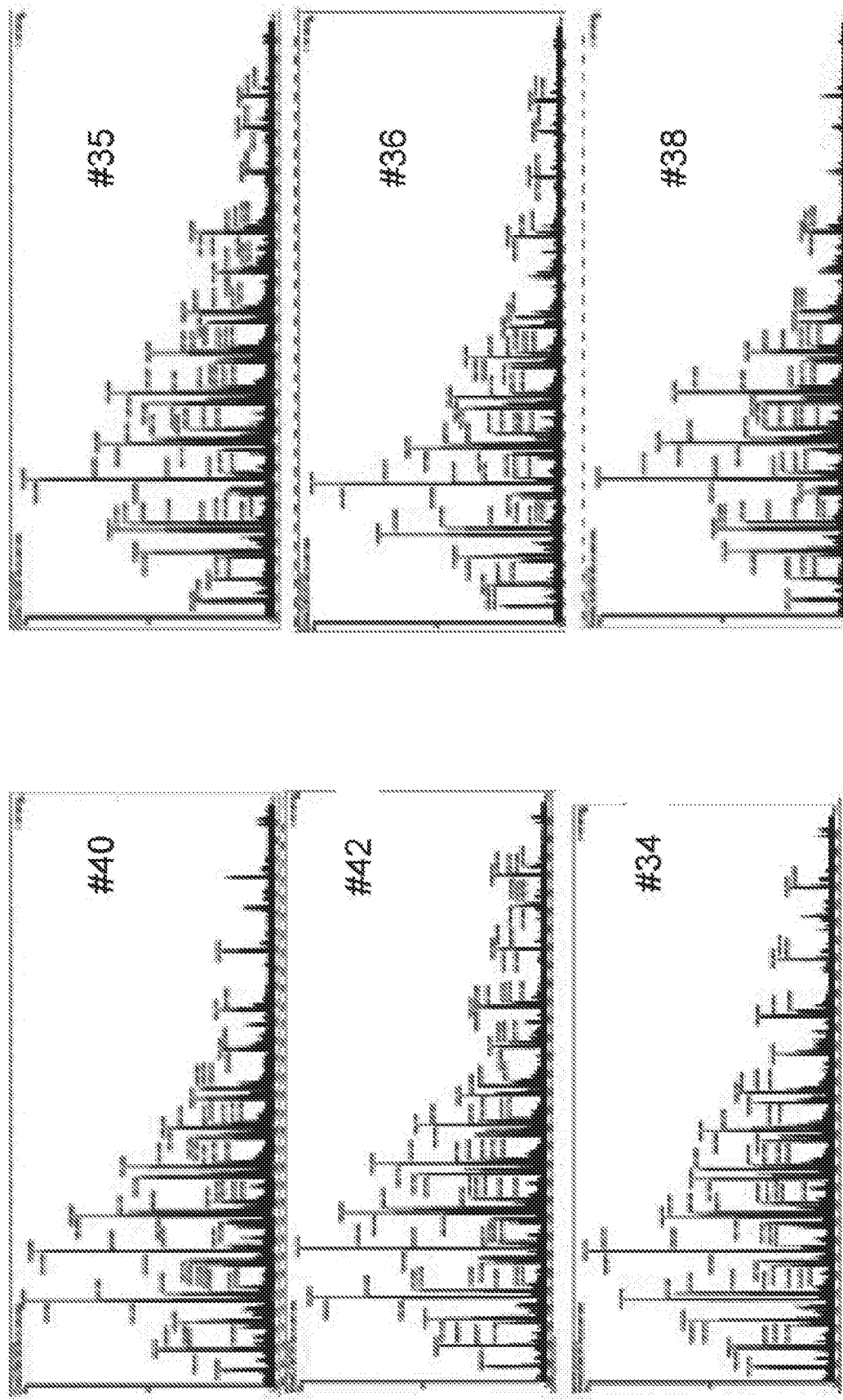
FIG. 47 are graphs showing glycopeptide mass fingerprints for asfotase alfa produced from 20K and 2K batches (N286 in T35). 2K Batch Numbers: #35, #36 and #38; 20K Batch Numbers: #40, #42 and #34.
Figure 48:
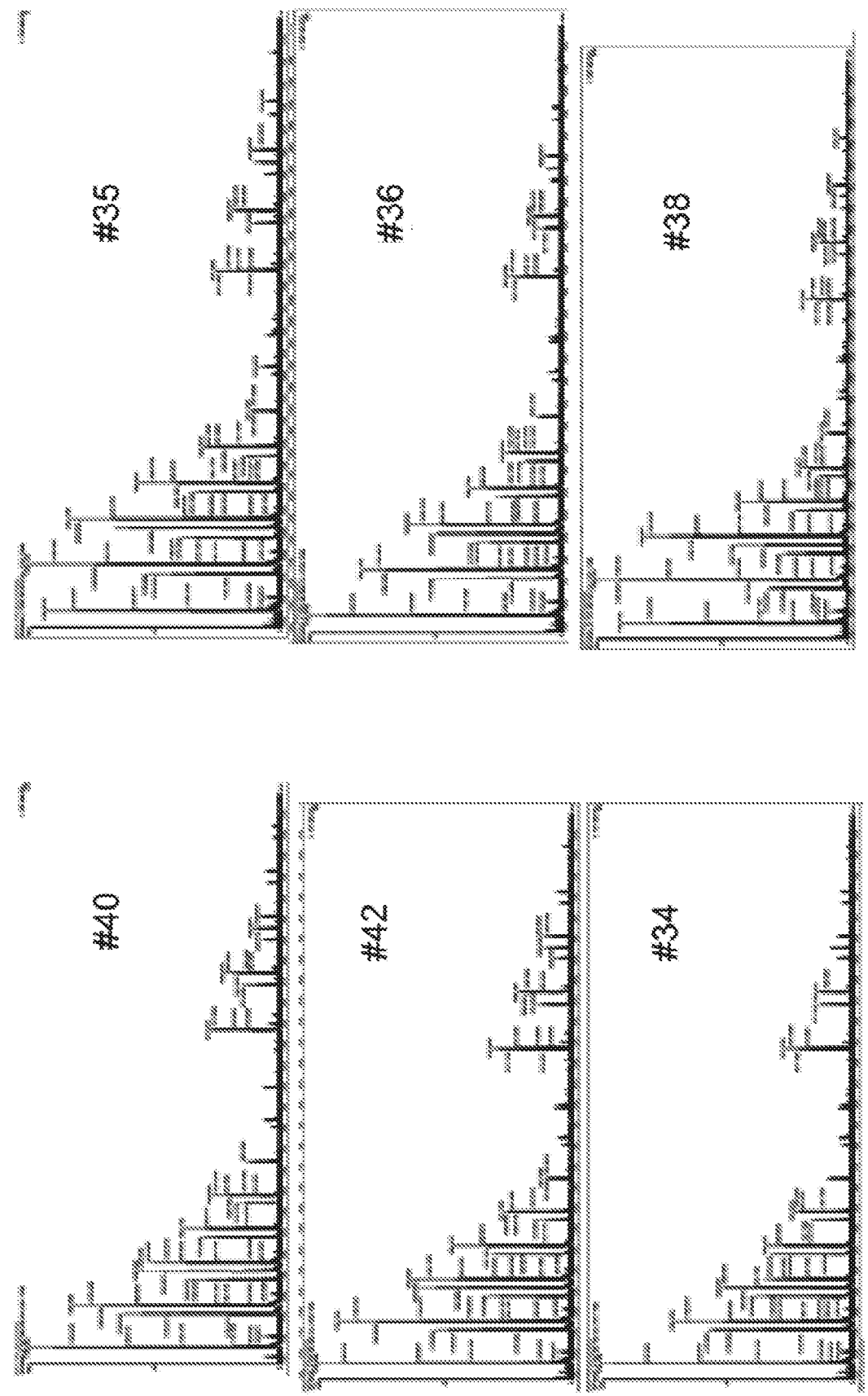
FIG. 48 are graphs showing glycopeptide mass fingerprints for asfotase alfa produced from 20K and 2K batches (N413 in T45-46). 2K Batch Numbers: #35, #36 and #38; 20K Batch Numbers: #40, #42 and #34.
Figure 49:
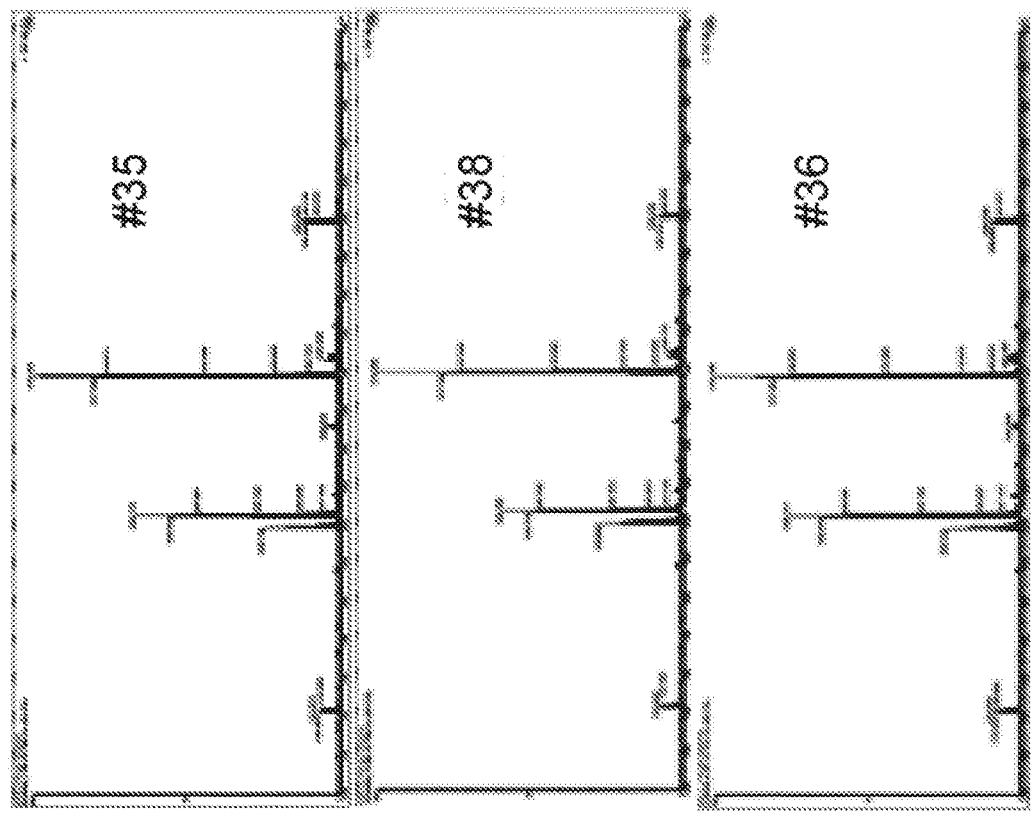
FIG. 49 are graphs showing glycopeptide mass fingerprints for asfotase alfa produced from 20K and 2K batches (N564 in T55). 2K Batch Numbers: #35, #36 and #38; 20K Batch Numbers: #40, #42 and #34.
Figure 49:
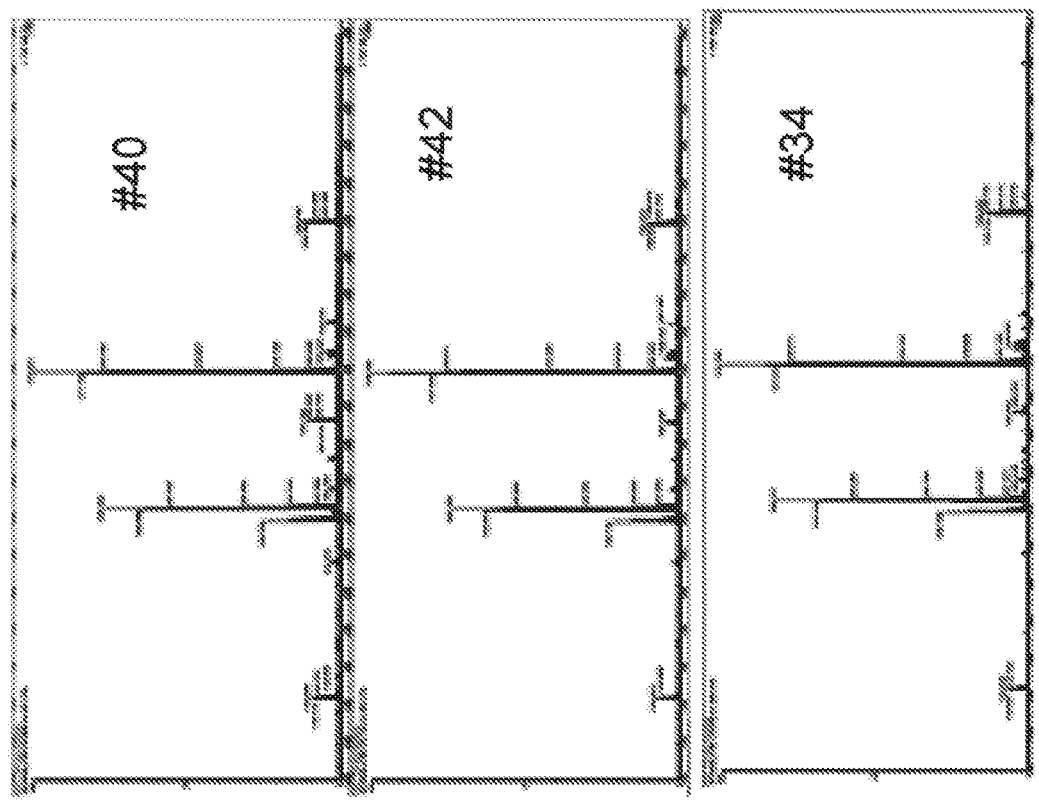
Figure 50:
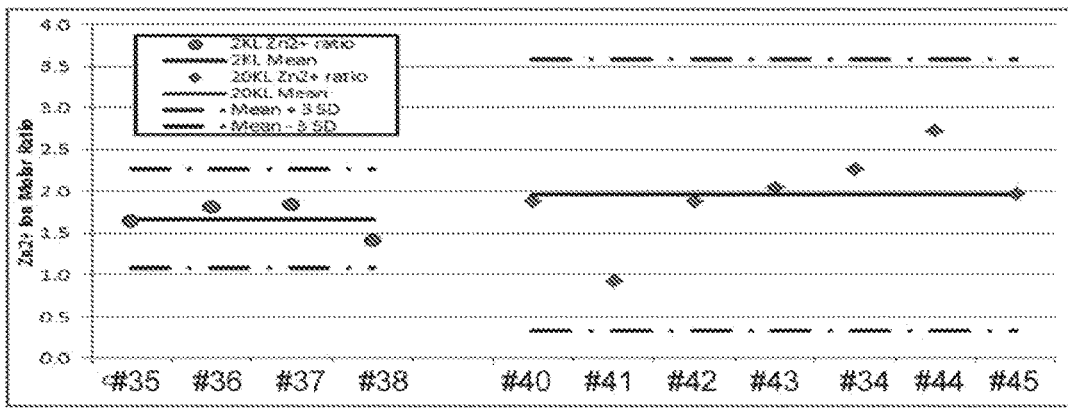
FIG. 50 are graphs comparing the ICP metal ion molar ratio for zinc (panel A), magnesium (panel B), and calcium (panel C) of asfotase alfa produced from 2K and 20K batches.
Figure 50:
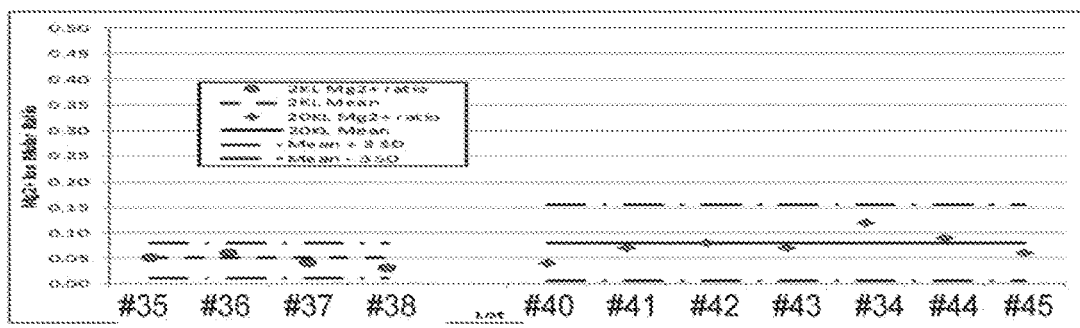
Figure 50:
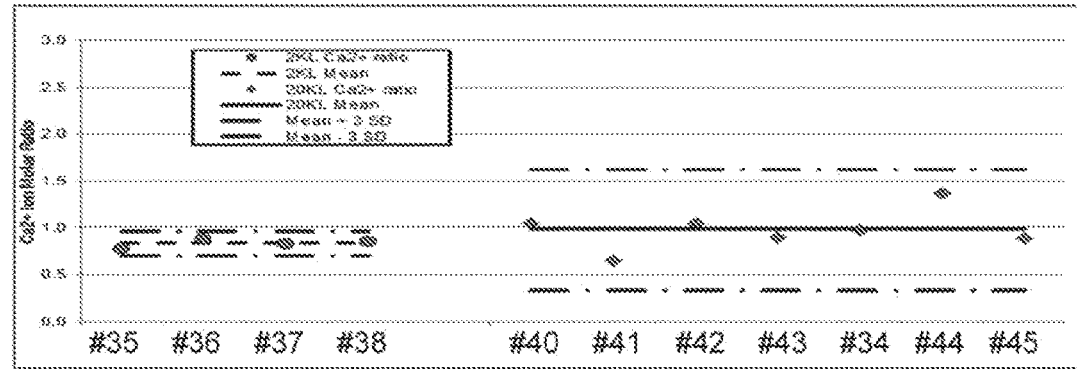
Figure 51:
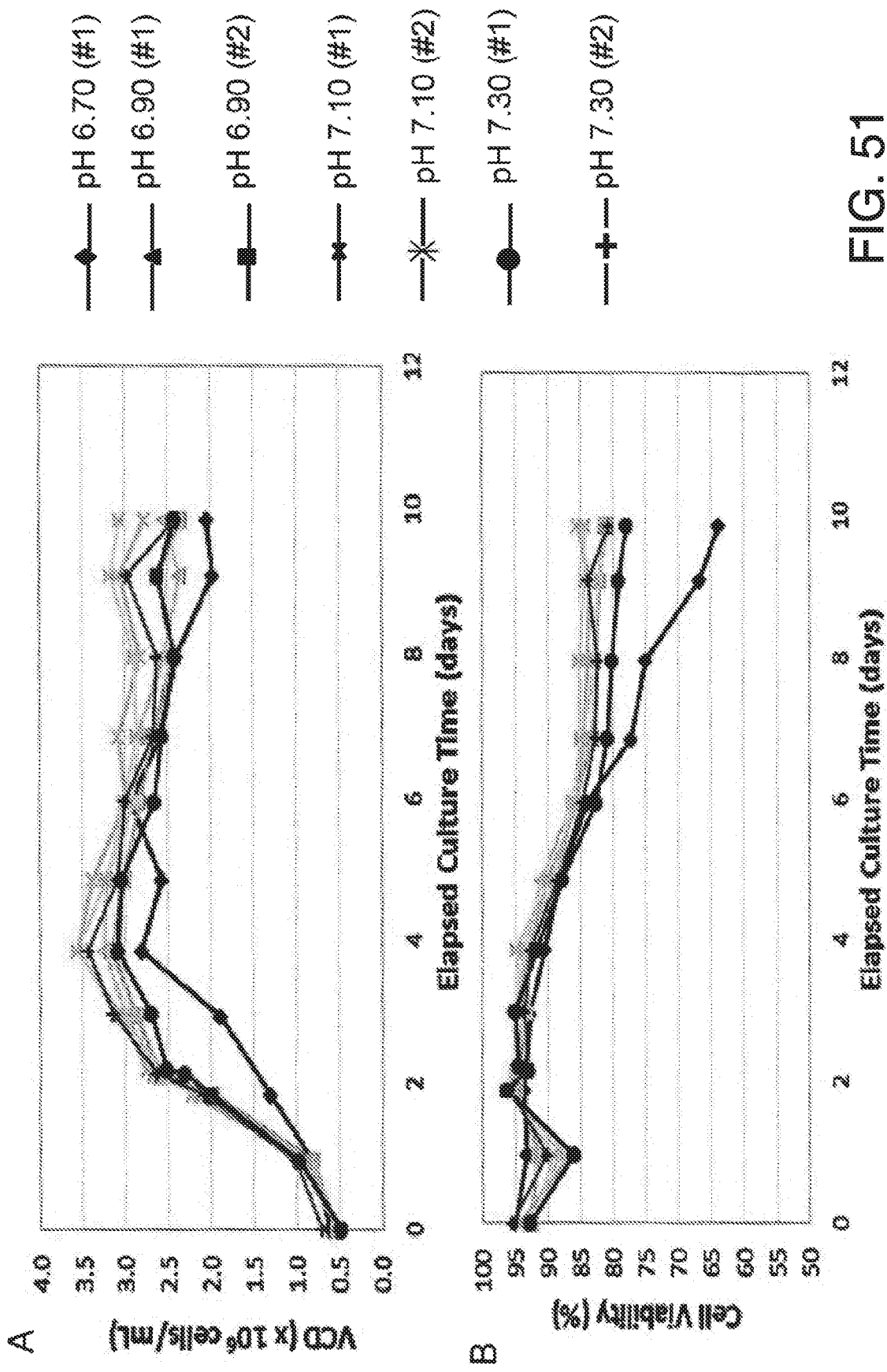
FIG. 51A is graph comparing the viable cell density (VCD) through culture time under different pH conditions.
FIG. 51B is graph comparing the cell viability through culture time under different pH conditions.
Figure 52:
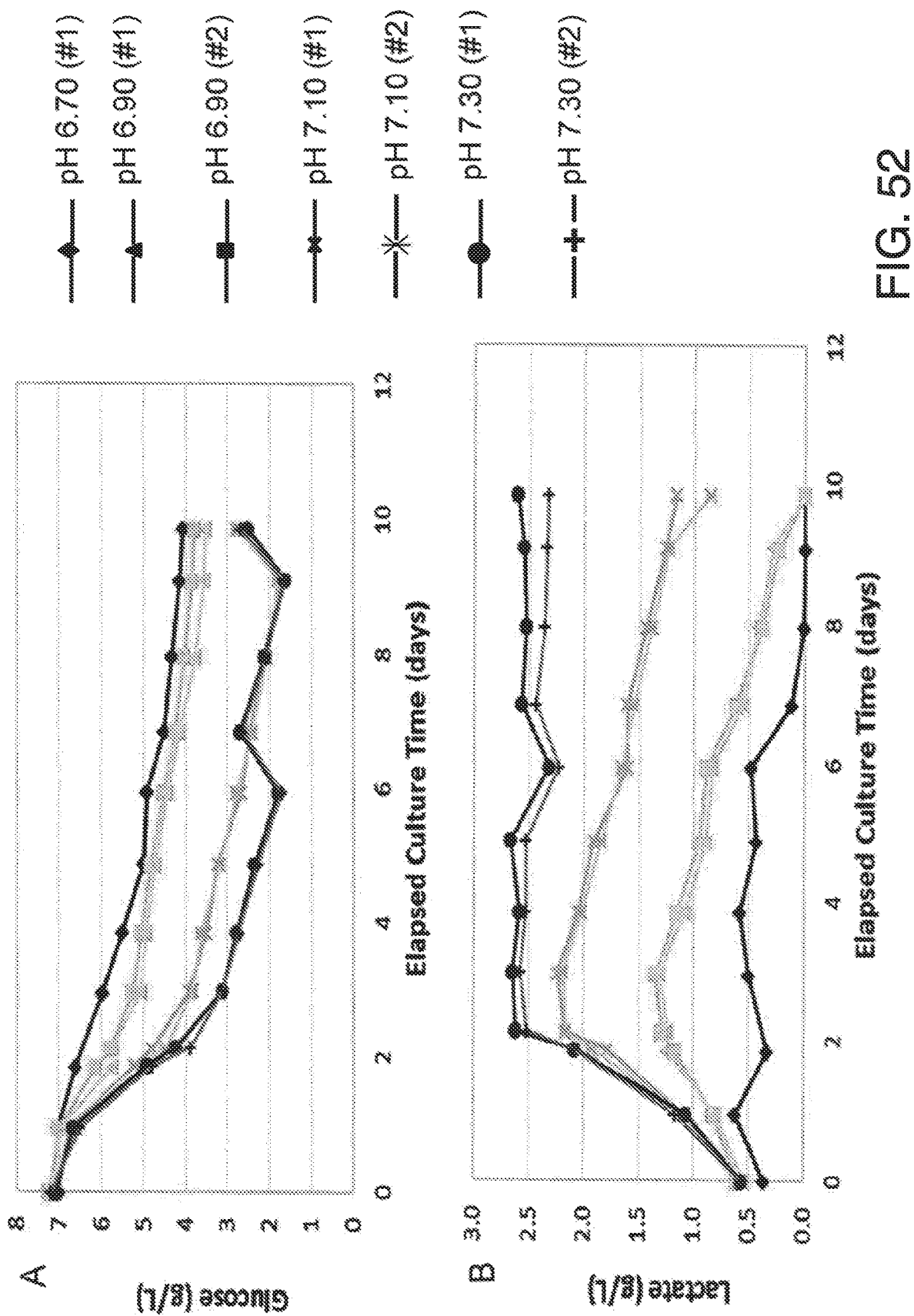
FIG. 52A is a graph showing the glucose concentration in the bioreactors through the elapsed culture time.
FIG. 52B is a graph showing the lactate concentration in the bioreactors through the elapsed culture time.
Figure 53:
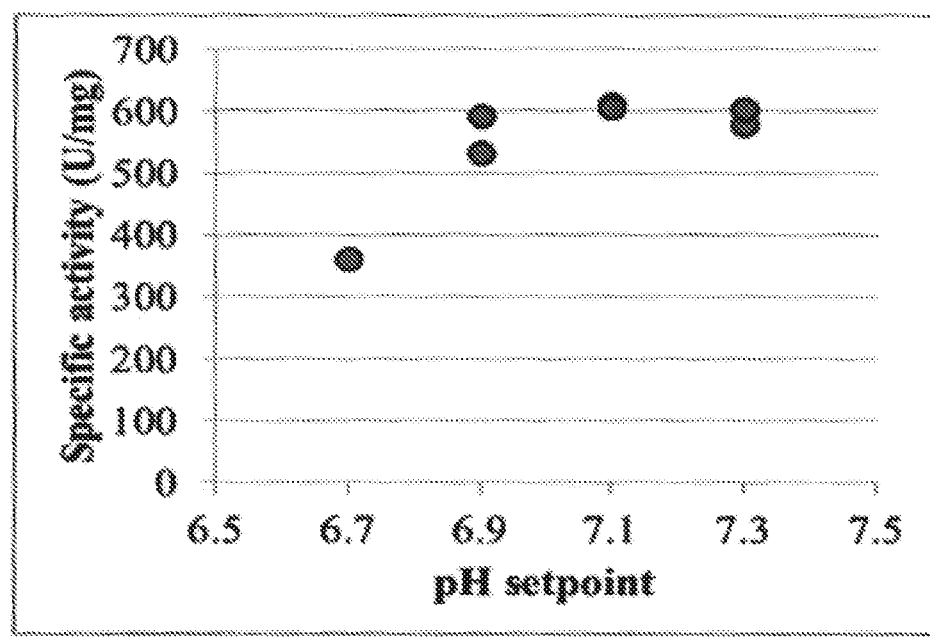
FIG. 53 is a graph comparing specific activity profiles under different pH conditions.

Capillary Isoelectric Focusing (cIEF)

cIEF separates proteins based on their isoelectric points and was used to monitor asfotase alfa charge variants. Asfotase alfa samples at a final concentration of 0.5 mg/mL in a buffer containing urea, methyl cellulose, sucrose, pharmalytes, and pI markers were analyzed using a capillary electrophoresis system. The samples were focused for 0.1 minute at 1500 V and then for 14 minutes at 3000 V. The separated protein variants were detected using UV absorption at 280 nm. An electropherogram from the representative batch of asfotase alfa is shown in FIG. 43. Six peaks were observed by cIEF. Typically, Peak 1 has a broad pI range. Additional shoulders were observed for peaks 4 and 5. This result demonstrated that asfotase alfa is highly heterogeneous with regard to charge, which was expected, because of the presence of multiple glycosylation sites with various numbers and levels of sialic acids at each site. The pI of each peak and their relative percentage of asfotase alfa of the representative batch are summarized in Table 25.

TABLE 25 pI and Relative Percentage of Peaks Observed by cIEF

| Peaks | pI   | %     |
|-------|------|-------|
| 1     | 6.60 | 36.64 |
| 2     | 6.65 | 8.66  |
| 3     | 6.68 | 11.78 |
| 4     | 6.73 | 16.71 |
| 5     | 6.80 | 11.24 |
| 6     | 6.85 | 15.27 |

Product-Related Substance

Structural heterogeneity of asfotase alfa due to post-translational modification is expected as it is expressed in CHO cell line. As described previously, heterogeneity of asfotase alfa is reflected as charge variants, where six peaks are observed when analyzed by cIEF. The consistent pattern of charge profiles of asfotase alfa has been demonstrated in clinical and PV batches. As determined by AUC, SDS-PAGE, SEC and AEX, using representative material, asfotase alfa is at a minimum of 96% purity, suggesting that multiple peaks observed by cIEF are fully representative of the produced asfotase alfa and that all peaks are product-related substance.

Product-Related Impurities

Product-related impurities are molecular variants that do not have the properties comparable to the desired asfotase alfa with respect to activity, efficacy, and safety (Guidance for Industry, Q6B specifications: test procedures and acceptance criteria for biotechnological/biological products, August 1999, ICH). Product-related impurities have been observed by three assays and the characteristics of each impurity are summarized in Table 26.

TABLE 26

Summary of Asfotase Alfa Product-Related Impurities

| Methods  | Impurities                                            |
|----------|-------------------------------------------------------|
| SDS-PAGE | Bands with molecular weight other than the main band  |
| SEC      | Aggregates                                            |
| AEX      | Truncated molecule                                    |

Characterization of SDS-PAGE Bands

Asfotase alfa was analyzed by both non-reduced and reduced SDS-PAGE. The results of SDS-PAGE analysis suggests that band 1 corresponds to intact asfotase alfa, band 2 corresponds to intact asfotase alfa with only one enzyme arm, and band 3 corresponds to the reduced form (monomer) of asfotase alfa (data not shown).

As expected, peptides from both the enzyme portion and the IgG1-Fc portion were observed from the band on reduced SDS-PAGE. This result, in addition to the apparent molecular weight of the band on reduced SDS-PAGE, indicates that the main band corresponds to asfotase alfa in its reduced form. Band characterization is summarized in Table 27.

TABLE 27

Summary of SDS-PAGE Band Characterization

| SDS-PAGE | Band Description | Apparent Molecular Weights | MAIDI-TOF and LC-MS analysis of bands after in-gel digestion | Species |
|---|---|---|---|---|
| Non-Reduced | Band 1 (Main band) | Approximately 200-220 kDa | Confirmed band 1 as asfotase alfa (61.9% sequence coverage) | Asfotase alfa, based on the apparent molecular weight and sequence coverage. |
|  | Band 2 | Approximately 125 kDa | Confirmed band 2 is asfotase alfa-related (13.8% sequence coverage) | Presumably truncated asfotase alfa based on the apparent molecular weight that is between asfotase alfa homodimer and its single polypeptide chain. |
|  | Band 3 | Approximately 95-105 kDa | Confirmed band 3 is asfotase alfa-related (7.4% sequence coverage) | Probably a single polypeptide chain of asfotase alfa. |
| Reduced | Main Band | Approximately 95-105 kDa | Confirmed the main band as asfotase alfa (65.4% sequence coverage) | Reduced asfotase alfa (single polypeptide chain) The hypothesized truncated form detected by non-reduced SDS-PAGE was not detected by reduced SDS-PAGE because of its low abundance. |

Characterization of SEC Peaks

SEC-HPLC was used as a purity assay by separating high molecular weight species (aggregates), asfotase alfa dimer, and low molecular weight species. On a typical SEC chromatogram, the most abundant peak corresponds to asfotase alfa homo-dimer. The peak that eluted before the main peak corresponds to a high molecular weight species. The peak that eluted after the main peak corresponds to a low molecular weight species. Fractions corresponding to both high molecular weight species and the main peaks were collected and analyzed by SDS-PAGE followed by in-gel digestion and mass spectrometry analysis. Matching the observed peptide molecular weights to the theoretical molecular weights derived from the known amino acid sequence revealed sequence coverage of 86.6% for the main peak and 70.7% for the high molecular weight species. Therefore, it is concluded that the high molecular weight species represents product-related impurities.

Characterization AEX Peaks

AEX was used to monitor the charge variants of asfotase alfa. The five AEX fractions along with the starting material were analyzed by GP-HPLC and by non-reduced and reduced SDS-PAGE (data not shown). The data suggests AEX basic peaks contain mainly asfotase alfa and possibly a small percentage of high molecular weight species. AEX acidic peak contains asfotase alfa high molecular weight species. Basic and acidic species are product-related as confirmed by peptide finger printing by MALDI-TOF analysis.

Asfotase alfa has been well characterized using multiple analytical techniques. Its identity was confirmed by N-terminal sequencing, amino acid analysis, and molecular weight analysis by MALDI-TOF and ESI-MS. The purity of the produced asfotase alfa was monitored by AUC, SDS-PAGE, GP-HPLC and AEX. The size of asfotase alfa was evaluated by MALDI-TOF and SEC-MALS analysis of the molecule with the oligosaccharides. In addition, molecular weight analyses of asfotase alfa were also performed by AUC and SDS-PAGE. Consistent higher molecular weights of asfotase alfa were observed by these orthogonal methods, suggesting extensive glycosylation of the molecule at multiple sites, which was confirmed by analysis of glycosylation. Higher order structures of asfotase alfa were determined by both far-UV and near-UV CD. The hydrodynamic size of the molecule can also be determined from the analyses of both AUC and SEC-MALS, which further confirmed that asfotase alfa exists as a covalent dimer. Low amount of aggregates were detected by SEC, AUC and SEC-MALS. The native disulfide bond structure and the location of free cysteine at 102 was confirmed by LC-MS analysis of the non-reducing peptide maps. The presence of only one major free cysteine was further confirmed by the assessment of the total amount of free sulfhydryl. LC-MS analysis demonstrated that the active site serine residue was partially phosphorylated. Three metals including zinc, calcium and magnesium, as reported in the literature, were detected in asfotase alfa drug substance. Glycosylation of asfotase alfa was extensively analyzed by free glycan analysis using MALDI-TOF, normal-phase HPLC analysis of 2-AB labeled oligosaccharides, LC-MS analysis of glycopeptides, and total sialic acid measurement. All six glycosylation sites per monomer of asfotase alfa were found to associate with a heterogeneous population of oligosaccharides. Charge profile, heterogeneity caused mainly by the presence of sialic acid, was analyzed by cIEF, where six peaks were observed. Product-related substance is reflected by the observation of six peaks by cIEF. Low levels of product-related impurities were detected by SEC, AEX and SDS-PAGE.

Example 9. Comparability of Asfotase Alfa Manufactured at 2,000 L (2K) and 20,000 L (20K) Scales In this Example, asfotase alfa drug substance was manufactured using 2,000 L (2K) and 20,000 L (20K) processes. To demonstrate comparability among asfotase alfa produced at different scales, three batches of asfotase alfa produced using a 2K (#35, #36 and #38) process and three batches of asfotase alfa produced using a 20K process (#40, #42, and #34) were analyzed for their physicochemical properties side-by-side, where possible, using the methods described in Table 28. The specific batches of 2K and 20K were chosen based on clinical use, and previously-tested batches have proved batch-to-batch consistency for all 2K and 20K batches.

The tested physicochemical properties established asfotase alfa purity, charge variants, size, identity, structure, glycosylation and activity. The test results are summarized in Table 29. Manufacturing comparability was further evaluated using a side-by-side forced degradation study, where the degradation pathways and kinetics of the above-mentioned 2K and 20K batches were compared. The samples were incubated at 40° C. for 0, 14, 24, and 48 hours and were analyzed by the methods listed in Table 30. The test results for the temperature forced degradation study are summarized in Table 31.

The overall results demonstrate that asfotase alfa manufactured using 2K and 20K processes are comparable.

TABLE 28

| Asfotase Alfa Physicochemical Tests | |
|---|---|
| Test Category | Test |
| Purity | Analytical Ultracentrifugation |
| Purity | SDS-PAGE/LoC (Lab on Chip) |
| Purity | SDS-PAGE |
| Purity | GP-HPLC |
| Purity | Anion Exchange Chromatography |
| Charge Profile | Capillary Isoelectric Focusing (cIEF) |
| Size | Size-Exclusion Chromatography-Multi-Angle Light Scattering (SEC-MALS) |
| Size | Intact Molecular Weight Analysis (MALDI-ToF-MS) |
| Identity | Deglycosylated/Reduced & Deglycosylated Molecular Weight Analysis (MALDI-ToF-MS) |
| Identity | Deglycosylated/Reduced & Deglycosylated Molecular Weight Analysis (ESI-ToF-MS) |
| Structure | Circular Dichroism Spectrometry |
| Structure | Disulfide bonding and Free thiol by LC/MS |
| Structure | Metal Analysis (ICP-MS/ICP-AES) |
| Structure | Phosphorylation Site Identification and Quantitation via UPLC-MSe |
| Glycosylation | MALDI-Free Glycan |
| Glycosylation | 2-AB labeled N-linked Oligosaccharides profiling by HPLC |
| Glycosylation | Glycopeptide Profile and Site Occupancy (UPLC-QToF-MS) |
| Glycosylation | Total Sialic Acid Content |
| Activity | pNPP Activity |
| Activity | HA Binding |
| Activity | PPi Enzyme Kinetic assay |

TABLE 29

Asfotase Alfa Physicochemical Summary

| Test | | 2K #35 | 2K #36 | 2K #38 | 2K Mean | 2K SD | 20K #40 | 20K #42 | 20K #34 | 20K Mean | 20K SD |
|---|---|---|---|---|---|---|---|---|---|---|---|
| Concentration (mg/mL) Analytical Ultracentrifugation | | 93.5 | 99.9 | 99.8 | NA | NA | 107.6 | 94.5 | 101.6 | NA | NA |
| % Monomer of asfotase alfa* | | 96.5 | 95.9 | 94.5 | 95.6 | 1.0 | 96.0 | 97.6 | 96.8 | 96.8 | 0.8 |
| % Dimer of asfotase alfa | | 2.9 | 3.3 | 3.9 | 3.37 | 0.5 | 3.4 | 2.3 | 2.9 | 2.9 | 0.6 |
| % Trimer of asfotase alfa | | 0.3 | 0.8 | 1.6 | 0.9 | 0.7 | 0.6 | 0.1 | 0.3 | 0.3 | 0.3 |
| SDS-PAGE/LoC | | | | | | | | | | | |
| Non-Reduced (%) | | 100.0 | 100.0 | 100.0 | 100.0 | 0.0 | 100.0 | 100.0 | 100.0 | 100.0 | 0.0 |
| Reduced (%) | | 99.8 | 99.8 | 99.8 | 99.8 | 0.0 | 99.8 | 99.8 | 99.9 | 99.8 | 0.1 |
| SDS-PAGE | | | | | | | | | | | |
| Non-Reduced (%) | | 100.0 | 100.0 | 100.0 | 100.0 | 0.0 | 100.0 | 100.0 | 100.0 | 100.0 | 0.0 |
| Reduced (%) | | 100.0 | 100.0 | 100.0 | 100.0 | 0.0 | 100.0 | 100.0 | 100.0 | 100.0 | 0.0 |
| GP-HPLC | | | | | | | | | | | |
| Dimer (%)* | | 96.1 | 97.1 | 96.2 | 96.5 | 0.6 | 98.2 | 98.9 | 98.6 | 98.6 | 0.4 |
| Aggregate (%) | | 2.4 | 2.9 | 3.8 | 3.0 | 0.7 | 1.8 | 1.1 | 1.4 | 1.4 | 0.4 |
| Fragment (%) | | 1.5 | 0.0 | 0.0 | 0.5 | 0.9 | 0.0 | 0.0 | 0.0 | 0.0 | 0.0 |
| AEX | | | | | | | | | | | |
| % Main Peak Area | | 94.29 | 94.60 | 93.62 | 94.17 | 0.50 | 95.68 | 96.84 | 96.63 | 96.38 | 0.62 |
| cIEF | | | | | | | | | | | |
| Peak 1 | pI | 6.61 | 6.59 | 6.62 | 6.61 | 0.02 | 6.59 | 6.59 | 6.60 | 6.59 | 0.01 |
| | % | 33.55 | 29.01 | 33.09 | 31.88 | 2.50 | 24.46 | 24.40 | 36.64 | 28.50 | 7.05 |
| Peak 2 | pI | 6.65 | 6.64 | 6.66 | 6.65 | 0.01 | 6.63 | 6.63 | 6.65 | 6.64 | 0.01 |
| | % | 10.79 | 9.54 | 10.24 | 10.19 | 0.63 | 8.53 | 8.96 | 8.66 | 8.72 | 0.22 |
| Peak 3 | pI | 6.69 | 6.68 | 6.70 | 6.69 | 0.01 | 6.67 | 6.67 | 6.68 | 6.67 | 0.01 |
| | % | 12.36 | 13.49 | 13.62 | 13.16 | 0.69 | 12.97 | 10.60 | 11.78 | 11.78 | 1.19 |
| Peak 4 | pI | 6.73 | 6.73 | 6.76 | 6.74 | 0.02 | 6.72 | 6.72 | 6.73 | 6.72 | 0.01 |
| | % | 17.21 | 18.71 | 17.09 | 17.67 | 0.90 | 18.79 | 20.25 | 16.71 | 18.58 | 1.78 |
| Peak 5 | pI | 6.80 | 6.80 | 6.80 | 6.80 | 0.00 | 6.79 | 6.79 | 6.80 | 6.79 | 0.01 |
| | % | 10.29 | 11.78 | 11.21 | 11.09 | 0.75 | 14.62 | 13.27 | 11.24 | 13.04 | 1.70 |
| Peak 6 | pI | 6.84 | 6.85 | 6.85 | 6.85 | 0.01 | 6.84 | 6.84 | 6.85 | 6.84 | 0.01 |
| | % | 15.81 | 17.47 | 14.74 | 16.01 | 1.38 | 20.62 | 22.53 | 15.27 | 19.47 | 3.76 |

TABLE 29-continued

Asfotase Alfa Physicochemical Summary

| | 2K | | | | | | 20K | | | | |
|---|---|---|---|---|---|---|---|---|---|---|---|
| Test | #35 | #36 | #38 | 2K Mean | 2K SD | #40 | #42 | #34 | 20K Mean | 20K SD |
| SEC-MALS | | | | | | | | | | |
| Mw (kDa) Dimer | 185.5 | 188.5 | 193.6 | 189.2 | 4.1 | 187.0 | 189.4 | 194.1 | 190.2 | 3.6 |
| Mw (kDa) High Molecular Weight Species | 789.6 | 1054.0 | 1047.0 | 963.5 | 150.7 | 673.4 | 579.1 | 722.1 | 658.2 | 72.7 |
| MALDI-ToF MW. (Da) | | | | | | | | | | |
| Glycosylated | 180984 | 180853 | 180869 | 180902 | 71 | 179649 | 180252 | 180157 | 180019 | 324 |
| Deglycosylated | 161122 | 160980 | 161048 | 161050 | 71 | 160778 | 160725 | 161140 | 160881 | 226 |
| Deglyco and Reduced | 80534 | 80493 | 80562 | 80530 | 35 | 80563 | 80509 | 80545 | 80539 | 27 |
| ESI-ToF MW (Da) | | | | | | | | | | |
| Deglyco | 161137.80 | 161136.05 | 161138.33 | 161137.39 | 1.19 | 161136.69 | 161136.46 | 161138.69 | 161137.28 | 1.23 |
| Deglyco and Reduced | 80575.23 | 80575.16 | 80576.18 | 80575.52 | 0.57 | 80574.65 | 80574.86 | 80574.77 | 80574.76 | 0.11 |
| Circular Dichroism | | | | | | | | | | |
| Near-UV Features (nm): | Near UV (nm) | Near UV (nm) | Near UV (nm) | Near UV (nm) | Near UV (nm) | Near UV (nm) | Near UV (nm) | Near UV (nm) | Near UV (nm) | Near UV (nm) |
| $\lambda$max 1 | 291.0 | 290.5 | 290.5 | 290.7 | 0.3 | 290.5 | 290.5 | 290.5 | 290.5 | 0.0 |
| $\lambda$max 2 | 285.5 | 285.5 | 285.0 | 285.3 | 0.3 | 285.5 | 286.0 | 285.5 | 285.5 | 0.5 |
| $\lambda$max 3 | 268.0 | 268.5 | 268.0 | 268.2 | 0.3 | 268.0 | 268.5 | 268.5 | 268.3 | 0.3 |
| $\lambda$max 4 | 261.0 | 261.5 | 261.0 | 261.2 | 0.3 | 261.5 | 260.5 | 261.0 | 261.0 | 0.5 |
| $\lambda$max 5 | 256.5 | 256.5 | 257.0 | 256.7 | 0.3 | 257.0 | 257.0 | 257.0 | 257.0 | 0.0 |
| $\lambda$min 1 | 293.0 | 293.0 | 293.0 | 293.0 | 0.0 | 292.5 | 292.5 | 293.0 | 292.7 | 0.3 |
| $\lambda$min 2 | 287.0 | 287.0 | 286.5 | 286.8 | 0.3 | 286.5 | 286.5 | 286.5 | 286.5 | 0.0 |
| $\lambda$min 3 | 281.0 | 281.0 | 280.0 | 280.7 | 0.6 | 281.0 | 280.5 | 280.0 | 280.5 | 0.5 |
| CD Far-UV Feature | Far UV (nm) | Far UV (nm) | Far UV (nm) | Far UV (nm) | Far UV (nm) | Far UV (nm) | Far UV (nm) | Far UV (nm) | Far UV (nm) | Far UV (nm) |
| signal intensity $\lambda$210 | −7550 | −7210 | −6830 | −7012 | 365 | −7520 | −7340 | −7320 | −7288 | 274 |
| signal intensity $\lambda$220 | −8410 | −8180 | −7680 | −7934 | 355 | −8450 | −8270 | −8400 | −8250 | 263 |
| $\lambda$210/$\lambda$220 ratio | 0.9 | 0.88 | 0.89 | 0.88 | 0.01 | 0.89 | 0.89 | 0.87 | 0.88 | 0.01 |
| Deconvolution | Decon | Decon | Decon | Decon | Decon | Decon | Decon | Decon | Decon | Decon |
| $\alpha$-helix | 0.197 | 0.193 | 0.181 | 0.190 | 0.008 | 0.206 | 0.198 | 0.201 | 0.202 | 0.004 |
| 3/10 helix | 0.049 | 0.046 | 0.046 | 0.047 | 0.002 | 0.047 | 0.045 | 0.046 | 0.046 | 0.001 |
| $\beta$-sheet | 0.192 | 0.196 | 0.199 | 0.196 | 0.004 | 0.182 | 0.188 | 0.193 | 0.188 | 0.006 |
| Turns | 0.146 | 0.144 | 0.152 | 0.147 | 0.004 | 0.153 | 0.150 | 0.141 | 0.148 | 0.006 |
| Poly (Pro)II Structure | 0.060 | 0.064 | 0.061 | 0.062 | 0.002 | 0.060 | 0.066 | 0.059 | 0.062 | 0.004 |
| Unordered protein | 0.351 | 0.357 | 0.358 | 0.355 | 0.004 | 0.350 | 0.350 | 0.358 | 0.353 | 0.005 |
| Total | 0.995 | 1.000 | 0.997 | 0.997 | 0.003 | 0.998 | 0.997 | 0.998 | 0.998 | 0.001 |

TABLE 29-continued

Asfotase Alfa Physicochemical Summary

| Test | 2K | | | | | 20K | | | | |
|---|---|---|---|---|---|---|---|---|---|---|
| | #35 | #36 | #38 | 2K Mean | 2K SD | #40 | #42 | #34 | 20K Mean | 20K SD |
| Disulfide Bonding and Free Thiol Analysis (LC/MS) | | | | | | | | | | |
| T16ssT21 | 15479 | 14499 | 14976 | 14985 | 490 | 11128 | 14424 | 15068 | 13540 | 2114 |
| T48ss | 1222 | 1261 | 442 | 975 | 462 | 728 | 1141 | 1345 | 1071 | 314 |
| T50ssT58 | 17743 | 15660 | 15268 | 16224 | 1330 | 14527 | 15217 | 17669 | 15804 | 1651 |
| T52ssT58 | 17922 | 17324 | 18066 | 17771 | 393 | 17530 | 16264 | 15593 | 16462 | 984 |
| T66ssT71 | 4205 | 3576 | 3482 | 3754 | 393 | 2852 | 3611 | 4077 | 3513 | 618 |
| T13* | 13768 | 11442 | 13817 | 13009 | 1357 | 10623 | 13261 | 12453 | 12112 | 1352 |
| T16* | 4792 | 4107 | 4602 | 4500 | 354 | 4110 | 4428 | 3729 | 4089 | 350 |
| T21* | 7332 | 6144 | 7307 | 6928 | 679 | 3332 | 5123 | 5423 | 4626 | 1131 |
| T52* | 1317 | 1096 | 1366 | 1260 | 144 | 820 | 1181 | 1140 | 1047 | 198 |
| T71* | 1408 | 966 | 1463 | 1279 | 272 | 795 | 1070 | 1167 | 1011 | 193 |
| T13ssT13 | 90 | 100 | 92 | 94 | 5 | 17 | 33 | 70 | 40 | 27 |
| T13ssT16 | 5870 | 4884 | 5636 | 5463 | 515 | 3538 | 5356 | 4365 | 4420 | 910 |
| T13ssT21 | 4060 | 3893 | 3661 | 3871 | 200 | 1161 | 1931 | 3321 | 2138 | 1095 |
| Total Free Cysteine | | | | | | | | | | |
| # Free Cys per half molecule | 0.7 | 0.6 | 0.6 | 0.6 | 0.06 | 0.7 | 0.7 | 0.7 | 0.7 | 0 |
| MALDI Free Glycan Species | m/z (M + Na)+ | m/z (M + Na)+ | m/z (M + Na)+ | m/z (M + Na)+ | | m/z (M + Na)+ | m/z (M + Na)+ | m/z (M + Na)+ | m/z (M + Na)+ | |
| M3 | 933.45 | 933.36 | 933.39 | 933.40 | 0.05 | 933.4 | 933.38 | 933.38 | 933.39 | 0.01 |
| A1 | 1136.52 | 1136.50 | 1136.52 | 1136.51 | 0.01 | 1136.48 | 1136.52 | 1136.42 | 1136.47 | 0.05 |
| M5 | 1257.61 | 1257.51 | 1257.54 | 1257.55 | 0.05 | 1257.49 | 1257.53 | 1257.43 | 1257.48 | 0.05 |
| FA1 | 1282.66 | 1282.56 | 1282.58 | 1282.60 | 0.05 | 1282.54 | 1282.58 | 1282.48 | 1282.53 | 0.05 |
| A1G1 | 1298.61 | 1298.54 | 1298.56 | 1298.57 | 0.03 | 1298.51 | 1298.63 | 1298.55 | 1298.55 | 0.08 |
| A2 | 1339.60 | 1339.59 | 1339.60 | 1339.60 | 0.01 | 1339.57 | 1339.61 | 1339.50 | 1339.56 | 0.06 |
| FA1G1 | 1444.71 | 1444.69 | 1444.64 | 1444.68 | 0.03 | 1444.58 | 1444.65 | 1444.52 | 1444.58 | 0.07 |
| FA2 | 1485.66 | 1485.65 | 1485.66 | 1485.66 | 0.01 | 1485.64 | 1485.68 | 1485.56 | 1485.62 | 0.06 |
| A2G1 | 1501.65 | 1501.65 | 1501.67 | 1501.66 | 0.01 | 1501.61 | 1501.67 | 1501.56 | 1501.61 | 0.06 |
| A3 | 1542.70 | 1542.68 | 1542.69 | 1542.69 | 0.01 | 1542.60 | 1542.70 | 1542.58 | 1542.63 | 0.06 |
| FA2G1 | 1647.73 | 1647.71 | 1647.73 | 1647.72 | 0.01 | 1647.66 | 1647.74 | 1647.61 | 1647.67 | 0.07 |
| A2G2 | 1663.72 | 1663.69 | 1663.73 | 1663.71 | 0.02 | 1663.62 | 1663.74 | 1663.60 | 1663.66 | 0.07 |
| FA3 | 1688.76 | 1688.75 | 1688.76 | 1688.76 | 0.01 | 1688.69 | 1688.76 | 1688.64 | 1688.70 | 0.06 |
| A3G1 | 1704.75 | 1704.74 | 1704.77 | 1704.75 | 0.01 | 1704.67 | 1704.75 | 1704.63 | 1704.69 | 0.06 |
| A4 | 1745.77 | 1745.76 | 1745.79 | 1745.77 | 0.02 | 1745.70 | 1745.75 | 1745.64 | 1745.70 | 0.06 |
| FA2G2 | 1809.79 | 1809.77 | 1809.82 | 1809.79 | 0.02 | 1809.69 | 1809.79 | 1809.65 | 1809.71 | 0.07 |
| FA3G1 | 1850.82 | 1850.80 | 1850.83 | 1850.82 | 0.01 | 1850.72 | 1850.79 | 1850.69 | 1850.74 | 0.06 |
| A3G2 | 1866.79 | 1866.79 | 1866.83 | 1866.80 | 0.02 | 1866.70 | 1866.79 | 1866.67 | 1866.72 | 0.06 |
| FA4 | 1891.84 | 1891.83 | 1891.86 | 1891.84 | 0.01 | 1891.74 | 1891.84 | 1891.71 | 1891.77 | 0.07 |
| A4G1 | 1907.85 | 1907.82 | 1907.87 | 1907.85 | 0.02 | 1907.71 | 1907.83 | 1907.69 | 1907.75 | 0.07 |
| FA2G2 | 2012.88 | 2012.86 | 2012.89 | 2012.88 | 0.01 | 2012.73 | 2012.86 | 2012.72 | 2012.78 | 0.07 |
| A3G3 | 2028.86 | 2028.85 | 2028.89 | 2028.87 | 0.02 | 2028.71 | 2028.84 | 2028.72 | 2028.77 | 0.07 |

TABLE 29-continued

Asfotase Alfa Physicochemical Summary

| Test | 2K | | | | | 20K | | | | |
|---|---|---|---|---|---|---|---|---|---|---|
| | #35 | #36 | #38 | 2K Mean | 2K SD | #40 | #42 | #34 | 20K Mean | 20K SD |
| FA4G1 | 2053.89 | 2053.89 | 2053.91 | 2053.90 | 0.01 | 2053.77 | 2053.88 | 2053.75 | 2053.81 | 0.07 |
| A4G2 | 2069.96 | 2069.90 | 2069.94 | 2069.93 | 0.03 | 2069.77 | 2069.90 | 2069.74 | 2069.81 | 0.08 |
| FA3G3 | 2174.91 | 2174.90 | 2174.94 | 2174.92 | 0.02 | 2174.78 | 2174.92 | 2174.77 | 2174.83 | 0.08 |
| FA4G2 | 2215.93 | 2215.92 | 2215.95 | 2215.93 | 0.01 | 2215.77 | 2215.92 | 2215.80 | 2215.84 | 0.07 |
| A4G3 | 2231.93 | 2231.87 | 2231.96 | 2231.92 | 0.04 | 2231.80 | 2231.90 | 2231.80 | 2231.84 | 0.05 |
| FA4G3 | 2377.96 | 2378.01 | 2377.98 | 2377.98 | 0.02 | 2377.76 | 2377.96 | 2377.84 | 2377.87 | 0.09 |
| A4G4 | 2393.94 | 2393.92 | 2393.99 | 2393.95 | 0.03 | 2393.78 | 2393.98 | 2393.81 | 2393.87 | 0.10 |
| FA4G1L1 | 2418.96 | 2418.91 | 2419.04 | 2418.97 | 0.06 | 2418.98 | 2419.02 | 2418.93 | 2418.98 | 0.05 |
| FA4G4 | 2539.94 | 2540.00 | 2539.98 | 2539.97 | 0.03 | 2539.82 | 2539.97 | 2539.89 | 2539.91 | 0.06 |
| FA4G2L1 | 2580.97 | 2581.05 | 2580.97 | 2581.00 | 0.04 | 2580.78 | 2580.97 | 2580.94 | 2580.92 | 0.08 |
| FA4G3L1 | 2742.95 | 2742.88 | 2742.94 | 2742.92 | 0.03 | 2742.77 | 2743.08 | 2742.90 | 2742.95 | 0.13 |
| FA4G4L1 | 2904.83 | 2904.79 | 2904.87 | 2904.83 | 0.04 | 2904.79 | 2904.94 | 2904.89 | 2904.89 | 0.06 |
| FA4G4L2 | 3270.47 | 3270.40 | 3270.54 | 3270.47 | 0.06 | 3270.63 | 3270.01 | 3269.87 | 3270.08 | 0.32 |
| 2AB labeled Glycans Peak Area % | | | | | | | | | | |
| M3 | 0.05 | 0.18 | 0.05 | 0.09 | 0.08 | 0.17 | 0.11 | 0.02 | 0.10 | 0.08 |
| A1 | 1.52 | 2.32 | 1.55 | 1.80 | 0.45 | 2.79 | 2.34 | 1.90 | 2.43 | 0.37 |
| FA1 | 9.16 | 13.55 | 7.98 | 10.23 | 2.94 | 11.67 | 11.46 | 11.58 | 11.57 | 0.11 |
| A2 | 0.29 | 0.55 | 0.49 | 0.44 | 0.14 | 0.60 | 0.53 | 0.26 | 0.50 | 0.14 |
| FA2 | 25.81 | 22.26 | 20.98 | 23.02 | 2.50 | 24.60 | 25.11 | 25.55 | 24.99 | 0.40 |
| M5/A3 | 5.3 | 6.61 | 6.1 | 6.00 | 0.66 | 6.44 | 6.30 | 5.18 | 6.13 | 0.54 |
| A2G1 | 1.23 | 1.67 | 1.14 | 1.35 | 0.28 | 1.49 | 1.43 | 1.25 | 1.42 | 0.10 |
| FA3 | 4.1 | 4.2 | 6.49 | 4.93 | 1.35 | 3.90 | 4.31 | 2.67 | 3.82 | 0.67 |
| FA2G1 | 3.8 | 3.2 | 2.68 | 3.23 | 0.56 | 3.37 | 3.54 | 4.58 | 3.68 | 0.51 |
| FA2G1 | 3.57 | 3.43 | 2.32 | 3.11 | 0.68 | 4.11 | 3.86 | 4.59 | 4.11 | 0.30 |
| FA4 | 4.35 | 4.31 | 6.31 | 4.99 | 1.14 | 3.63 | 4.15 | 2.68 | 3.65 | 0.60 |
| A2G2 | 2.28 | 2.62 | 2.21 | 2.37 | 0.22 | 2.24 | 2.24 | 2.46 | 2.28 | 0.10 |
| FA3G1 | 2.99 | 1.61 | 3.69 | 2.76 | 1.06 | 3.05 | 3.19 | 2.25 | 2.95 | 0.40 |
| FA2G2 | 7.39 | 6.71 | 5.08 | 6.39 | 1.19 | 5.73 | 6.80 | 7.03 | 6.42 | 0.64 |
| FA4G1 | 2.33 | 2.46 | 4.51 | 3.10 | 1.22 | 3.73 | 2.13 | 3.42 | 3.03 | 0.83 |
| FA3G3 | 2.28 | 2.15 | 3.01 | 2.48 | 0.46 | 2.29 | 2.36 | 1.71 | 2.20 | 0.28 |
| FA3G3 | 3.68 | 3.45 | 3.78 | 3.64 | 0.17 | 3.19 | 3.41 | 3.01 | 3.24 | 0.17 |
| FA4G3 | 2.65 | 2.41 | 2.94 | 2.67 | 0.27 | 2.41 | 2.36 | 2.13 | 2.33 | 0.12 |
| FA4G3 | 0.99 | 1.15 | 1.51 | 1.22 | 0.27 | 0.84 | 0.93 | 0.89 | 0.89 | 0.05 |
| FA4G4 | 5.74 | 5.39 | 5.75 | 5.63 | 0.21 | 4.76 | 4.78 | 5.35 | 4.89 | 0.26 |
| FA4G4L1 | 3.43 | 3.05 | 3.69 | 3.39 | 0.32 | 2.73 | 2.64 | 3.54 | 2.86 | 0.39 |
| FA4G4L2 | 1.49 | 1.34 | 1.68 | 1.50 | 0.17 | 1.22 | 1.13 | 1.87 | 1.31 | 0.31 |
| UNKNOWN | 0.38 | 0.41 | 0.48 | 0.42 | 0.05 | 0.36 | 0.29 | 0.61 | 0.38 | 0.13 |

TABLE 29-continued

Asfotase Alfa Physicochemical Summary

Glycopeptide Profile and Site Occupancy (UPLC-QToF-MS)
Glycopeptide Masses Observed in Reduced/Alkylated Trypsin Digested Test

| Approximate Retention Time (min) | Tryptic Peptide | Glycan | glycopeptide m/z (M + H)+ | 2K #35 m/z (M + H)+ | 2K #36 m/z (M + H)+ | 2K #38 m/z (M + H)+ | 2K Mean m/z (M + H)+ | 2K SD m/z (M + H)+ | 20K #40 m/z (M + H)+ | 20K #42 m/z (M + H)+ | 20K #34 m/z (M + H)+ | 20K Mean m/z (M + H)+ | 20K SD m/z (M + H)+ |
|---|---|---|---|---|---|---|---|---|---|---|---|---|---|
| 39.7-40.7 | T15-16 | FA1 | 3078.34 | 3078.31 | 3078.33 | 3078.31 | 3078.32 | 0.01 | 3078.31 | 3078.33 | 3078.32 | 3078.32 | 0.01 |
| | | FA2 | 3281.42 | 3281.40 | 3281.40 | 3281.39 | 3281.40 | 0.01 | 3281.38 | 3281.41 | 3281.40 | 3281.40 | 0.01 |
| | | FA2G1 | 3443.47 | 3443.46 | 3443.46 | 3443.45 | 3443.45 | 0.01 | 3443.44 | 3443.47 | 3443.45 | 3443.45 | 0.01 |
| | | FA3 | 3484.50 | 3484.48 | 3484.48 | 3484.48 | 3484.48 | 0.00 | 3484.46 | 3484.49 | 3484.48 | 3484.48 | 0.01 |
| | | FA2G2 | 3605.53 | 3605.51 | 3605.51 | 3605.51 | 3605.51 | 0.00 | 3605.49 | 3605.52 | 3605.51 | 3605.51 | 0.01 |
| | | FA3G1 | 3646.55 | 3646.54 | 3646.54 | 3646.53 | 3646.54 | 0.01 | 3646.52 | 3646.54 | 3646.54 | 3646.53 | 0.01 |
| | | FA4 | 3687.58 | 3687.57 | 3687.56 | 3687.55 | 3687.56 | 0.01 | 3687.55 | 3687.57 | 3687.57 | 3687.56 | 0.01 |
| | | FA3G2 | 3808.61 | 3808.59 | 3808.60 | 3808.59 | 3808.59 | 0.01 | 3808.57 | 3808.60 | 3808.60 | 3808.59 | 0.01 |
| | | FA4G1 | 3849.63 | 3849.62 | 3849.62 | 3849.61 | 3849.62 | 0.01 | 3849.60 | 3849.63 | 3849.62 | 3849.62 | 0.01 |
| | | FA3G3 | 3970.66 | 3970.65 | 3970.65 | 3970.64 | 3970.65 | 0.01 | 3970.62 | 3970.65 | 3970.65 | 3970.64 | 0.02 |
| 17.4-17.9 | T26-27 | A2 | 2755.12 | 2755.11 | 2755.11 | 2755.10 | 2755.11 | 0.01 | 2755.10 | 2755.12 | 2755.11 | 2755.11 | 0.01 |
| | | FA2 | 2901.18 | 2901.16 | 2901.16 | 2901.16 | 2901.16 | 0.00 | 2901.15 | 2901.17 | 2901.16 | 2901.16 | 0.01 |
| | | FA2G1 | 3063.23 | 3063.21 | 3063.21 | 3063.21 | 3063.21 | 0.00 | 3063.21 | 3063.22 | 3063.21 | 3063.22 | 0.01 |
| | | FA3 | 3104.26 | 3104.25 | 3104.25 | 3104.24 | 3104.24 | 0.01 | 3104.23 | 3104.26 | 3104.25 | 3104.24 | 0.01 |
| | | FA2G2 | 3225.28 | 3225.28 | 3225.28 | 3225.27 | 3225.28 | 0.00 | ND | 3225.28 | 3225.27 | 3225.28 | 0.00 |
| | | FA3G1 | 3266.31 | 3266.29 | 3266.29 | 3266.30 | 3266.29 | 0.00 | 3266.28 | 3266.30 | 3266.29 | 3266.29 | 0.01 |
| | | FA4 | 3307.34 | 3307.32 | 3307.33 | 3307.32 | 3307.32 | 0.00 | 3307.30 | 3307.33 | 3307.32 | 3307.32 | 0.01 |
| | | FA4G1 | 3469.39 | 3469.38 | 3469.38 | 3469.37 | 3469.37 | 0.01 | 3469.36 | 3469.39 | 3469.38 | 3469.37 | 0.02 |
| | | FA4G2 | 3631.43 | 3631.43 | 3631.44 | 3631.42 | 3631.43 | 0.01 | 3631.41 | 3631.44 | 3631.43 | 3631.43 | 0.01 |
| | | FA4G3 | 3793.49 | 3793.48 | 3793.49 | 3793.49 | 3793.49 | 0.00 | 3793.46 | 3793.50 | 3793.47 | 3793.48 | 0.02 |
| 28.6-29.9 | T33 | A1 | 2191.92 | 2191.93 | 2191.98 | 2191.94 | 2191.94 | 0.03 | 2191.91 | 2191.93 | 2191.93 | 2191.92 | 0.01 |
| | | A2 | 2394.99 | 2395.00 | 2395.06 | 2395.00 | 2395.02 | 0.04 | 2394.99 | 2395.01 | 2395.00 | 2395.00 | 0.01 |
| | | A2G1 | 2557.05 | 2557.06 | 2557.12 | 2557.05 | 2557.08 | 0.04 | 2557.05 | 2557.07 | 2557.06 | 2557.06 | 0.01 |
| | | A3 | 2598.07 | 2598.07 | 2598.14 | 2598.09 | 2598.10 | 0.03 | 2598.06 | 2598.08 | 2598.07 | 2598.07 | 0.01 |
| | | A2G2 | 2719.10 | 2719.11 | 2719.18 | 2719.10 | 2719.13 | 0.04 | 2719.10 | 2719.12 | 2719.11 | 2719.11 | 0.01 |
| | | A3G1 | 2760.13 | 2760.14 | 2760.20 | 2760.13 | 2760.16 | 0.04 | 2760.12 | 2760.15 | 2760.14 | 2760.14 | 0.01 |
| | | A4 | 2801.15 | 2801.16 | 2801.23 | 2801.15 | 2801.18 | 0.04 | 2801.15 | 2801.17 | 2801.16 | 2801.16 | 0.01 |
| 99.5-102.8 | T35 | A2 | 3496.66 | 3496.64 | 3496.65 | 3496.63 | 3496.64 | 0.01 | 3496.63 | 3496.65 | 3496.65 | 3496.64 | 0.01 |
| | | A3 | 3699.74 | 3699.73 | 3699.73 | 3699.72 | 3699.73 | 0.01 | 3699.73 | 3699.73 | 3699.73 | 3699.73 | 0.01 |
| | | FA3 | 3845.80 | 3845.79 | 3845.78 | 3845.77 | 3845.78 | 0.01 | 3845.77 | 3845.79 | 3845.79 | 3845.79 | 0.01 |
| | | A4 | 3902.82 | 3902.81 | 3902.80 | 3902.80 | 3902.80 | 0.01 | 3902.78 | 3902.81 | 3902.80 | 3902.80 | 0.02 |
| | | FA3G1 | 4007.85 | 4007.85 | 4007.84 | 4007.83 | 4007.84 | 0.01 | 4007.83 | 4007.85 | 4007.85 | 4007.84 | 0.01 |
| | | FA4 | 4048.88 | 4048.88 | 4048.88 | 4048.86 | 4048.87 | 0.01 | 4048.86 | 4048.88 | 4048.87 | 4048.87 | 0.01 |
| | | FA4G1 | 4210.93 | 4210.93 | 4210.93 | 4210.91 | 4210.92 | 0.01 | 4210.92 | 4210.93 | 4210.93 | 4210.93 | 0.01 |
| 46.3-47.0 | T45-46 | FA2 | 4548.04 | 4547.99 | 4548.00 | 4547.97 | 4547.99 | 0.01 | 4547.97 | 4548.01 | 4547.99 | 4547.99 | 0.02 |
| | | FA2G1 | 4710.09 | 4710.04 | 4710.05 | 4710.03 | 4710.04 | 0.01 | 4710.03 | 4710.06 | 4710.05 | 4710.05 | 0.02 |
| | | FA3 | 4751.11 | 4751.07 | 4751.08 | 4751.05 | 4751.06 | 0.01 | 4751.05 | 4751.09 | 4751.08 | 4751.07 | 0.02 |
| | | FA2G2 | 4872.14 | 4872.09 | 4872.10 | 4872.08 | 4872.09 | 0.01 | 4872.08 | 4872.11 | 4872.10 | 4872.10 | 0.01 |

TABLE 29-continued

Asfotase Alfa Physicochemical Summary

|  |  | Test |  | 2K | | | | | | | 20K | | | | | |
|---|---|---|---|---|---|---|---|---|---|---|---|---|---|---|---|---|
|  |  |  |  | #35 | #36 | #38 | 2K Mean | 2K SD | #40 | #42 | #34 | 20K Mean | 20K SD |
|  |  | FA3G1 | 4913.17 | 4913.12 | 4913.13 | 4913.11 | 4913.12 | 0.01 | 4913.11 | 4913.14 | 4913.13 | 4913.13 | 0.02 |
|  |  | FA4 | 4954.19 | 4954.15 | 4954.16 | 4954.13 | 4954.15 | 0.01 | 4954.18 | 4954.17 | 4954.21 | 4954.18 | 0.02 |
|  |  | FA3G2 | 5075.22 | 5075.17 | 5075.18 | 5075.16 | 5075.17 | 0.01 | 5075.16 | 5075.20 | 5075.18 | 5075.18 | 0.02 |
|  |  | FA4G1 | 5116.25 | 5116.20 | 5116.21 | 5116.19 | 5116.20 | 0.01 | 5116.18 | 5116.22 | 5116.21 | 5116.21 | 0.02 |
|  |  | FA4G2 | 5278.29 | 5278.25 | 5278.26 | 5278.25 | 5278.25 | 0.01 | 5278.23 | 5278.27 | 5278.26 | 5278.26 | 0.02 |
| 19.6-20.0 | T55 | A1 | 2284.91 | 2284.92 | 2284.92 | 2284.91 | 2284.92 | 0.00 | 2284.90 | 2284.92 | 2284.92 | 2284.91 | 0.01 |
|  |  | A2 | 2487.99 | 2488.00 | 2488.00 | 2487.99 | 2488.00 | 0.00 | 2487.98 | 2488.00 | 2488.00 | 2487.99 | 0.01 |
|  |  | FA2 | 2634.05 | 2634.06 | 2634.06 | 2634.05 | 2634.06 | 0.00 | 2634.05 | 2634.06 | 2634.06 | 2634.05 | 0.01 |
|  |  | FA2G1 | 2796.10 | 2796.12 | 2796.12 | 2796.12 | 2796.12 | 0.00 | 2796.10 | 2796.12 | 2796.12 | 2796.11 | 0.01 |

Glycopeptide Profile and Site Occupancy (UPLC-QToF-MS) Relative Glycoform Contributions at each N-Linked Oligosaccharide Site

| Approximate Retention Time (min) | Tryptic Peptide | Glycan | Relative % Observed | Relative % Observed | Relative % Observed | Relative % Observed | Relative % Observed | Relative % Observed | Relative % Observed | Relative % Observed | Relative % Observed | Relative % Observed |
|---|---|---|---|---|---|---|---|---|---|---|---|---|
|  |  |  | #35 | #36 | #38 | 2K Mean | 2K SD | #40 | #42 | #34 | 20K Mean | 20K SD |
| 39.7-40.7 | T15-16 | FA1 | 5 | 8 | 6 | 6.4 | 1.7 | 12 | 8 | 10 | 10.0 | 1.6 |
|  |  | FA2 | 16 | 18 | 19 | 17.7 | 1.3 | 18 | 18 | 18 | 17.6 | 0.1 |
|  |  | FA2G1 | 11 | 11 | 8 | 9.9 | 1.6 | 12 | 11 | 11 | 11.5 | 0.7 |
|  |  | FA3 | 12 | 12 | 17 | 13.4 | 2.8 | 10 | 10 | 8 | 9.3 | 0.8 |
|  |  | FA2G2 | 10 | 11 | 9 | 10.1 | 1.1 | 12 | 9 | 11 | 10.7 | 1.3 |
|  |  | FA3G1 | 7 | 7 | 7 | 7.1 | 0.2 | 9 | 7 | 7 | 7.7 | 1.0 |
|  |  | FA4 | 7 | 7 | 10 | 7.5 | 1.8 | 5 | 5 | 3 | 4.4 | 0.9 |
|  |  | FA3G2 | 5 | 6 | 3 | 4.2 | 1.8 | 4 | 5 | 5 | 4.5 | 0.8 |
|  |  | FA4G1 | 6 | 5 | 5 | 5.3 | 0.9 | 4 | 5 | 4 | 4.2 | 0.4 |
|  |  | FA4G2 | 4 | 3 | 3 | 3.4 | 0.4 | 1 | 5 | 6 | 3.7 | 2.6 |
| 17.4-17.9 | T26-27 | A2 | 10 | 12 | 9 | 10.4 | 1.7 | 12 | 11 | 10 | 10.7 | 0.7 |
|  |  | FA2 | 5 | 6 | 7 | 6.3 | 1.0 | 8 | 8 | 6 | 7.5 | 1.0 |
|  |  | FA2G1 | 4 | 5 | 3 | 4.0 | 0.8 | 2 | 6 | 7 | 5.0 | 2.6 |
|  |  | FA3 | 14 | 13 | 19 | 15.3 | 3.1 | 15 | 12 | 9 | 12.1 | 2.9 |
|  |  | FA2G2 | 6 | 7 | 5 | 6.0 | 1.1 | 0 | 6 | 8 | 4.7 | 4.2 |
|  |  | FA3G1 | 8 | 7 | 7 | 7.0 | 0.7 | 9 | 7 | 7 | 7.8 | 1.2 |
|  |  | FA4 | 10 | 9 | 13 | 10.9 | 2.1 | 8 | 7 | 5 | 6.8 | 1.3 |
|  |  | FA4G1 | 9 | 7 | 9 | 8.4 | 1.0 | 7 | 7 | 7 | 7.0 | 0.3 |
|  |  | FA4G2 | 6 | 6 | 5 | 5.8 | 0.5 | 7 | 6 | 7 | 6.4 | 0.4 |
|  |  | FA4G3 | 4 | 3 | 3 | 3.3 | 0.8 | 5 | 4 | 5 | 4.6 | 0.7 |
| 28.6-29.9 | T33 | A1 | 11 | 12 | 10 | 10.7 | 1.1 | 18 | 16 | 17 | 17.1 | 1.1 |
|  |  | A2 | 23 | 24 | 24 | 23.5 | 0.5 | 21 | 22 | 21 | 21.3 | 0.9 |
|  |  | A2G1 | 14 | 13 | 11 | 12.5 | 1.6 | 14 | 13 | 14 | 13.7 | 0.8 |
|  |  | A3 | 8 | 7 | 15 | 10.0 | 4.0 | 5 | 6 | 5 | 5.3 | 0.5 |

TABLE 29-continued

Asfotase Alfa Physicochemical Summary

| | | | 2K | | | | | | 20K | | | |
|---|---|---|---|---|---|---|---|---|---|---|---|---|
| | Test | #35 | #36 | #38 | 2K Mean | 2K SD | #40 | #42 | #34 | 20K Mean | 20K SD |
| | A2G2 | 12 | 12 | 10 | 11.3 | 0.9 | 11 | 10 | 13 | 11.5 | 1.3 |
| | A3G1 | 6 | 5 | 5 | 5.4 | 0.2 | 5 | 4 | 5 | 4.8 | 0.4 |
| | A4 | 4 | 3 | 3 | 3.9 | 1.0 | 2 | 3 | 2 | 2.2 | 0.5 |
| 99.5-102.8 T35 | A2 | 7 | 9 | 7 | 7.6 | 1.1 | 9 | 9 | 8 | 9.0 | 0.6 |
| | A3 | 11 | 13 | 14 | 12.7 | 1.4 | 10 | 11 | 9 | 9.8 | 0.7 |
| | FA3 | 8 | 8 | 10 | 8.8 | 1.3 | 8 | 8 | 7 | 7.9 | 0.7 |
| 46.3-47.0 T45-46 | A4 | 4 | 4 | 5 | 4.1 | 0.4 | 3 | 3 | 3 | 3.1 | 0.3 |
| | FA3G1 | 5 | 5 | 5 | 5.0 | 0.3 | 5 | 5 | 5 | 5.4 | 0.1 |
| | FA4 | 8 | 7 | 10 | 8.2 | 1.7 | 6 | 7 | 6 | 6.3 | 0.5 |
| | FA4G1 | 6 | 5 | 6 | 5.6 | 0.6 | 5 | 6 | 6 | 5.4 | 0.5 |
| | FA2 | 17 | 17 | 16 | 16.5 | 0.0 | 17 | 18 | 22 | 18.7 | 2.6 |
| | FA2G1 | 9 | 10 | 7 | 8.6 | 1.8 | 13 | 10 | 12 | 11.9 | 1.4 |
| | FA3 | 17 | 18 | 21 | 18.5 | 2.2 | 20 | 18 | 15 | 17.8 | 2.6 |
| | FA2G2 | 6 | 7 | 5 | 6.2 | 1.0 | 7 | 6 | 8 | 6.8 | 1.1 |
| | FA3G1 | 11 | 10 | 9 | 9.9 | 1.0 | 12 | 11 | 11 | 11.5 | 0.8 |
| | FA4 | 14 | 13 | 17 | 14.8 | 2.2 | 2 | 12 | 1 | 4.8 | 6.0 |
| | FA3G2 | 5 | 5 | 4 | 4.8 | 0.8 | 5 | 5 | 6 | 5.7 | 0.7 |
| | FA4G1 | 9 | 8 | 9 | 8.6 | 0.5 | 8 | 8 | 7 | 7.8 | 0.5 |
| | FA4G2 | 5 | 4 | 4 | 4.2 | 0.4 | 4 | 5 | 5 | 4.5 | 0.3 |
| 19.6-20.0 T55 | A1 | 4 | 4 | 4 | 4.2 | 0.1 | 3 | 5 | 3 | 3.7 | 0.9 |
| | A2 | 38 | 37 | 33 | 36.0 | 2.6 | 29 | 44 | 42 | 38.4 | 8.0 |
| | FA2 | 36 | 41 | 44 | 40.1 | 3.7 | 40 | 29 | 32 | 33.7 | 5.5 |
| | FA2G1 | 7 | 6 | 5 | 5.6 | 0.9 | 5 | 6 | 8 | 6.2 | 1.4 |
| Total Sialic Acid per Monomer (mol/mol) LC-MSe Phosphorylation | | 2.8 | 2.0 | 1.8 | 2.20 | 0.53 | 1.1 | 1.5 | 2.1 | 1.57 | 0.50 |
| Peak Area T13 non-Phos† | | 2611 | 2190 | 2137 | | | 2800 | 2672 | 2579 | | |
| Peak Area T13 S93 Phos‡ | | 1370 | 1215 | 967 | | | 1375 | 1260 | 1324 | | |
| % Phosphorylated | | 34.4 | 35.7 | 31.2 | 33.8 | 2.3 | 32.9 | 32.0 | 33.9 | 32.9 | 1.0 |
| ICP-MS Ion Molar Ratio | | | | | | | | | | | |
| Zn2+ | | 1.63 | 1.81 | 1.41 | 1.62 | 0.20 | 1.88 | 1.88 | 2.27 | 2.01 | 0.23 |
| Mg2+ | | 0.05 | 0.05 | 0.03 | 0.05 | 0.02 | 0.04 | 0.08 | 0.12 | 0.08 | 0.04 |
| Ca2+ | | 0.77 | 0.87 | 0.85 | 0.83 | 0.05 | 1.04 | 1.04 | 0.97 | 1.02 | 0.04 |

TABLE 29-continued

Asfotase Alfa Physicochemical Summary

| | 2K | | | | | 20K | | | |
|---|---|---|---|---|---|---|---|---|---|
| Test | #35 | #36 | #38 | 2K Mean | 2K SD | #40 | #42 | #34 | 20K Mean | 20K SD |
| Specific Activity (pNPP) | | | | | | | | | | |
| (U/mg) | 877.0 | 896.0 | 812.0 | 861.7 | 44.0 | 875.0 | 991.0 | 1079.0 | 981.7 | 102.3 |
| HA Binding | | | | | | | | | | |
| % Binding PPi | 92 | 92 | 89 | 91 | 2 | 97 | 92 | 85 | 91 | 5 |
| Sample $K_m$ | 90.8 | 88.9 | 73.5 | 94.5 | 8.1 | 81.0 | 41.1 | 90.3 | 70.8 | 26.1 |
| Head-to-head Reference $K_m$ | 81.7 | 81.7 | 62.3 | 75.2 | 11.2 | 69.3 | 38.3 | 79.6 | 62.4 | 21.5 |
| $K_m$ % of: Reference | 111% | 109% | 118% | 129% | 33% | 117% | 107% | 113% | 113% | 5% |
| Sample $K_{cat}$ | 125.7 | 141.5 | 103.7 | 123.6 | 19.0 | 125.7 | 100.0 | 137.0 | 131.4 | 19.0 |
| Head-to-head Reference $K_{cat}$ | 124.0 | 124.0 | 107.6 | 118.5 | 9.5 | 116.0 | 99.0 | 114.9 | 115.5 | 9.5 |
| $K_{cat}$ % of Reference | 101% | 114% | 96% | 104% | 9% | 108% | 101% | 119% | 114% | 9% |

†Peptide Mods: Cys102 COMe; Molecular formula: C102H159N27O38S1; Monoisotopic Mass: 2402.106.
‡Peptide Mods: Cys102 COMe S93 PO4; Molecular formula: C102H160N27O41SIP1; Monoisotopic Mass: 2482.0723.
*Monomer of asfotase alfa as reported by analytical ultracentrifugation is equivalent/synonymous to 'dimer' by GP-HPLC and SEC-MALS.

TABLE 30

Asfotase Alfa Temperature Forced Degradation Tests

| Assay Category | Assay | Time Points for each assay | | | |
|---|---|---|---|---|---|
| | | T0 | T12 ± 3 | T24 ± 3 | T48 ± 3 |
| Purity | SDS-PAGE Reduced/Non-Reduced | x | | | x |
| Purity and Impurities | HPLC Gel Permeation | x | x | x | x |
| Impurities | AEX | x | x | x | x |
| Impurities | RP-HPLC | x | x | x | x |
| Impurities | Peptide Mapping | x | | | x |
| Potency | Specific Activity (pNPP) | x | x | x | x |

TABLE 31

Summary of Asfotase Alfa Temperature Forced Degradation Results

| | 2K | | | | | 20K | | | | |
|---|---|---|---|---|---|---|---|---|---|---|
| Test | #35 | #36 | #38 | 2K Mean | 2K SD | #40 | #42 | #34 | 20K Mean | 20K SD |
| RP-HPLC % Main Peak Area (RT ~21.2 minutes) | | | | | | | | | | |
| T0 | 99.07 | 99.61 | 99.45 | 99.38 | 0.28 | 99.61 | 99.64 | 99.65 | 99.63 | 0.02 |
| T14 | 89.21 | 88.98 | 80.86 | 86.35 | 4.76 | 90.88 | 91.65 | 91.35 | 91.29 | 0.39 |
| T24 | 82.96 | 83.01 | 75.33 | 80.43 | 4.42 | 87.09 | 86.68 | 86.32 | 86.70 | 0.39 |
| T48 | 73.28 | 72.24 | 67.48 | 71.00 | 3.09 | 76.25 | 78.70 | 76.87 | 77.27 | 1.27 |
| AEX % Main Peak Area | | | | | | | | | | |
| T0 | 93.90 | 94.60 | 94.20 | 94.23 | 0.35 | 96.00 | 96.80 | 96.50 | 96.43 | 0.40 |
| T14 | 87.00 | 86.40 | 77.70 | 83.70 | 5.20 | 96.10 | 94.10 | 92.60 | 94.27 | 1.76 |
| T24 | 76.40 | 77.20 | 67.30 | 73.63 | 5.50 | 82.40 | 83.00 | 81.70 | 82.37 | 0.65 |
| T48 | 61.47 | 63.89 | 56.87 | 60.74 | 3.57 | 68.80 | 72.10 | 69.00 | 69.97 | 1.85 |
| GP-HPLC % Main Peak Area | | | | | | | | | | |
| T0 | 96.0 | 96.2 | 95.9 | 96.0 | 0.2 | 97.5 | 98.2 | 97.8 | 97.8 | 0.4 |
| T14 | 84.7 | 85.3 | 74.3 | 81.4 | 6.2 | 87.2 | 88.7 | 88.1 | 88.0 | 0.8 |
| T24 | 77.5 | 77.6 | 67.4 | 74.2 | 5.9 | 80.7 | 82.2 | 81.2 | 81.4 | 0.8 |
| T48 | 63.8 | 62.9 | 57.4 | 61.4 | 3.5 | 68.0 | 71.9 | 69.5 | 69.8 | 2.0 |
| Specific Activity (pNPP) (U/mg) | | | | | | | | | | |
| T0 | 901 | 900 | 781 | 861 | 69 | 938 | 949 | 1084 | 990 | 81 |
| T14 | 793 | 795 | 684 | 757 | 64 | 613 | 679 | 801 | 698 | 95 |
| T24 | 747 | 793 | 600 | 713 | 101 | 577 | 585 | 732 | 631 | 87 |
| T48 | 524 | 543 | 458 | 508 | 45 | 386 | 505 | 369 | 420 | 74 |
| SDS-PAGE Non-Reduced % Main Band | | | | | | | | | | |
| T0 | 100.0 | 100.0 | 100.0 | 100.0 | 0.0 | 100.0 | 100.0 | 100.0 | 100.0 | 0.0 |
| T48 | 96.0 | 97.5 | 97.0 | 96.8 | 0.8 | 97.1 | 97.1 | 97.8 | 97.3 | 0.4 |
| Reduced % Main Band | | | | | | | | | | |
| T0 | 100.0 | 100.0 | 100.0 | 100.0 | 0.0 | 100.0 | 100.0 | 100.0 | 100.0 | 0.0 |
| T48 | 100.0 | 100.0 | 100.0 | 100.0 | 0.0 | 100.0 | 100.0 | 100.0 | 100.0 | 0.0 |

Purity

Analytical Ultracentrifugation (AUC)

The % monomer levels determined by analytical ultracentrifugation were comparable between the 2K and the 20K batches. All the values were in the range of 94.5% to 97.6% with a 20K mean of 96.8% and a 2K mean of 95.6%. The difference is within the assay variability of AUC as previously demonstrated for the analysis of an IgG1 antibody (see Pekar and Sukumar 2007 Quantitation of aggregates in therapeutic proteins using sedimentation velocity analytical ultracentrifugation: Practical considerations that affect precision and accuracy. *Analytical Biochemistry*, 367: 225-237), which is also a glycoprotein with a similar molecular weight. GP-HPLC data (shown below) indicates comparable % of monomer, which further indicates that the slight difference among batches detected by AUC was due to intra-assay variation (such as difference between instrument cells). A small additional peak at 2.5 (s) was detected for asfotase alfa produced from exemplary Process #35, which was an artifact of the c(s) analysis. The shift of the #35 peak, corresponding to the dimer of asfotase alfa (approximately 11 (s)), is considered within the error limits of the method. The asfotase alfa AUC data were acquired by the University of Connecticut, Analytical Ultracentrifugation Facility, Biotechnology Bioservices Center. This method distinguishes asfotase alfa monomer from aggregates consisting of dimeric or larger species and their relative % based on continuous sedimentation coefficient distribution.

SDS-PAGE/LoC (Lab on Chip)

The main band % determined by SDS-PAGE: LABCHIP® (PerkinElmer) GXII Protein Assay for both non-reduced and reduced was comparable between the 2K batches and the 20K batches. As summarized in Table 29, the mean main band % was 100.0% (non-reduced) and 99.8% (reduced) for the three 2K batches and 100.0% (non-reduced) and 99.8% (reduced) for 20K batches. In addition, comparable band patterns were observed for the 2K and 20K batches as demonstrated by electropherograms of both the non-reduced and reduced analyses. This test separates the protein based on its molecular mass and provides analysis of the purity of the intact protein expressed as a percent main band. The assay was performed following LabChip GXII Protein Assay Quick Guide, HT Protein Express LabChip Kit, Version 2 (revised March 2010).

SDS-PAGE

The three 2K batches and three 20K batches were analyzed side-by-side using SDS-PAGE. Analysis by densitometry resulted in the main band accounting for 100% for all the batches for both the non-reduced and reduced SDS-PAGE. In addition to the main band, a faint band below the quantitation limit with apparent molecular weight higher than that of the asfotase alfa dimer was observed for all batches. Only one band was observed for all batches by reduced SDS-PAGE. This test separates the protein based on its molecular mass and provides analysis of the purity of the intact protein expressed as a percent main band. The protein sample was separated on a gel, stained with Coomassie Blue Stain for visualization, destained and analyzed by densitometry. Molecular weight of asfotase alfa, degradation products, and process related impurities were estimated by comparison with known molecular weight standards. Quantitative measurements of separated proteins are performed by scanning and analyzing with densitometric analysis.

showed overlaid peaks for 2K and 20K batches at the same retention times, suggesting that products from all batches had the same species. This method separates protein in order of increasing net surface anionic charge. Proteins separated are detected by ultraviolet absorbance at 280 nm and then quantified as peak area percent.

Charge Profile

Capillary Isoelectric Focusing (cIEF)

The peak profiles and the relative % of each peak of the 2K and 20K batches were comparable when asfotase alfa was analyzed by cIEF. All samples exhibit six prominent peaks ranging from isoelectric point (pI) of ~6.57 to ~6.85 and these peaks are referred to as peaks 1, 2, 3, 4, 5 and 6 from left to right. Peak areas detected in 2K and 20K batches for each charged variant species are comparable as shown in Table 29. Comparability between the cIEF peak % of the 2K and 20K batches was confirmed using a T-Test analysis of all batches as shown in Table 32 (all p-values were >0.05 indicating that any observed differences between lots is not significant). The cIEF electropherograms of 2K and 20K batches showed similar peak profiles in the same pI ranges. cIEF provides semi-quantitative separation of charged-variant species based on protein isoform pI's. The separated proteins were detected at 280 nm absorbance.

TABLE 32

T-Test of the cIEF Peak % of 2K and 20K Batches

|  |  |  | cIEF Peak | | | | | |
|---|---|---|---|---|---|---|---|---|
|  |  |  | Peak 1 | Peak 2 | Peak 3 | Peak 4 | Peak 5 | Peak 6 |
| T-Test of Peak % of 2K and 20K batches | 2K Batches | #35 | 33.55 | 10.79 | 12.36 | 17.21 | 10.29 | 15.81 |
|  |  | #36 | 29.01 | 9.54 | 13.49 | 18.71 | 11.78 | 17.47 |
|  |  | #37 | 27.97 | 11.38 | 12.25 | 18.96 | 11.97 | 17.47 |
|  |  | #38 | 33.09 | 10.24 | 13.62 | 17.09 | 11.21 | 14.74 |
|  |  | #39 | 27.87 | 6.02 | 11.96 | 12.93 | 15.33 | 25.90 |
|  | 20K Batches | #40 | 24.46 | 8.53 | 12.97 | 18.79 | 14.62 | 20.62 |
|  |  | #41 | 35.52 | 6.87 | 15.94 | 11.42 | 12.69 | 17.56 |
|  |  | #42 | 24.40 | 8.96 | 10.60 | 20.25 | 13.27 | 22.53 |
|  |  | #43 | 32.50 | 9.65 | 11.60 | 18.00 | 11.64 | 16.60 |
|  |  | #34 | 36.64 | 8.66 | 11.78 | 16.71 | 11.24 | 15.27 |
|  |  | #44 | 24.90 | 10.48 | 15.39 | 18.20 | 9.74 | 21.30 |
|  |  | #45 | 27.40 | 10.10 | 11.65 | 20.94 | 9.50 | 20.40 |
| T-Test P-Value |  |  | 0.74 | 0.57 | 0.91 | 0.65 | 0.79 | 0.67 |

GP-HPLC

The purity of asfotase alfa was analyzed side-by-side by GP-HPLC. The 2K mean (96.5%) and the 20K mean (98.6%) are shown in Table 29. The % asfotase alfa of the 20K batches is slightly higher than that of the 2K batches. However, batch data showed similar % dimer, suggesting that the slightly lower % dimer of 2K batches mainly due to differences in sample history such as material age. The GP-HPLC chromatogram also showed comparable products from the 2K and 20K batches. Same peaks at the same retention times indicate the same species were observed. This method distinguishes asfotase alfa from larger species and smaller fragments.

Anion Exchange Chromatography (AEX)

The % of the main peak by AEX for all 2K batches and 20K batches were within a narrow range of 93.62% to 96.84% as shown in Table 29. The 2K mean was 94.17% and the 20K mean was 96.38% of main peak area. Slightly higher % of the main peak was observed for the 20K batches due to a decrease in the late eluting peak. The slightly higher level of the main peak in the 20K batches demonstrates higher purity of the product. The AEX chromatogram Molecular Size Size Exclusion Chromatography—Multi-Angle Light Scattering (SEC-MALS)

The molecular weights of asfotase alfa determined by SEC-MALS of the 2K and 20K batches were comparable. The mean molecular weight of the 2K batches is 189.2 kDa and the mean molecular weight of the 20K batches is 189.2 kDa as shown In Table 29. Similar peak profiles were observed for all the batches on UV chromatograms (the sample from batch #36 was run at a later date, due to sample availability, resulting in a non-perfect match of its peak profiles with the other samples). The SEC-MALS method combines an SEC column to separate protein species by size with a MALS instrument to determine molecular weight of peaks. High variation in the molecular weights of the high molecular weight species (listed in Table 29), as determined by the light scattering signal and refractive index (RI), is due to higher method variation for determination of low abundant species. Based on UV chromatograms, the relative retention times of the high molecular weight species to asfotase alfa are similar for all six batches, which indicate that the molecular weights of the high molecular weight species should also be similar.

Intact Molecular Weight Analysis (MALDI-ToF-MS)

The mean molecular weight of the 2K batches was 180,902 Da and the mean molecular weight of the 20K batches was 180,019 Da as shown in Table 29. The molecular weights of 20K batches and 2K batches are within the 1% mass accuracy of the externally calibrated MALDI-ToF and thus are comparable. The slightly higher trending of the 2K molecular weight is likely due to the presence of slightly higher amount of larger oligosaccharides such as oligosaccharides with sialic acid. The MALDI-ToF Intact Molecular weight (IMW) spectra for the asfotase alfa 2K and 20K batches also detected the same peak profiles. Batch #36 was analyzed on a separate occasion using a different instrument calibration but was included for completeness of comparability. Additional masses present in the spectra are due to assay induced fragmentation and or multiple charged ions. Intensity differences observed for identified species are a result of matrix crystallization and laser effects. This method identifies the molecule on the basis of molecular weight. Test samples were solid phase-extracted and mixed with sDHB matrix solution and co-precipitated on the MALDI target. This dried sample was ionized with a laser into a ToF mass spectrometer. An m/z spectrum was collected from each sample and the intact m/z was converted to molecular weight.

Identity

Deglycosylated/Reduced & Deglycosylated Molecular Weight Analysis (MALDI-ToF-MS)

The molecular weight for deglycosylated asfotase alfa was calculated from the primary amino acid sequence of the two identical polypeptide amino acid sequences of 726 amino acids using NIST molecular weights and isotope percentages with 20 cysteines forming 10 disulfide bonds. Deglycosylated asfotase alfa molecular weight was calculated to be 161,135.20 Da.

The molecular weights of deglycosylated asfotase alfa from the 20K batches and from the 2K batches were all within 1% of the calculated deglycosylated molecular weight (the mass accuracy of the externally calibrated MALDI-TOF) as shown in Table 29. The mean molecular weight of 20K batches was 160,881 Da and the mean molecular weight of the 2K batches was 161,050 Da as shown in Table 29. The MALDI-ToF spectra for the 2K and 20 K batches detected similar peak profiles. Additional masses present in the spectra were due to assay induced fragmentation, incomplete deglycosylation, and/or multiply charged ions. Intensity differences observed for identified species are a result of matrix crystallization and laser effects.

The molecular weight for reduced and deglycosylated asfotase alfa was calculated from the primary amino acid sequence of the polypeptide amino acid sequence of 726 amino acids using NIST molecular weights and isotope percentages. Reduced and deglycosylated asfotase alfa molecular weight was calculated to be 80,577.68 Da.

The molecular weight values for reduced and deglycosylated asfotase alfa 20K batches compares with 2K batches and all values were within 1% of the calculated reduced and deglycosylated molecular weight (the mass accuracy of the externally calibrated MALDI-ToF) as shown in Table 29. The mean of 2K batches was 80,530 Da and the mean of the 20K batches was 80,539 Da. The MALDI-ToF spectra for the 2K and 20K batches detected comparable peak profiles. Additional masses present in the spectra are due to assay induced fragmentation and or multiple charged ions. Intensity differences observed for identified species are a result of matrix crystallization and laser effects. This method identifies the molecule on the basis of molecular weight. Test samples were solid phase-extracted and mixed with sDHB matrix solution and co-precipitated on the MALDI target. This dried sample was ionized with a laser into a ToF mass spectrometer. An m/z spectrum was collected from each sample and the intact m/z was converted to molecular weight.

The molecular weights of deglycosylated asfotase alfa of the 2K and 20K batches were comparable and all values are within the 100 ppm of the calculated deglycosylated molecular weight (which is the mass accuracy of the externally calibrated ESI-ToF-MS) as shown in Table 29. The mean molecular weight of the 2K batches was 161,137.39 Da and the mean molecular weight of the 20K batches was 161,137.28 Da and the values were consistent with the calculated deglycosylated molecular weight of 161,135.20 Da. The reduced and deglycosylated molecular weight values for the main peak of the 2K batches were comparable to that of the 20K batches and all values are well within the 100 ppm of the calculated reduced and deglycosylated molecular weight (which is the mass accuracy of the externally calibrated ESI-ToF-MS) as shown in Table 29. The mean molecular weight of the 2K batches was 80,575.52 Da and the mean molecular weight of the 20K batches was 80,574.76 Da. The values are consistent with the calculated reduced and deglycosylated molecular weight value for asfotase alfa of 80,577.68 Da. This method identifies the molecule on the basis of intact molecular weight. Test samples were injected onto a C4 RP-HPLC column and eluted with an aqueous:organic solvent gradient. The eluate was then electrosprayed into a ToF mass spectrometer and a spectrum from the upper half of the chromatographic peak was deconvoluted to provide the intact molecular weight.

The zinc and magnesium ion molar ratios determined by Inductively Coupled Plasma-Mass Spectrometry (ICP-MS) for the three 20K and three 2K batches were comparable as shown in Table 29. The calcium ion molar ratios determined by Inductively Coupled Plasma-Atomic Emission Spectroscopy (ICP-AES) for the 20K and 2K batches were comparable as shown in Table 29. The ion molar ratios for zinc and calcium were also in agreement with literature, where two zinc and one calcium were associated with each alkaline phosphatase enzyme monomer (see E. Mornet et al. 2001 "Structural evidence for a functional role of human tissue non-specific alkaline phosphatase in bone mineralization." *JBC*, 276: 31171-31178; and B. Stec, K M. Holtz and ER. Kantrowitz. 2000 "A revised mechanism for the alkaline phosphatase reaction involving three metal ions." *JMB*, 299: 1303-1311). The magnesium ion molar ratio for all batches was surprisingly lower than the expected value reported in literature. ICP-AES was chosen for calcium analysis as ICP-AES does not suffer from the argon poly atomic interferences observed for calcium isotopes in ICP-MS. The asfotase alfa ICP data were acquired commercially. These methods determined the amount of magnesium, zinc and calcium (µg/mL) from which the molar ion ratios were calculated for asfotase alfa.

Phosphorylation Site Identification and Quantitation Via UPLC-MSe

The site and the relative percentage of phosphorylation were determined by UPLC-MS tryptic peptide mapping. Alkaline phosphatase is known to contain a serine residue in the active site that can form a serine-phosphate intermediate (see pp 28-29 of Millán, José Luis. 2006 "Mammalian Alkaline Phosphatases." Wiley-VCH). The same serine residue 93 was found to be phosphorylated in all batches at a percentage in the range of 35.7% to 31.2% as shown in Table 29. The percentage of phosphorylation was found not to correlate with asfotase alfa specific activity (pNPP), HA binding, $K_m$, and $K_{cat}$ (data not shown). Based on the lack of correlation, the phosphorylated intermediate is not a rate limiting step for the activity of asfotase alfa. The confirmation and identification of a phosphorylation site at S93 in asfotase alfa was confirmed via UPLC-MSe peptide mapping. The theoretical sequence of asfotase alfa and the predicted tryptic cleavages were used for the analysis. The resultant LC-MSe data was collected and processed using Waters Biopharmalynx v.1.2. Biopharmalynx software (Waters) identified the 13th tryptic peptide from the primary sequence (T13), which contains S93, the active site serine from the enzymatic portion of the molecule as having Cys102 capped with ac, and S93 existing as both phosphorylated and non-phosphorylated. Once identified as part of the peptide map, extracted ion chromatograms (EIC's) were pulled for each of these peptides and smoothed and integrated. From the resulting EIC peak areas, the ratio of phosphorylated peptide peak area to total peak area gives a relative percentage of the phosphorylation at S93. Confirmation of the +80 Da associated with phosphorylated serine side chain was made by examining the MSC fragmentation pattern generated for the proposed phosphorylated T13 peptide as shown in FIG. 36. This fragmentation pattern confirmed that S93 was shifted by +80 Da (the mass of a phosphorylation) observed by the y12 and y13 ions. Each batch of asfotase alfa was reduced and alkylated then digested with trypsin. Detection was performed by ESI-Q-ToF-MS using a Waters Acquity UPLC and Synapt Q-ToF mass spectrometer, operating in positive ion electrospray mode.

Glycosylation

N-Linked Oligosaccharides Mass Profiling (MALDI-ToF-MS)

Released oligosaccharides from the three 2K batches and the three 20K batches were analyzed by MALDI-ToF and the results are shown in Table 29. The same glycan species at similar relative percentage was observed in the 20K batches and 2K batches. This method identifies the glycans associated with the drug substance by molecular weights. The glycans were enzymatically cleaved from the drug substance using PNGase-F digestion and subsequent acidification. The glycans were then solid pase extracted and mixed with the super 3,4-dihydroxybenzoic acid matrix solution and co-precipitated on the MALDI target. This dried sample was ionized with a laser into a ToF mass spectrometer. An m/z (M+Na)+spectrum was collected.

2-AB Labeled N-Linked Oligosaccharides Profiling (HPLC)

The types of glycoforms and the relative percentage of each glycoform were analyzed by 2-AB labeling and HPLC analysis. The results are shown in Table 29. Peak at the same retention times and with similar relative percentage was observed in all batches (data not shown) suggesting the same types of oligosaccharides and similar levels. Batch #36 sample was run at a later date. As an example, the percentage of the major glycoform FA2 was plotted against enzymatic activities. No correlation was observed between percent FA2 and Specific Activity (pNPP), HA Binding, $K_m$, and $K_{cat}$ (data not shown).

This assay characterizes the glycosylation pattern by determining the oligosaccharides associated with the drug molecule on the basis of the retention time and peak area of the fluorescently tagged free-oligosaccharides. The free oligosaccharides from drug substance were released enzymatically and tagged with 2-aminobenzamide (2-AB) by reductive amination. Samples were then injected on to an HPLC system with a Ludger column and the 2AB tagged oligosaccharides were separated and detected with a fluorescence detector, 330 nm excitation 420 nm emission. The chromatograms of each batch were compared and peak area of each resolved peak was used to determine relative amount of each oligosaccharide from each batch.

Glycopeptide Profile by UPLC-QToF-AMS

The oligosaccharide profile at each glycosylation site was evaluated by analysis of glycopeptides by UPLC-MS. Tissue non-specific alkaline phosphatase (TNAP) has five N-glycosylation sites (see pp 54-55 of Millan, 2006 Wiley-VCH). Asfotase alfa contains an additional N-glycosylation site in the Fc region providing a total of six N-glycosylation sites per monomer. FIG. 44 through FIG. 49 show the glycopeptide fingerprint profiles for N123 in T15-16, N213 in T26-27, N254 in T33, N286 in T35, N413 in T45-46 and N564 in T55. UPLC-Q-ToF-MS glycopeptide fingerprints of the summed N-linked oligosaccharides provided detailed characterization of the N-glycosylation. Identification of glycopeptide species by mass analysis and relative quantitation of each species was performed by transforming the multiple charge states observed in the raw glycopeptide mass fingerprint spectra into singly charged and deisotoped spectra for each site. The results of these transformations are shown in Table 29. It lists all masses observed for the glycoforms and their relative % for glycoforms contributing ≥5% to the total glycoform content at each observed N-linked oligosaccharide site. In this assay, asfotase alfa was reduced and alkylated then digested with trypsin. Detection was performed by ESI-Q-ToF-MS using a Waters Acquity UPLC and Synapt Q-ToF mass spectrometer, operating in positive ion electrospray mode. The theoretical sequence of asfotase alfa and the predicted tryptic cleavages were used for the analysis. Molecular weights for the theoretical glycopeptides were calculated using NIST molecular weights and isotope percentages. Glycopeptides are observed as collections of related glycoforms with closely related elution times and thus requires summation of spectra to ensure the complete glycopeptide complement for a particular site is observed. Site-specific summed spectra (glycopeptide mass fingerprints) were obtained for each of the most abundant peptide species containing each of the N-linked oligosaccharide sites in asfotase alfa for each batch tested.

Total Sialic Acid Content (TSAC)

Total sialic acid content was determined by HPAE-PAD. As shown in Table 29, sialic acid content for each batch is within the specification of 0.9-3.5 mole sialic acid per mole of monomer. Considering the variation of the sialic acid content due to its relatively lower amount, the 2K batches and 20K batches were comparable. No correlation was observed between TSAC value and Specific Activity (pNPP), HA Binding, $K_m$, and $K_{cat}$.

Activity

Specific Activity (pNPP)

Specific activity of asfotase alfa was determined for the three 20K and three 2K batches. The mean specific activity of the 20K batches is 981.7 U/mg and 861.7 U/mg for the three 2 K batches. The specific activity of all batches was within the specification of 620-1250 U/mg and was comparable for the 20K and 2K batches. This method is used for the determination of asfotase alfa enzymatic activity using pNPP as a substrate. Asfotase alfa is a recombinant protein that has one domain from the human tissue non-specific alkaline phosphatase enzyme. This domain is catalytically active and hydrolyzes phosphate esters. The assay is performed at enzyme saturation to reach and maintain Vmax for duration of the measurement. The pNPP is hydrolyzed into a yellow colored product (maximal absorbance at 405 nm).

The rate of reaction is directly proportional to the enzyme activity. One unit (U) corresponds to 1 μmol of pNPP formed per minute under the employed method conditions. The Specific Activity by pNPP (enzymatic activity per mg protein) was calculated from the enzymatic activity and the Protein Concentration by $A_{280}$. The results are shown in Table 29.

Hydroxyapatite Binding

The % hydroxyapatite binding determined by the HA Binding Assay of asfotase alfa 2K batches were comparable with the 20K batches with all values in the range of 85-97%. The mean % HA binding is 91% for both the 20K and 2K batches (Table 29). The HA binding assay measures the enzymatic activity of asfotase alfa complex for pNPP when bound to hydroxyapatite. A synthetic substrate, para-Nitrophenyl Phosphate (pNPP), when hydrolyzed by asfotase alfa, produces a yellow colored product that can be quantifiable by absorbance at 405 nm. This assay was performed at substrate saturation in order to reach and maintain the Vmax for the duration of the reaction.

PPi Enzyme Kinetic Assay Using Physiological Relevant Substance

The kinetic parameters $K_m$ and $K_{cat}$ were determined by PPi Kinetic Assay. Samples were run on a number of occasions head-to-head with the reference standard. For comparison, $K_m$ and $K_{cat}$ are graphed as a percent of the reference standard value run at the time of sample testing (Table 29). All $K_m$ values were within 30% of the reference standard value run side-by-side and are considered comparable. All $K_{cat}$ values were within 20% of the reference standard run side-by-side and are considered comparable. The $K_m$% of reference and $K_{cat}$% of reference for the 2K batches were comparable to the 20K batches. PPi Kinetic Assay measures the purified asfotase alfa potency (enzymatic activity) using PPi, a natural alkaline phosphatase substrate and determines kinetic constants $K_m$ and $K_{cat}$ of PPi hydrolysis under physiological conditions (37° C., pH 7.4).

Temperature Forced Degradation

To further ensure comparability of the 2K and the 20K batches, side-by-side forced degradation study was performed to compare the degradation pathways and kinetics. Three 2K batches (#35, #36, and #38) and three 20K batches (#40, #42, and #34), detailed in Table 33, were used for the study. Some batches required the use of drug product (DP) material due to limited BDS sample availability.

Batches #35, #36, #40, #42, and #34 were diluted using asfotase alfa formulation buffer (25 mM sodium phosphate and 150 mM sodium chloride, pH 7.4) to 40 mg/mL to match the protein concentration of batch #38. To achieve substantial levels of degradations to establish degradation kinetics, forced degradation conditions were chosen based on preliminary forced degradation condition screening. Aliquots (200 μL) were created for each test assay at each time point (0, 14, 24 and 48 hours). The T0 aliquots were held at 5° C. until testing. The rest of the sample aliquots were incubated at 40° C. for 14, 24 and 48 hours. Samples were analyzed by SDS-PAGE, GP-HPLC, AEX, RP-HPLC, Peptide Mapping, and Potency as listed in Table 30 to determine comparability. The test results for the temperature forced degradation study are listed in Table 31 for the three 20K batches and three 2K batches.

TABLE 33

Batches Used for the Degradation Study

| Name | Concentration mg/mL |
|---|---|
| #35 | 90.9 |
| #36 | 96.4 |
| #38 | 40.0 |
| #40 | 107.6 |
| #42 | 92.9 |
| #34 | 101.6 |

SDS-PAGE (Non-Reduced and Reduced)

T0 and T48 hour samples were analyzed by SDS-PAGE (non-reduced and reduced) for purity. The main band % by non-reduced SDS-PAGE was 100% for all batches at T=0 and decreased to a mean of 97.3% for 20K batches and 96.8% for 2K batches as shown in Table 31. The trend of degradation is comparable for the 20K and 2K batches. High molecular weight species was detected in the T48 hour sample for all six batches. This species disappeared upon reduction. This result suggests the formation of disulfide bond-related aggregates is a degradation pathway for all batches. No extra bands were observed by reduced SDS-PAGE for both the 20K and 2K batches at T=0 and T=48 hours, indicating no degradation in the peptide bonds. This test separates the protein based on its molecular mass and provides analysis of the purity of the intact protein expressed as a percent main band. The protein sample is separated on a gel, stained with Coomassie Blue Stain for visualization, destained and analyzed by densitometry. Molecular weight of asfotase alfa, degradation products, and process related impurities are estimated by comparison with known molecular weight standards. Quantitative measurements of separated proteins are performed by scanning and analyzing with densitometric analysis.

GP-HPLC

Degradation to form aggregates and fragments caused by thermal stress was monitored by GP-HPLC and the results are shown in Table 31. The peak profiles for all batches at T=0 were similar suggesting the presence of the same species. Thermal stress resulted in the appearance of a peak at approximately 6 minutes, corresponding to large aggregates, which increased over time. The peak profiles of all batches at T=14 hours, T=24 hours and T=48 hours were similar, which indicates similar degradation pathway. The slopes of decrease of the main peak over time for all batches were similar taking into account the fact that the materials used were at different ages. Similar slope indicates similar degradation kinetics.

Anion Exchange Chromatography (AEX)

Degradation of asfotase alfa was also monitored by AEX, which separates proteins based on charge. The same peak profiles were observed for all batches at T=0, suggesting the same species in all batches. Thermal stress resulted in the increase of peaks in the retention time window of approximately 22-26 minutes. Comparable peaks profiles for all batches were observed for all batches at T=14 hours, T=24 hours and at T=48 hours, which indicates formation of the same species by thermal degradation. Similar slopes of degradation, monitored by decrease of the main peak, were observed for all batches taking into account the slight difference at T=0 (as disclosed previously) and the age difference of different batches.

RP-HPLC

When analyzed by RP-HPLC, a mean peak in the retention time window of approximately 21.2-21.3 minutes was observed for all batches, indicating the same species in all batches. The main peak was the only major peak observed for all batches at T=0. Thermal stress resulted in an increase in a peak eluting immediately after the main peak. The same peak from thermal degradation observed for all batches at T=14, T=24 and T=48 hours suggests the same degradation pathway. Degradation kinetics as monitored by the decrease of the main peak was comparable for all batches as evidenced by similar slopes of all batches.

Peptide Mapping

T0, T24 and T48 hour samples for 20K and 2K batches were analyzed by peptide mapping for evaluation of potential chemical degradation. There was no observed significant difference between 20K and 2K at all the time points (T=0 hour and T=48 hours). This method denatures, reduces and alkylates protein with guanidine hydrochloride, dithiothreitol and iodoacetate, followed by digestion with the protease trypsin. The peptide fragments produced are separated by gradient reversed phase HPLC and detected at 210 nm.

Specific Activity (pNPP)

Specific activity (pNPP) of asfotase alfa 20K batches and 2K batches was determined by enzymatic assay after 40° C. incubation at each time point (T0, T14, T24, and T48). The activities of the 20K batches were comparable with the 2K batches at each time point. Decrease in the activity caused by thermal stress follows similar slopes for all batches over time. Protein phosphatase, enzyme controls the removal of phosphate ($PO_4^{3-}$) group from protein molecules. pNPP Phosphatase Assay was used to detect phosphatase activity and to compare 20K and 2K batches. This method is used for the determination of asfotase alfa enzymatic activity using pNPP as a substrate. Asfotase alfa is a recombinant protein that has one domain from the human tissue non-specific alkaline phosphatase enzyme. This domain is catalytically active and hydrolyzes phosphate esters. The assay is performed at enzyme saturation to reach and maintain Vmax for duration of the measurement. The pNPP is hydrolyzed into a yellow colored product (maximal absorbance at 405 nm). The rate of reaction is directly proportional to the enzyme activity. One unit (U) corresponds to 1 μmol of pNPP formed per minute under the employed method conditions. The Specific Activity by pNPP (enzymatic activity per mg protein) is calculated from the enzymatic activity and the Protein Concentration by $A_{280}$.

Comparability of asfotase alfa manufactured at 20K scale and asfotase alfa manufactured at 2K scale was established. Three batches from each scale was analyzed side-by-side, if possible, using physicochemical methods to evaluate asfotase alfa purity, impurities, charge variants, size, structure, glycosylation, disulfide bond, free thiols and activity. In addition, side-by-side forced degradation study was carried out to evaluate the degradation pathways and kinetics. The results demonstrate that the manufactured products at 20K and 2K scales were comparable.

The purity of the batches was assessed by analytical ultracentrifugation, SDS-PAGE/LoC, SDS-PAGE, GP-HPLC, and AEX. The results showed comparable purity for all the batches. The same types of aggregates at very low comparable levels were detected in all batches by AUC, SDS-PAGE and GP-HPLC.

Charge variants, common for recombinant proteins, were evaluated by cIEF. The same species at comparable levels was observed for all batches, suggesting consistent level of posttranslational modifications.

The molecular size of the batches was assessed by SEC-MALS, and intact MALDI-ToF molecular weight. Identity was confirmed by deglycosylated/reduced & deglycosylated MALDI-ToF molecular weight and deglycosylated/reduced & deglycosylated ESI-ToF molecular weight. Structure was also evaluated by CD, disulfide bonding and free thiols (LC/MS), total free thiol assay, metal content analysis (ICP-MS/ICP-AES), and phosphorylation site occupancy. Comparable molecular weights and comparable hydrodynamic size were obtained for all batches, indicating similar modifications and similar conformation of asfotase alfa of all batches.

Asfotase alfa glycosylation was assessed by MALDI-ToF free glycan, 2AB labeled oligosaccharide fHPLC, LC-MS glycopeptide analysis, and total sialic acid content. The same oligosaccharide species at comparable levels were obtained for all batches.

The activity of the drug substance was assessed by specific activity (pNPP), HA binding and PPi activity. The results showed that that asfotase alfa 20K batches were comparable to asfotase alfa 2K batches.

Lastly, the same degradation pathway and similar degradation kinetics of the 20K and 2K batches was observed by the side-by-side forced degradation study using thermal stress.

In summary, asfotase alfa 20K batches and 2K batches are comparable as demonstrated by extended characterization using multiple orthogonal methods and side-by-side forced degradation study. Thus, material from 20K batches should have comparable safety and efficiency as material from the 2K batches.

Example 10. Additional Comparability of Asfotase Alfa Manufactured at 2,000 L (2K) and 20,000 L (20K) Scales Seven batches of asfotase alfa were produced at the 20,000 L scale, and five additional batches of asfotase alfa were produced using the 2,000 L scale. The products for both scales were analyzed and found to be comparable (data not shown).

What is claimed is:

1. A method for producing a population of recombinant polypeptides, comprising:
   a) providing a 100 L to 25,000 L fed-batch bioreactor comprising
      i) cells capable of expressing the recombinant polypeptides, wherein the recombinant polypeptides are asfotase alfa having the sequence of SEQ ID NO: 1, and
      ii) a culture medium suitable for conducting such expression, the culture medium comprising from about 25 μM to about 300 μM zinc; and
   b) culturing the cells under conditions suitable to express the recombinant polypeptides; wherein the pH of the culture medium is about 6.7 to about 7.1, wherein zinc is added into said culture medium such that the zinc concentration in the culture medium is maintained at a concentration of about 25 μM to about 300 μM of zinc, wherein the zinc is added into said culture medium in at least one bolus, continuously, or semi-continuously;
   wherein the recombinant polypeptides comprise a total sialic acid content (TSAC) between about 0.9 to about 3.5 mol sialic acid/mol protein monomer; and
   wherein the bioreactor comprises a molar ratio of zinc per mole of recombinant polypeptide of from about 0.5 to about 3.0.

2. The method of claim 1, wherein the zinc concentration in the culture medium is maintained at a concentration of from about 25 μM to about 150 μM of zinc.

3. The method of claim 2, wherein the zinc concentration in the culture medium is maintained at a concentration of from about 60 μM to about 150 μM of zinc.

4. The method of claim 3, wherein the zinc concentration in the culture medium is maintained at a concentration of about 28 μM of zinc.

5. The method of claim 1, wherein the pH of said culture medium is maintained at from about 6.8 to about 7.0.

6. The method of claim 1, wherein the pH of said culture medium is maintained at about 6.9.

7. The method of claim 1, further comprising adding at least one, two, three, or four feed bolus(es) to the culture medium during culturing.

8. The method of claim 7, wherein at least four feed boluses are added to the culture medium.

9. The method of claim 1, further comprising culturing the cells at a first temperature until reaching a cell density of at least about $2.5 \times 10^6$ viable cells, and shifting to a second temperature which is lower than the first temperature for recombinant polypeptide expression.

10. The method of claim 9, wherein the first temperature is from about 35° C. to about 37.5° C.

11. The method of claim 9, wherein the second temperature is from about 29° C. to about 35° C.

12. The method of claim 9, wherein the first temperature is about 37° C. and the second temperature is about 30° C.

13. The method of claim 9, wherein the first temperature is about 36.5° C. and the second temperature is about 33° C.

14. The method of claim 1, wherein the cells are selected from the group consisting of CHO, NS0/1, PER.C6, COS-7, human embryonic kidney (HEK), HEK 293, 293 HEK cells subcloned for growth in suspension culture, BHK, TM4, CVI, VERO-76, HeLa, MDCK, BRL 3A, W138, Hep G2, MMT 060562, TRI, MRC 5, FS4, and Hep G2 cells.

15. The method of claim 14, wherein the cells are CHO cells.

16. The method of claim 1, wherein the fed-batch reactor is 2,000 L to 20,000 L.

17. The method of claim 1, wherein the population of asfotase alfa polypeptides have a specific activity (pNPP) of 620 to 1250 units/mg.

18. The method of claim 1, wherein the population of asfotase alfa polypeptides have a mean TSAC value from 1.2 to 3.0 mol sialic acid/mol protein monomer.

* * * * *

UNITED STATES PATENT AND TRADEMARK OFFICE
CERTIFICATE OF CORRECTION

| | | |
|---|---|---|
| PATENT NO. | : 11,352,612 B2 | Page 1 of 1 |
| APPLICATION NO. | : 15/751498 | |
| DATED | : June 7, 2022 | |
| INVENTOR(S) | : Jaluria et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1051 days.

Signed and Sealed this
Twenty-first Day of January, 2025

Coke Morgan Stewart
*Acting Director of the United States Patent and Trademark Office*

SEQUENCE LISTING

```
<160> NUMBER OF SEQ ID NOS: 1

<210> SEQ ID NO 1
<211> LENGTH: 726
<212> TYPE: PRT
<213> ORGANISM: Artificial Sequence
<220> FEATURE:
<223> OTHER INFORMATION: Synthetic polypeptide

<400> SEQUENCE: 1
```

```
Leu Val Pro Glu Lys Glu Lys Asp Pro Lys Tyr Trp Arg Asp Gln Ala
1               5                   10                  15

Gln Glu Thr Leu Lys Tyr Ala Leu Glu Leu Gln Lys Leu Asn Thr Asn
                20                  25                  30

Val Ala Lys Asn Val Ile Met Phe Leu Gly Asp Gly Met Gly Val Ser
            35                  40                  45

Thr Val Thr Ala Ala Arg Ile Leu Lys Gly Gln Leu His His Asn Pro
        50                  55                  60

Gly Glu Glu Thr Arg Leu Glu Met Asp Lys Phe Pro Phe Val Ala Leu
65                  70                  75                  80

Ser Lys Thr Tyr Asn Thr Asn Ala Gln Val Pro Asp Ser Ala Gly Thr
                85                  90                  95

Ala Thr Ala Tyr Leu Cys Gly Val Lys Ala Asn Glu Gly Thr Val Gly
            100                 105                 110

Val Ser Ala Ala Thr Glu Arg Ser Arg Cys Asn Thr Thr Gln Gly Asn
        115                 120                 125

Glu Val Thr Ser Ile Leu Arg Trp Ala Lys Asp Ala Gly Lys Ser Val
    130                 135                 140

Gly Ile Val Thr Thr Arg Val Asn His Ala Thr Pro Ser Ala Ala
145                 150                 155                 160

Tyr Ala His Ser Ala Asp Arg Asp Trp Tyr Ser Asp Asn Glu Met Pro
                165                 170                 175

Pro Glu Ala Leu Ser Gln Gly Cys Lys Asp Ile Ala Tyr Gln Leu Met
            180                 185                 190

His Asn Ile Arg Asp Ile Asp Val Ile Met Gly Gly Gly Arg Lys Tyr
        195                 200                 205

Met Tyr Pro Lys Asn Lys Thr Asp Val Glu Tyr Glu Ser Asp Glu Lys
    210                 215                 220

Ala Arg Gly Thr Arg Leu Asp Gly Leu Asp Leu Val Asp Thr Trp Lys
225                 230                 235                 240

Ser Phe Lys Pro Arg Tyr Lys His Ser His Phe Ile Trp Asn Arg Thr
                245                 250                 255

Glu Leu Leu Thr Leu Asp Pro His Asn Val Asp Tyr Leu Leu Gly Leu
            260                 265                 270

Phe Glu Pro Gly Asp Met Gln Tyr Glu Leu Asn Arg Asn Asn Val Thr
        275                 280                 285

Asp Pro Ser Leu Ser Glu Met Val Val Ala Ile Gln Ile Leu Arg
    290                 295                 300

Lys Asn Pro Lys Gly Phe Phe Leu Leu Val Glu Gly Gly Arg Ile Asp
305                 310                 315                 320

His Gly His His Glu Gly Lys Ala Lys Gln Ala Leu His Glu Ala Val
                325                 330                 335

Glu Met Asp Arg Ala Ile Gly Gln Ala Gly Ser Leu Thr Ser Ser Glu
            340                 345                 350

Asp Thr Leu Thr Val Val Thr Ala Asp His Ser His Val Phe Thr Phe
        355                 360                 365

Gly Gly Tyr Thr Pro Arg Gly Asn Ser Ile Phe Gly Leu Ala Pro Met
    370                 375                 380

Leu Ser Asp Thr Asp Lys Lys Pro Phe Thr Ala Ile Leu Tyr Gly Asn
385                 390                 395                 400

Gly Pro Gly Tyr Lys Val Val Gly Gly Glu Arg Glu Asn Val Ser Met
                405                 410                 415
```

```
Val Asp Tyr Ala His Asn Asn Tyr Gln Ala Gln Ser Ala Val Pro Leu
            420                 425                 430

Arg His Glu Thr His Gly Gly Glu Asp Val Ala Val Phe Ser Lys Gly
        435                 440                 445

Pro Met Ala His Leu Leu His Gly Val His Glu Gln Asn Tyr Val Pro
    450                 455                 460

His Val Met Ala Tyr Ala Ala Cys Ile Gly Ala Asn Leu Gly His Cys
465                 470                 475                 480

Ala Pro Ala Ser Ser Leu Lys Asp Lys Thr His Thr Cys Pro Pro Cys
            485                 490                 495

Pro Ala Pro Glu Leu Leu Gly Gly Pro Ser Val Phe Leu Phe Pro Pro
            500                 505                 510

Lys Pro Lys Asp Thr Leu Met Ile Ser Arg Thr Pro Glu Val Thr Cys
        515                 520                 525

Val Val Val Asp Val Ser His Glu Asp Pro Glu Val Lys Phe Asn Trp
    530                 535                 540

Tyr Val Asp Gly Val Glu Val His Asn Ala Lys Thr Lys Pro Arg Glu
545                 550                 555                 560

Glu Gln Tyr Asn Ser Thr Tyr Arg Val Val Ser Val Leu Thr Val Leu
            565                 570                 575

His Gln Asp Trp Leu Asn Gly Lys Glu Tyr Lys Cys Lys Val Ser Asn
            580                 585                 590

Lys Ala Leu Pro Ala Pro Ile Glu Lys Thr Ile Ser Lys Ala Lys Gly
        595                 600                 605

Gln Pro Arg Glu Pro Gln Val Tyr Thr Leu Pro Pro Ser Arg Glu Glu
    610                 615                 620

Met Thr Lys Asn Gln Val Ser Leu Thr Cys Leu Val Lys Gly Phe Tyr
625                 630                 635                 640

Pro Ser Asp Ile Ala Val Glu Trp Glu Ser Asn Gly Gln Pro Glu Asn
            645                 650                 655

Asn Tyr Lys Thr Thr Pro Pro Val Leu Asp Ser Asp Gly Ser Phe Phe
        660                 665                 670

Leu Tyr Ser Lys Leu Thr Val Asp Lys Ser Arg Trp Gln Gln Gly Asn
    675                 680                 685

Val Phe Ser Cys Ser Val Met His Glu Ala Leu His Asn His Tyr Thr
    690                 695                 700

Gln Lys Ser Leu Ser Leu Ser Pro Gly Lys Asp Ile Asp Asp Asp Asp
705                 710                 715                 720

Asp Asp Asp Asp Asp Asp
                725
```